United States Patent
Brizgys et al.

(10) Patent No.: US 9,050,344 B2
(45) Date of Patent: Jun. 9, 2015

(54) THERAPEUTIC COMPOUNDS

(71) Applicant: Gilead Sciences, Inc., Foster City, CA (US)

(72) Inventors: Gediminas Brizgys, San Mateo, CA (US); Chien-Hung Chou, Livermore, CA (US); Randall L. Halcomb, Foster City, CA (US); Yunfeng Eric Hu, San Mateo, CA (US); Qi Liu, Union City, CA (US); John R. Somoza, San Francisco, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/151,758

(22) Filed: Jan. 9, 2014

(65) Prior Publication Data
US 2014/0221347 A1 Aug. 7, 2014

Related U.S. Application Data

(60) Provisional application No. 61/750,763, filed on Jan. 9, 2013.

(51) Int. Cl.

| | |
|---|---|
| A61K 31/5377 | (2006.01) |
| C07D 401/14 | (2006.01) |
| C07D 401/12 | (2006.01) |
| C07D 403/14 | (2006.01) |
| A61K 31/4439 | (2006.01) |
| A61K 31/444 | (2006.01) |
| A61K 31/506 | (2006.01) |
| A61K 45/06 | (2006.01) |
| C07D 403/12 | (2006.01) |
| C07D 405/14 | (2006.01) |
| C07D 491/107 | (2006.01) |

(52) U.S. Cl.
CPC .......... *A61K 31/5377* (2013.01); *C07D 401/14* (2013.01); *C07D 401/12* (2013.01); *C07D 403/14* (2013.01); *A61K 31/4439* (2013.01); *A61K 31/444* (2013.01); *A61K 31/506* (2013.01); *A61K 45/06* (2013.01); *C07D 403/12* (2013.01); *C07D 405/14* (2013.01); *C07D 491/107* (2013.01)

(58) Field of Classification Search
CPC .............. A61K 31/444; A61K 31/496; A61K 31/5377; C07D 401/14
USPC ...................... 514/210.21; 544/297
See application file for complete search history.

(56) References Cited

U.S. PATENT DOCUMENTS

| | | |
|---|---|---|
| 2013/0165489 A1 | 6/2013 | Cocklin et al. |
| 2014/0142085 A1 | 5/2014 | Bondy et al. |
| 2014/0221346 A1 | 8/2014 | Halcomb et al. |
| 2014/0221417 A1 | 8/2014 | Bondy et al. |
| 2014/0221421 A1 | 8/2014 | Bondy et al. |

FOREIGN PATENT DOCUMENTS

| | | |
|---|---|---|
| WO | WO-2004/050643 A2 | 6/2004 |
| WO | WO-2004/050643 A3 | 6/2004 |
| WO | WO-2009/062285 A1 | 5/2009 |
| WO | WO-2010/130034 A1 | 11/2010 |
| WO | WO-2012/003497 A1 | 1/2012 |
| WO | WO-2012/003498 A1 | 1/2012 |
| WO | WO-2012/145728 A1 | 10/2012 |
| WO | WO-2013/006738 A1 | 1/2013 |
| WO | WO-2013/006792 A1 | 1/2013 |
| WO | WO-2013/159064 A1 | 10/2013 |
| WO | WO-2014/016358 A1 | 1/2014 |

OTHER PUBLICATIONS

Berge, S.M. et al. (Jan. 1977). "Pharmaceutical Salts," *J. Pharma. Sci.* 66(1):1-19.
Hammer, S. et al. (Aug. 6, 2008). "Antiretroviral Treatment of Adult HIV Infection. 2008 Recommendations of the International AIDS Society: USA Panel," *JAMA* 300(5):555-570.
International Search Report mailed on Mar. 11, 2014 for PCT Patent Application No. PCT/US2014/010938, filed on Jan. 9, 2014, three pages.
Lemke, C.T. et al. (Jun. 2012). "Distinct Effects of Two HIV-1 Capsid Assembly Inhibitor Families That Bind the Same Site Within the N-Terminal Domain of the Viral CA Protein," *J. Virol.* 86(12):6643-6655.
Smith, R.J. et al. (Feb. 5, 2010; e-pub. Jan. 14, 2010). "Evolutionary Dynamics of Complex Networks of HIV Drug-Resistant Strains: The Case of San Francisco," *Science* 327(5966):697-701.
Taiwo, B. (Sep. 2009; e-pub. Jan. 10, 2009). "Understanding Transmitted HIV Resistance Through the Experience in the USA," *Int'l J. of Infectious Diseases* 13(5):552-559.
Written Opinion of the International Searching Authority mailed on Mar. 11, 2014 for PCT Patent Application No. PCT/US2014/010938, filed on Jan. 9, 2014, five pages.
Restriction Requirement mailed on Jul. 28, 2014, for U.S. Appl. No. 14/151,752, filed Jan. 9, 2014, six pages.

*Primary Examiner* — Taofiq A Solola
(74) *Attorney, Agent, or Firm* — Timothy A. Marquart

(57) ABSTRACT

Compounds of formula I:

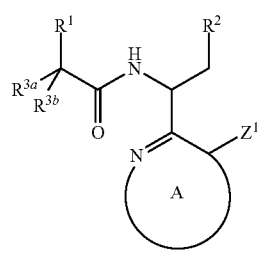

or pharmaceutically acceptable salts thereof are disclosed. Also disclosed are pharmaceutical compositions comprising a compound of formula I, processes for preparing compounds of formula I, intermediates useful for preparing compounds of formula I and therapeutic methods for treating a Retroviridae viral infection including an infection caused by the HIV virus.

17 Claims, No Drawings

THERAPEUTIC COMPOUNDS

CROSS REFERENCE TO RELATED APPLICATION

This application claims the benefit of and priority to U.S. Provisional Application Ser. No. 61/750,763, filed Jan. 9, 2013, the disclosure of which is hereby incorporated by reference in its entirety.

BACKGROUND

Positive-single stranded RNA viruses comprising the Retroviridae family include those of the subfamily Orthoretrovirinae and genera *Alpharetrovirus, Betaretrovirus, Gamaretrovirus, Deltaretrovirus, Epsilonretrovirus, Lentivirus,* and *Spumavirus* which cause many human and animal diseases. Among the *Lentivirus,* HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments do lead to the emergence of HIV strains that are resistant to current therapies (Taiwo, B., *International Journal of Infectious Diseases* 2009, 13:552-559; Smith, R. J., et al., *Science* 2010, 327:697-701). Therefore, there is a pressing need to discover new antiretroviral agents that are active against emerging drug-resistant HIV variants.

SUMMARY

Provided herein are compounds and methods for the treatment of a viral infection.

One embodiment provides a compound of formula If:

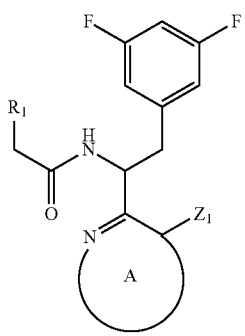

If wherein:

A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with $Z^3$ group;

$R^1$ is

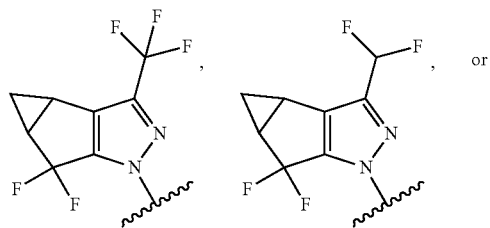

$Z^1$ is aryl, heteroaryl, or heterocycle, wherein any aryl, heteroaryl and heterocycle of $Z^1$ is optionally substituted with $(C_1-C_8)$alkyl, oxo, halogen, —C(O)NH$_2$, —NHS(O)$_2$CH$_3$, or —N(COCH$_3$)(S(O)$_2$CH$_3$);

$Z^2$ is —NR$_{q3}$R$_{r3}$, —NHCOR$_{p3}$, —NHCO$_2$R$_{p3}$, —NHS(O)$_2$ R$_{p3}$, —NHS(O)$_2$OR$_{p3}$, —NHS(O)$_2$NR$_{q3}$R$_{r3}$ or —SCH$_3$;

R$_{q3}$ and R$_{r3}$ are each independently H or $(C_1-C_4)$alkyl, wherein any $(C_1-C_4)$alkyl of R$_{q3}$ or R$_{r3}$ is optionally substituted with —OH, or R$_{q3}$ and R$_{r3}$ together with the nitrogen to which they are attached form a heterocycle or heteroaryl, wherein the heterocycle or heteroaryl is optionally substituted with $(C_1-C_4)$alkyl, —OH, —NH$_2$, or oxo;

R$_{p3}$ is $(C_1-C_4)$alkyl or $(C_1-C_4)$haloalkyl; and each $Z^3$ is independently halogen, $(C_1-C_4)$alkyl, —OH, —CN, $(C_1-C_4)$heteroalkyl or $(C_1-C_4)$haloalkyl; and or a pharmaceutically acceptable salt thereof.

One embodiment provides a compound of formula I

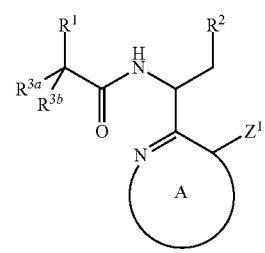

I wherein:

A is a 6-membered heteroaryl with of one or two nitrogen atoms, wherein the 6-membered heteroaryl is substituted with one $Z^1$ group at the position shown, one $Z^2$ group, and optionally substituted with one or more (e.g., 1 or 2) $Z^3$ groups;

$R^1$ is aryl, heteroaryl or heterocycle, wherein any aryl, heteroaryl or heterocycle of $R^1$ is optionally substituted with one or more (e.g., 1, 2, 3, 4 or 5) $Z^4$ groups;

$R^2$ is phenyl, 5-membered heteroaryl, 6-membered heteroaryl or $(C_3-C_7)$carbocycle wherein any phenyl, 5-membered heteroaryl, 6-membered heteroaryl or $(C_3-C_7)$carbocycle of $R^2$ is optionally substituted with one or more (e.g., 1, 2 or 3) $Z^5$ groups;

each $R^{3a}$ and $R^{3b}$ is independently selected from H, halogen, $(C_1-C_3)$alkyl, and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is selected from aryl, heteroaryl, and heterocycle, wherein any aryl, heteroaryl and heterocycle of $Z^1$ is optionally substituted with one or more (e.g., 1, 2, 3, 4 or 5) $Z^{1a}$ or $Z^{1b}$;

each $Z^{1a}$ is independently selected from $(C_3-C_7)$carbocycle, aryl, heteroaryl, heterocycle, halogen, —CN, —OR$_{n1}$, —OC(O)R$_{p1}$, —OC(O)NR$_{q1}$R$_{r1}$, —SR$_{n1}$, —S(O) R$_{p1}$, —S(O)$_2$OH, —S(O)$_2$R$_{p1}$, —S(O)$_2$NR$_{q1}$R$_{r1}$,

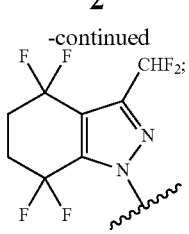

—$NR_{q1}R_{r1}$, —$NR_{n1}COR_N$, —$NR_{n1}CO_2R_{p1}$, —$NR_{n1}CONR_{q1}R_{r1}$, —$NR_{n1}S(O)_2R_{p1}$, —$NR_{n1}S(O)_2OR_{p1}$, —$NR_{n1}S(O)_2NR_{q1}R_{r1}$, $NO_2$, —$C(O)R_{n1}$, —$C(O)OR_{n1}$, —$C(O)NR_oR_{r1}$ and —$S(O)_2NR_{n1}COR_{p1}$, wherein any ($C_3$-$C_7$)carbocycle, aryl, heteroaryl and heterocycle of $Z^{1a}$ is optionally substituted with one or more (e.g., 1, 2, 3, 4 or 5) $Z^{1c}$ or $Z^{1d}$ groups;

each $Z^{1b}$ is independently selected from ($C_1$-$C_8$)alkyl, ($C_2$-$C_8$)alkenyl and ($C_2$-$C_8$)alkynyl, wherein any ($C_1$-$C_8$)alkyl, ($C_2$-$C_8$)alkenyl and ($C_2$-$C_8$)alkynyl of $Z^{1b}$ is optionally substituted with one or more (e.g., 1, 2, 3, 4 or 5) $Z^{1c}$ groups;

each $Z^{1c}$ is independently selected from ($C_3$-$C_7$)carbocycle, aryl, heteroaryl, heterocycle, halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O_2NR_{q2}R_{r2}$, $NO_2$, —$C(O)R_{n2}$, —$C(O)OR_{n2}$, —$C(O)NR_{q2}R_{r2}$, haloaryl, haloheteroaryl, haloheterocycle and ($C_1$-$C_8$)heteroalkyl;

each $Z^{1d}$ is independently selected from ($C_1$-$C_8$)alkyl, ($C_2$-$C_8$)alkenyl, ($C_2$-$C_8$)alkynyl and ($C_1$-$C_8$)haloalkyl;

each $R_{n1}$ is independently selected from H, ($C_1$-$C_8$)alkyl, ($C_2$-$C_8$)alkenyl, ($C_2$-$C_8$)alkynyl, ($C_3$-$C_7$)carbocycle, heterocycle, heteroaryl and aryl, wherein any ($C_3$-$C_7$)carbocycle, aryl, heteroaryl and heterocycle of $R_{n1}$ is optionally substituted with one or more (e.g., 1, 2, 3, 4 or 5) $Z^{1c}$ or $Z^{1d}$ groups, and wherein any ($C_1$-$C_8$)alkyl, ($C_2$-$C_8$)alkenyl and ($C_2$-$C_8$)alkynyl of $R_{n1}$ is optionally substituted with one or more (e.g., 1, 2, 3, 4 or 5) $Z^{1c}$ groups;

each $R_{p1}$ is independently selected from ($C_1$-$C_8$)alkyl, ($C_2$-$C_8$)alkenyl, ($C_2$-$C_8$)alkynyl, ($C_3$-$C_7$)carbocycle, heterocycle, heteroaryl and aryl, wherein any ($C_3$-$C_7$)carbocycle, aryl, heteroaryl and heterocycle of $R_{p1}$ is optionally substituted with one or more (e.g., 1, 2, 3, 4 or 5) $Z^{1c}$ or $Z^{1d}$ groups, and wherein any ($C_1$-$C_8$)alkyl, ($C_2$-$C_8$)alkenyl and ($C_2$-$C_8$)alkynyl of $R_{p1}$ is optionally substituted with one or more (e.g., 1, 2, 3, 4 or 5) $Z^{1c}$ groups;

$R_{q1}$ and $R_{n1}$ are each independently selected from H, ($C_1$-$C_8$)alkyl, ($C_2$-$C_8$)alkenyl, ($C_2$-$C_8$)alkynyl, ($C_3$-$C_7$)carbocycle, heterocycle, heteroaryl and aryl, wherein any ($C_3$-$C_7$)carbocycle, aryl, heteroaryl and heterocycle of $R_{q1}$ or $R_{n1}$ is optionally substituted with one or more (e.g., 1, 2, 3, 4 or 5) $Z^{1c}$ or $Z^{1d}$ groups, and wherein any ($C_1$-$C_8$)alkyl, ($C_2$-$C_8$)alkenyl and ($C_2$-$C_8$)alkynyl of $R_{q1}$ or $R_{r1}$ is optionally substituted with one or more (e.g., 1, 2, 3, 4 or 5) $Z^{1c}$ groups, or $R_{q1}$ and $R_{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1c}$ or $Z^{1d}$ groups;

each $R_{n2}$ is independently selected from H, ($C_1$-$C_8$)alkyl, ($C_2$-$C_8$)alkenyl, ($C_2$-$C_8$)alkynyl, ($C_3$-$C_7$)carbocycle, heterocycle, heteroaryl, aryl, haloaryl, haloheteroaryl, haloheterocycle, ($C_1$-$C_8$)haloalkyl and ($C_1$-$C_8$)heteroalkyl;

each $R_{p2}$ is independently selected from ($C_1$-$C_8$)alkyl, ($C_2$-$C_8$)alkenyl, ($C_2$-$C_8$)alkynyl, ($C_3$-$C_7$)carbocycle, heterocycle, heteroaryl, aryl, haloaryl, haloheteroaryl, haloheterocycle, ($C_1$-$C_8$)haloalkyl and ($C_1$-$C_8$)heteroalkyl;

$R_{q2}$ and $R_{r2}$ are each independently selected from H, ($C_1$-$C_8$)alkyl, ($C_2$-$C_8$)alkenyl, ($C_2$-$C_8$)alkynyl, ($C_3$-$C_7$)carbocycle, heterocycle, heteroaryl, aryl, haloaryl, haloheteroaryl, haloheterocycle, ($C_1$-$C_8$)haloalkyl and ($C_1$-$C_8$)heteroalkyl, or $R_{q2}$ and $R_{r2}$ together with the nitrogen to which they are attached form a 5, 6 or 7-membered heterocycle;

$Z^2$ is selected from —$OR_{s3}$—$OC(O)R_{p3}$, —$OC(O)NR_{q3}R_{r3}$, —$SR_{n3}$, —$S(O)R_{p3}$, —$S(O)_2R_{p3}$, —$S(O)_2NR_{q3}R_{r3}$, —$NR_{q3}R_{r3}$, —$NR_{n3}COR_{p3}$, —$NR_{n3}CO_2R_{p3}$, —$NR_{n3}S(O)_2R_{p3}$, —$NR_{n3}S(O)_2OR_{p3}$ and —$NR_{n3}S(O)_2NR_{q3}R_{r3}$;

each $Z^{2a}$ is independently selected from ($C_3$-$C_7$)carbocycle, aryl, heteroaryl, heterocycle, halogen, —CN, —$OR_{n4}$, —$OC(O)R_{p4}$, —$OC(O)NR_{q4}R_{r4}$, —$SR_{n4}$, —$S(O)R_{p4}$, —$S(O)_2OH$, —$S(O)_2R_{p4}$, —$S(O)_2NR_{q4}R_{r4}$, —$NR_{q4}R_{r4}$, —$NR_{n4}COR_{p4}$, —$NR_{n4}CO_2R_{p4}$, —$NR_{n4}CONR_{q4}R_{r4}$, —$NR_{n4}S(O)_2R_{p4}$, —$NR_{n4}S(O)_2OR_{p4}$, —$NR_{n4}S(O)_2NR_{q4}R_{r4}$, $NO_2$, —$C(O)R_{n4}$, —$C(O)OR_{n4}$, —$C(O)NR_{q4}R_{r4}$, wherein any ($C_3$-$C_7$)carbocycle, aryl, heteroaryl and heterocycle of $Z^{2a}$ is optionally substituted with one or more (e.g., 1, 2, 3, 4 or 5) $Z^{2b}$ or $Z^{2c}$ groups;

each $Z^{2b}$ is independently selected from ($C_1$-$C_4$)alkyl, ($C_1$-$C_4$)heteroalkyl and ($C_1$-$C_4$)haloalkyl;

each $Z^{2c}$ is independently selected from halogen, —CN, —$OR_{n4}$, —$OC(O)R_{p4}$, —$OC(O)NR_{q4}R_{r4}$, —$SR_{n4}$, —$S(O)R_{p4}$, —$S(O)_2OH$, —$S(O)_2R_{p4}$, —$S(O)_2NR_{q4}R_{r4}$, —$NR_{q4}R_{r4}$, —$NR_{n4}COR_{p4}$, —$NR_{n4}CO_2R_{p4}$, —$NR_{n4}CONR_{q4}R_{r4}$, —$NR_{n4}S(O)_2R_{p4}$, —$NR_{n4}S(O)_2OR_{p4}$, —$NR_{n4}S(O)_2NR_{q4}R_{r4}$, $NO_2$, —$C(O)R_{n4}$, —$C(O)OR_{n4}$, —$C(O)NR_{q4}R_{r4}$;

each $R_{n3}$ is independently selected from H, ($C_1$-$C_4$)alkyl, ($C_2$-$C_4$)alkenyl, ($C_2$-$C_4$)alkynyl, ($C_3$-$C_7$)carbocycle, heterocycle, heteroaryl and aryl, wherein any ($C_3$-$C_7$)carbocycle, aryl, heteroaryl and heterocycle of $R_{n3}$ is optionally substituted with one or more (e.g., 1, 2, 3, 4 or 5) $Z^{2b}$ or $Z^{2c}$ groups, and wherein any ($C_1$-$C_4$)alkyl, ($C_2$-$C_4$)alkenyl or ($C_2$-$C_4$)alkynyl of $R_{n3}$ is optionally substituted with one or more (e.g., 1, 2, 3, 4 or 5) $Z^{2a}$ groups;

each $R_{p3}$ is independently selected from ($C_1$-$C_4$)alkyl, ($C_1$-$C_4$)haloalkyl, ($C_2$-$C_4$)alkenyl, ($C_2$-$C_4$)alkynyl, ($C_3$-$C_7$)carbocycle, heterocycle, heteroaryl and aryl, wherein any ($C_3$-$C_7$)carbocycle, aryl, heteroaryl and heterocycle of $R_{p3}$ is optionally substituted with one or more (e.g., 1, 2, 3, 4 or 5) $Z^{2b}$ or $Z^{2c}$ groups, and wherein any ($C_1$-$C_4$)alkyl, ($C_2$-$C_4$)alkenyl and ($C_2$-$C_4$)alkynyl of $R_{p3}$ is optionally substituted with one or more (e.g., 1, 2, 3, 4 or 5) $Z^{2a}$ groups;

$R_{q3}$ and $R_{r3}$ are each independently selected from H, ($C_1$-$C_4$)alkyl, ($C_2$-$C_4$)alkenyl, ($C_3$-$C_7$)carbocycle, heterocycle, heteroaryl and aryl, wherein any ($C_3$-$C_7$)carbocycle, aryl, heteroaryl and heterocycle of $R_{q3}$ or $R_{r3}$ is optionally substituted with one or more (e.g., 1, 2, 3, 4 or 5) $Z^{2b}$ or $Z^{2c}$ groups, and wherein any ($C_1$-$C_4$)alkyl and ($C_2$-$C_4$)alkenyl of $R_{q3}$ or $R_{r3}$ is optionally substituted with one or more (e.g., 1, 2, 3, 4 or 5) $Z^{2a}$ groups, or $R_{q3}$ and $R_{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups;

each $R_{s3}$ is independently selected from ($C_2$-$C_4$)alkenyl, ($C_2$-$C_4$)alkynyl, ($C_3$-$C_7$)carbocycle, heterocycle, heteroaryl and aryl, wherein any ($C_3$-$C_7$)carbocycle, aryl, heteroaryl and heterocycle of $R_{s3}$ is optionally substituted with one or more (e.g., 1, 2, 3, 4 or 5) $Z^{2b}$ or $Z^{2c}$ groups, and wherein any ($C_2$-$C_4$)alkenyl or ($C_2$-$C_4$)alkynyl of $R_{s3}$ is optionally substituted with one or more (e.g., 1, 2, 3, 4 or 5) $Z^{2a}$ groups, or $R_{s3}$ is ($C_1$-$C_4$)alkyl substituted with one or more (e.g., 1, 2, 3, 4 or 5) $Z^{2a}$ groups;

each $R_{n4}$ is independently selected from H, ($C_1$-$C_4$)alkyl, ($C_2$-$C_8$)alkenyl, ($C_2$-$C_8$)alkynyl, ($C_1$-$C_4$)haloalkyl and ($C_1$-$C_4$)heteroalkyl;

each $R_{p4}$ is independently selected from ($C_1$-$C_8$)alkyl, ($C_2$-$C_4$)alkenyl, ($C_2$-$C_4$)alkynyl, (($C_1$-$C_4$)haloalkyl and ($C_1$-$C_4$) heteroalkyl; and $R_{q4}$ and $R_{r4}$ are each independently selected from H, ($C_1$-$C_4$)alkyl, ($C_2$-$C_4$)alkenyl, ($C_2$-$C_4$)alkynyl, ($C_1$-$C_4$)haloalkyl and ($C_1$-$C_4$)heteroalkyl;

each $Z^3$ is independently selected from halogen, $(C_1\text{-}C_4)$alkyl, —OH, —CN, $(C_1\text{-}C_4)$heteroalkyl and $(C_1\text{-}C_4)$haloalkyl;

each $Z^4$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, aryl, heteroaryl, heterocycle, halogen, —CN, —$OR_{n5}$, —$OC(O)R_{p5}$, —$OC(O)NR_{q5}R_{r5}$, —$SR_{n5}$, —$S(O)R_{p5}$, —$S(O)_2OH$, —$S(O)_2R_{p5}$, —$S(O)_2NR_{q5}R_{r5}$, —$NR_{q5}R_{r5}$, —$NR_{n5}COR_{p5}$, —$NR_{n5}CO_2R_{p5}$, —$NR_{n5}CONR_{q5}R_{r5}$, —$NR_{n5}S(O)_2R_{p5}$, —$NR_{n5}S(O)_2OR_{p5}$, —$NR_{n5}S(O)_2NR_{q5}R_{r5}$, $NO_2$, —$C(O)R_{n5}$, —$C(O)OR_{n5}$, —$C(O)NR_{q5}R_{r5}$ and —$B(OR_{q5})(OR_{r5})$ wherein any $(C_3\text{-}C_7)$carbocycle, aryl, heteroaryl and heterocycle of $Z^4$ is optionally substituted with one or more (e.g., 1, 2, 3, 4 or 5) $Z^{4a}$ or $Z^{4b}$ groups, and wherein any $(C_1\text{-}C_8)$alkyl, $(C_2\text{-}C_8)$alkenyl and $(C_2\text{-}C_8)$alkynyl of $Z^4$ is optionally substituted with one or more (e.g., 1, 2, 3, 4 or 5) $Z^{4a}$ groups;

each $Z^{4a}$ is independently selected from $(C_3\text{-}C_7)$carbocycle, aryl, heteroaryl, heterocycle, halogen, —CN, —$OR_{n6}$, —$OC(O)R_{p6}$, —$OC(O)NR_{q6}R_{r6}$, —$SR_{n6}$, —$S(O)R_{p6}$, —$S(O)_2OH$, —$S(O)_2R_{p6}$, —$S(O)_2NR_{q6}R_{r6}$, —$NR_{q6}R_{r6}$, —$NR_{n6}COR_{p6}$, —$NR_{n6}CO_2R_{p6}$, —$NR_{n6}CONR_{q6}R_{r6}$, —$NR_{n6}S(O)_2R_{p6}$, —$NR_{n6}S(O)_2OR_{p6}$, —$NR_{n6}S(O)_2NR_{q6}R_{r6}$, $NO_2$, —$C(O)R_{n6}$, —$C(O)OR_{n6}$, and —$C(O)NR_{q6}R_{r6}$, wherein any $(C_3\text{-}C_7)$carbocycle, aryl, heteroaryl and heterocycle of $Z^{4a}$ is optionally substituted with one or more (e.g., 1, 2, 3, 4 or 5) $Z^{4c}$ or $Z^{4d}$ groups;

each $Z^{4b}$ is independently selected from $(C_1\text{-}C_4)$alkyl, $(C_2\text{-}C_4)$alkenyl and $(C_2\text{-}C_4)$alkynyl, wherein any $(C_1\text{-}C_4)$alkyl, $(C_2\text{-}C_4)$alkenyl and $(C_2\text{-}C_4)$alkynyl of $Z^{4b}$ is optionally substituted with one or more (e.g., 1, 2, 3, 4 or 5) $Z^{4c}$ groups;

each $Z^{4c}$ is independently selected from $(C_3\text{-}C_7)$carbocycle, aryl, heteroaryl, heterocycle, halogen, —CN, —$OR_{n7}$, —$OC(O)R_{p7}$, —$OC(O)NR_qR_{r7}$, —$SR_{n7}$, —$S(O)R_{p7}$, —$S(O)_2OH$, —$S(O)_2R_{p7}$, —$S(O)_2NR_{q7}R_{r7}$, —$NR_{q7}R_{r7}$, —$NR_{n7}COR_{p7}$, —$NR_{n7}CO_2R_{p7}$, —$NR_{n7}CONR_{q7}R_{r7}$, —$NR_{n7}S(O)_2R_{p7}$, —$NR_{n7}S(O)_2OR_{p7}$, —$NR_{n7}S(O)_2NR_{q7}R_{r7}$, $NO_2$, —$C(O)R_{n7}$, —$C(O)OR_{n7}$, —$C(O)NR_{q7}R_{r7}$, haloaryl, haloheteroaryl, haloheterocycle and $(C_1\text{-}C_4)$heteroalkyl;

each $Z^{4d}$ is independently selected from $(C_1\text{-}C_4)$alkyl, $(C_2\text{-}C_4)$alkenyl, $(C_2\text{-}C_4)$alkynyl, and $(C_1\text{-}C_4)$haloalkyl;

each $R_{n5}$ is independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n5}$ is optionally substituted with one or more (e.g., 1, 2, 3, 4 or 5) $Z^{4a}$ or $Z^{4b}$ groups, and wherein any $(C_1\text{-}C_4)$alkyl, $(C_2\text{-}C_4)$alkenyl and $(C_2\text{-}C_4)$alkynyl of $R_{n5}$ is optionally substituted with one or more (e.g., 1, 2, 3, 4 or 5) $Z^{4a}$ groups;

each $R_{p5}$ is independently selected from $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl, or heterocycle of $R_{p5}$ is optionally substituted with one or more (e.g., 1, 2, 3, 4 or 5) $Z^{4a}$ or $Z^{4b}$ groups, and wherein any $(C_1\text{-}C_4)$alkyl, $(C_2\text{-}C_4)$alkenyl or $(C_2\text{-}C_4)$alkynyl of $R_{p5}$ is optionally substituted with one or more (e.g., 1, 2, 3, 4 or 5) $Z^{4a}$ groups;

$R_{q5}$ and $R_{r5}$ are each independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{q5}$ or $R_{r5}$ is optionally substituted with one or more (e.g., 1, 2, 3, 4 or 5) $Z^{4a}$ or $Z^{4b}$ groups, and wherein any $(C_1\text{-}C_4)$alkyl, $(C_2\text{-}C_4)$alkenyl and $(C_2\text{-}C_4)$alkynyl of $R_{q5}$ or $R_{r5}$ is optionally substituted with one or more (e.g., 1, 2, 3, 4 or 5) $Z^{4a}$ groups, or $R_{q5}$ and $R_{r5}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{4a}$ or $Z^{4b}$ groups;

each $R_{n6}$ is independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n6}$ is optionally substituted with one or more (e.g., 1, 2, 3, 4 or 5) $Z^{4c}$ or $Z^{4d}$ groups, and wherein any $(C_1\text{-}C_4)$alkyl, $(C_2\text{-}C_4)$alkenyl and $(C_2\text{-}C_4)$alkynyl of $R_{n6}$ is optionally substituted with one or more (e.g., 1, 2, 3, 4 or 5) $Z^{4c}$ groups;

each $R_{p6}$ is independently selected from $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{p6}$ is optionally substituted with one or more (e.g., 1, 2, 3, 4 or 5) $Z^{4c}$ or $Z^{4d}$ groups, and wherein any $(C_1\text{-}C_4)$alkyl, $(C_2\text{-}C_4)$alkenyl and $(C_2\text{-}C_4)$alkynyl of $R_{p6}$ is optionally substituted with one or more (e.g., 1, 2, 3, 4 or 5) $Z^{4c}$ groups;

$R_{q6}$ and $R_{r6}$ are each independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{q6}$ or $R_{r6}$ is optionally substituted with one or more (e.g., 1, 2, 3, 4 or 5) $Z^{4c}$ or $Z^{4d}$ groups, and wherein any $(C_1\text{-}C_4)$alkyl, $(C_2\text{-}C_4)$alkenyl and $(C_2\text{-}C_4)$alkynyl of $R_{q6}$ or $R_{r6}$ is optionally substituted with one or more (e.g., 1, 2, 3, 4 or 5) $Z^{4c}$ groups, or $R_{q6}$ and $R_{r6}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{4c}$ or $Z^{4d}$ groups;

each $R_{n7}$ is independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl, aryl, haloaryl, haloheteroaryl, haloheterocycle, $(C_1\text{-}C_4)$haloalkyl and $(C_1\text{-}C_4)$heteroalkyl;

each $R_{p7}$ is independently selected from $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl, aryl, haloaryl, haloheteroaryl, haloheterocycle, $(C_1\text{-}C_4)$haloalkyl and $(C_1\text{-}C_4)$heteroalkyl;

$R_{q7}$ and $R_{r7}$ are each independently selected from H, $(C_1\text{-}C_4)$alkyl, $(C_2\text{-}C_4)$alkenyl, $(C_2\text{-}C_4)$alkynyl, $(C_3\text{-}C_7)$carbocycle, heterocycle, heteroaryl, aryl, haloaryl, haloheteroaryl, haloheterocycle, $(C_1\text{-}C_4)$haloalkyl and $(C_1\text{-}C_4)$heteroalkyl, or $R_{q7}$ and $R_{r7}$ together with the nitrogen to which they are attached form a 5, 6 or 7-membered heterocycle;

each $Z^5$ is independently selected from $(C_1\text{-}C_6)$alkyl, halogen, —CN, and —$OR_8$, wherein any $(C_1\text{-}C_6)$alkyl of $Z^5$ is optionally substituted with one or more (e.g., 1, 2, 3, 4 or 5) halogen; and each $R_{n8}$ is independently selected from H, $(C_1\text{-}C_3)$alkyl, $(C_1\text{-}C_3)$haloalkyl and $(C_3\text{-}C_7)$carbocycle;

or a salt thereof. In certain embodiments, a salt is a pharmaceutically acceptable salt.

One embodiment provides a pharmaceutical composition comprising a compound of formula I or a pharmaceutically acceptable salt thereof, and a pharmaceutically acceptable carrier.

One embodiment provides a method for treating a Retroviridae viral infection (e.g., an HIV viral infection) in a mammal (e.g., a human), comprising administering a compound of formula I, or a pharmaceutically acceptable salt thereof, to the mammal.

One embodiment provides a method for inhibiting the proliferation of the HIV virus, treating AIDS or delaying the onset of AIDS or ARC symptoms in a mammal (e.g., a human), comprising administering a compound of formula I, or a pharmaceutically acceptable salt thereof, to the mammal.

One embodiment provides a method for treating an HIV infection in a mammal (e.g., a human), comprising administering a compound of formula I, or a pharmaceutically acceptable salt thereof, to the mammal.

One embodiment provides a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

One embodiment provides a compound of formula I, or a pharmaceutically acceptable salt thereof for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

One embodiment provides a compound of formula I, or a pharmaceutically acceptable salt thereof for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

One embodiment provides a compound of formula I, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms.

One embodiment provides a compound of formula I, or a pharmaceutically acceptable salt thereof, for use in the prophylactic or therapeutic treatment of a Retroviridae virus infection (e.g., an HIV virus infection).

One embodiment provides the use of a compound of formula I, or a pharmaceutically acceptable salt thereof, for the manufacture of a medicament for a Retroviridae virus infection (e.g., an HIV virus infection) in a mammal (e.g., a human).

One embodiment provides processes and intermediates disclosed herein that are useful for preparing compounds of formula I or salts thereof. In certain embodiments, a salt is a pharmaceutically acceptable salt.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2$$CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)$$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2$$CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (—($CH_2$)$_7$$CH_3$).

"Alkenyl" is a straight or branched hydrocarbon with at least one site of unsaturation, e.g., a carbon-carbon, $sp^2$ double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon with at least one site of unsaturation, i.e. a carbon-carbon, sp triple bond. For example, an alkynyl group can have 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "heteroalkyl" as used herein refers to an alkyl as defined herein, wherein one or more of the carbon atoms of the alkyl are replaced by an O, S, or $NR_q$, (or if the carbon atom being replaced is a terminal carbon with an OH, SH or $NR_{q2}$) wherein each $R_q$ is independently H or $(C_1-C_6)$alkyl.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl$(C_1-C_6)$alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl4,5,6,7-tetrahydro-1H-indazole and 3b,4,4a,5-tetrahydro-1H-cyclopropa[3,4]cyclopenta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl $(C_1-C_6)$alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl$(C_1-C_6)$alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. $(C_3-C_7)$carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl$(C_1-C_6)$alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

The term "haloaryl" as used herein refers to an aryl as defined herein, wherein one or more hydrogen atoms of the aryl are each replaced independently by a halo substituent. Such a range includes one halo substituent on the aryl group to complete halogenation of the aryl group.

The term "haloheteroaryl" as used herein refers to a heteroaryl as defined herein, wherein one or more hydrogen atoms of the heteroaryl are each replaced independently by a halo substituent. Such a range includes one halo substituent on the heteroaryl group to complete halogenation of the heteroaryl group.

The term "haloheterocycle" as used herein refers to a heterocycle as defined herein, wherein one or more hydrogen atoms of the heterocycle are each replaced independently by a halo substituent. Such a range includes one halo substituent on the heterocycle group to complete halogenation of the heterocycle group.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH ~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Also, such compositions thus include racemic mixtures of all stereoisomers, including enantiomers, diastereomers, and atropisomers. In addition, the compounds disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Accordingly, in one embodiment, a composition disclosed herein is greater than 50% a single enantiomer. In another embodiment, a composition disclosed herein is at least 80% a single enantiomer. In another embodiment, a composition disclosed herein is at least 90% a single enantiomer. In another embodiment, a composition disclosed herein is at least 98% a single enantiomer. In another embodiment, a composition disclosed herein is at least 99% a single enantiomer. In another embodiment, a composition disclosed herein is greater than 50% a single diastereomer. In another embodiment, a composition disclosed herein is at least 80% a single diastereomer. In another embodiment, a composition disclosed herein is at least 90% a single diastereomer. In another embodiment, a composition disclosed herein is at least 98% a single diastereomer. In another embodiment, a composition disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Protecting Groups

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

"Pharmaceutically acceptable salt" refers to a salt of a compound that is pharmaceutically acceptable and that possesses (or can be converted to a form that possesses) the desired pharmacological activity of the parent compound. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napththalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their un-ionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$.

Specific values listed below for radicals, substituents, and ranges in the embodiments of the invention are for illustration only; they do not exclude other defined values or other values within defined ranges for the radicals and substituents.

Compounds of Formula I.

A specific group of compounds of formula I are compounds of formula Ia.

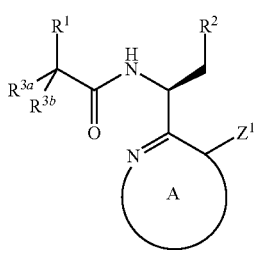

Ia or a salt thereof. In certain embodiments, a salt is a pharmaceutically acceptable salt.

Another specific group of compounds of formula I are compounds of formula Ib.

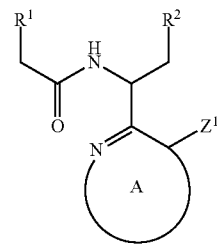

Ib or a salt thereof. In certain embodiments, a salt is a pharmaceutically acceptable salt.

Another specific group of compounds of formula I are compounds of formula Ic.

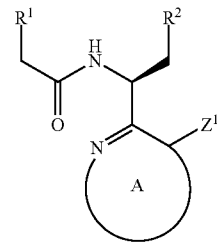

Ic or a salt thereof. In certain embodiments, a salt is a pharmaceutically acceptable salt.

Another specific group of compounds of formula I are compounds of formula Id.

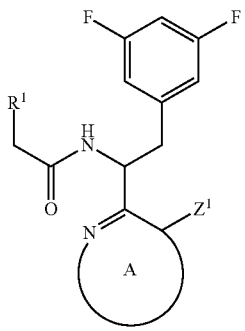

Id or a salt thereof. In certain embodiments, a salt is a pharmaceutically acceptable salt.

Another specific group of compounds of formula I are compounds of formula Ie.

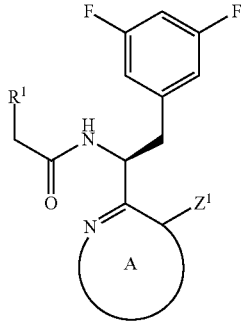

Ie or a salt thereof. In certain embodiments, a salt is a pharmaceutically acceptable salt.

Specific values listed below are values for compounds of formula I as well as all related formulas (e.g., formulas Ia, Ib, Ic, Id, Ie).

A specific value for $R^{3a}$ and $R^{3b}$ is H.

A specific value for $R^2$ is phenyl or a 5-membered heteroaryl, wherein any phenyl or 5-membered heteroaryl of $R^2$ is optionally substituted with one or more $Z^5$ groups. In certain embodiments, $R^2$ is phenyl or a 5-membered heteroaryl, wherein any phenyl or 5-membered heteroaryl of $R^2$ is optionally substituted with two $Z^5$ groups.

A specific value for $R^2$ is phenyl optionally substituted with one or more $Z^5$ groups. In certain embodiments, $R^2$ is phenyl optionally substituted with two $Z^5$ groups.

A specific value for $Z^5$ is halo.

A specific value for $Z^5$ is fluoro.

A specific value for $R^2$ is 3,5-difluorophenyl.

A specific value for A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or more (e.g., 1 or 2) $Z^3$ groups. In certain embodiments, A is pyridinyl, pyrazinyl, or pyridazinyl.

In certain embodiments, A is optionally substituted with one $Z^3$ group.

A specific value for A is pyridinyl or pyrimidinyl, wherein any pyridinyl or pyrimidinyl of A is substituted with one $Z^1$ group, one $Z^2$ group, and optionally substituted with one or more (e.g., 1 or 2) $Z^3$ groups.

A specific value for A is selected from:

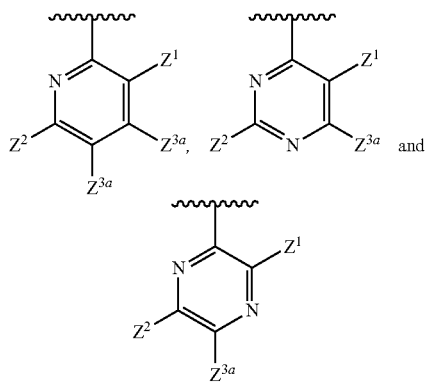

wherein each $Z^{3a}$ is independently selected from H and $Z^3$.

A specific value for A is:

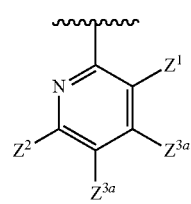

wherein each $Z^{3a}$ is independently selected from H and $Z^3$.

A specific value for A is:

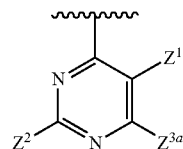

wherein each $Z^{3a}$ is independently selected from H and $Z^3$.

A specific value for A is:

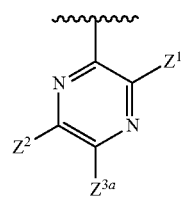

wherein each $Z^{3a}$ is independently selected from H and $Z^3$.

In certain embodiments, A is:

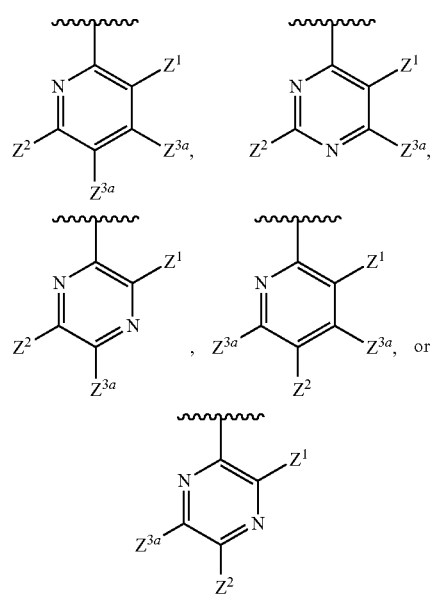

wherein each $Z^{3a}$ is independently H or $Z^3$.

In certain embodiments, A is:

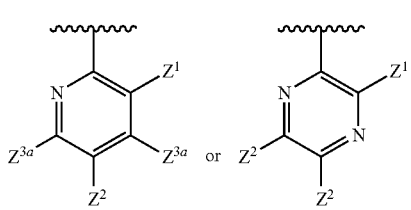

wherein each $Z^{3a}$ is independently H or $Z^3$.

In certain embodiments, A is:

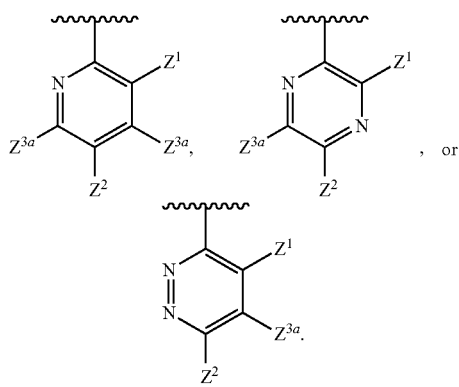

wherein each $Z^{3a}$ is independently H or $Z^3$.

A specific value for $Z^{3a}$ is H.

A specific value for $Z^1$ is selected from phenyl, monocyclic-heteroaryl and bicyclic-heterocycle, wherein any phenyl, monocyclic-heteroaryl, and bicyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, monocyclic-heteroaryl and bicyclic-heterocycle, wherein the monocyclic-heteroaryl and bicyclic-heterocycle have 2-12 carbon atoms and 1-5 heteroatoms in the ring system, and wherein any phenyl, monocyclic-heteroaryl and bicyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, monocyclic-heteroaryl and bicyclic-heterocycle, wherein the monocyclic-heteroaryl and bicyclic-heterocycle have 4-8 carbon atoms and 1-3 heteroatoms in the ring system, and wherein any phenyl, monocyclic-heteroaryl and bicyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, monocyclic-heteroaryl and bicyclic-heteroheterocycle, wherein the monocyclic-heteroaryl and bicyclic-heterocycle have 1-12 carbon atoms and 1-5 heteroatoms in the ring system, and wherein any phenyl, monocyclic-heteroaryl and bicyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, isoindolinyl-1-one and pyridinyl, wherein any phenyl, isoindolinyl-1-one and pyridinyl of $Z^1$ is optionally substituted with one or more (e.g., 1, 2, 3, 4 or 5) $Z^{1a}$ or $Z^{1b}$ groups.

A specific value for $Z^1$ is phenyl, wherein the phenyl is optionally substituted with one or more (e.g., 1, 2, 3, 4 or 5) $Z^{1a}$ or $Z^{1b}$ groups.

In certain embodiments, $Z^1$ is optionally substituted with one to three $Z^{1a}$ or $Z^{1b}$ groups.

In certain embodiments, each $Z^{1a}$ is independently halogen, —$OR_{n1}$, —$S(O)_2NR_{q1}R_{r1}$, —$NR_{q1}R_{r1}$, —$NR_{n1}S(O)_2R_{p1}$ or —$C(O)NR_{q1}R_{r1}$, and each $Z^{1b}$ is $(C_1-C_3)$alkyl, wherein any $(C_1-C_3)$alkyl of $Z^{1b}$ is optionally substituted with one $Z^{1c}$ group. In certain embodiments, $Z^1$ is a heterocycle substituted with an oxo group.

A specific value for $Z^{1a}$ is independently selected from halogen, —$OR_{n1}$, —$S(O)_2NR_{q1}R_{r1}$, and —$C(O)NR_{q1}R_{r1}$, and each $Z^{1b}$ is $(C_1-C_8)$alkyl, wherein any $(C_1-C_8)$alkyl of $Z^{1b}$ is optionally substituted with one or more (e.g., 1, 2, 3, 4 or 5) $Z^{1c}$ groups.

In certain embodiments, each $Z^{1a}$ is independently halogen, —$OR_{n1}$, —$S(O)_2NR_{q1}R_{r1}$, —$NR_{n1}S(O)_2R_{p1}$, or —$C(O)NR_{q1}R_{r1}$, and each $Z^{1b}$ is $(C_1-C_8)$alkyl, wherein any $(C_1-C_4)$alkyl of $Z^{1b}$ is optionally substituted with one to three $Z^{1c}$ groups.

A specific value for $Z^{1c}$ is —$OR_2$. In certain embodiments, each $R_{n2}$ is independently H, $(C_1-C_3)$alkyl, aryl, or $(C_1-C_3)$haloalkyl.

A specific group of compounds of formula I are compounds wherein $R_{q1}$ and $R_{r1}$ are each H, $R_{n1}$ is phenyl or $(C_1-C_8)$alkyl wherein any $(C_1-C_8)$alkyl of $R_{n1}$ is optionally substituted with one or more (e.g., 1, 2, 3, 4 or 5) halogen, and $R_{n2}$ is H.

A specific value for each $R_{q1}$ and $R_{r1}$ is H.

A specific value for $R_{n1}$ is phenyl or $(C_1-C_8)$alkyl wherein any $(C_1-C_8)$alkyl of $R_{n1}$ is optionally substituted with one or more (e.g. 1, 2, 3, 4 or 5) halogen.

A specific value for $R_{n2}$ is H.

A specific value for $Z^1$ is selected from:

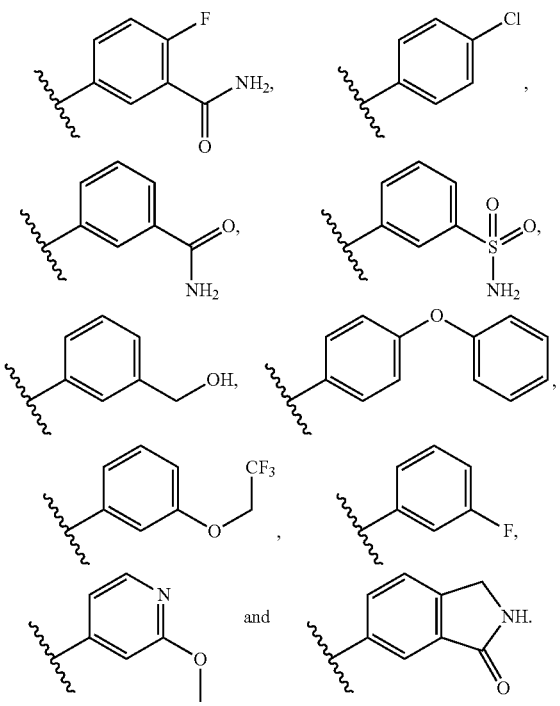

In certain embodiments, $Z^1$ is:

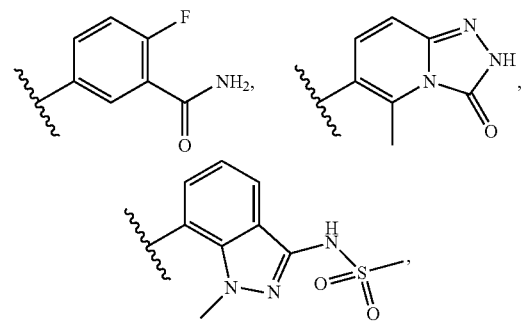

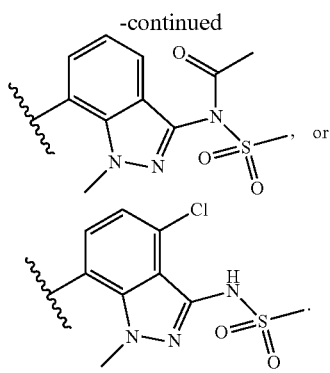

In certain embodiments, $Z^2$ is $-OC(O)R_{p3}$, $-SR_{n3}$, $-NR_{q3}R_{r3}$, $-NR_{n3}CO_2R_{p3}$, or $-NR_{n3}S(O)_2R_{p3}$. In certain embodiments, $Z^2$ is $-SR_{n3}$, $-NR_{q3}R_{r3}$, $-NR_{n3}CO_2R_{p3}$, or $-NR_{n3}S(O)_2R_{p3}$. In certain embodiments, $Z^2$ is $-NR_{q3}R_{r3}$, $-NR_{n3}CO_2R_{p3}$, or $-NR_{n3}S(O)_2R_{p3}$.

A specific value for $Z^2$ is selected from $-OC(O)R_{p3}$ and $-NR_{q3}R_{r3}$.

A specific value for $Z^2$ is $-OC(O)R_{p3}$.

A specific value for $R_{p3}$ is $(C_1-C_4)$alkyl, wherein any $(C_1-C_4)$alkyl, is optionally substituted with one or more (e.g., 1, 2, 3, 4 or 5) $Z^{2a}$ groups.

A specific value for $R_{p3}$ is $(C_1-C_4)$alkyl.

A specific value for $Z^2$ is $-NR_{q3}R_{r3}$.

A specific group of compounds of formula I are compounds wherein $R_{q3}$ and $R_{r3}$ are each independently selected from H, $(C_1-C_4)$alkyl and heterocycle, wherein any heterocycle of $R_{q3}$ or $R_{r3}$ is optionally substituted with one or more (e.g., 1, 2, 3, 4 or 5) $Z^{2b}$ or $Z^{2c}$ groups, and wherein any $(C_1-C_4)$alkyl of $R_{q3}$ or $R_{r3}$ is optionally substituted with one or more (e.g., 1, 2, 3, 4 or 5) $Z^{2a}$ groups, or $R_{q3}$ and $R_{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups.

In certain embodiments, $R_{q3}$ and $R_{r3}$ are each independently H, $(C_1-C_4)$alkyl or heterocycle, wherein any heterocycle of $R_{q3}$ or $R_{r3}$ is optionally substituted with one or two $Z^{2b}$ or $Z^{2c}$ groups, and wherein any $(C_1-C_4)$alkyl of $R_{q3}$ or $R_{r3}$ is optionally substituted with one or two $Z^{2a}$ groups, or $R_{q3}$ and $R_{r3}$ together with the nitrogen to which they are attached form a heterocycle or heteroaryl, wherein the heterocycle or heteroaryl is optionally substituted with one or two $Z^{2b}$ or $Z^{2c}$ groups.

In certain embodiments, $Z^2$ is $-NR_{q3}R_{r3}$, wherein $R_{q3}$ and $R_{r3}$ together with the nitrogen to which they are attached form a heterocycle, the heterocycle is substituted with oxo group. In certain embodiments, the heterocycle is substituted with one or two oxo groups. In certain embodiments, $Z^2$ is $-NR_{q3}R_{r3}$, wherein $R_{q3}$ and $R_{r3}$ together with the nitrogen to which they are attached form a heterocycle, wherein the heterocycle is a multiple ring system connected by spiro bond. In certain embodiments, $Z^2$ is $-NR_{q3}R_{r3}$, wherein $R_{q3}$ and $R_{r3}$ together with the nitrogen to which they are attached form a heterocycle, wherein the heterocycle is a bicyclic heterocyclic, wherein the two cyclic groups of the heterocycle are connected by spiro bond.

A specific group of compounds of formula I are compounds wherein $R_{q3}$ and $R_{r3}$ are each independently selected from H, $(C_1-C_4)$alkyl and monocyclic heterocycle, wherein any monocyclic heterocycle of $R_{q3}$ or $R_{r3}$ is optionally substituted with one or more (e.g., 1, 2, 3, 4 or 5) $Z^{2b}$ or $Z^{2c}$ groups, and wherein any $(C_1-C_4)$alkyl of $R_{q3}$ or $R_{r3}$ is optionally substituted with one or more (e.g., 1, 2, 3, 4 or 5) $Z^{2a}$ groups, or $R_{q3}$ and $R_{r3}$ together with the nitrogen to which they are attached form a monocyclic heterocycle, bicyclic heterocycle or monocyclic heteroaryl, wherein the monocyclic heterocycle, bicyclic heterocycle or monocyclic heteroaryl is optionally substituted with one or more (e.g., 1, 2, 3, 4 or 5) $Z^{2b}$ or $Z^{2c}$ groups.

A specific group of compounds of formula I are compounds wherein $R_{q3}$ and $R_{r3}$ are each independently selected from H, $(C_1-C_4)$alkyl and monocyclic heterocycle, wherein the monocyclic heterocycle has 1-5 carbon atoms and 1-4 heteroatoms in the ring system, wherein any monocyclic heterocycle of $R_{q3}$ or $R_{r3}$ is optionally substituted with one or more (e.g., 1, 2, 3, 4 or 5) $Z^{2b}$ or $Z^{2c}$ groups, and wherein any $(C_1-C_4)$alkyl of $R_{q3}$ or $R_{r43}$ is optionally substituted with one or more (e.g., 1, 2, 3, 4 or 5) $Z^{2a}$ groups, or $R_{q3}$ and $R_{r3}$ together with the nitrogen to which they are attached form a monocyclic heterocycle, bicyclic heterocycle or monocyclic heteroaryl, wherein the monocyclic-heteroaryl, bicyclic-heteroaryl and bicyclic-heterocycle have 1-8 carbon atoms and 1-4 heteroatoms in the ring system and wherein the monocyclic heterocycle, bicyclic heterocycle or monocyclic heteroaryl is optionally substituted with one or more (e.g., 1, 2, 3, 4 or 5) $Z^{2b}$ or $Z^{2c}$ groups.

A specific value for each $Z^{2a}$ is independently selected from $(C_3-C_7)$carbocycle, monocyclic heteroaryl, monocyclic heterocycle, $-OR_{n4}$, and $-NR_{q4}R_{r4}$, wherein any $(C_3-C_7)$carbocycle, heteroaryl and heterocycle of $Z^{2a}$ is optionally substituted with one or more (e.g., 1, 2, 3, 4 or 5) $Z^{2b}$ or $Z^{2c}$ groups.

In certain embodiments, each $Z^{2a}$ is independently $(C_3-C_7)$carbocycle, monocyclic heteroaryl, monocyclic heterocycle, $-OR_{n4}$, or $-NR_{q4}R_{r4}$, wherein any $(C_3-C_7)$carbocycle, heteroaryl and heterocycle of $Z^{2a}$ is optionally substituted with one or two $Z^{2b}$ or $Z^{2c}$ groups.

A specific group of compounds of formula I are compounds wherein each $Z^{2a}$ is independently selected from $(C_3-C_7)$carbocycle, monocyclic heteroaryl, monocyclic heterocycle, $-OR_{n4}$, and $-NR_{q4}R_{r4}$, wherein the monocyclic heteroaryl and monocyclic heterocycle have 1-5 carbon atoms and 1-4 heteroatoms in the ring system, wherein any $(C_3-C_7)$carbocycle, heteroaryl and heterocycle of $Z^{2a}$ is optionally substituted with one or more (e.g., 1, 2, 3, 4 or 5) $Z^{2b}$ or $Z^{2c}$ groups, and wherein each $Z^{2c}$ is $-OR_{n4}$.

In certain embodiments, each $Z^{2a}$ is independently $(C_3-C_7)$carbocycle, monocyclic heteroaryl, monocyclic heterocycle, $-OR_{n4}$, or $-NR_{q4}R_{r4}$, wherein the monocyclic heteroaryl and monocyclic heterocycle have 1-5 carbon atoms and 1-4 heteroatoms in the ring system, wherein any $(C_3-C_7)$carbocycle, heteroaryl and heterocycle of $Z^{2a}$ is optionally substituted with one or two $Z^{2b}$ or $Z^{2c}$ groups, and wherein each $Z^{2c}$ is $-OR_{n4}$.

A specific group of compounds of formula I are compounds wherein each $R_{n4}$ is independently selected from H, $(C_1-C_4)$alkyl, and $(C_1-C_4)$heteroalkyl, and wherein $R_{q4}$ and $R_{r4}$ are each $(C_1-C_4)$alkyl.

A specific value for $Z^2$ is selected from:

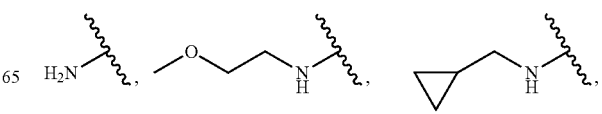

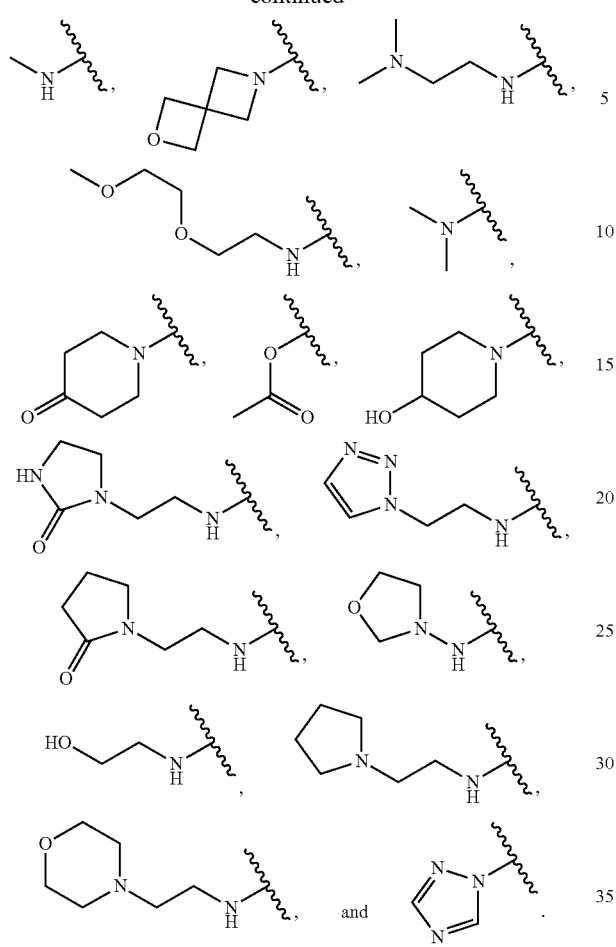
In certain embodiments, $Z^2$ is:
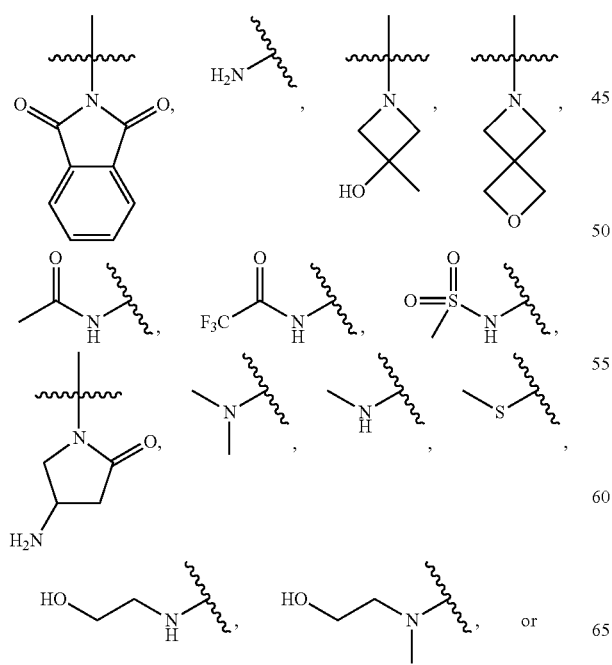
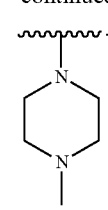
A specific value for A is selected from:
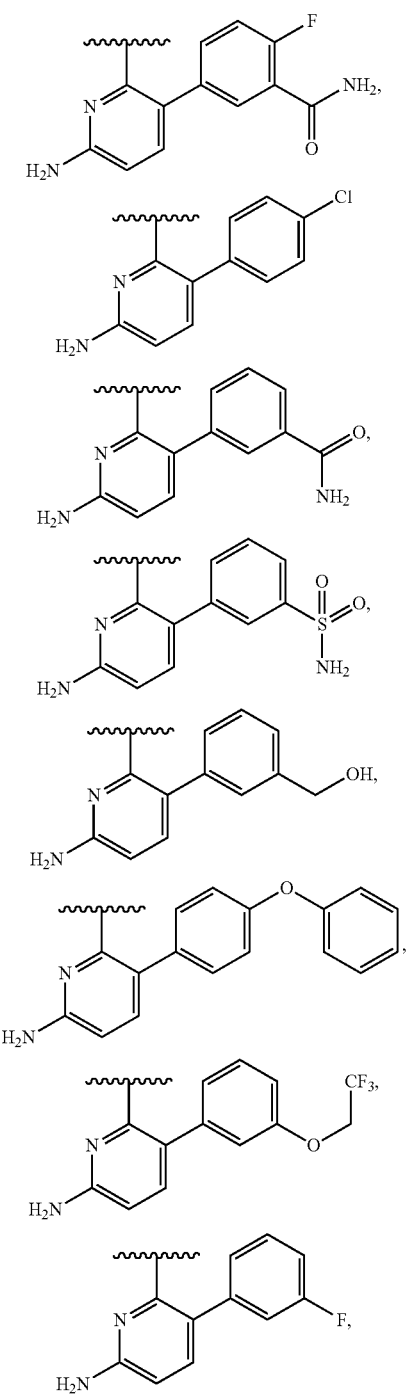

25
-continued
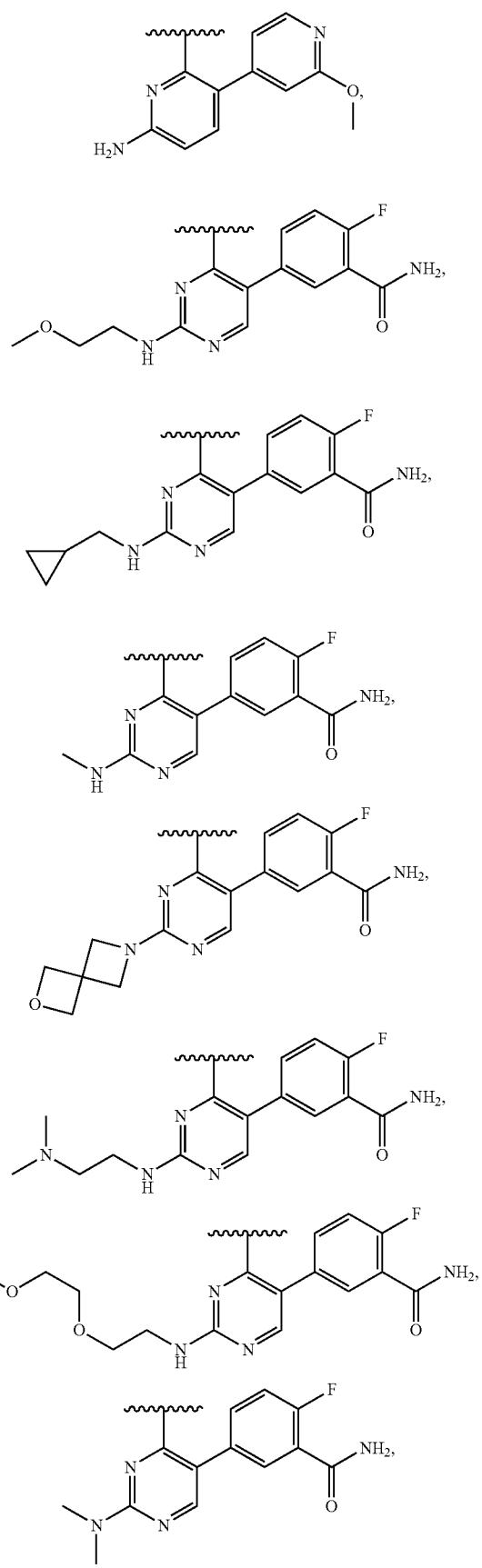
26
-continued
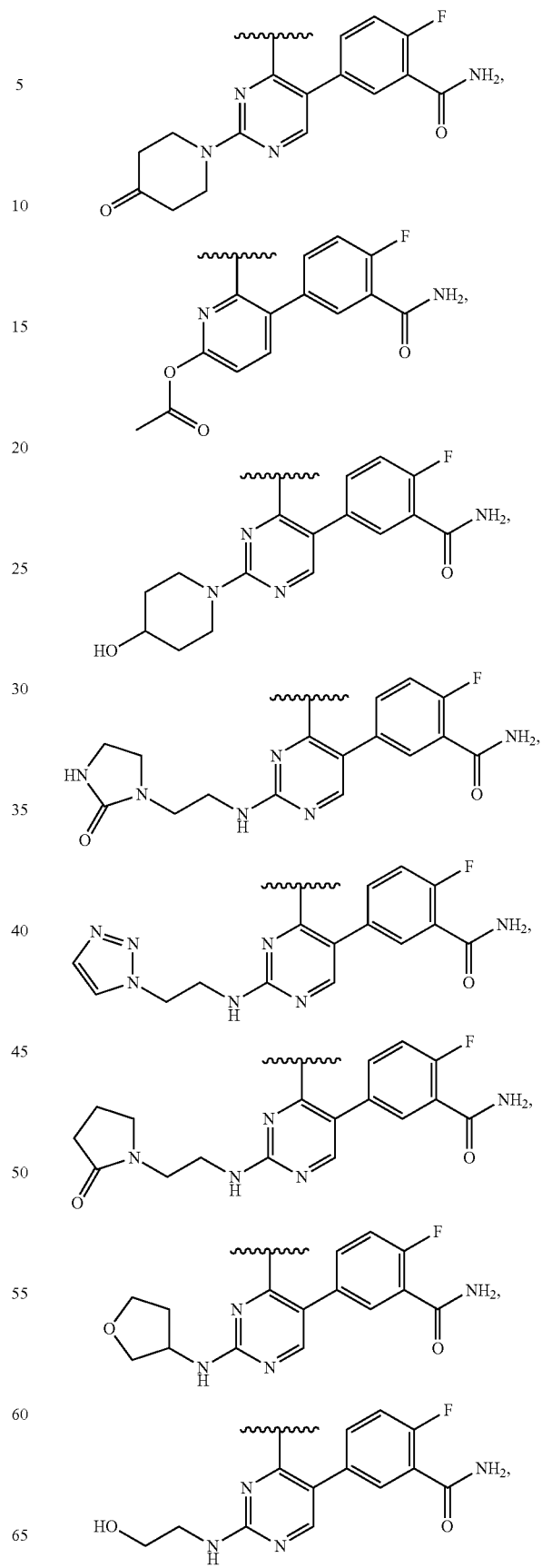

-continued

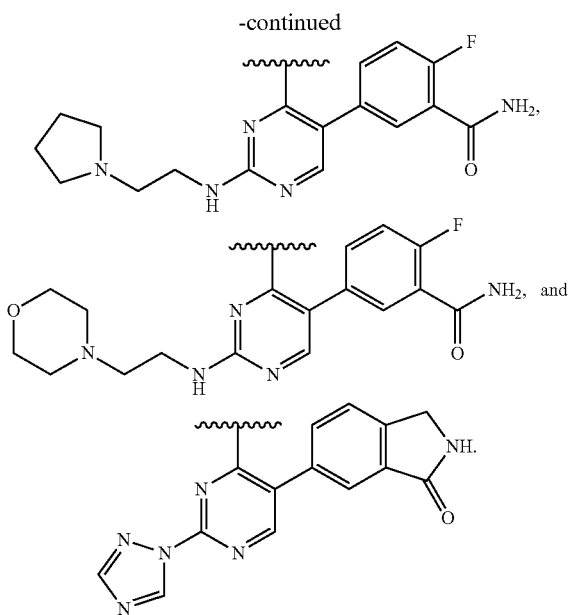

A specific value for $R^1$ is a heteroaryl, wherein any heteroaryl of $R^1$ is optionally substituted with one or more (e.g., 1, 2, 3, 4 or 5) $Z^4$ groups.

A specific value for $R^1$ is a bicyclic-heteroaryl, wherein any bicyclic-heteroaryl of $R^1$ is optionally substituted with one or more (e.g., 1, 2, 3, 4 or 5) $Z^4$ groups.

A specific value for $R^1$ is a bicyclic-heteroaryl or tricyclic-heteroaryl, wherein any bicyclic-heteroaryl or tricyclic-heteroaryl of $R^1$ is optionally substituted with one or more (e.g., 1, 2, 3, 4 or 5) $Z^4$ groups.

A specific value for $R^1$ is a bicyclic-heteroaryl, wherein the bicyclic-heteroaryl of $R^1$ contains at least one partially unsaturated ring, and wherein any bicyclic-heteroaryl of $R^1$ is optionally substituted with one or more (e.g., 1, 2, 3, 4 or 5) $Z^4$ groups.

A specific value for $R^1$ is a bicyclic-heteroaryl or tricyclic-heteroaryl, wherein the bicyclic-heteroaryl or tricyclic-heteroaryl of $R^1$ contains at least one partially unsaturated ring, and wherein any bicyclic-heteroaryl or tricyclic-heteroaryl of $R^1$ is optionally substituted with one or more (e.g., 1, 2, 3, 4 or 5) $Z^4$ groups.

A specific value for $R^1$ is a bicyclic-heteroaryl, wherein the bicyclic-heteroaryl has 4-9 carbon atoms and 1-5 heteroatoms in the ring system, and wherein any bicyclic-heteroaryl of $R^1$ is optionally substituted with one or more (e.g., 1, 2, 3, 4 or 5) $Z^4$ groups.

A specific value for $R^1$ is a bicyclic-heteroaryl or tricyclic-heteroaryl, wherein the bicyclic-heteroaryl or tricyclic-heteroaryl has 4-9 carbon atoms and 1-5 heteroatoms in the ring system, and wherein any bicyclic-heteroaryl or tricyclic-heteroaryl of $R^1$ is optionally substituted with one or more (e.g., 1, 2, 3, 4 or 5) $Z^4$ groups.

A specific value for $R^1$ is a bicyclic-heteroaryl, wherein the bicyclic-heteroaryl has 6-9 carbon atoms and 1-3 heteroatoms in the ring system, and wherein any bicyclic-heteroaryl of $R^1$ is optionally substituted with one or more (e.g., 1, 2, 3, 4 or 5) $Z^4$ groups.

A specific value for $R^1$ is a bicyclic-heteroaryl or tricyclic-heteroaryl, wherein the bicyclic-heteroaryl or tricyclic-heteroaryl has 6-9 carbon atoms and 1-3 heteroatoms in the ring system, and wherein any bicyclic-heteroaryl or tricyclic-heteroaryl of $R^1$ is optionally substituted with one or more (e.g., 1, 2, 3, 4 or 5) $Z^4$ groups.

In certain embodiments, the bicyclic-heteroaryl or tricyclic-heteroaryl has 9 carbon atoms and 1 or 2 heteroatoms in the ring system.

In certain embodiments, $R^1$ is optionally substituted by two to five $Z^4$ groups. In certain embodiments, each $Z^4$ is independently $(C_1-C_3)$alkyl or halogen, wherein any $(C_1-C_3)$alkyl of $Z^3$ is optionally substituted with 1-3 halogen.

A specific value for $R^1$ is selected from indolyl and 4,5,6,7-tetrahydro-indazolyl, wherein any indolyl and 4,5,6,7-tetrahydro-indazolyl of $R^1$ is optionally substituted with one or more (e.g., 1, 2, 3, 4 or 5) $Z^4$ groups.

A specific value for $R^1$ is selected from indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole, wherein any indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole of $R^1$ is optionally substituted with one or more (e.g., 1, 2, 3, 4 or 5) $Z^4$ groups.

A specific value for $R^1$ is selected from indol-3-yl and 4,5,6,7-tetrahydro-1H-indazol-1-yl, wherein any indol-3-yl and 4,5,6,7-tetrahydro-1H-indazol-1-yl of $R^1$ is optionally substituted with one or more (e.g., 1, 2, 3, 4 or 5) $Z^4$ groups.

A specific value for $R^1$ is selected from indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl, wherein any indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl of $R^1$ is optionally substituted with one or more (e.g., 1, 2, 3, 4 or 5) $Z^4$ groups.

A specific value for each $Z^4$ is independently selected from $(C_1-C_6)$alkyl and halogen, wherein any $(C_1-C_6)$alkyl of $Z^4$ is optionally substituted with one or more (e.g., 1, 2, 3, 4 or 5) halogen.

A specific value for each $Z^4$ is independently selected from $(C_1-C_6)$alkyl, —CN and halogen, wherein any $(C_1-C_6)$alkyl of $Z^4$ is optionally substituted with one or more (e.g., 1, 2, 3, 4 or 5) halogen.

A specific value for each $Z^4$ is independently selected from fluoro, trifluoromethyl and difluoromethyl.

A specific value for each $Z^4$ is independently selected from fluoro, trifluoromethyl, —CN and difluoromethyl.

A specific value for $R^1$ is selected from:

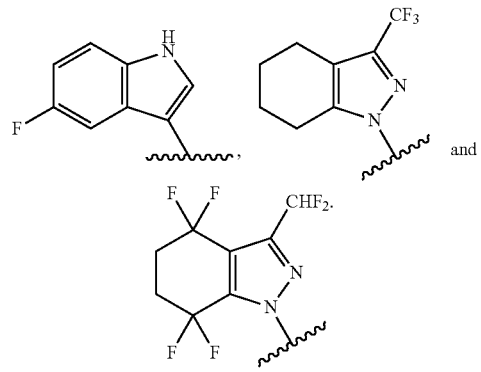

A specific value for $R^1$ is selected from:

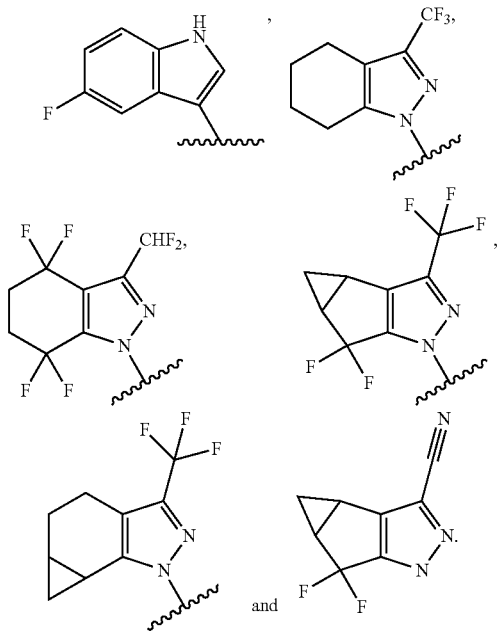

A specific value for $R^1$ is selected from:

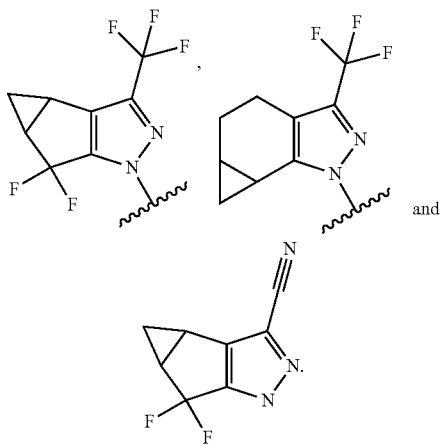

In one variation of formula I, $R^{3a}$ and $R^{3b}$ are each H and A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or more $Z^3$ groups. In another variation, $R^{3a}$ and $R^{3b}$ are each H and A is pyridinyl, pyrimidinyl, or pyrazinyl, wherein any pyridinyl, pyrimidinyl, or pyrazinyl of A is substituted with one $Z^1$ group, one $Z^2$ group, and optionally substituted with one or more $Z^3$ groups. In another variation, $R^{3a}$ and $R^{3b}$ are each H and A is pyridinyl or pyrimidinyl, wherein any pyridinyl or pyrimidinyl of A is substituted with one $Z^1$ group, one $Z^2$ group, and optionally substituted with one or more $Z^3$ groups.

In one variation of formula I, $R^{3a}$ and $R^{3b}$ are each H and A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or two $Z^3$ groups. In another variation, $R^{3a}$ and $R^{3b}$ are each H and A is pyridinyl, pyrimidinyl, or pyrazinyl, wherein any pyridinyl, pyrimidinyl, or pyrazinyl of A is substituted with one $Z^1$ group, one $Z^2$ group, and optionally substituted with one or two $Z^3$ groups. In another variation, $R^{3a}$ and $R^{3b}$ are each H and A is pyridinyl or pyrimidinyl, wherein any pyridinyl or pyrimidinyl of A is substituted with one $Z^1$ group, one $Z^2$ group, and optionally substituted with one or two $Z^3$ groups.

In one variation of formula I, A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or more $Z^3$ groups; and $R^2$ is phenyl or a 5-membered heteroaryl, wherein any phenyl or 5-membered heteroaryl of $R^2$ is optionally substituted with two $Z^5$ groups. In another variation, A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or more $Z^3$ groups; $R^2$ is phenyl or a 5-membered heteroaryl, wherein any phenyl or 5-membered heteroaryl of $R^2$ is optionally substituted with two $Z^5$ groups; and each $Z^5$ is halo.

In one variation of formula I, A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or two $Z^3$ groups; and $R^2$ is phenyl or a 5-membered heteroaryl, wherein any phenyl or 5-membered heteroaryl of $R^2$ is optionally substituted with two $Z^5$ groups. In another variation, A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or two $Z^3$ groups; $R^2$ is phenyl or a 5-membered heteroaryl, wherein any phenyl or 5-membered heteroaryl of $R^2$ is optionally substituted with two $Z^5$ groups; and each $Z^5$ is halo.

In another variation, A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with one or two $Z^3$ groups; and $R^1$ is a bicyclic-heteroaryl or tricyclic-heteroaryl, wherein the bicyclic-heteroaryl or tricyclic-heteroaryl has 4-9 carbon atoms and 1-5 heteroatoms in the ring system, and wherein any bicyclic-heteroaryl or tricyclic-heteroaryl of $R^1$ is optionally substituted with one to five $Z^4$ groups.

One embodiment provides a compound of formula If

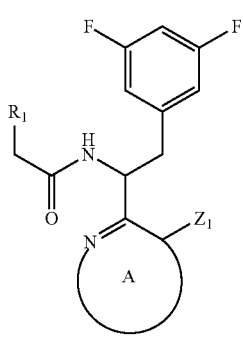

A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with $Z^3$ group;

$R^1$ is

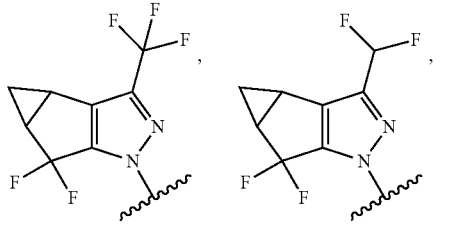

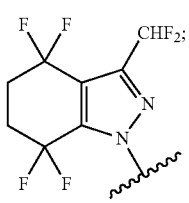

$Z^1$ is aryl, heteroaryl, or heterocycle, wherein any aryl, heteroaryl and heterocycle of $Z^1$ is optionally substituted with $(C_1-C_8)$alkyl, oxo, halogen, —C(O)NH$_2$, —NHS(O)$_2$CH$_3$, or —N(COCH$_3$)(S(O)$_2$CH$_3$);

$Z^2$ is —NR$_{q3}$R$_{r3}$, —NHCOR$_{p3}$, —NHCO$_2$R$_{p3}$, —NHS(O)$_2$ R$_{p3}$, —NHS(O)$_2$OR$_{p3}$, —NHS(O)$_2$NR$_{q3}$R$_{r3}$ or —SCH$_3$;

R$_{q3}$ and R$_{r3}$ are each independently H or $(C_1-C_4)$alkyl, wherein any $(C_1-C_4)$alkyl of R$_{q3}$ or R$_{r3}$ is optionally substituted with —OH, or R$_{q3}$ and R$_{r3}$ together with the nitrogen to which they are attached form a heterocycle or heteroaryl, wherein the heterocycle or heteroaryl is optionally substituted with $(C_1-C_4)$alkyl, —OH, —NH$_2$, or oxo;

R$_{p3}$ is $(C_1-C_4)$alkyl or $(C_1-C_4)$haloalkyl; and each $Z^3$ is independently halogen, $(C_1-C_4)$alkyl, —OH, —CN, $(C_1-C_4)$heteroalkyl or $(C_1-C_4)$haloalkyl; and or a pharmaceutically acceptable salt thereof.

A specific group of compounds of formula If are compounds of formula Ig.

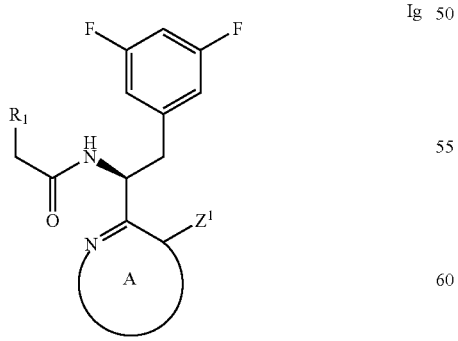

or a pharmaceutically acceptable salt thereof.

A specific group of compounds of formula If are compounds of formula Ih.

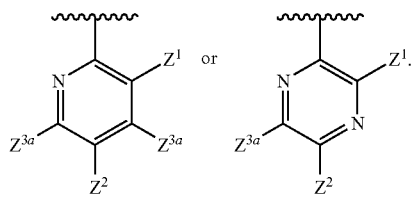

or a pharmaceutically acceptable salt thereof.

Specific values listed below are values for compounds of formula If as well as all related formulas (e.g., formulas Ig and Ih).

In certain embodiments of formula If, A is pyridinyl, pyrimidinyl, or pyrazinyl. In certain embodiments, A is:

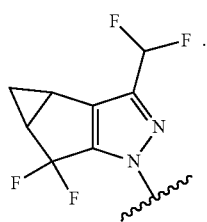 [SMILES: *n1nc(C(F)F)c2c1C(F)(F)C1CC21 ; "."]

In certain embodiments of formula If, $R^1$ is

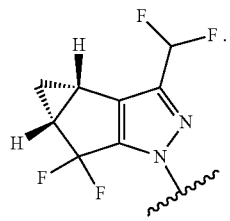

In certain embodiments of formula If, $R^1$ is

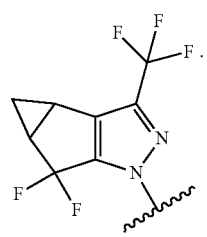 [SMILES: *n1nc(C(F)(F)F)c2c1C(F)(F)C1CC21 ; "."]

In certain embodiments, $R^1$ is

In certain embodiments, $R^1$ is
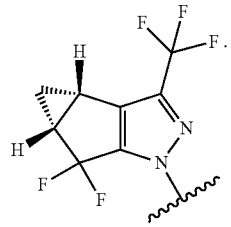
In certain embodiments of formula If, $R^1$ is
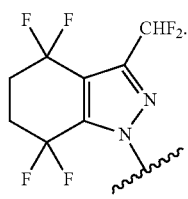 [SMILES: *n1nc(C(F)F)c2c1C(F)(F)CCC2(F)F]
In certain embodiments of formula If, $Z^1$ is:
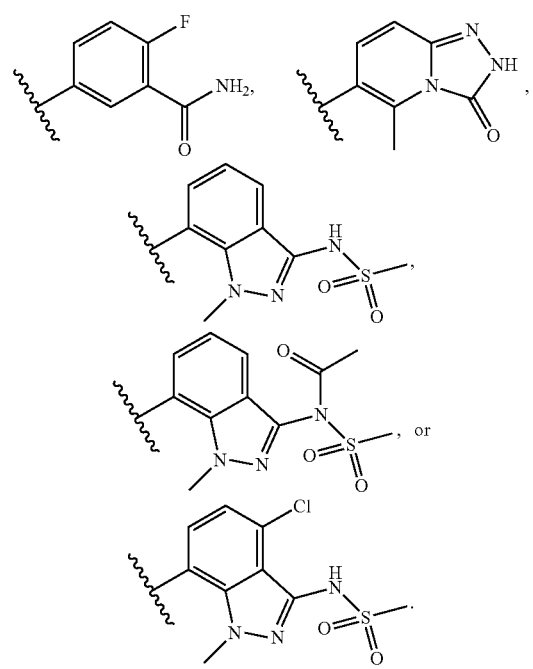
In certain embodiments of formula If, $Z^2$ is:
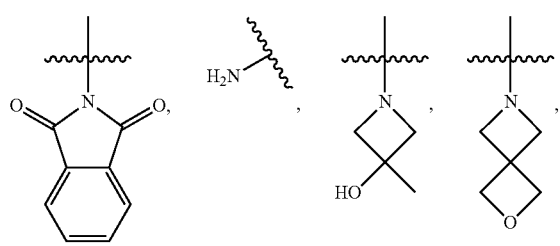
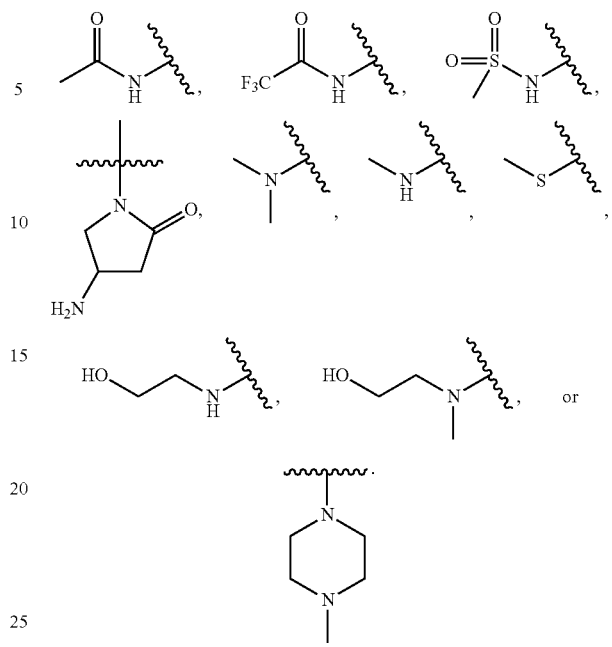
In one embodiment the compound of formula I is selected from:
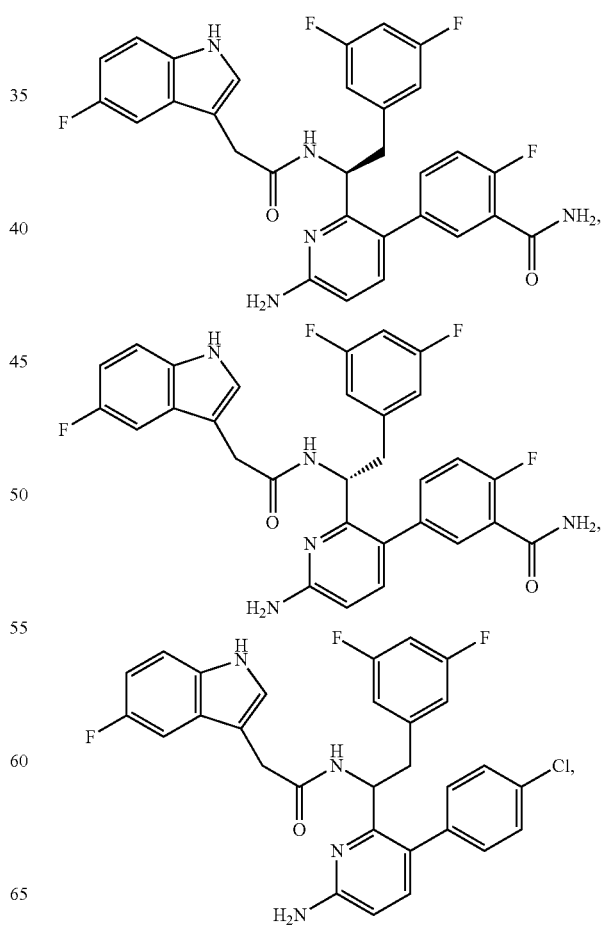

35
-continued
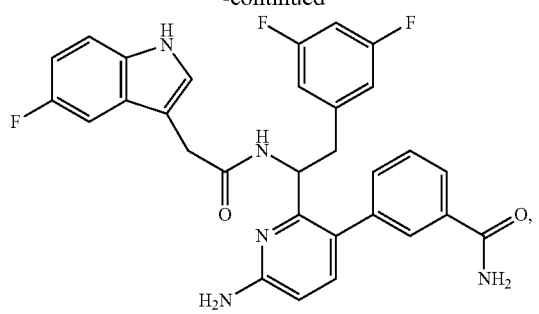
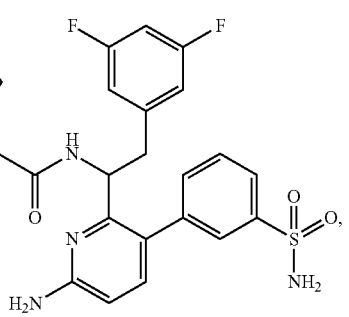
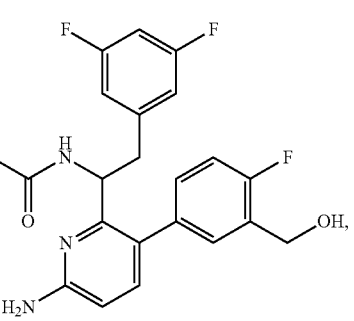
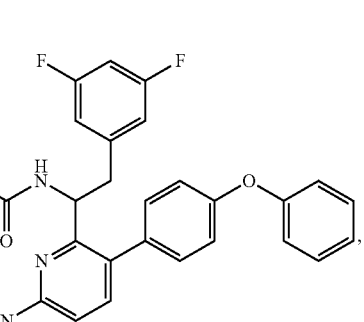
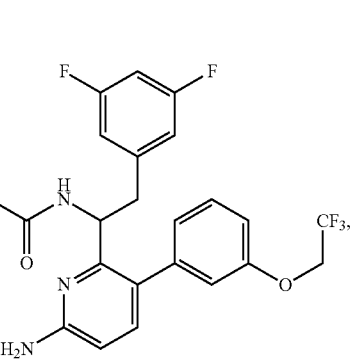
36
-continued
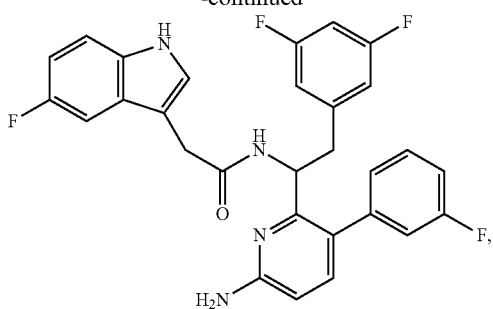
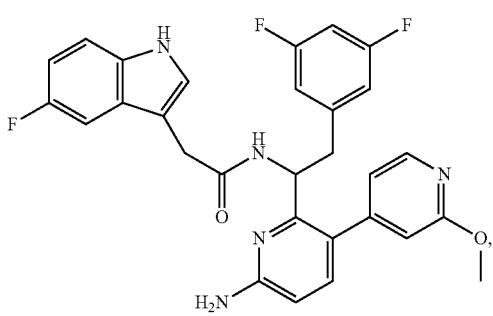
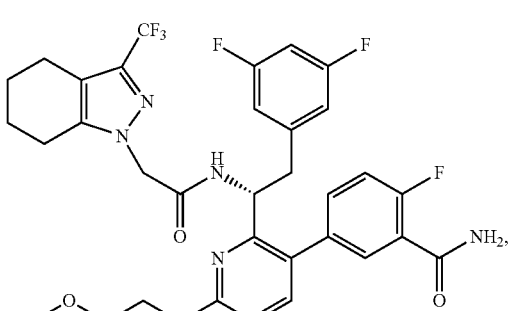
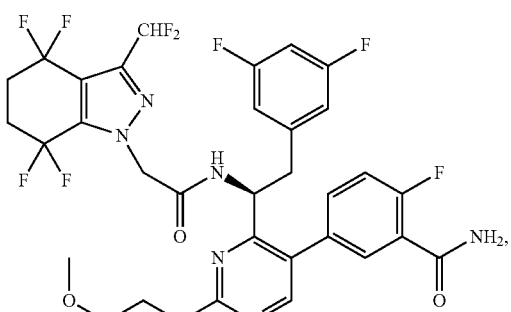
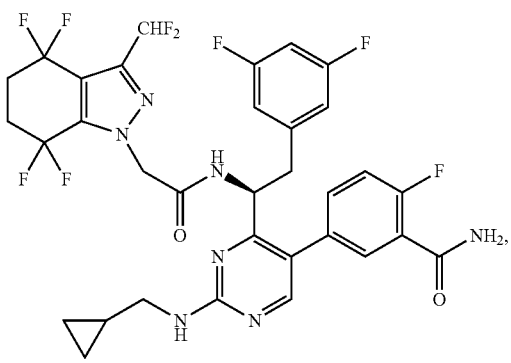

37
-continued
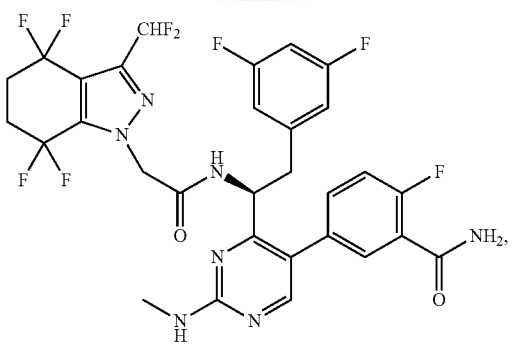
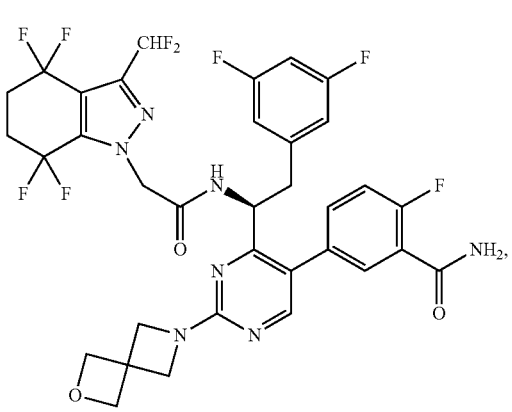
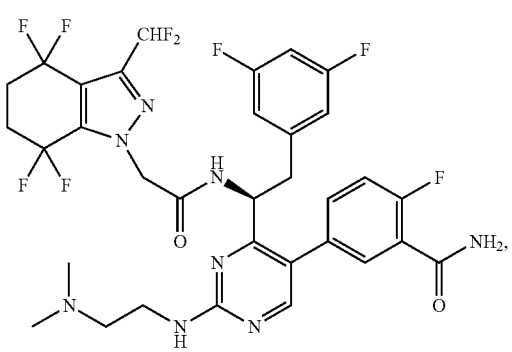
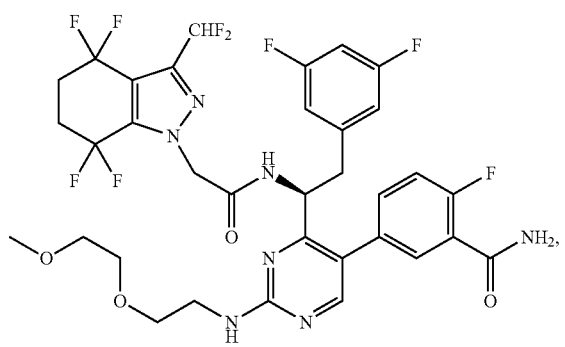
38
-continued
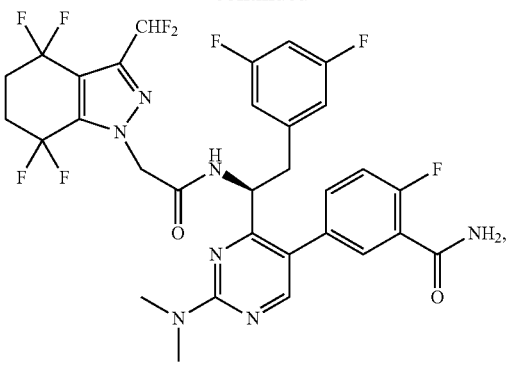
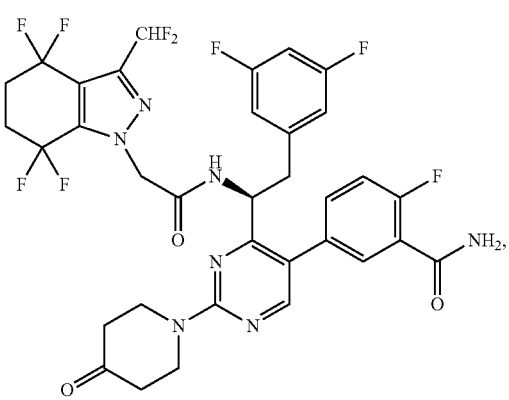
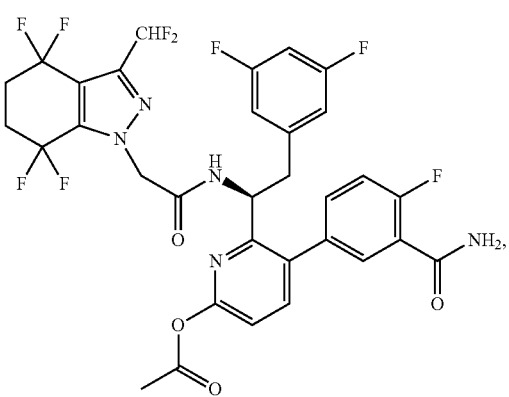
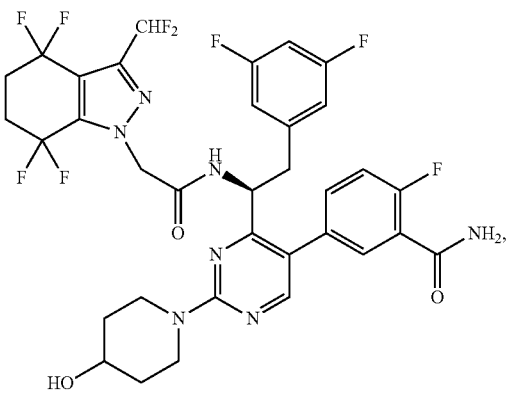

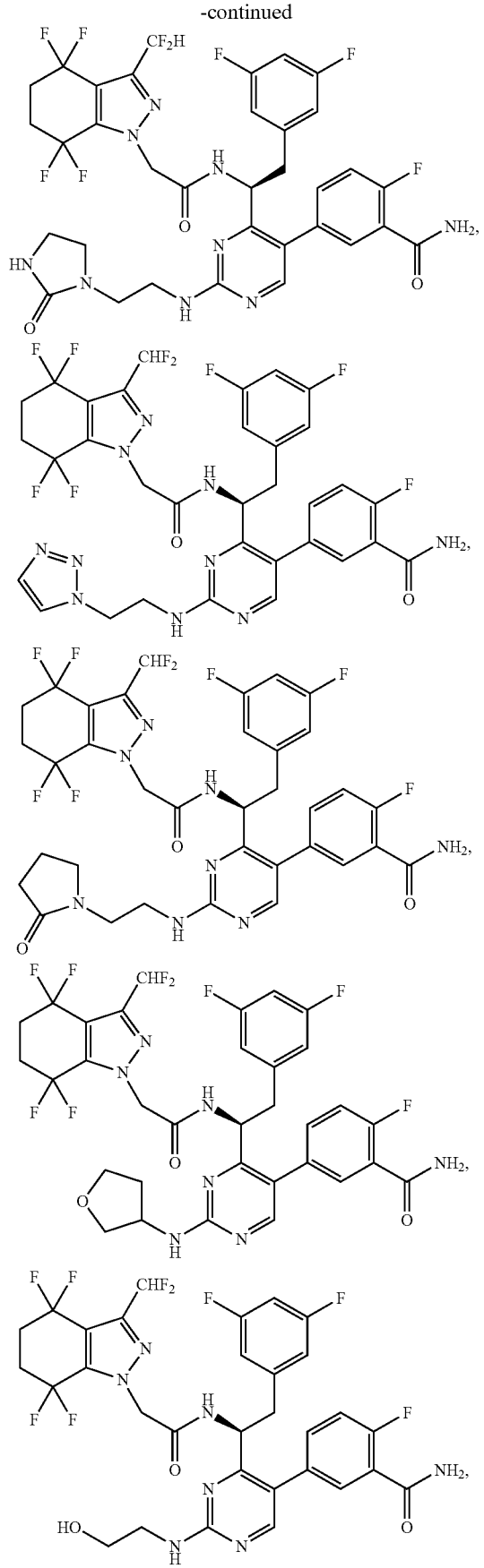
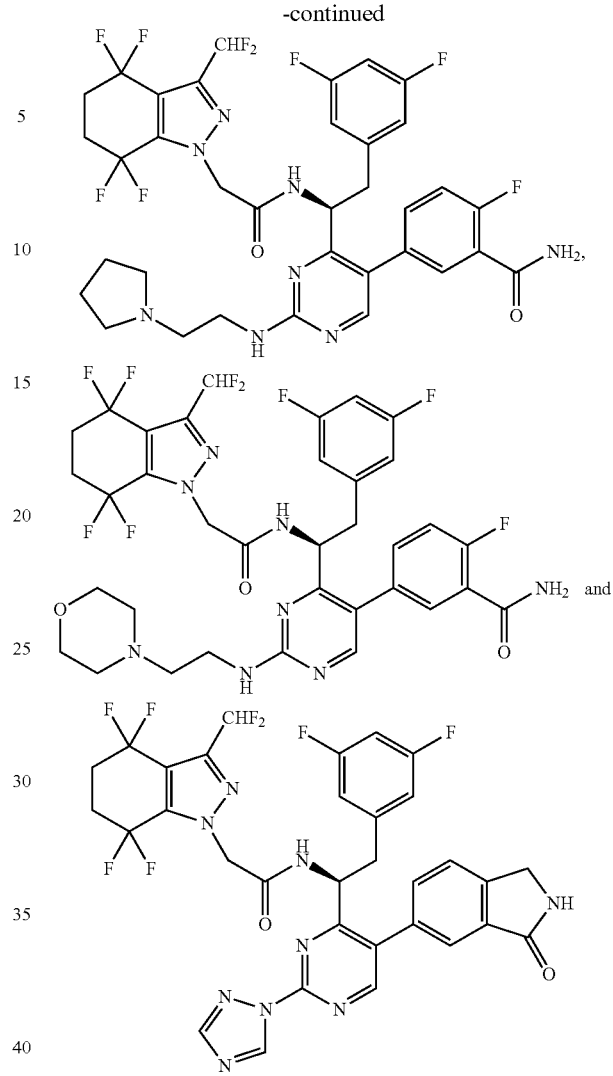
and salts thereof. In certain embodiments, a salt is a pharmaceutically acceptable salt.
In one embodiment, a compound is:
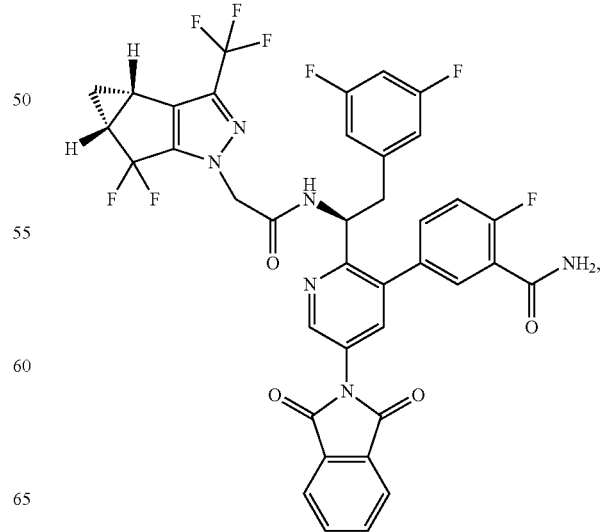

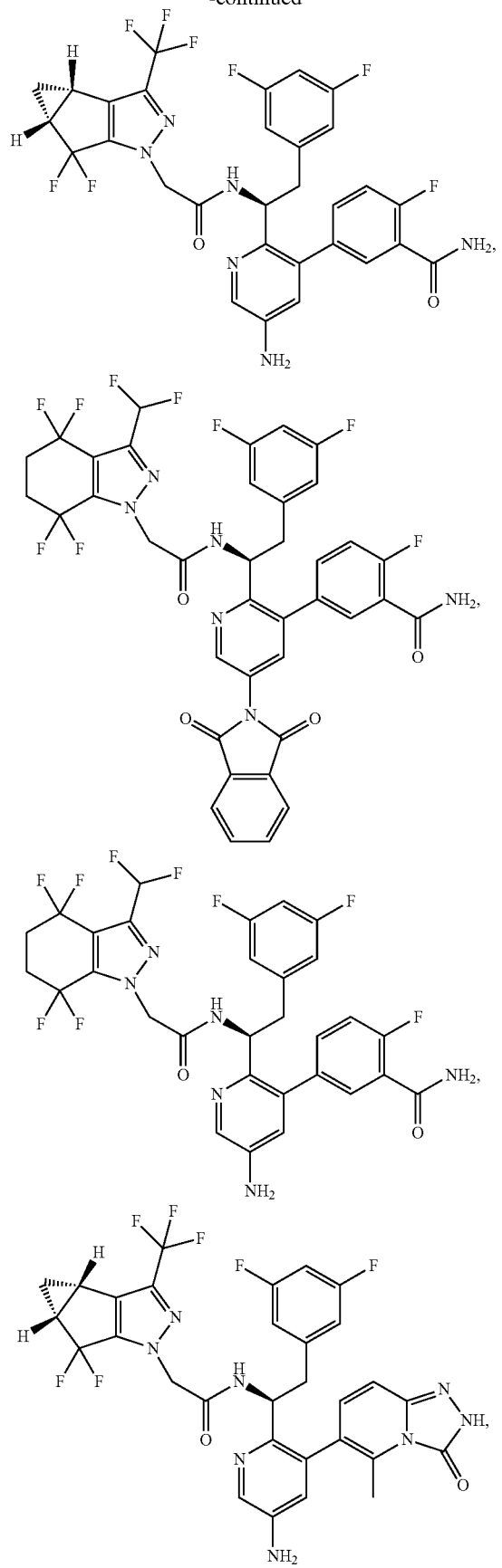
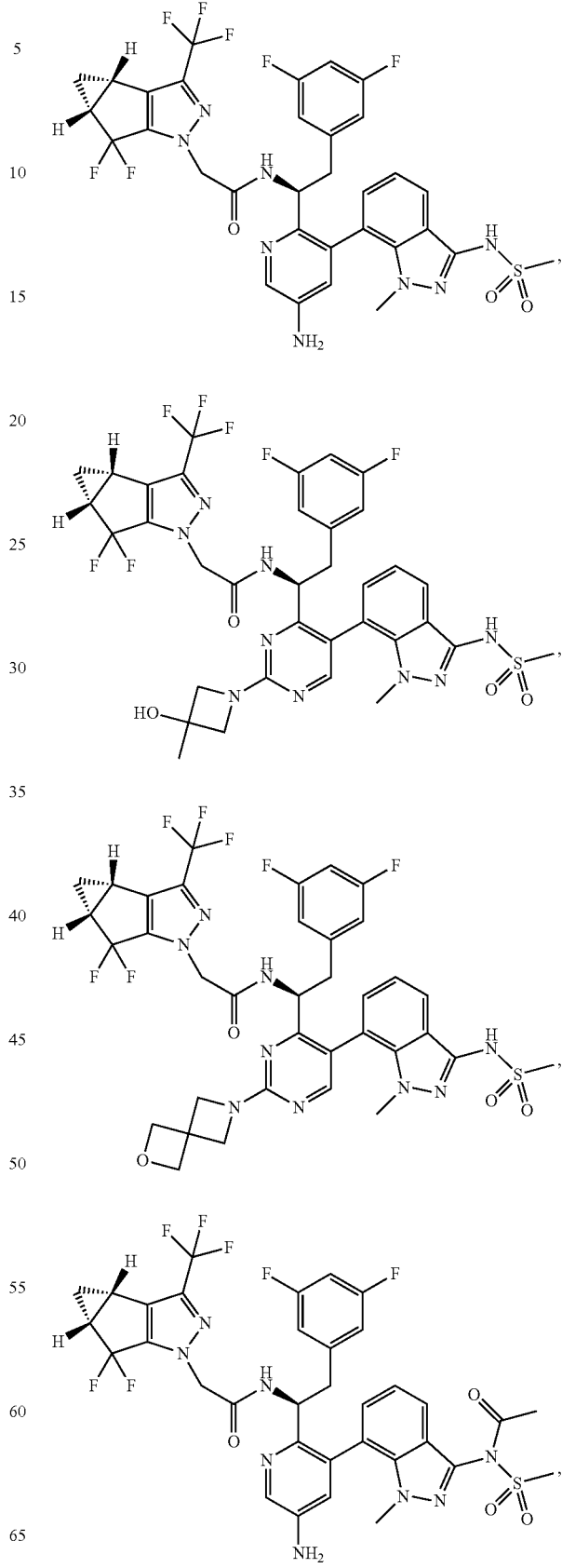

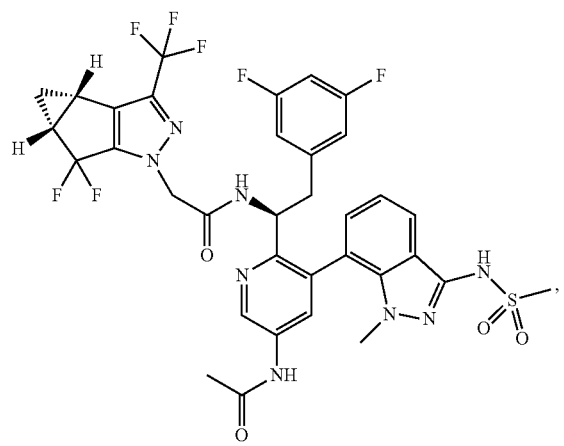
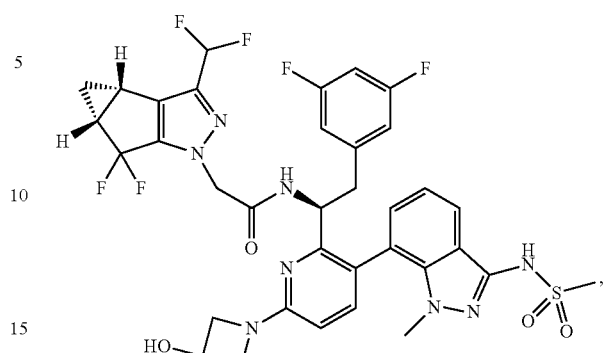
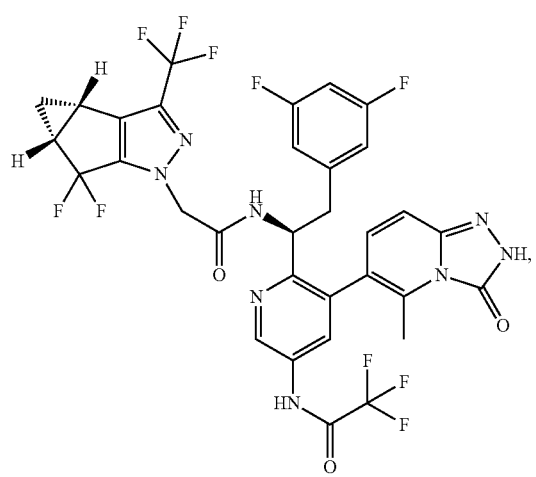
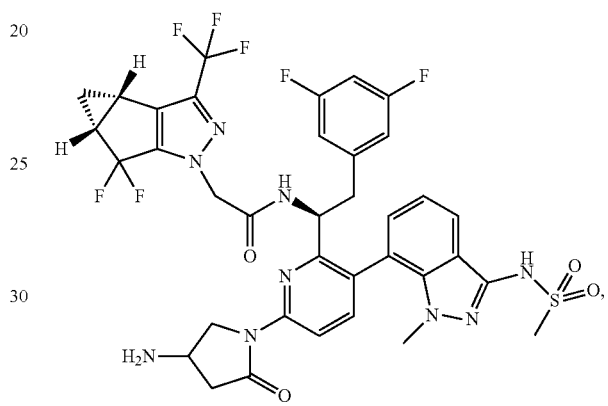
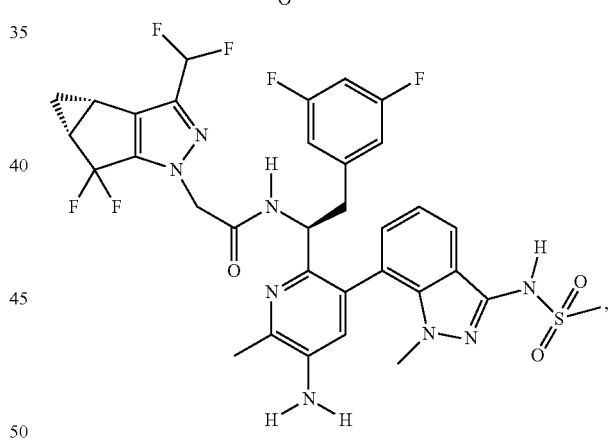
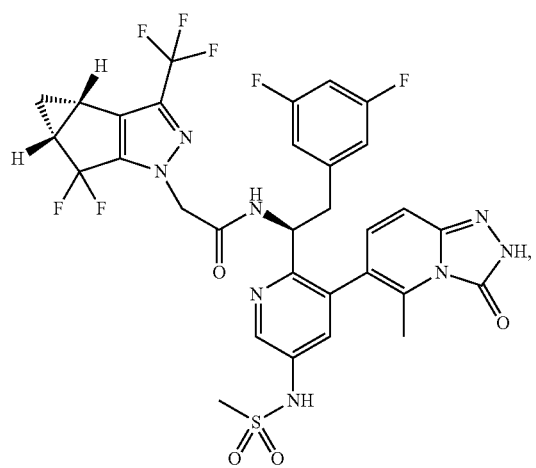
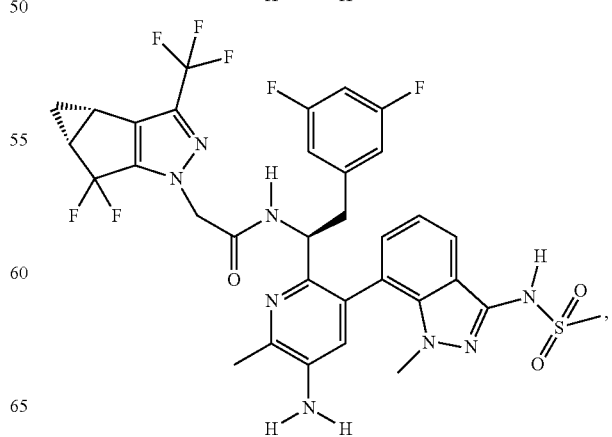

45
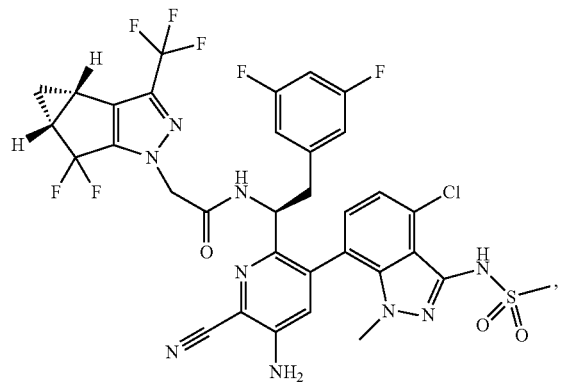
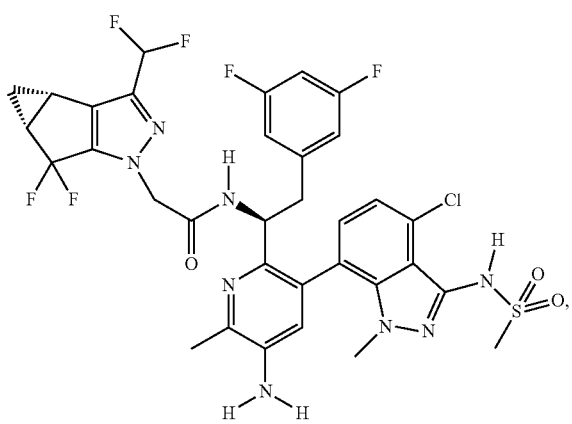
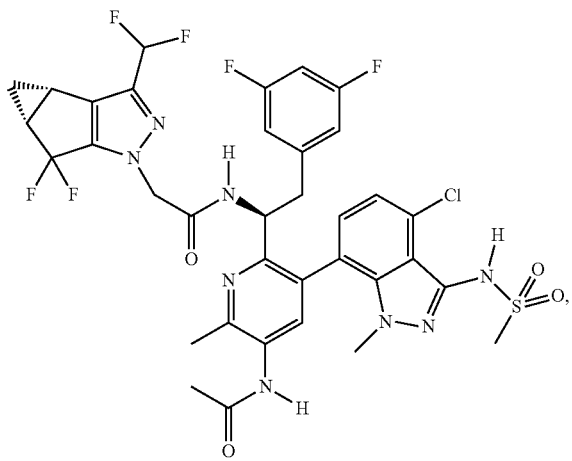
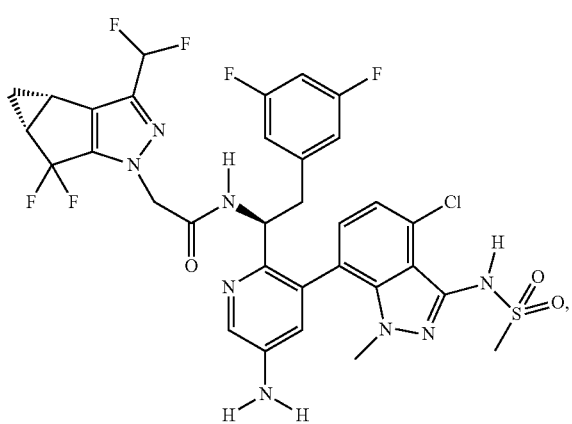
46
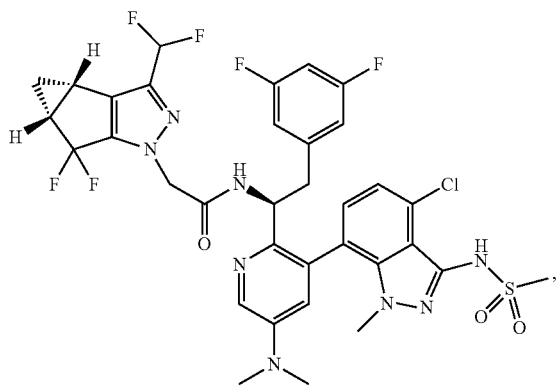
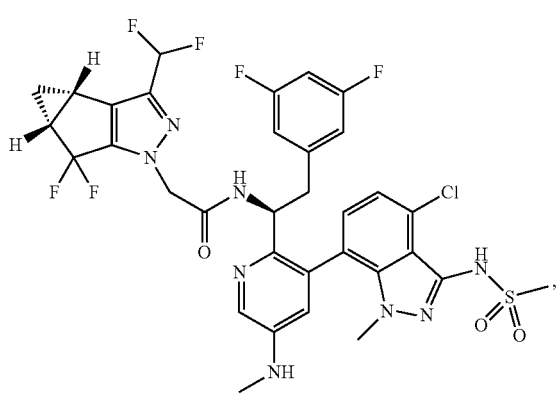
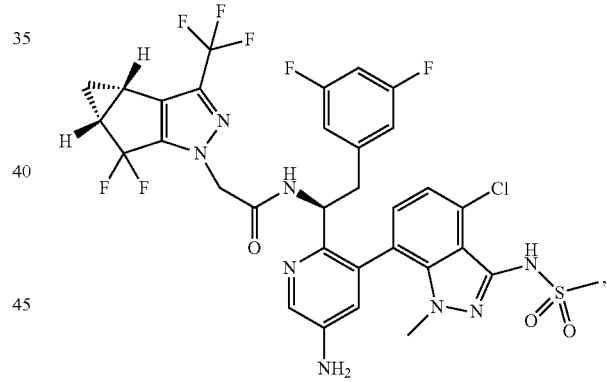
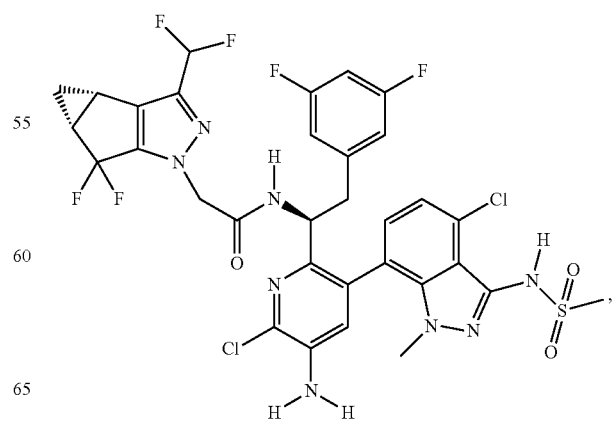

47
-continued
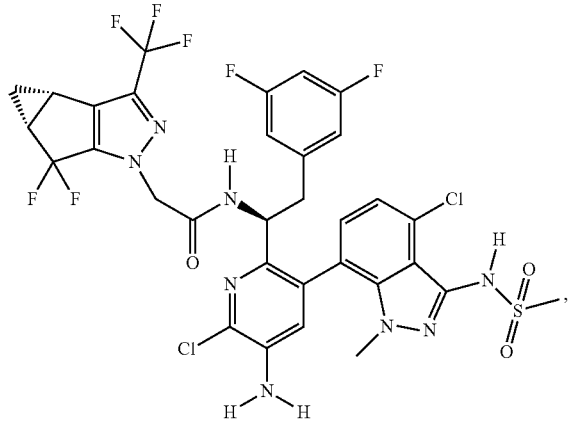
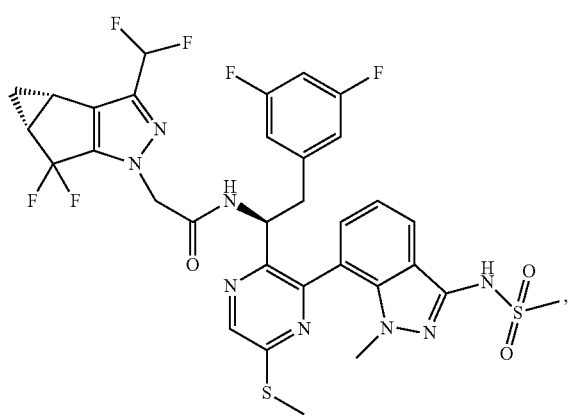
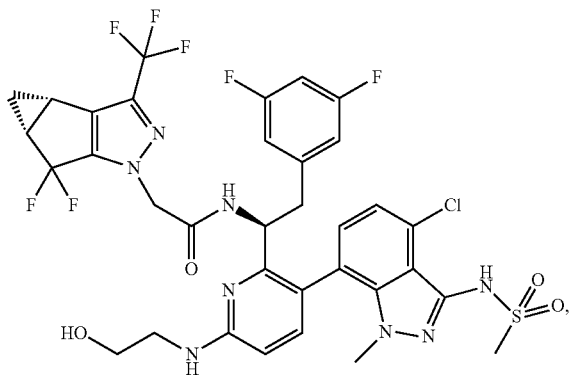
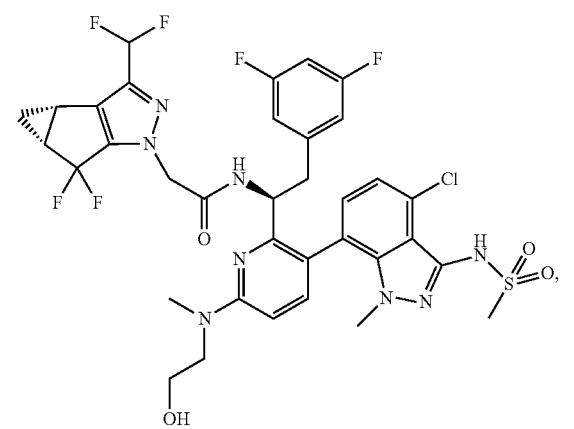
48
-continued
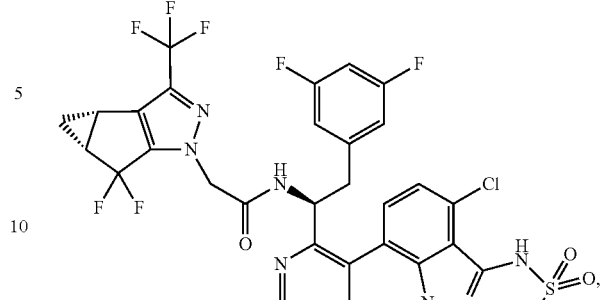
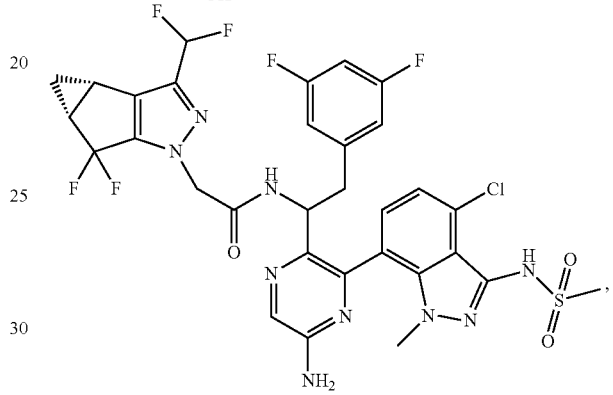
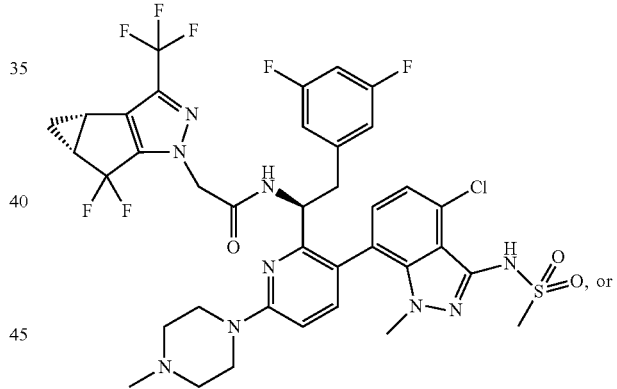
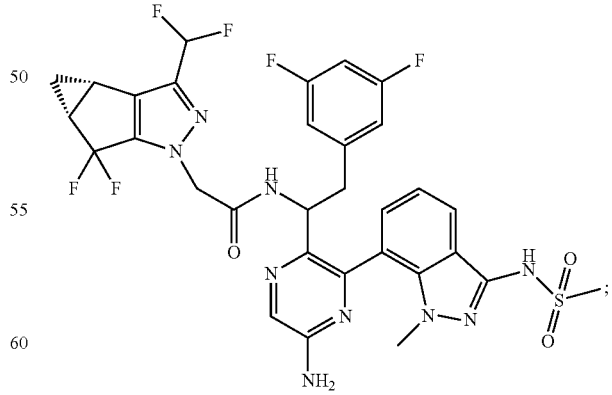
and pharmaceutically acceptable salts thereof.
General Synthetic Procedures
The following scheme describes methods that are useful for preparing compounds of formula I.

Scheme 1

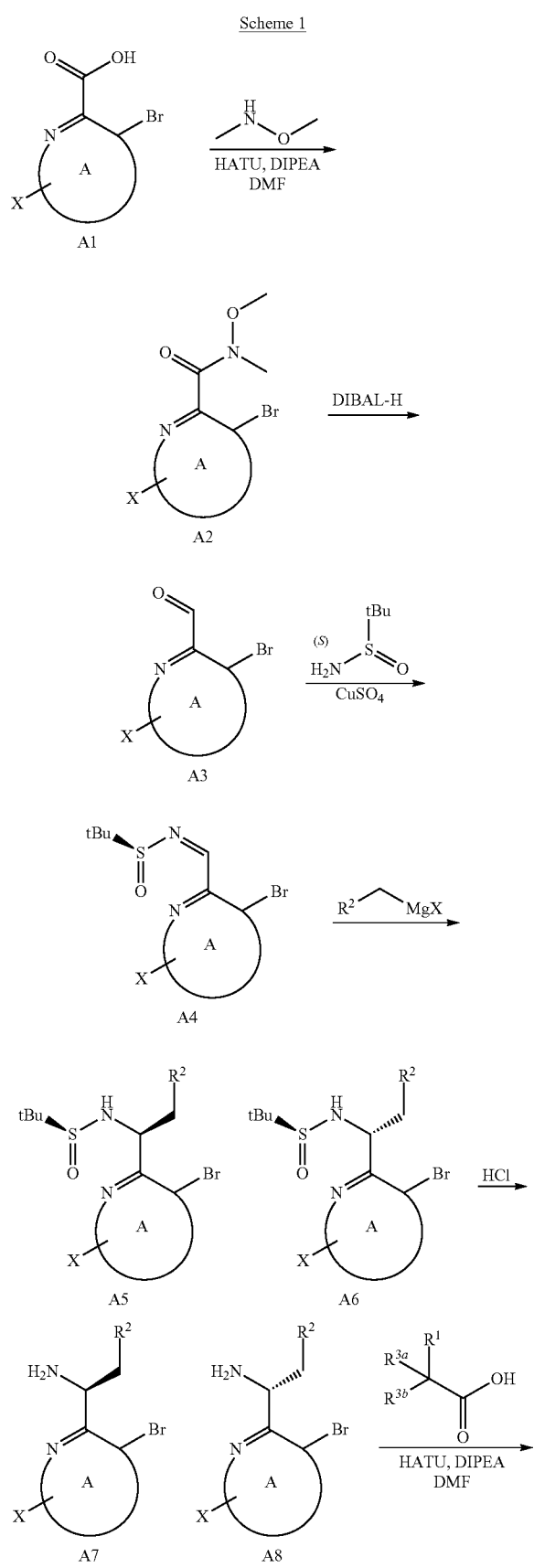

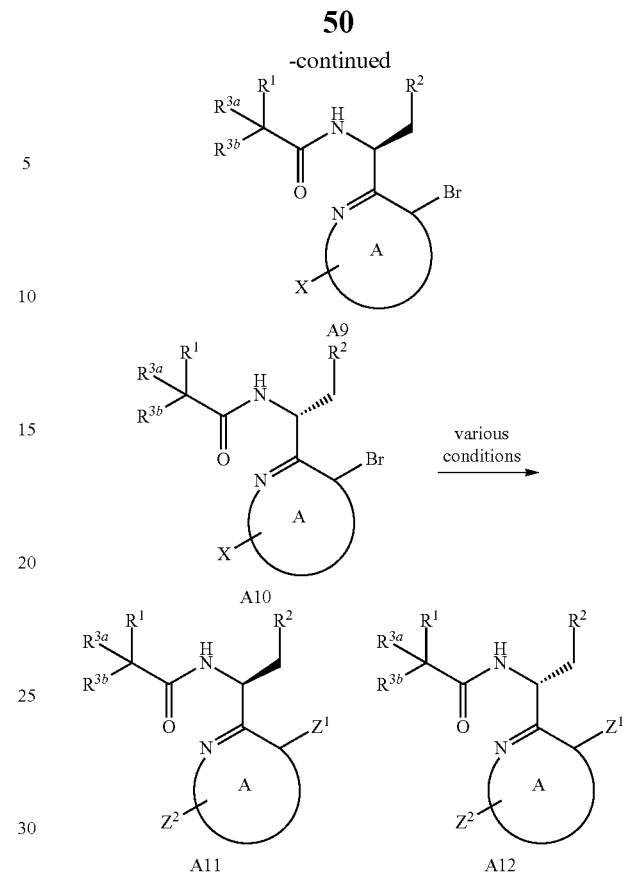

Scheme 1 describes a general stereoselective route which can be used to prepare compounds of formula I. Heteroaryl acids of formula A1 (where X represents diversifiable chemical group such as $NH_2$, SH, or halogen that may be suitably protected) can be converted to the corresponding aldehydes then condensed with a chiral auxiliary to provide a stereoselective addition of a nucleophilic reagent. Depicted in Scheme 1 is the conversion of a heteroaryl acid A1 containing two diversifiable functional groups to the corresponding aldehyde. This is followed by the condensation of the aldehyde A3 with (S) tert-butane sulfinamide and the addition of a Grignard reagent to provide a mixture of A5 and A6 enriched in A5. This mixture may be separated by column chromatography on silica gel to provide pure diastereomers. Removal of the auxiliary provides amines A7 and A8 which can be coupled to a variety of carboxylic acids to provide heteroaryl compounds of formula A9 and A10. Diversification of A9 and A10 may be accomplished by a variety of methods including alkylation, acylation, cyanation, nucleophilic aromatic displacement, and metal catalyzed cross coupling reactions such as Suzuki couplings, Buchwald-Hartwig type couplings, and Sonogashira couplings.

Combination Therapy

In one embodiment, the invention provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In one embodiment, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In one embodiment, combination pharmaceutical agents comprising a compound disclosed herein, or a pharmaceutically acceptable salt thereof, in combination with one or more additional therapeutic agents are provided.

One embodiment provides pharmaceutical compositions comprising a compound disclosed herein, or a pharmaceutically acceptable salt thereof, in combination with at least one additional therapeutic agent, and a pharmaceutically acceptable carrier. In one embodiment, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, capsid polymerization inhibitors or capsid disrupting compounds such as those disclosed in US 2013/0165489 (University of Pennsylvania), and WO 2013/006792 (Pharma Resources), pharmacokinetic enhancers, and other drug for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MW-150, TMC-120, rilpivirene, BILR 355 BS, VRX 840773, lersivirine (UK-453061), RDEA806, KMO23 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), tenofovir alafenamide (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by reference in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5 mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS119, ALG 889, and PA-1050040 (PA-040).

In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In some embodiments, one or more of the compounds disclosed herein are combined with one or more other active therapeutic agents in a unitary dosage form for simultaneous or sequential administration to a patient. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units including but not limited to capsules, cachets or tablets each containing a predetermined amount of the active ingredient.

Pharmaceutical formulations according to the present invention comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

The antiviral properties of a compound of the invention may be determined using Test A described below.

Test A: Antiviral Assay in MT4 Cells

For the antiviral assay, 40 µL of 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were defined as the compound concentration that caused a 50% decrease in luminescence signal, a measure of HIV-1 replication. Percent inhibition of virus-induced cell killing calculated from the dose response curve at 3 µM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity (Test A) as depicted in the table below. Shown below are the corresponding values for CC50 and percent inhibition of virus-induced cell killing in the presence of 31.1M drug concentration.

| Compound | % inhibition at 3 µM | CC50 (nM) |
| --- | --- | --- |
| 1H | 98 | 22082 |
| 2 | 0 | 25239 |
| 3 | 87 | 9337 |
| 4 | 94 | 13074 |
| 5 | 87 | 28652 |
| 6 | 59 | 14439 |
| 7 | 37 | 11466 |
| 8 | 50 | 11677 |
| 9 | 41 | 17525 |
| 10 | 38 | 23835 |
| 11J | 0 | 16271 |
| 12E | 86 | 18198 |
| 13B | 42 | 7722 |
| 14B | 89 | 28633 |
| 15B | 70 | 36296 |
| 16B | 41 | 15417 |
| 17B | 83 | 48760 |
| 18B | 16 | 38913 |
| 19C | 26 | >51513 |
| 20B | 1 | >53192 |
| 21 | 41 | 22526 |

-continued

| Compound | % inhibition at 3 µM | CC50 (nM) |
| --- | --- | --- |
| 22B | 93 | 34113 |
| 23F | 77 | 32713 |
| 24 | 79 | 37217 |
| 25 | 69 | 37675 |
| 26 | 86 | 19885 |
| 27 | n.d. | 3500 |
| 28 | 81 | 14089 |
| 29D | 101 | 39974 |
| 30K | 48 | >53192 |
| 31 | 96 | 19489 |
| 32 | 37 | >53192 |
| 33 | 85 | 13304 |
| 34 | 89 | 22374 |
| 35 | 93 | 23944 |
| 36C | 94 | 32201 |
| 37 | 95 | 34040 |
| 38B | 98 | 40834 |
| 39 | 92 | 29550 |
| 40 | 96 | 24115 |
| 41E | 91 | >49982 |
| 42K | 92 | 18896 |
| 43B | 83 | 16860 |
| 44 | 107 | 31990 |
| 45 | 110 | 21462 |
| 46F | 109 | 12479 |
| 47C | 107 | 18105 |
| 48 | 93 | 20719 |
| 49C | 93 | 28143 |
| 50 | 86 | 34213 |
| 51 | 79 | 16569 |
| 52 | 104 | 21528 |
| 53B | 91 | 15025 |
| 54 | 92 | 12139 |
| 55G | 107 | 22094 |
| 56 | 95 | 24258 |
| 57G | 81 | 29458 |
| 58 | 86 | 12755 |
| 59D | 85 | >46781 |
| 60C | 90 | 9108 |
| 61 | 75 | >53192 |

(n.d.—not determined)

The data above represent an average over time of each assay for each compound. For certain compounds, multiple assays have been conducted over the life of the project. Thus, the data reported in the tables include the data reported in the priority document, as well as data from assays run in the intervening period.

In one embodiment, the compounds demonstrate >10% inhibition at 3 µM. In one embodiment, the compounds demonstrate >30% inhibition at 3 µM. In one embodiment, the compounds demonstrate >50% inhibition at 3 µM. In one embodiment, the compounds demonstrate >70% inhibition at 3 µM. It is to be understood that the compounds disclosed herein can be grouped according to their % inhibition as described above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

Example 1 and 2

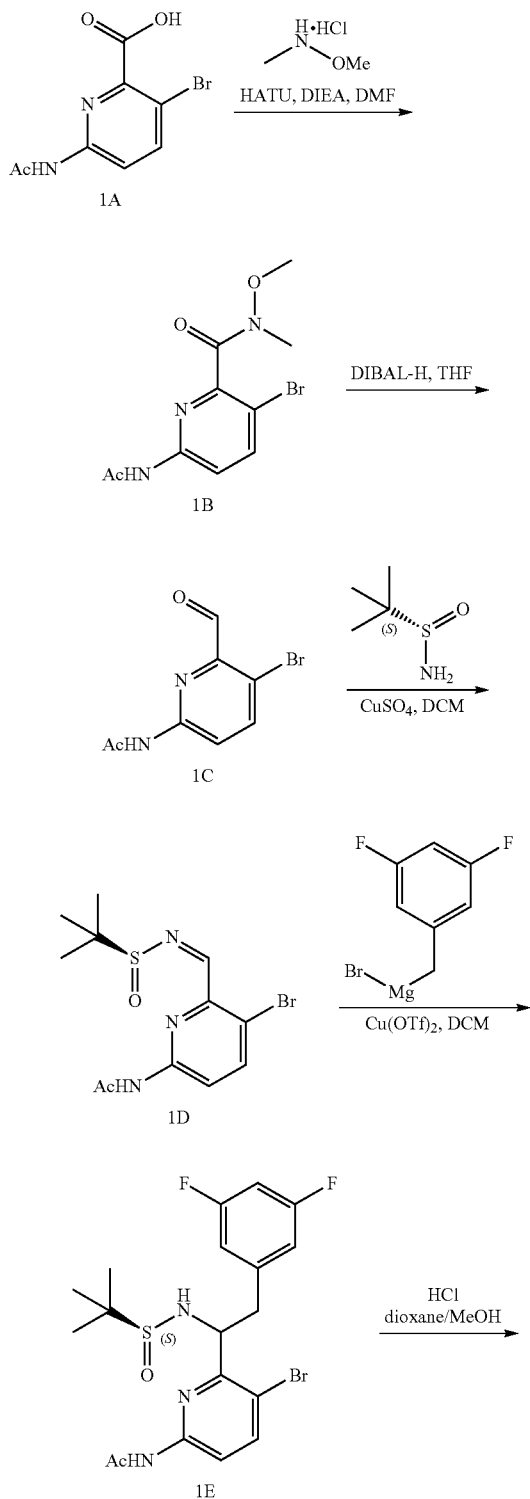

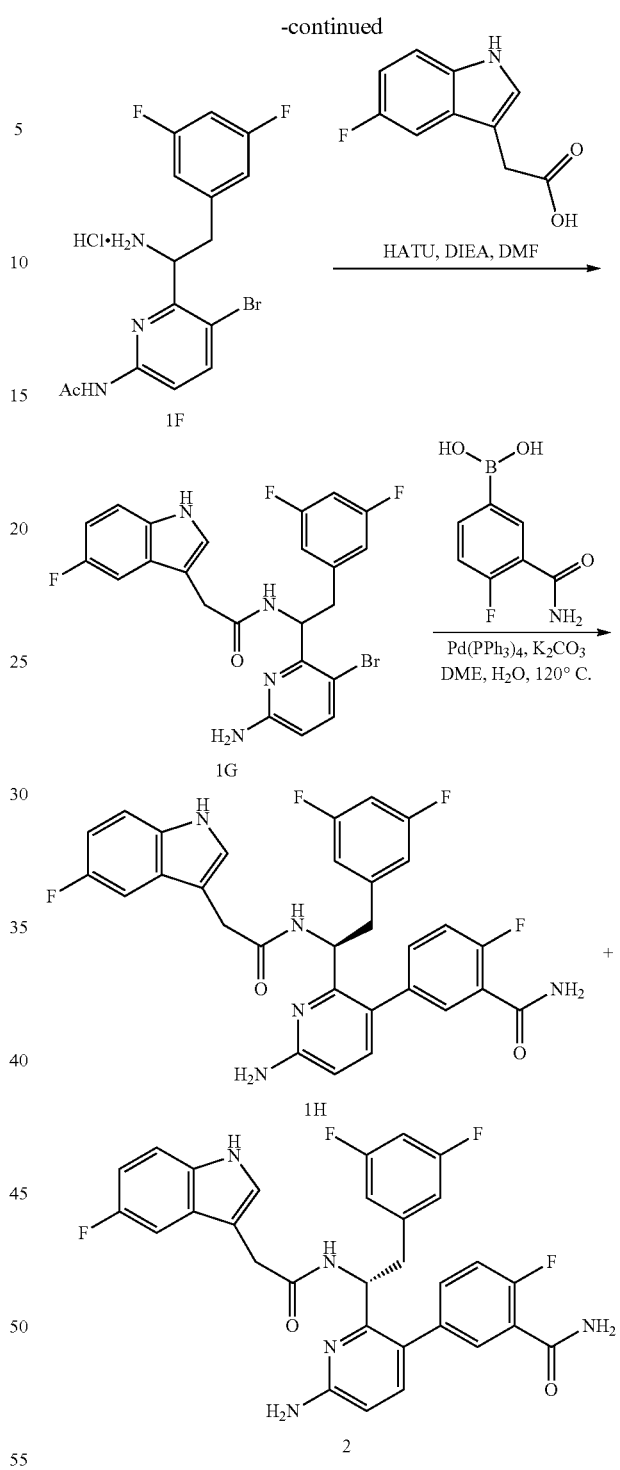

Synthesis of 6-acetamido-3-bromo-N-methoxy-N-methylpicolinamide (1B)

HATU (1-[Bis(dimethylamino)methylene]-1H-1,2,3-triazolo[4,5-b]pyridinium 3-oxid hexafluorophosphate) (4.56 g, 12.0 mmol) was added to a solution of 6-acetamido-3-bromopicolinic acid (2.6 g, 10.0 mmol) and DIPEA (N,N-diisopropylethylamine)(5.2 ml, 30 mmol) in DCM (dichloromethane)(10 ml). After 10 minutes, N,O-dimethylhydroxylamine hydrochloride (1.5 g, 15.0 mmol) was added to the reaction. The reaction was stirred at room temperature for 5 min. The reaction mixture was partitioned between EtOAc (ethyl acetate) and saturated NH₄Cl solution. The organic phase was washed with brine, dried over Na₂SO₄, filtered and concentrated in vacuo. The crude material was used in the next step without further purification. MS (m/z) 302.1 [M+H]⁺. ¹H NMR (400 MHz, cd3cl) δ 8.14 (s, 1H), 8.13 (d, J=8.4 Hz, 1H), 7.85 (d, J=8.4 Hz, 1H), 3.56 (s, 3H), 3.37 (s, 3H), 2.20 (s, 3H).

Synthesis of
N-(5-bromo-6-formylpyridin-2-yl)acetamide (1C)

To the crude material from last step (1B, 2.6 g, 8.6 mmol) in THF (tetrahydrofuran)(30 mL) was added DIBAL-H (di-isobutylaluminium hydride)(13 mmol, 1.5 equiv) dropwise at 70° C. The reaction was stirred for 1 h and was then quenched with NH₄Cl solution. The reaction mixture was partitioned between EtOAc and saturated NH₄Cl solution. The organic phase was washed with brine, dried over Na₂SO₄, filtered and concentrated in vacuo. The crude material was used in the next step without further purification. MS (m/z) 244.1 [M+H]⁺.

Synthesis of (S)—N-(5-bromo-6-(((tert-butylsulfinyl)imino)methyl)pyridin-2-yl)acetamide (1D)

Copper(II) sulfate (anhydrous 2.8 g, 17.2 mmol) was added to a solution of N-(5-bromo-6-formylpyridin-2-yl)acetamide (crude material, assume 8.6 mmol) and (S)-2-methylpropane-2-sulfinamide (1.2 g, 9.4 mmol) in DCM (30 ml). The suspension was stirred overnight at room temperature. The reaction was filtered and washed with DCM (3×20 ml). The filtrate was concentrated. The crude product was purified by flash column (30% EtOAc/Hexanes). MS (m/z) 346.1 [M+H]⁺.

Synthesis of (S)—N-(5-bromo-6-(2-(3,5-difluorophenyl)-1-(1,1-dimethylethylsulfinamido)ethyl)pyridin-2-yl)acetamide (1E)

(3,5-Difluorobenzyl)magnesium bromide (0.25 M in ether, 10 ml, 2.5 mmol) was added dropwise to a solution of (S)—N-(5-bromo-6-(((tert-butylsulfinyl)imino)methyl)pyridin-2-yl)acetamide (1D, 0.47 g, 1.36 mmol) in DCM (5 ml) at 78° C. The reaction was stirred for 3 h at −78° C. Ammonium chloride (aq, 10 mL) was added to the reaction and the mixture was allowed to warm to r.t. The mixture was extracted with EtOAc (2×30 mL). The organic layer was dried over Na₂SO₄, filtered and concentrated. The crude product contained a mixture of diastereomers which were used in the next step without further purification. MS (m/z) 474.1 [M+H]⁺.

Synthesis of N-(6-(1-amino-2-(3,5-difluorophenyl)ethyl)-5-bromopyridin-2-yl)acetamide hydrochloride (1F)

(S)—N-(5-Bromo-6-(2-(3,5-difluorophenyl)-1-(1,1-dimethylethylsulfinamido)ethyl)pyridin-2-yl)acetamide (1E, crude material from last step) was treated with a mixture of 2 ml of 1.25 M HCl in MeOH (methanol)/1 ml of 4 M HCl in dioxane for 1 hour. The solvent was removed in vacuo. The crude material was used without further purification. MS (m/z) 369.9 [M+H]⁺.

Synthesis of N-(1-(6-amino-3-bromopyridin-2-yl)-2-(3,5-difluorophenyl)ethyl)-2-(5-fluoro-1H-indol-3-yl)acetamide (1G)

HATU (741 mg, 1.95 mmol) was added to a solution of 2-(5-fluoro-1H-indol-3-yl)acetic acid (251 mg, 1.3 mmol) and DIPEA (1.2 mL, 6.5 mmol) in DMF (dimethylformamide)(5 mL). After 10 minutes, N-(6-(1-amino-2-(3,5-difluorophenyl)ethyl)-5-bromopyridin-2-yl)acetamide hydrochloride (1F, 480 mg, 1.3 mmol) in 2 mL of DMF was added. The reaction was stirred for 1 h at room temperature. The DMF solution was filtered and purified by RP HPLC using a C18 column and a gradient of 20% B to 85% B over 25 minutes (A=0.1% TFA/H₂O, B=0.1% TFA/acetonitrile) to provide the desired product (acetyl group was removed during reverse phase purification). ¹H NMR (400 MHz, CDCl₃) δ 8.14 (s, 1H), 7.71 (d, J=9.2 Hz, 1H), 7.52 (d, J=8.6 Hz, 1H), 7.26 (m, 3H), 7.16 (s, 1H), 6.89 (t, J=8.6 Hz, 2H), 6.64-6.46 (m, 4H), 5.62 (d, J=8.1 Hz, 1H), 3.59 (s, 2H), 3.01-2.90 (m, 2H). MS (m/z) 502.5 [M+H]⁺.

Synthesis of (S)-5-(6-amino-2-(2-(3,5-difluorophenyl)-1-(2-(5-fluoro-1H-indol-3-yl)acetamido)ethyl)pyridin-3-yl)-2-fluorobenzamide (1H) and (R)-5-(6-amino-2-(2-(3,5-difluorophenyl)-1-(2-(5-fluoro-1H-indol-3-yl)acetamido)ethyl)pyridin-3-yl)-2-fluorobenzamide (2)

A suspension of N-(1-(6-amino-3-bromopyridin-2-yl)-2-(3,5-difluorophenyl)ethyl)-2-(5-fluoro-1H-indol-3-yl)acetamide (1G, 30 mg, 0.06 mmol), potassium carbonate (0.06 mL, 2M in water), (3-carbamoyl-4-fluorophenyl)boronic acid (13 mg, 0.072 mmol) and tetrakis(triphenylphosphine) palladium (1.0 mg, 0.0009 mmol) in DME (dimethyl ether) (1.0 mL) was degassed for 30 minutes. The mixture was submitted to microwave heating at 120° C. for 30 min. The reaction was cooled and filtered through celite. The filtrate was extracted with EtOAc (2×10 mL). The organic layer was dried over Na₂SO₄, filtered and concentrated. The crude product was purified by reverse phase HPLC to give a mixture of enantiomers. MS (m/z) 562.4 [M+H]⁺. ¹H NMR (400 MHz, CDCl₃) δ 8.08 (s, 1H), 7.71 (d, J=7.9 Hz, 2H), 7.62 (s, 1H), 7.45 (d, J=9.2 Hz, 1H), 7.28-7.15 (m, 3H), 7.10 (s, 1H), 6.91 (s, 1H), 6.82 (t, J=8.4 Hz, 2H), 6.58 (d, J=9.0 Hz, 1H), 6.52-6.40 (m, 2H), 6.22-6.05 (m, 3H), 5.16 (d, J=8.1 Hz, 1H), 3.52 (s, 2H), 3.01-2.87 (m, 1H), 2.83-2.78 (m, 1H).

The mixture of enantiomers were separated by chiral chromatography (Chiralcel AZ-H, Heptane:IPA 70:30) to gave (S)-5-(6-amino-2-(2-(3,5-difluorophenyl)-1-(2-(5-fluoro-1H-indol-3-yl)acetamido)ethyl)pyridin-3-yl)-2-fluorobenzamide (1H, slow eluting peak) and (R)-5-(6-amino-2-(2-(3,5-difluorophenyl)-1-(2-(5-fluoro-1H-indol-3-yl)acetamido)ethyl)pyridin-3-yl)-2-fluorobenzamide (2, fast eluting peak).

Example 3

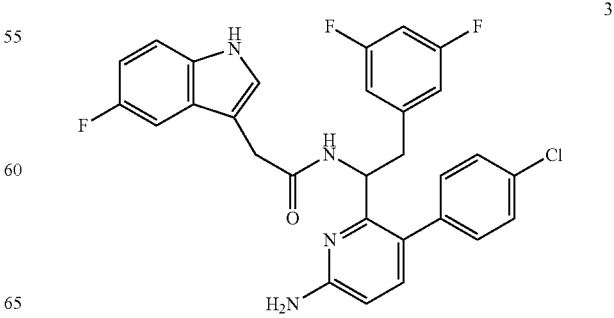

Synthesis of N-(1-(6-amino-3-(4-chlorophenyl)pyridin-2-yl)-2-(3,5-difluorophenyl)ethyl)-2-(5-fluoro-1H-indol-3-yl)acetamide (3)

The title compound was prepared according to the method presented for the synthesis of compound IH of Example 1 utilizing 1G and 4-chlorophenyl boronic acid. $^1$H NMR (400 MHz, CDCl$_3$) δ 8.17 (s, 1H), 7.63 (d, J=8.1 Hz, 1H), 7.52 (d, J=9.0 Hz, 1H), 7.45 (d, J=8.5 Hz, 2H), 7.31-7.23 (m, 6H), 7.19 (s, 1H), 6.89 (t, J=10.0 Hz, 2H), 6.65 (d, J=8.9 Hz, 1H), 6.52 (t, J=8.9 Hz, 1H), 6.26 (d, J=5.9 Hz, 2H), 5.27 (dd, J=16.5, 8.2 Hz, 1H), 3.61 (s, 2H), 3.00 (dd, J=13.6, 9.3 Hz, 1H), 2.85 (dd, J=13.7, 7.5 Hz, 1H). MS (m/z) 535.4 [M+H]$^+$.

Example 4

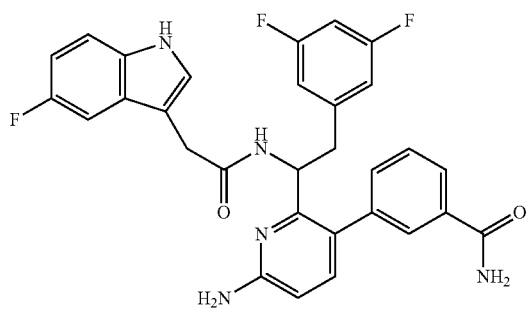

4

Synthesis of 3-(6-amino-2-(2-(3,5-difluorophenyl)-1-(2-(5-fluoro-1H-indol-3-yl)acetamido)ethyl)pyridin-3-yl)benzamide (4)

The title compound was prepared according to the method presented for the synthesis of compound 1H of Example 1 utilizing 1G and 3-(4,4,5,5-tetramethyl-1,3,2-dioxaborolan-2-yl)benzamide. $^1$H NMR (400 MHz, CDCl$_3$) δ 8.06-7.95 (m, 4H), 7.50-7.38 (m, 2H), 7.26-7.20 (m, 1H), 7.13 (m, 1H), 6.89-6.81 (m, 3H), 6.60 (d, J=8.9 Hz, 1H), 6.50-6.39 (m, 2H), 6.07 (d, J=5.8 Hz, 2H), 5.43 (d, J=8.8 Hz, 1H), 3.59 (s, 2H), 2.88 (dd, J=13.6, 9.3 Hz, 1H), 2.76 (dd, J=13.7, 7.5 Hz, 1H). MS (m/z) 535.4 [M+H]$^+$.

Example 5

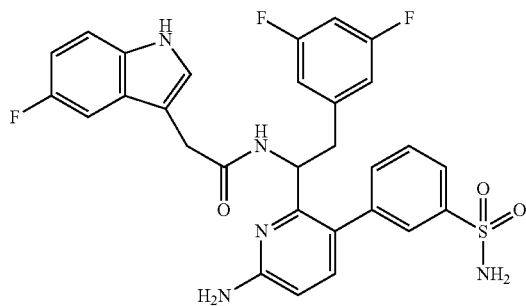

5

Synthesis of N-(1-(6-amino-3-(3-sulfamoylphenyl)pyridin-2-yl)-2-(3,5-difluorophenyl)ethyl)-2-(5-fluoro-1H-indol-3-yl)acetamide (5)

The title compound was prepared according to the method presented for the synthesis of compound 1H of Example 1 utilizing 1G and (3-sulfamoylphenyl)boronic acid. $^1$H NMR (400 MHz, CDCl$_3$) δ 8.15 (s, 1H), 8.03 (d, J=7.7 Hz, 1H), 7.96 (s, 2H), 7.91 (m, 1H), 7.57 (m, 3H), 7.24 (m, 1H), 6.92 (d, J=9.3 Hz, 2H), 6.70 (d, J=8.7 Hz, 1H), 6.54 (s, 1H), 6.20 (d, J=5.7 Hz, 2H), 5.54 (s, 2H), 5.33 (d, J=9.0 Hz, 1H), 3.63 (s, 2H), 2.99-2.85 (m, 2H). MS (m/z) 580.0 [M+H]$^+$.

Example 6

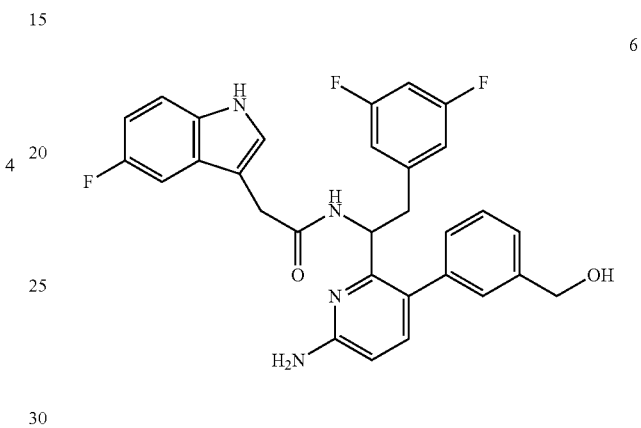

6

Synthesis of N-(1-(6-amino-3-(3-(hydroxymethyl)phenyl)pyridin-2-yl)-2-(3,5-difluorophenyl)ethyl)-2-(5-fluoro-1H-indol-3-yl)acetamide (6)

The title compound was prepared according to the method presented for the synthesis of compound 1H of Example 1 utilizing 1G and (3-(hydroxymethyl)phenyl)boronic acid. $^1$H NMR (400 MHz, CDCl$_3$) δ 8.09 (s, 1H), 7.65 (d, J=8.9 Hz, 1H), 7.52 (d, J=9.1 Hz, 1H), 7.42-7.38 (m, 2H), 7.38-7.16 (m, 1H), 7.11 (s, 1H), 7.02 (s, 1H), 6.81 (d, J=9.5 Hz, 2H), 6.58 (d, J=8.8 Hz, 1H), 6.43 (s, 1H), 6.17 (m, 2H), 5.35-5.24 (m, 1H), 4.71 (s, 2H), 3.53 (s, 2H), 2.96-2.84 (m, 1H), 2.81 (d, J=7.1 Hz, 1H). MS (m/z) 531.2 [M+H]$^+$.

Example 7

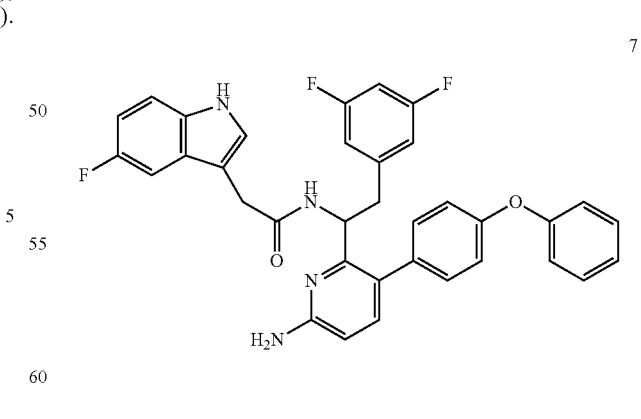

7

Synthesis of N-(1-(6-amino-3-(4-phenoxyphenyl)pyridin-2-yl)-2-(3,5-difluorophenyl)ethyl)-2-(5-fluoro-1H-indol-3-yl)acetamide (7)

The title compound was prepared according to the method presented for the synthesis of compound 1H of Example 1 utilizing 1G and (4-phenoxyphenyl)boronic acid. $^1$H NMR (400 MHz, CDCl$_3$) δ 8.03 (s, 1H), 7.65 (d, J=7.8 Hz, 1H), 7.49 (d, J=9.0 Hz, 1H), 7.32 (t, J=7.8 Hz, 2H), 7.29-7.18 (m, 1H), 7.10 (m, 2H), 7.01 (m, 5H), 6.82 (t, J=9.1 Hz, 4H), 6.56 (d, J=8.9 Hz, 1H), 6.43 (s, 1H), 6.19 (d, J=6.4 Hz, 2H), 5.30 (d, J=8.0 Hz, 1H), 3.52 (s, 2H), 2.97-2.85 (m, 1H), 2.75 (dd, J=14.0, 6.9 Hz, 1H). MS (m/z) 592.8 [M+H]$^+$.

Example 8

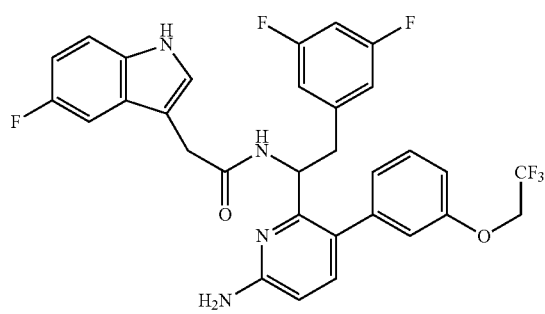

Synthesis of N-(1-(6-amino-3-(3-(2,2,2-trifluoroethoxy)phenyl)pyridin-2-yl)-2-(3,5-difluorophenyl)ethyl)-2-(5-fluoro-1H-indol-3-yl)acetamide (8)

The title compound was prepared according to the method presented for the synthesis of compound 1H of Example 1 utilizing 1G and (3-(2,2,2-trifluoroethyl)phenyl)boronic acid. $^1$H NMR (400 MHz, DMSO) δ 10.96 (s, 1H), 7.61-7.55 (m, 3H), 7.30 (dd, J=8.7, 4.6 Hz, 2H), 7.26-7.11 (m, 2H), 7.11-6.95 (m, 4H), 6.87 (t, J=9.4 Hz, 1H), 6.47 (m, 2H), 5.02 (d, J=6.6 Hz, 1H), 4.79-4.61 (m, 2H), 2.91 (m, 2H). MS (m/z) 599.2 [M+H]$^+$.

Example 9

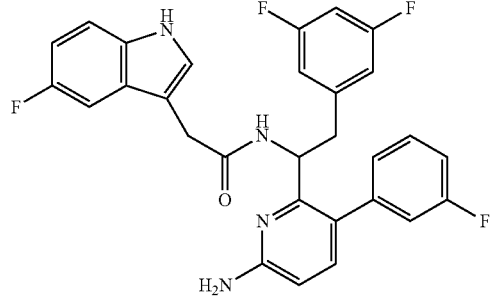

Synthesis of N-(1-(6-amino-3-(3-fluorophenyl)pyridin-2-yl)-2-(3,5-difluorophenyl)ethyl)-2-(5-fluoro-1H-indol-3-yl)acetamide (9)

The title compound was prepared according to the method presented for the synthesis of compound 1H of Example 1 utilizing 1G and (3-fluorophenyl)boronic acid. $^1$H NMR (400 MHz, DMSO) δ 10.95 (s, 1H), 8.42 (s, 1H), 7.63-7.32 (m, 3H), 7.32-7.26 (m, 2H), 7.17 (dd, J=22.4, 9.7 Hz, 3H), 6.98-6.81 (m, 4H), 6.47 (d, J=6.7 Hz, 2H), 5.03 (d, J=6.8 Hz, 1H), 2.98-2.82 (m, 2H). MS (m/z) 519.4 [M+H]$^+$.

Example 10

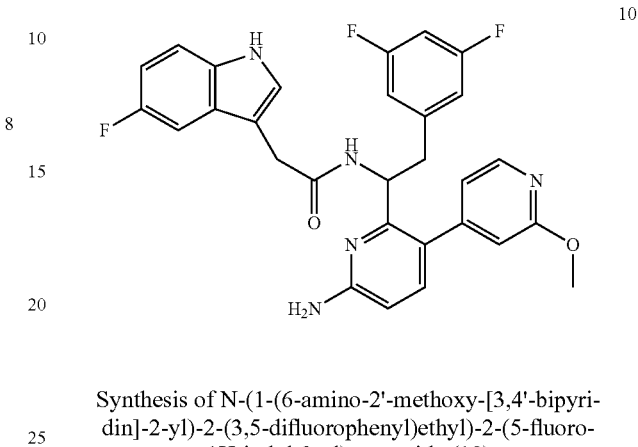

Synthesis of N-(1-(6-amino-2'-methoxy-[3,4'-bipyridin]-2-yl)-2-(3,5-difluorophenyl)ethyl)-2-(5-fluoro-1H-indol-3-yl)acetamide (10)

The title compound was prepared according to the method presented for the synthesis of compound 1H of Example 1 utilizing 1G and (2-methoxypyridin-4-yl)boronic acid. $^1$H NMR (400 MHz, DMSO) δ 10.89 (s, 1H), 7.96 (d, J=5.2 Hz, 1H), 7.25 (dd, J=8.9, 4.3 Hz, 2H), 7.14-7.10 (m, 3H), 6.88-6.80 (m, 3H), 6.67 (d, J=5.2 Hz, 1H), 6.45-6.38 (m, 5H), 5.00 (d, J=7.3 Hz, 1H), 3.75 (s, 2H), 2.89 (m, 2H). MS (m/z) 532.4 [M+H]$^+$.

Example 11

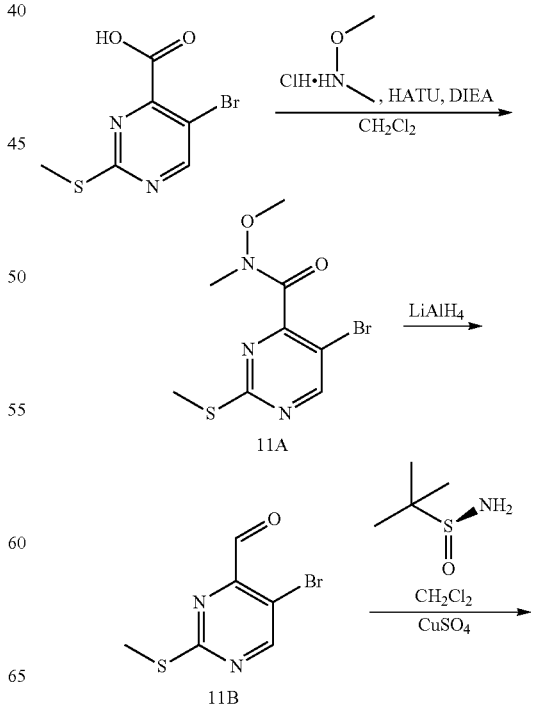

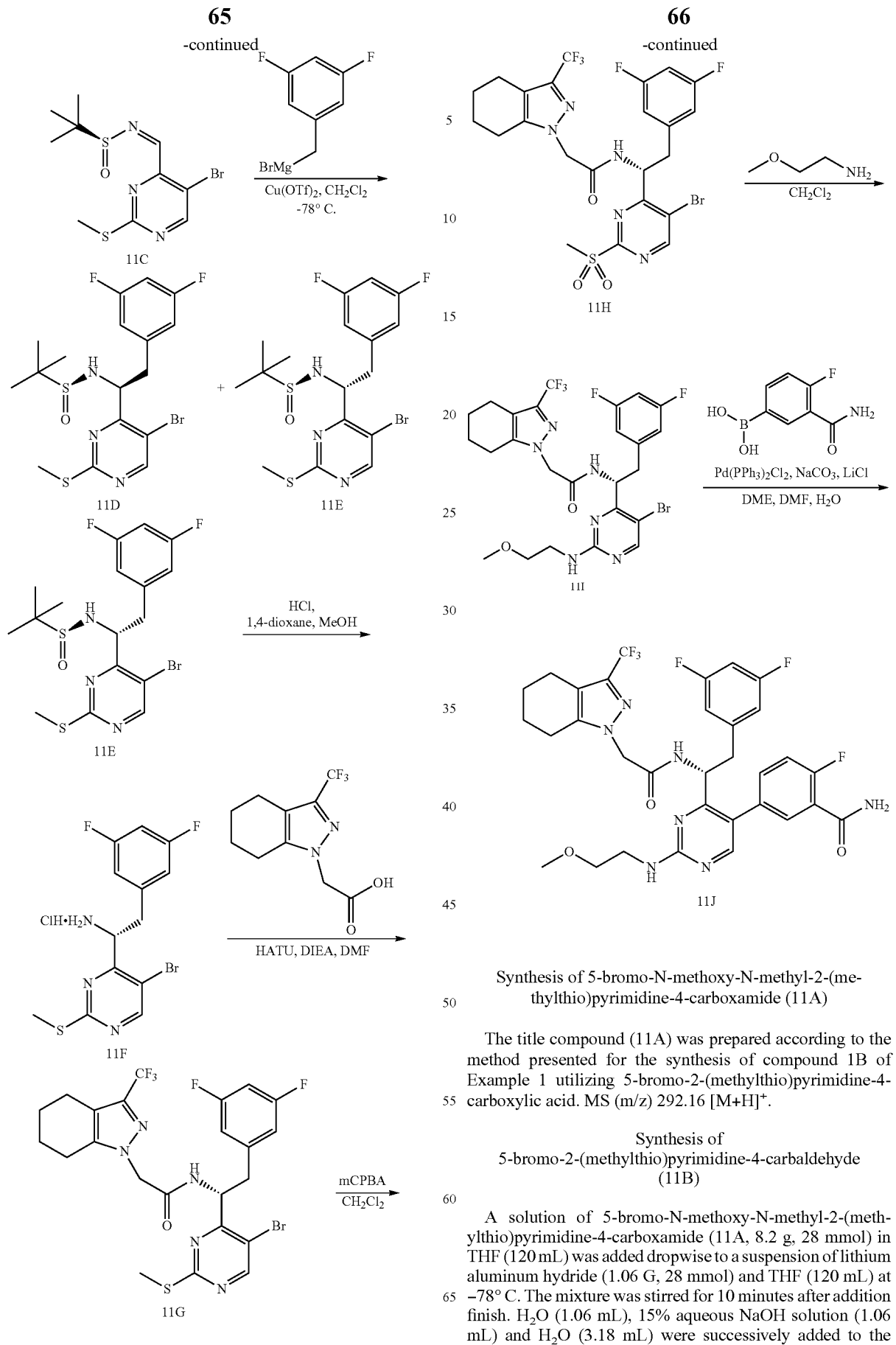

Synthesis of 5-bromo-N-methoxy-N-methyl-2-(methylthio)pyrimidine-4-carboxamide (11A)

The title compound (11A) was prepared according to the method presented for the synthesis of compound 1B of Example 1 utilizing 5-bromo-2-(methylthio)pyrimidine-4-carboxylic acid. MS (m/z) 292.16 [M+H]$^+$.

Synthesis of 5-bromo-2-(methylthio)pyrimidine-4-carbaldehyde (11B)

A solution of 5-bromo-N-methoxy-N-methyl-2-(methylthio)pyrimidine-4-carboxamide (11A, 8.2 g, 28 mmol) in THF (120 mL) was added dropwise to a suspension of lithium aluminum hydride (1.06 G, 28 mmol) and THF (120 mL) at −78° C. The mixture was stirred for 10 minutes after addition finish. H$_2$O (1.06 mL), 15% aqueous NaOH solution (1.06 mL) and H$_2$O (3.18 mL) were successively added to the mixture at 0° C. very slowly. The resulting precipitate was filtered and washed with THF. The filtrate was concentrated in vacuo to afford crude of the title compound. MS (m/z): 233.14, [M+H]+.

Synthesis of (S)—N-((5-bromo-2-(methylthio)pyrimidin-4-yl)methylene)-2-methylpropane-2-sulfinamide (11C)

The title compound (11C) was prepared according to the method presented for the synthesis of compound 1D of Example 1 utilizing 11B. MS (m/z) 337.7 [M+H]+.

Synthesis of (S)—N—((R)-1-(5-bromo-2-(methylthio)pyrimidin-4-yl)-2-(3,5-difluorophenyl)ethyl)-2-methylpropane-2-sulfinamide (11E)

To a solution of (S)—N-((5-bromo-2-(methylthio)pyrimidin-4-yl)methylene)-2-methylpropane-2-sulfinamide (11C, 2.97 g. 8.8 mmol) in THF (18 mL) cooled to −78° C. was drop wise added 3,5-difluorobenzylmagnesium bromide (53 mL, 0.25 M in Ether, 13.3 mmol). After stirring at −78° C. for 10 min, NH4Cl (sat. aq.) (10 ml) was added to the reaction and warmed up to ambient temperature. Extracted with EtOAc and the organic layer was dried with Na2SO4(s). The solvent was removed and the residue was purified by flash column to yield the title compound (11E) and (S)—N—((S)-1-(5-bromo-2-(methylthio)pyrimidin-4-yl)-2-(3,5-difluorophenyl)ethyl)-2-methylpropane-2-sulfinamide (11D). MS (m/z) 465.87 [M+H]+

Synthesis of (R)-1-(5-bromo-2-(methylthio)pyrimidin-4-yl)-2-(3,5-difluorophenyl)ethanamine hydrochloride (11F)

The title compound (11F) was prepared according to the method presented for the synthesis of compound 1F of Example 1 utilizing 11E. MS (m/z) 361.66 [M+H]+.

Synthesis of ((R)—N-(1-(5-bromo-2-(methylthio)pyrimidin-4-yl)-2-(3,5-difluorophenyl)ethyl)-2-(3-(trifluoromethyl)-4,5,6,7-tetrahydro-1H-indazol-1-yl)acetamide (11G)

2-(3-(Trifluoromethyl)-4,5,6,7-tetrahydro-1H-indazol-1-yl)acetic acid (124 mg, 0.5 mmol) and 11F (200 mg, 0.5 mmol) were dissolved in 3 mL of DMF and cooled down to 0° C. To it were added N,N-diisopropylethylamine (435 µL, 2.5 mmol) and HATU (228 mg, 0.6 mmol). The reaction mixture was stirred at 0° C. for 5 minutes, and then partitioned between EtOAc and 5% LiCl aqueous solution. The organic layer was separated, washed with brine, dried over MgSO4, filtered and concentrated. The residue was dissolved in methylene chloride and to it added hexanes. The precipitate was collected by vacuum filtration and dried under high vacuum overnight to afford the title compound 11G. MS (m/z) 592.25 [M+H]+.

Synthesis of (R)—N-(1-(5-bromo-2-(methylsulfonyl)pyrimidin-4-yl)-2-(3,5-difluorophenyl)ethyl)-2-(3-(trifluoromethyl)-4,5,6,7-tetrahydro-1H-indazol-1-yl)acetamide (11H)

Compound 11G (198 mg, 0.33 mmol) was charged in dichloromethane (2 ml) at 0° C. mCPBA (meta-chloroperoxybenzoic acid) (185 mg, 0.8 mmol, content 77 percent; 2.5 eq.) was added a little at a time. The mixture was slowly warmed to room temperature and stirred for 4 h and then water was added. The reaction mixture was partitioned between dichloromethane and saturated NaHCO3 aqueous solution. The organic layer was separated and concentrated to afford the title product. MS (m/z) 622.98 [M+H]+.

Synthesis of (R)—N-(1-(5-bromo-2-((2-methoxyethyl)amino)pyrimidin-4-yl)-2-(3,5-difluorophenyl)ethyl)-2-(3-(trifluoromethyl)-4,5,6,7-tetrahydro-1H-indazol-1-yl)acetamide (11I)

2-Methoxyethylamine (0.086 ml, 1 mmol) was added at room temperature to a solution of compound 11H (62 mg, 0.1 mmol) in dichloromethane (5 mL). Stirring was continued at 45° C. for overnight. The solvent was evaporated and the crude product was purified by silica gel chromatography using an ethyl acetate/hexanes eluent to yield the title compound. MS (m/z) 618.00 [M+H]+.

Synthesis of (R)-5-(4-(2-(3,5-difluorophenyl)-1-(2-(3-(trifluoromethyl)-4,5,6,7-tetrahydro-1H-indazol-1-yl)acetamido)ethyl)-2-((2-methoxyethyl)amino)pyrimidin-5-yl)-2-fluorobenzamide (11J)

In a microwave tube were charged with compound 11I (29 mg, 0.1 mmol), (3-carbamoyl-4-fluorophenyl)boronic acid (27 mg, 0.15 mmol), LiCl (13 mg, 0.3 mmol), Na2CO3 (17 mg, 0.2 mmol), Pd(PPh3)2Cl2 (3.5 mg, 0.005 mmol). To the mixture was added 2 mL of DME/DMF/H2O (4/1/1). The mixture was heated up to 150° C. for 30 min in a Microwave Synthesizer. After cooled down and filtered through a syringe filter, purified on reverse phase HPLC eluting with acetonitrile and water (with 0.1% TFA) to afford the title product. 1H NMR (400 MHz, CD3OD) δ 8.61 (d, J=8.0 Hz, 1H), 8.07 (s, 1H), 7.48 (dd, J=6.9, 2.3 Hz, 1H), 7.40-7.33 (m, 1H), 7.22 (dd, J=10.7, 8.5 Hz, 1H), 6.70 (t, J=9.2 Hz, 1H), 6.45 (d, J=6.2 Hz, 2H), 5.24 (q, J=7.5 Hz, 1H), 4.76 (s, 2H), 3.85-3.56 (m, 4H), 3.41 (s, 3H), 3.01 (ddd, J=29.2, 13.3, 7.4 Hz, 2H), 2.63-2.34 (m, 4H), 1.88-1.60 (m, 4H). MS (m/z) 676.46 [M+H]+.

Example 12

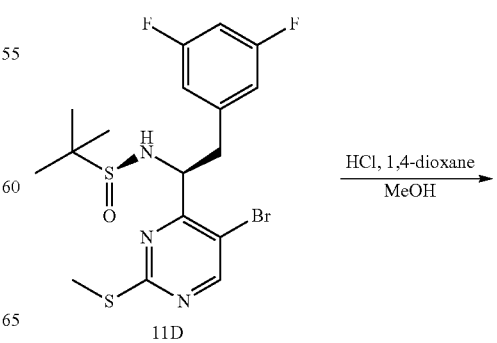

-continued

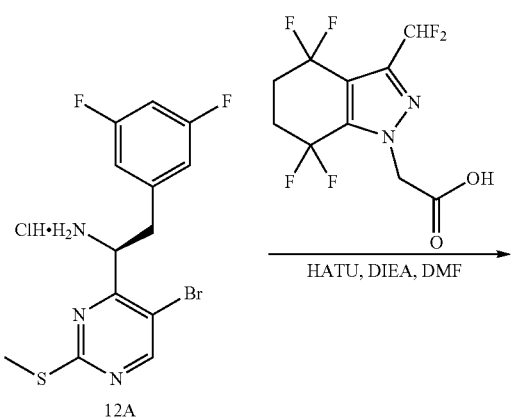

12A

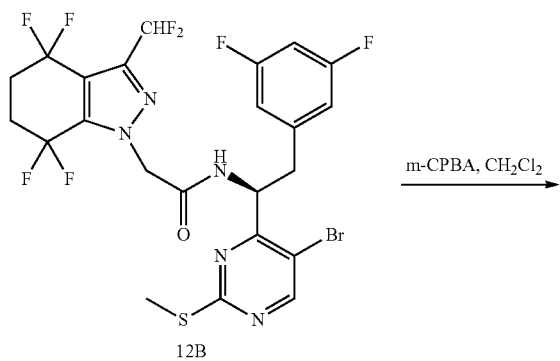

12B

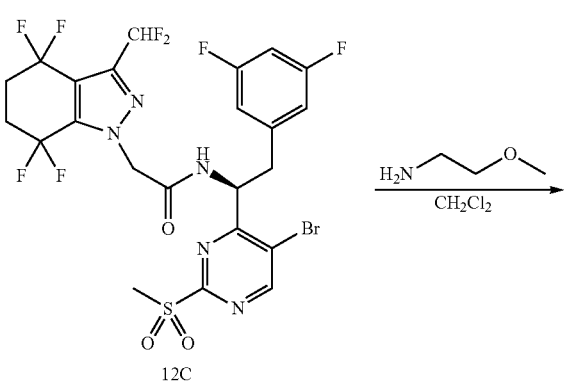

12C

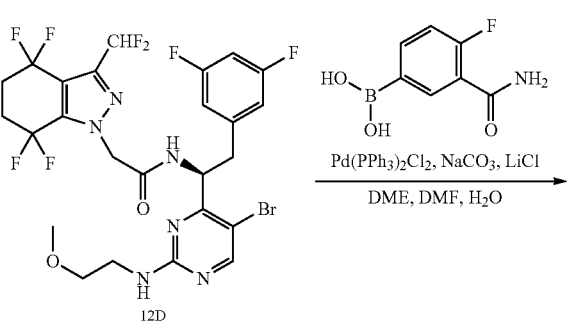

12D

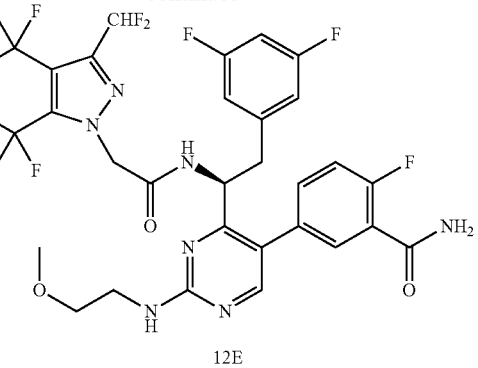

12E

Synthesis of (S)-1-(5-bromo-2-(methylthio)pyrimidin-4-yl)-2-(3,5-difluorophenyl)ethanamine hydrochloride (12A)

The title compound (12A) was prepared according to the method presented for the synthesis of compound 1F of Example 1 utilizing 11D. MS (m/z) 362.13 [M+H]$^+$.

Synthesis of (S)—N-(1-(5-bromo-2-(methylthio)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (12B)

The title compound (12B) was prepared according to the method presented for the synthesis of compound 11G of Example 11 utilizing 2-(3-(difluoromethyl)-4,4,7,7-tetrafluoro-4,5,6,7-tetrahydro-1H-indazol-1-yl)acetic acid and 12A. MS (m/z) 644.22 [M+H]$^+$.

Synthesis of (S)—N-(1-(5-bromo-2-(methylsulfonyl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (12C)

The title compound (12C) was prepared according to the method presented for the synthesis of compound 11H of Example 11 utilizing 12B. MS (m/z) 677.97 [M+H]$^+$.

Synthesis of (S)—N-(1-(5-bromo-2-((2-methoxyethyl)amino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (12D)

The title compound (12D) was prepared according to the method presented for the synthesis of compound 11I of Example 11 utilizing 12C. MS (m/z) 671.34 [M+H]$^+$.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-methoxyethyl)amino)pyrimidin-5-yl)-2-fluorobenzamide (12E)

The title compound (12E) was prepared according to the method presented for the synthesis of compound 11J of Example 11 utilizing 12D. $^1$H NMR (400 MHz, CD$_3$OD) δ 8.80 (d, J=8.0 Hz, 1H), 8.05 (s, 1H), 7.47-7.29 (m, 2H), 7.21 (dd, J=10.7, 8.6 Hz, 1H), 6.97-6.61 (m, 2H), 6.44 (d, J=6.1 Hz, 2H), 5.22 (dd, J=14.9, 7.7 Hz, 1H), 5.05 (s, 2H), 3.89-3.51

(m, 4H), 3.41 (s, 3H), 3.02 (ddd, J=20.2, 13.2, 7.5 Hz, 2H), 2.66-2.28 (m, 4H). MS (m/z) 730.24 [M+H]$^+$.

Example 13

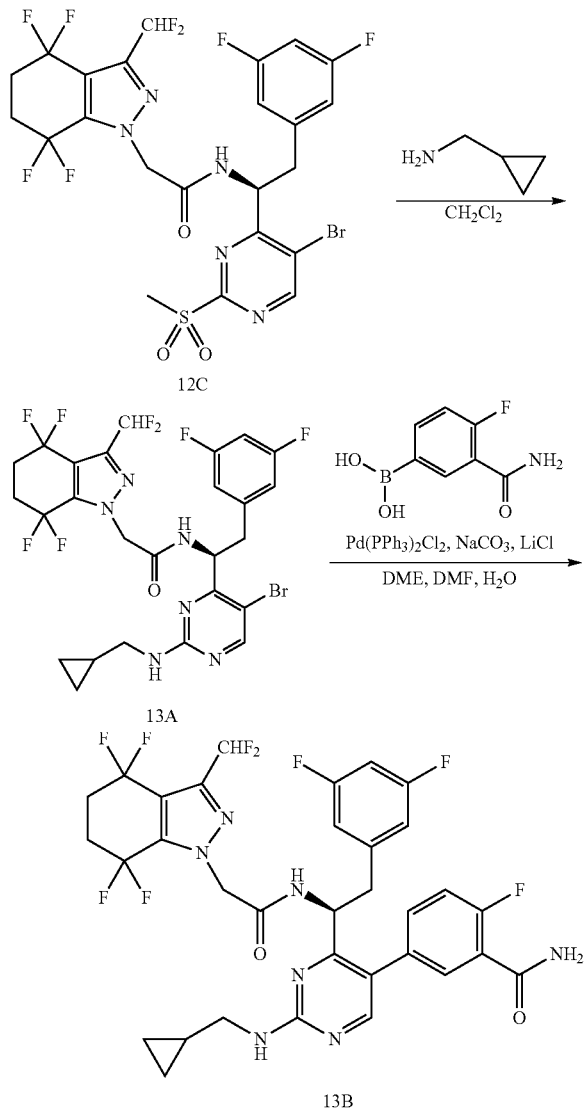

Synthesis of (S)—N-(1-(5-bromo-2-((cyclopropylmethyl)amino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (13A)

The title compound (13A) was prepared according to the method presented for the synthesis of compound 11I of Example 11 utilizing cyclopropylmethanamine and 12C. MS (m/z) 668.95 [M+H]$^+$.

Synthesis of (S)-5-(2-((cyclopropylmethyl)amino)-4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyrimidin-5-yl)-2-fluorobenzamide (13B)

The title compound (13B) was prepared according to the method presented for the synthesis of compound 11J of Example 11 utilizing 13A. $^1$H NMR (400 MHz, CD$_3$OD) δ 8.50 (d, J=7.7 Hz, 1H), 7.73 (s, 1H), 7.24-7.02 (m, 2H), 6.90 (dd, J=10.7, 8.6 Hz, 1H), 6.65-6.24 (m, 2H), 6.13 (d, J=6.1 Hz, 2H), 4.91 (m, 1H), 4.83-4.62 (m, 2H), 3.09 (m, 2H), 2.71 (ddd, J=20.2, 13.3, 7.4 Hz, 2H), 2.37-2.06 (m, 4H), 0.88 (m, 1H), 0.47-0.16 (m, 2H), 0.02 (q, J=5.1 Hz, 2H). MS (m/z) 726.30 [M+H]$^+$.

Example 14

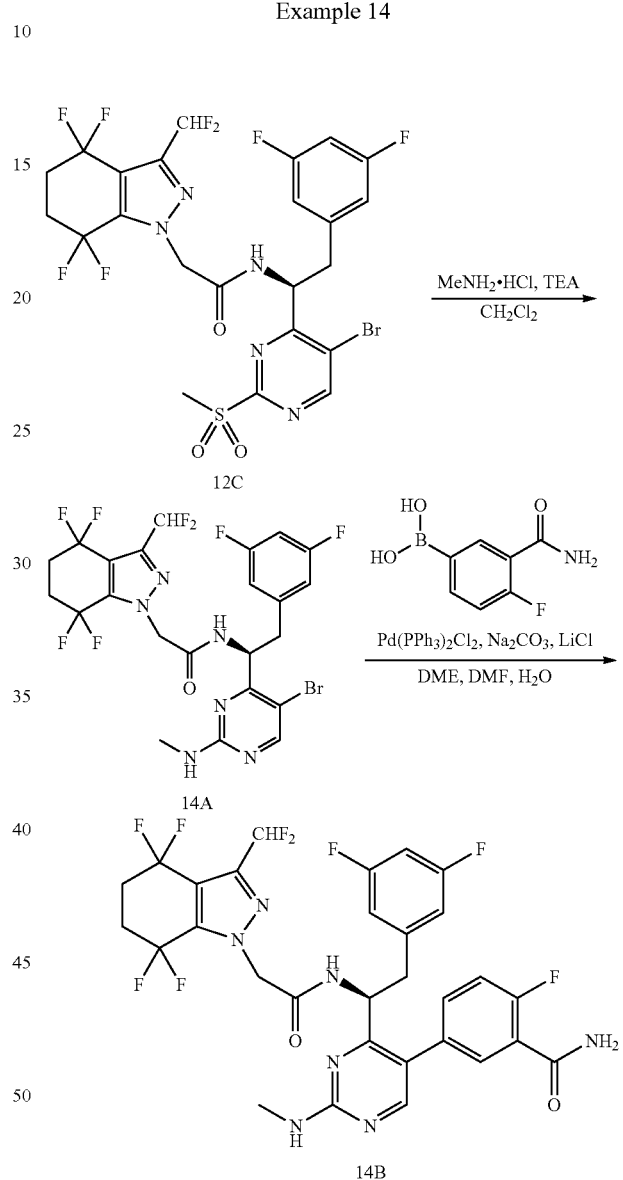

Synthesis of (S)—N-(1-(5-bromo-2-(methylamino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (14A)

To the mixture of compound 12C (68 mg, 0.1 mmol) and methylamine hydrochloride (34 mg, 0.5 mmol) in dichloromethane (5 ml) was added triethylamine (697 μL, 0.5 mmol). The reaction mixture was stirring at ambient temperature for 2 hours. The solvent was evaporated and the crude product was purified on reverse phase HPLC eluting with acetonitrile and water (with 0.1% TFA) to afford the title product. MS (m/z) 627.24 [M+H]+.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(methylamino)pyrimidin-5-yl)-2-fluorobenzamide (14B)

The title compound (14B) was prepared according to the method presented for the synthesis of compound 11J of Example 11 utilizing 14A. ¹H NMR (400 MHz, CD₃OD) δ 8.82 (d, J=7.9 Hz, 1H), 8.06 (s, 1H), 7.44 (m 7.37 (m, 1H), 7.23 (dd, J=10.7, 8.5 Hz, 1H), 6.73 (m, 2H), 6.46 (d, J=6.2 Hz, 2H), 5.23 (q, J=7.5 Hz, 1H), 5.04 (s, 2H), 3.17-2.89 (m, 5H), 2.65-2.29 (m, 4H). MS (m/z) 686.26 [M+H]+.

Example 15

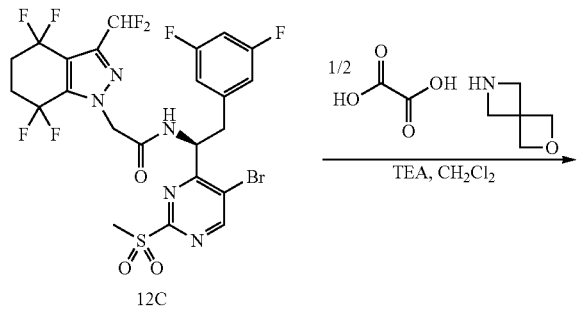

12C

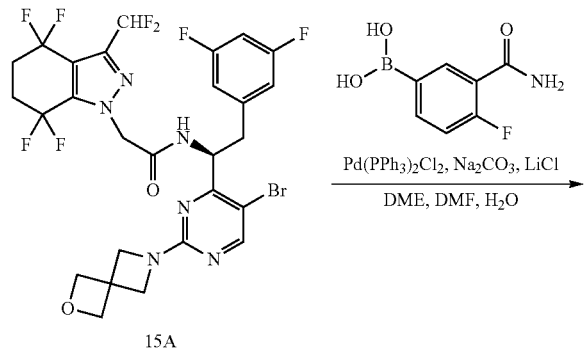

15A

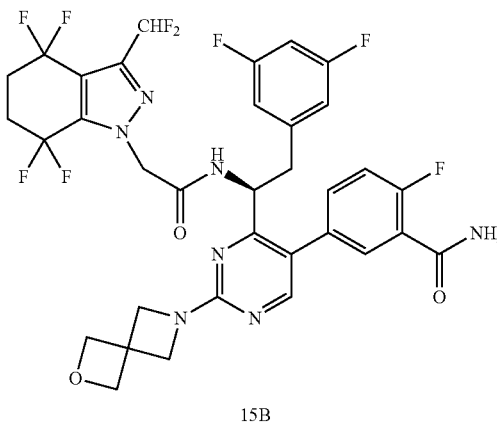

15B

Synthesis of (S)—N-(1-(5-bromo-2-(2-oxa-6-azaspiro[3.3]heptan-6-yl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (15A)

The title compound (15A) was prepared according to the method presented for the synthesis of compound 14A of Example 14 utilizing 12C and 2-oxa-6-azaspiro[3.3]heptane hemioxalate. MS (m/z) 695.04 [M+H]+.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(2-oxa-6-azaspiro[3.3]heptan-6-yl)pyrimidin-5-yl)-2-fluorobenzamide (15B)

The title compound (15B) was prepared according to the method presented for the synthesis of compound 11J of Example 11 utilizing 15A. ¹H NMR (400 MHz, CD₃OD) δ 8.69 (d, J=8.0 Hz, 1H), 8.09 (s, 1H), 7.45-7.31 (m, 2H), 7.21 (dd, J=10.7, 8.6 Hz, 1H), 7.03-6.63 (m, 2H), 6.42 (d, J=6.1 Hz, 2H), 5.23 (dd, J=15.1, 7.6 Hz, 1H), 5.05 (s, 2H), 4.88 (s, 4H), 4.39 (q, J=9.9 Hz, 4H), 3.00 (m, 2H), 2.50 (m, 4H). MS (m/z) 754.24 [M+H]+.

Example 16

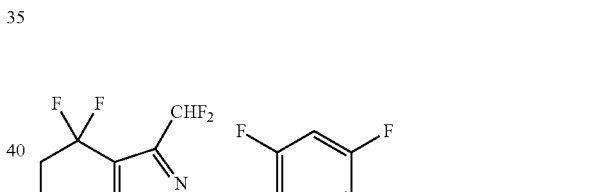

12C

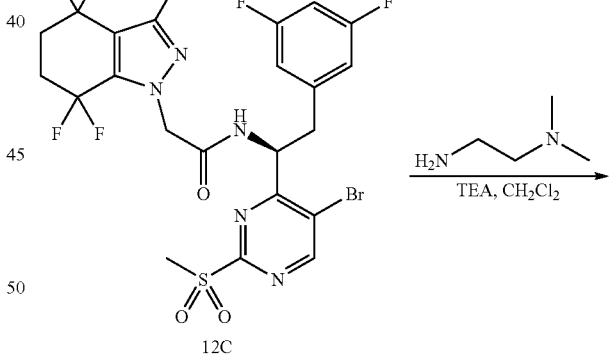

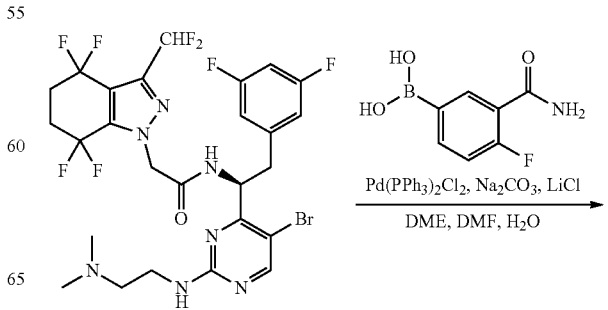

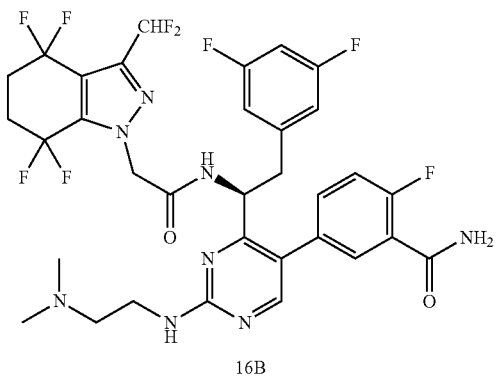

16B

Synthesis of (S)—N-(1-(5-bromo-2-((2-(dimethylamino)ethyl)amino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (16A)

The title compound (16A) was prepared according to the method presented for the synthesis of compound 14A of Example 14 utilizing 12C and N,N-dimethylethane-1,2-diamine. MS (m/z) 686.00 [M+H]⁺.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(dimethylamino)ethyl)amino)pyrimidin-5-yl)-2-fluorobenzamide (16B)

The title compound (16B) was prepared according to the method presented for the synthesis of compound 11J of Example 11 utilizing 16A. $^1$H NMR (400 MHz, —CD$_3$OD) δ 8.75 (d, J=7.4 Hz, 1H), 8.13 (s, 1H), 7.38 (m, 2H), 7.21 (dd, J=10.8, 8.4 Hz, 1H), 6.98-6.63 (m, 2H), 6.42 (m, 2H), 5.23 (d, J=7.6 Hz, 1H), 5.02 (q, J=16.8 Hz, 2H), 3.88 (m, 2H), 3.45 (t, J=5.5 Hz, 2H), 3.15-2.93 (m, 8H), 2.52 (m, 4H). MS (m/z) 743.60 [M+H]⁺.

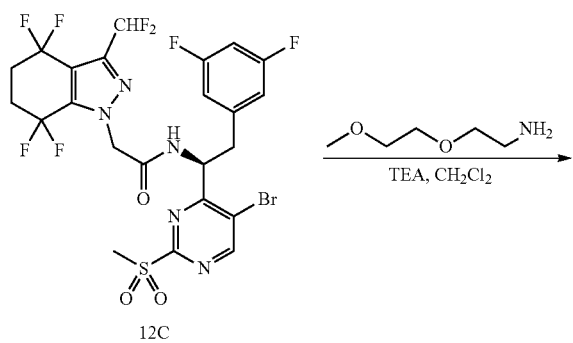

12C

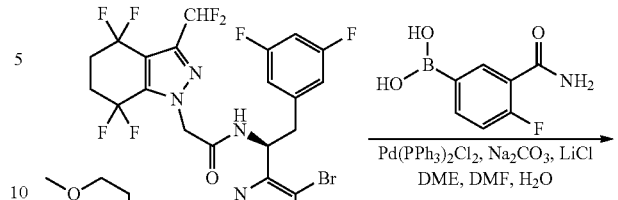

17A

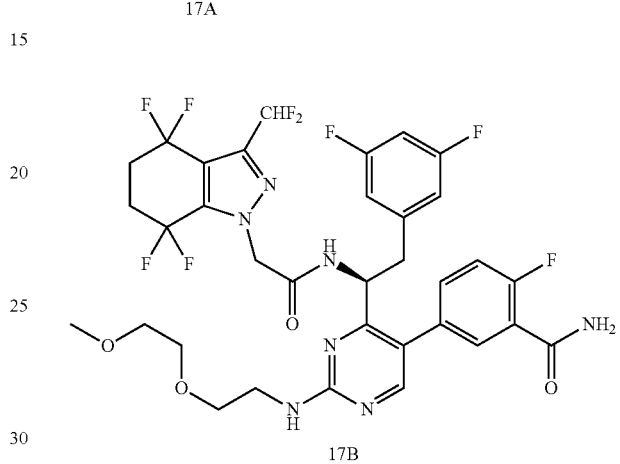

17B

Example 17

Synthesis of (S)—N-(1-(5-bromo-2-((2-(2-methoxyethoxy)ethyl)amino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (17A)

The title compound (17A) was prepared according to the method presented for the synthesis of compound 14A of Example 14 utilizing 12C and 2-(2-methoxyethoxy)ethanamine. MS (m/z) 716.15 [M+H]⁺.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(2-methoxyethoxy)ethyl)amino)pyrimidin-5-yl)-2-fluorobenzamide (17B)

The title compound (17B) was prepared according to the method presented for the synthesis of compound 11J of Example 11 utilizing 17A. $^1$H NMR (400 MHz, CD$_3$OD) δ 8.82 (d, J=8.2 Hz, 1H), 8.06 (s, 1H), 7.52-7.31 (m, 2H), 7.21 (dd, J=10.7, 8.5 Hz, 1H), 7.01-6.56 (m, 2H), 6.44 (d, J=6.0 Hz, 2H), 5.23 (t, J=6.7 Hz, 1H), 5.05 (s, 2H), 3.84-3.63 (m, 6H), 3.57 (m, 2H), 3.37 (s, 3H), 3.17-2.90 (m, 2H), 2.65-2.39 (m, 4H). MS (m/z) 774.58 [M+H]⁺.

Example 18

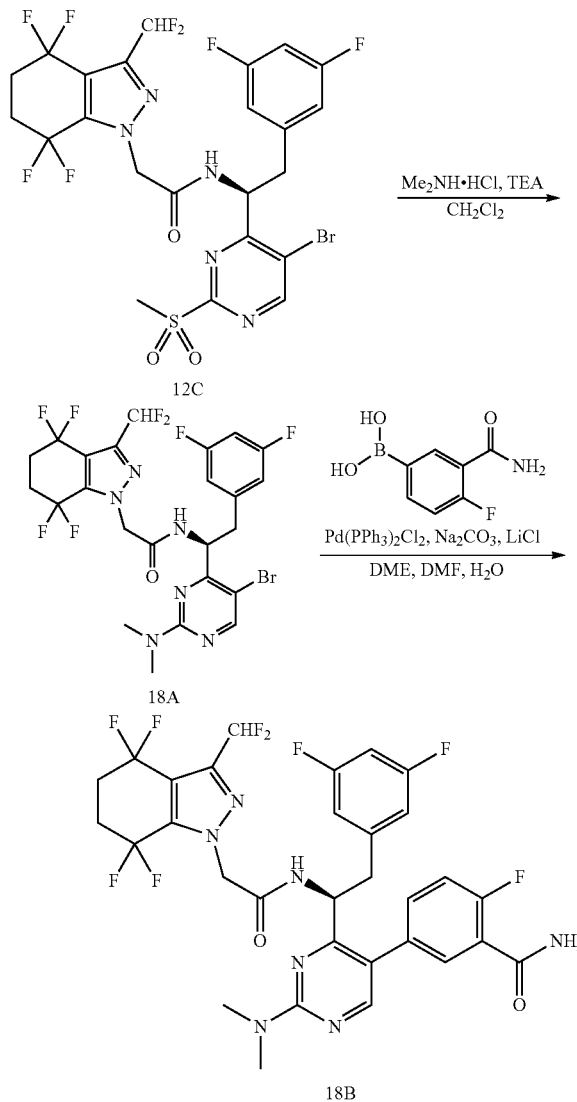

Synthesis of (S)—N-(1-(5-bromo-2-(dimethylamino) pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (18A)

The title compound (18A) was prepared according to the method presented for the synthesis of compound 14A of Example 14 utilizing 12C and dimethylamine hydrochloride. MS (m/z) 643.09 [M+H]$^+$.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(dimethylamino)pyrimidin-5-yl)-2-fluorobenzamide (18B)

The title compound (18B) was prepared according to the method presented for the synthesis of compound 11J of Example 11 utilizing 18A. $^1$H NMR (400 MHz, CD$_3$OD) δ 8.72 (d, J=7.8 Hz, 1H), 8.08 (s, 1H), 7.51-7.29 (m, 2H), 7.21 (dd, J=10.7, 8.5 Hz, 1H), 7.03-6.55 (m, 2H), 6.43 (d, J=6.2 Hz, 2H), 5.25 (dd, J=14.1, 6.5 Hz, 1H), 5.12-4.97 (m, 2H), 3.28 (s, 6H), 3.03 (m, 2H), 2.66-2.31 (m, 4H). MS (m/z) 700.56 [M+H]$^+$.

Example 19

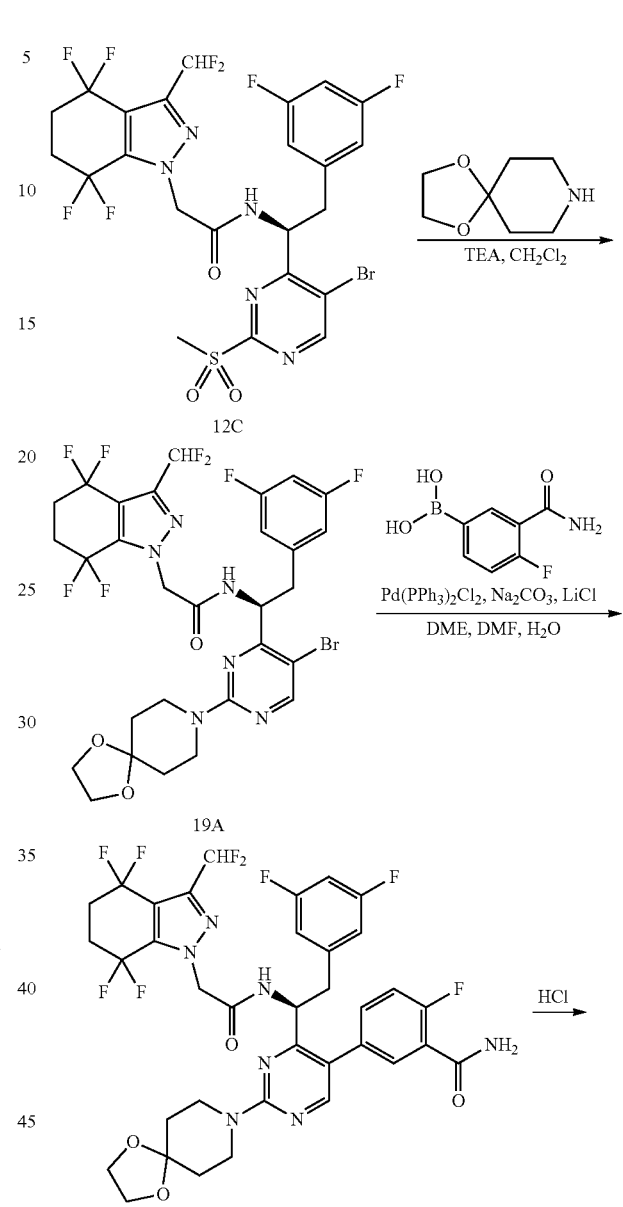

Synthesis of (S)—N-(1-(5-bromo-2-(1,4-dioxa-8-azaspiro[4.5]decan-8-yl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (19A)

The title compound (19A) was prepared according to the method presented for the synthesis of compound 14A of Example 14 utilizing 12C and 1,4-dioxa-8-azaspiro[4.5]decane. MS (m/z) 740.04 [M+H]$^+$.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(1,4-dioxa-8-azaspiro[4.5]decan-8-yl)pyrimidin-5-yl)-2-fluorobenzamide (19B)

The title compound (19B) was prepared according to the method presented for the synthesis of compound 11J of Example 11 utilizing 19A. MS (m/z) 798.63 [M+H]$^+$.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(4-oxopiperidin-1-yl)pyrimidin-5-yl)-2-fluorobenzamide (19C)

Compound 19B (40 mg, 0.05 mmol) was dissolved in 2 mL of THF and to it was added 1 mL of 6N HCl. The mixtures was stirred at ambient temperature for 16 hours and then extracted with ethyl acetate. The organic layer was separated, washed with brine, dried over MgSO$_4$, filtered and concentrated. The residue was purified by reverse phase HPLC eluting with acetonitrile/water (with 0.1% TFA) to afford the title compound. $^1$H NMR (400 MHz, CDCl$_3$) δ 8.21 (s, 1H), 7.71 (d, J=5.0 Hz, 1H), 7.46 (s, 1H), 7.33 (m, 1H), 7.30-7.18 (m, 1H), 7.11 (d, J=11.0 Hz, 1H), 6.98 (m, 1H), 6.78 (t, J=53.6 Hz, 1H), 6.58 (m, 1H), 6.20 (d, J=6.2 Hz, 2H), 5.37 (d, J=7.4 Hz, 1H), 5.11-4.89 (m, 2H), 4.22-3.98 (m, 4H), 2.83 (m, 2H), 2.54 (m, 8H). MS (m/z) 754.11 [M+H]$^+$.

Example 20

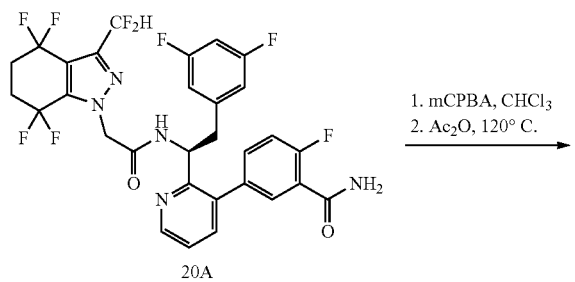

20A

Synthesis of (S)-5-(3-carbamoyl-4-fluorophenyl)-6-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridin-2-yl acetate (20B)

To a solution of (S)-5-(2-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridin-3-yl)-2-fluorobenzamide (50 mg, 0.076 mmol) in chloroform (1 mL) was added mCPBA (27.6 mg, 0.16 mmol). The reaction was heated at 60° C. for 30 min. After cooled to room temperature, the reaction mixture was partitioned between chloroform and saturated NaHCO$_3$ solution. The organic phase was washed with brine, dried over Na$_2$SO$_4$, filtered and concentrated in vacuo. The crude material was used in the next step without further purification. MS (m/z) 672.4 [M+H]$^+$.

The crude material from last step was dissolved in acetic anhydride (2 mL) and heated over night in a seal tube. The crude product was purified by reverse phase HPLC to give (S)-5-(3-carbamoyl-4-fluorophenyl)-6-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridin-2-yl acetate. MS (m/z) 714.13 [M+H]$^+$.

Example 21

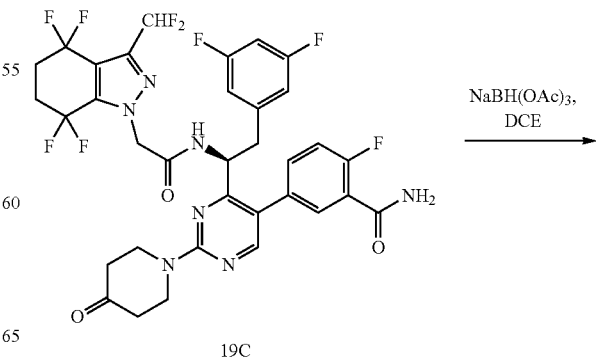

19C

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(4-hydroxypiperidin-1-yl)pyrimidin-5-yl)-2-fluorobenzamide (21A)

To a solution of compound 19C (18 mg, 0.023 mmol) in 1,2-dichloroethane (0.5 ml), was added acetic acid (13 μL, 0.23 mmol) and sodium triacetoxyborohydride (9.7 mg, 0.046 mmol) at room temperature. After being stirred for 3 hours, the mixture was treated with EtOAc (10 mL) and water (3 mL). The organic layer was washed with brine (2 mL), dried (MgSO₄), filtered, and concentrated under reduced pressure to furnish the crude product. This material was purified on reverse phase HPLC eluting with acetonitrile and water (with 0.1% TFA) to afford the title product. ¹H NMR (400 MHz, CD₃OD) δ 8.71 (d, J=8.5 Hz, 1H), 8.09 (s, 1H), 7.41 (dd, J=7.0, 2.3 Hz, 1H), 7.33 (m, 1H), 7.20 (dd, J=10.8, 8.5 Hz, 1H), 6.97-6.61 (m, 3H), 6.42 (d, J=6.2 Hz, 2H), 5.24 (t, J=7.2 Hz, 1H), 5.13-4.96 (m, 2H), 4.51 (m, 2H), 4.01-3.83 (m, 1H), 3.42 (m, 2H), 3.14-2.82 (m, 2H), 2.50 (m, 4H), 2.08-1.84 (m, 2H), 1.68-1.37 (m, 2H); MS (m/z) 756.22 [M+H]⁺.

Example 22

Synthesis of (S)—N-(1-(5-bromo-2-((2-(2-oxoimidazolidin-1-yl)ethyl)amino)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (22A)

The title compound (22A) was prepared according to the method presented for the synthesis of compound 14A of Example 14 utilizing 12C and 1-(2-aminoethyl)imidazolidin-2-one. MS (m/z) 725.15 [M+H]⁺.

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(2-oxoimidazolidin-1-yl)ethyl)amino)pyrimidin-5-yl)-2-fluorobenzamide (22B)

The title compound (22B) was prepared according to the method presented for the synthesis of compound 11J of Example 11 utilizing 22A. ¹H NMR (400 MHz, CD₃OD) δ 8.88 (m, 1H), 8.07 (s, 1H), 7.47-7.29 (m, 2H), 7.27-7.14 (m, 1H), 6.96-6.59 (m, 2H), 6.45 (d, J=6.4 Hz, 2H), 5.26 (m, 1H), 5.09 (s, 2H), 3.82-3.49 (m, 6H), 3.40 (m, 2H), 3.15-2.95 (m, 2H), 2.51 (m, 4H). MS (m/z) 784.22 [M+H]⁺.

Example 23

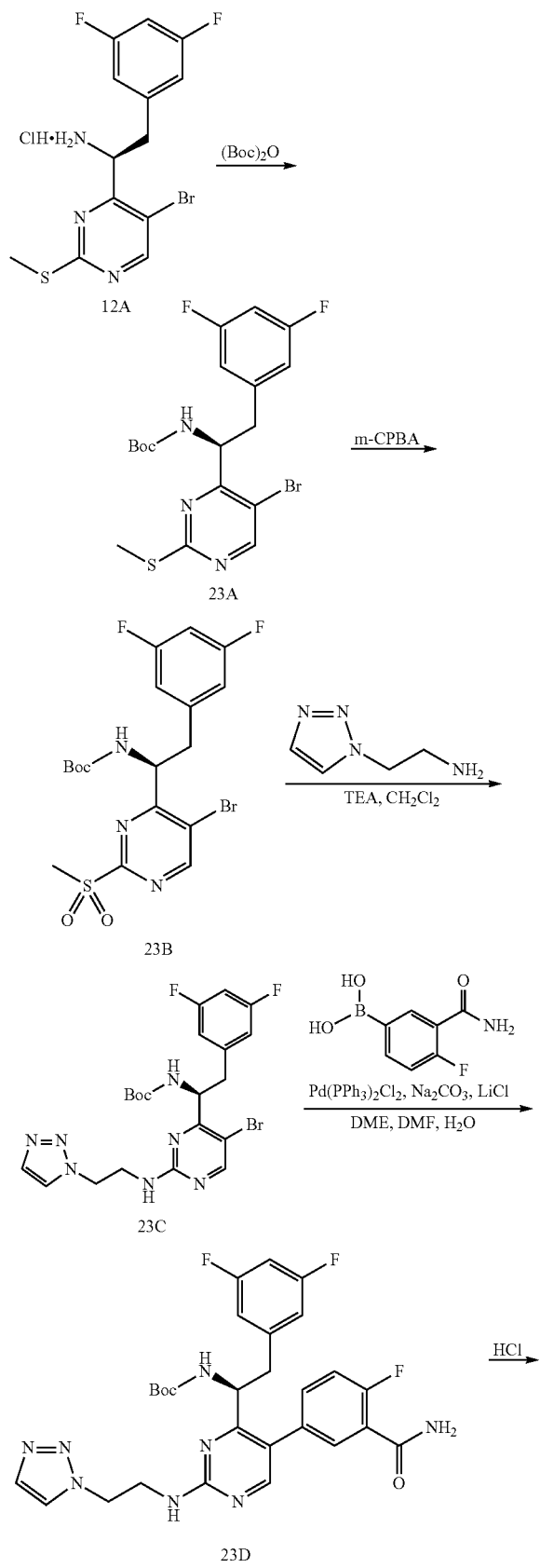

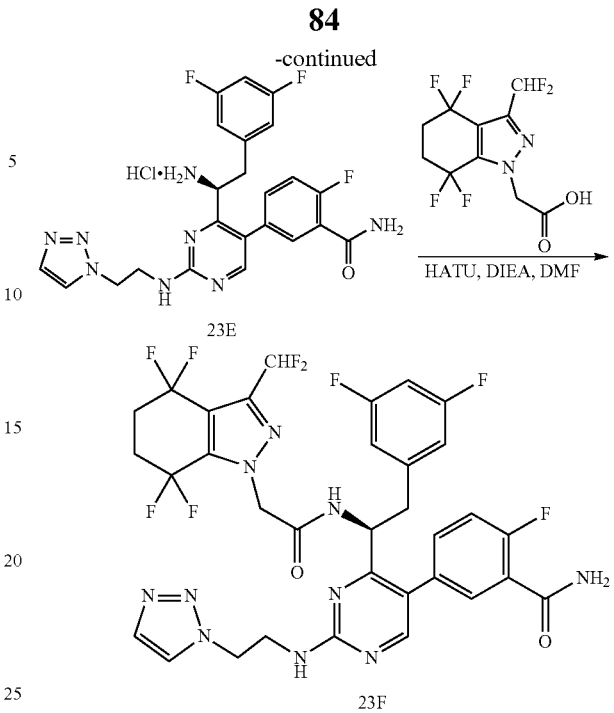

Synthesis of (S)-tert-butyl (1-(5-bromo-2-(methylthio)pyrimidin-4-yl)-2-(3,5-difluorophenyl)ethyl) carbamate (23A)

To the compound 12A (310 mg, 0.78 mmol) in dichloromethane (3 mL) was added triethylamine (0.22 mL, 1.56 mmol) and di-tert-butyldicarbonate (170 mg, 0.78 mmol). The mixture was stirred for one hour at ambient temperature then concentrated in vacuo.

The residue was purified by silica gel chromatography using an ethyl acetate/hexanes eluent to yield the title compound. MS (m/z) 459.86 [M+H]$^+$.

Synthesis of (S)-tert-butyl (1-(5-bromo-2-(methylsulfonyl)pyrimidin-4-yl)-2-(3,5-difluorophenyl) ethyl)carbamate (23B)

The title compound (23B) was prepared according to the method presented for the synthesis of compound 11H of Example 11 utilizing 23A. MS (m/z) 394.03 [M+H-Boc]$^+$.

Synthesis of (S)-tert-butyl (1-(2-((2-(1H-1,2,3-triazol-1-yl)ethyl)amino)-5-bromopyrimidin-4-yl)-2-(3,5-difluorophenyl)ethyl)carbamate (23C)

The title compound (23C) was prepared according to the method presented for the synthesis of compound 14A of Example 14 utilizing 23B and 2-(1H-1,2,3-triazol-1-yl)ethanamine. MS (m/z) 545.97 [M+Na]$^+$.

Synthesis of (S)-tert-butyl (1-(2-((2-(1H-1,2,3-triazol-1-yl)ethyl)amino)-5-(3-carbamoyl-4-fluorophenyl)pyrimidin-4-yl)-2-(3,5-difluorophenyl)ethyl) carbamate (23D)

In a microwave tube were charged with compound 23C (52 mg, 0.1 mmol), (3-carbamoyl-4-fluorophenyl)boronic acid (27 mg, 0.15 mmol), K$_2$CO$_3$ (41 mg, 0.3 mmol), Pd(dppf)Cl$_2$ (5 mg). To the mixture was added 2 mL of Toluene/2-propanol/H$_2$O (3/1/1). The mixture was heated up to 120° C. for 20 min in a Microwave Synthesizer. The mixture was partitioned between ethyl acetate and water. The organic layer was separated and concentrated to afford crude product used for next step without further purification. MS (m/z) 582.73 [M+H]⁺.

Synthesis of (S)-5-(2-((2-(1H-1,2,3-triazol-1-yl)ethyl)amino)-4-(1-amino-2-(3,5-difluorophenyl)ethyl)pyrimidin-5-yl)-2-fluorobenzamide hydrochloride (23E)

Compound 23D was dissolved in 2 mL of 4N HCl in dioxane and stirred at ambient temperature for overnight. The solvent was removed to afford the title product. (m/z) 483.08 [M+H]⁺.

Synthesis of (S)-5-(2-((2-(1H-1,2,3-triazol-1-yl)ethyl)amino)-4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyrimidin-5-yl)-2-fluorobenzamide (23F)

The title compound (23F) was prepared according to the method presented for the synthesis of compound 11G of Example 11 utilizing 2-(3-(difluoromethyl)-4,4,7,7-tetrafluoro-4,5,6,7-tetrahydro-1H-indazol-1-yl)acetic acid and 23E. $^1$H NMR (400 MHz, CD$_3$OD) δ 8.71 (d, J=7.6 Hz, 1H), 8.06 (s, 1H), 7.99 (s, 1H), 7.74 (s, 1H), 7.43-7.25 (m, 2H), 7.20 (dd, J=10.8, 8.5 Hz, 1H), 6.97-6.58 (m, 2H), 6.42 (d, J=6.2 Hz, 2H), 5.32-5.18 (m, 2H), 5.09 (s, 2H), 4.73 (m, 2H), 4.01 (m, 2H), 3.01 (m, 2H), 2.66-2.34 (m, 4H). MS (m/z) 767.06 [M+H]⁺.

Example 24

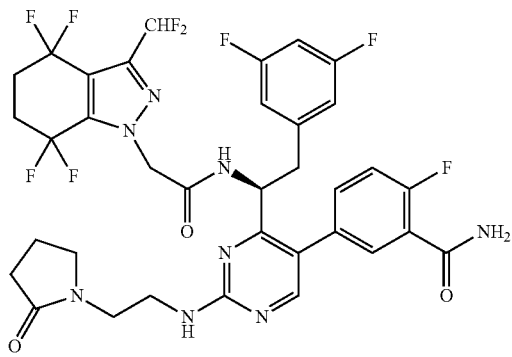

24

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(2-oxopyrrolidin-1-yl)ethyl)amino)pyrimidin-5-yl)-2-fluorobenzamide (24)

The title compound (24) was prepared according to the method presented for the synthesis of compound 23F of Example 23 starting with 1-(2-aminoethyl)pyrrolidin-2-one and 23B. MS (m/z) $^1$H NMR (400 MHz, CD$_3$OD) δ 8.84 (m, 1H), 8.07 (s, 1H), 7.50-7.27 (m, 2H), 7.24-7.11 (m, 1H), 6.97-6.61 (m, 2H), 6.45 (d, J=6.2 Hz, 2H), 5.27 (m, 1H), 5.10 (s, 2H), 3.57 (m, 6H), 3.18-2.87 (m, 2H), 2.51 (m, 4H), 2.41-2.28 (m, 2H), 2.12-1.89 (m, 2H). 783.12 [M+H]⁺.

Example 25

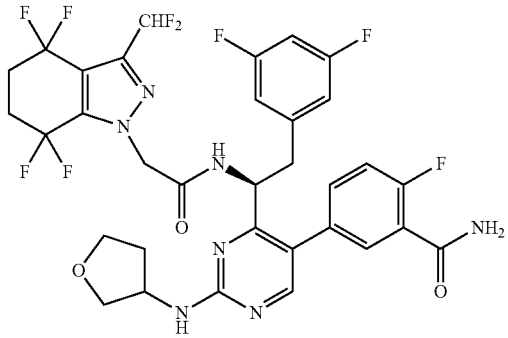

25

Synthesis of 5-(4-((S)-1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((tetrahydrofuran-3-yl)amino)pyrimidin-5-yl)-2-fluorobenzamide (25)

The title compound (25) was prepared according to the method presented for the synthesis of compound 23F of Example 23 starting with tetrahydrofuran-3-amine and 23B. $^1$H NMR (400 MHz, CD$_3$OD) δ 8.71 (d, J=7.6 Hz, 1H), 8.06 (s, 1H), 7.43-7.26 (m, 2H), 7.24-7.14 (m, 1H), 6.95-6.63 (m, 2H), 6.42 (d, J=5.9 Hz, 2H), 5.22 (m, 1H), 5.04 (s, 2H), 4.66 (m, 1H), 4.01 (m, 2H), 3.93-3.84 (m, 1H), 3.76 (m, 1H), 3.02 (m, 2H), 2.51 (m, 4H), 2.37 (m, 1H), 1.99 (m, 1H). MS (m/z) 742.15 [M+H]⁺.

Example 26

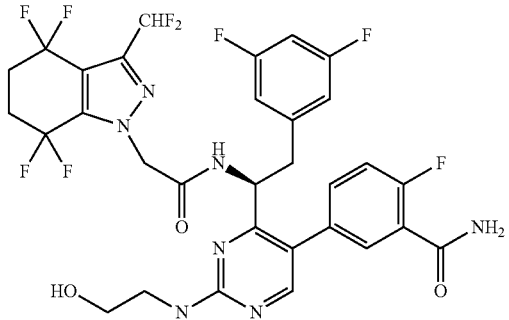

26

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-hydroxyethyl)amino)pyrimidin-5-yl)-2-fluorobenzamide (26)

The title compound (26) was prepared according to the method presented for the synthesis of compound 14B of Example 14 starting with 2-aminoethanol and 12C. ¹H NMR (400 MHz, CD₃OD) δ 8.83 (d, J=7.7 Hz, 1H), 8.06 (s, 2H), 7.49-7.32 (m, 2H), 7.21 (dd, J=10.7, 8.5 Hz, 1H), 7.02-6.58 (m, 2H), 6.45 (d, J=6.1 Hz, 2H), 5.22 (m, 1H), 5.05 (s, 2H), 3.86-3.58 (m, 4H), 3.18-2.85 (m, 2H), 2.66-2.23 (m, 4H). MS (m/z) 716.23 [M+H]⁺.

Example 27

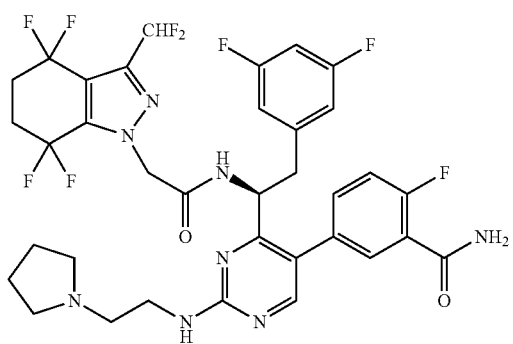

Synthesis of ((S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(pyrrolidin-1-yl)ethyl)amino)pyrimidin-5-yl)-2-fluorobenzamide (27)

The title compound (27) was prepared according to the method presented for the synthesis of compound 23F of Example 23 starting with 2-(pyrrolidin-1-yl)ethanamine and 23B. ¹H NMR (400 MHz, CD₃OD) δ 8.67 (d, J=7.8 Hz, 1H), 8.05 (s, 1H), 7.41-7.23 (m, 2H), 7.13 (dd, J=10.7, 8.5 Hz, 1H), 6.95-6.48 (m, 2H), 6.35 (d, J=6.2 Hz, 2H), 5.15 (m, 1H), 4.95 (q, J=16.7 Hz, 2H), 3.74 (m, 4H), 3.43 (m, 2H), 3.11 (m, 2H), 3.00-2.88 (m, 2H), 2.70-2.28 (m, 4H), 2.13-1.89 (m, 4H). MS (m/z) 769.29 [M+H]⁺.

Example 28

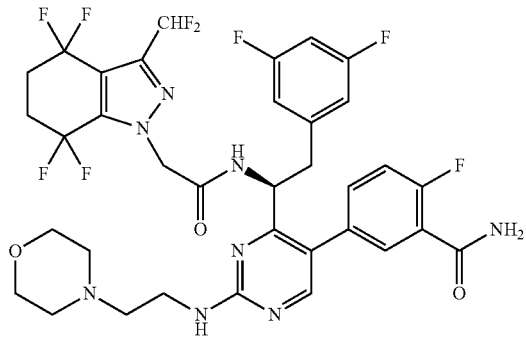

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-morpholinoethyl)amino)pyrimidin-5-yl)-2-fluorobenzamide (28)

The title compound (28) was prepared according to the method presented for the synthesis of compound 23F of Example 23 starting with 2-morpholinoethanamine and 23B. ¹H NMR (400 MHz, CD₃OD) δ 8.76 (d, J=7.8 Hz, 1H), 8.14 (s, 1H), 7.46-7.32 (m, 2H), 7.22 (dd, J=10.7, 8.5 Hz, 1H), 7.00-6.59 (m, 2H), 6.43 (d, J=6.2 Hz, 2H), 5.23 (m, 1H), 5.02 (q, J=16.6 Hz, 2H), 3.97 (m, 6H), 3.70-3.39 (m, 6H), 3.10-2.93 (m, 2H), 2.66-2.38 (m, 4H). MS (m/z) 785.29 [M+H]⁺.

Example 29

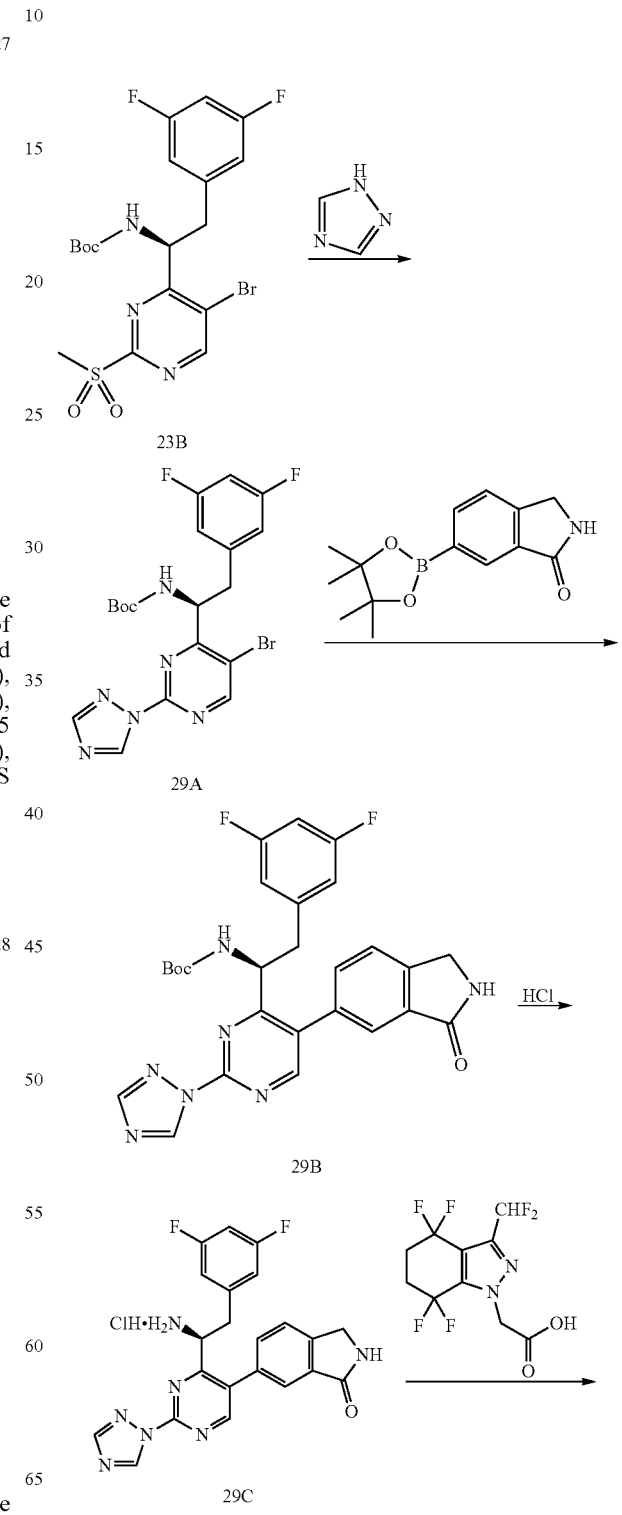

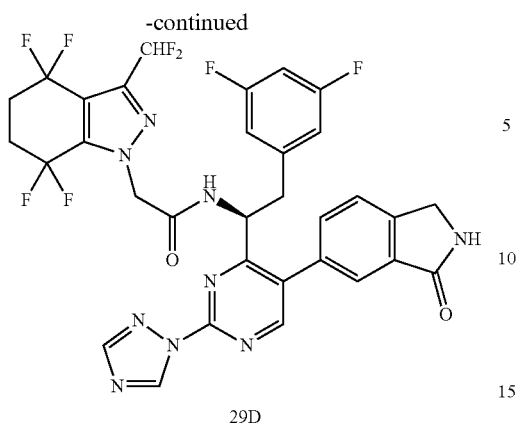

29D

Synthesis of (S)-tert-butyl (1-(5-bromo-2-(1H-1,2,4-triazol-1-yl)pyrimidin-4-yl)-2-(3,5-difluorophenyl)ethyl)carbamate (29A)

In a microwave tube were charged with compound 23B (100 mg, 0.2 mmol), 1H-1,2,4-triazole (42 mg, 0.6 mmol), triethylamine (84 μL, 0.6 mmol) and DMF (0.6 mL, The mixture was heated up to 120° C. for 15 min in a Microwave Synthesizer. After cooled down, it was partitioned between ethyl acetate and 5% of LiCl aqueous solution. The organic layer was separated and concentrated. The residue was purified on silica gel chromatography eluting with ethyl acetate and hexanes to afford the title compound. MS (m/z) 481.21 [M+H]+.

Synthesis of (S)-tert-butyl (2-(3,5-difluorophenyl)-1-(5-(3-oxoisoindolin-5-yl)-2-(1H-1,2,4-triazol-1-yl)pyrimidin-4-yl)ethyl)carbamate (29B)

In a microwave tube was charged with 29B (50 mg, 0.1 mmol), 6-(4,4,5,5-tetramethyl-1,3,2-dioxaborolan-2-yl)isoindolin-1-one (39 mg, 0.15 mmol), LiCl (13 mg, 0.3 mmol), Na₂CO₃ (25 mg, 0.3 mmol) and 3 mg of Pd(PPh₃)₂Cl₂. To the mixture was added 0.7 mL of 1,4-dioxane, 0.2 mL of methanol and 0.2 mL of H₂O. The mixture was heated up to 160° C. for 20 min in a Microwave Synthesizer. After cooled down, it was partitioned between ethyl acetate and water. The organic layer was separated and concentrated. The residue was purified on silica gel chromatography eluting with ethyl acetate and hexanes to afford the title compound. MS (m/z) 533.78 [M+H]+.

Synthesis of (S)-6-(4-(1-amino-2-(3,5-difluorophenyl)ethyl)-2-(1H-1,2,4-triazol-1-yl)pyrimidin-5-yl)isoindolin-1-one hydrochloride (29C)

The title compound (29C) was prepared according to the method presented for the synthesis of compound 23E of Example 23 utilizing 29B. MS (m/z) 434.11[M+H]+

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(5-(3-oxoisoindolin-5-yl)-2-(1H-1,2,4-triazol-1-yl)pyrimidin-4-yl)ethyl)acetamide (29D)

The title compound (29D) was prepared according to the method presented for the synthesis of compound 11G of Example 11 utilizing 29C. ¹H NMR (400 MHz, CD₃OD) δ 9.59 (s, 1H), 9.19 (d, J=8.4 Hz, 1H), 8.71 (s, 1H), 8.39 (s, 1H), 7.66 (q, J=7.9 Hz, 2H), 7.46 (s, 1H), 6.93-6.54 (m, 2H), 6.38 (d, J=6.2 Hz, 2H), 5.55 (q, J=7.6 Hz, 1H), 5.09 (s, 2H), 4.52 (s, 2H), 3.20-2.91 (m, 2H), 2.47 (m, 4H). MS (m/z) 718.08 [M+H]+

Example 30

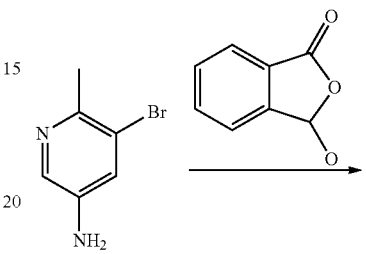

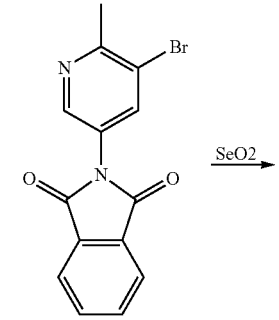

30A

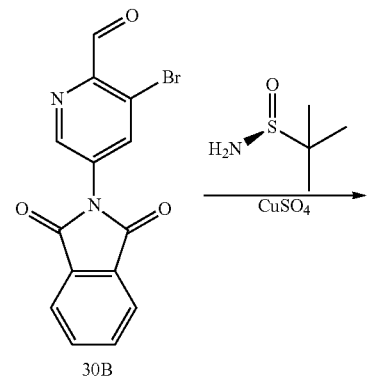

30B

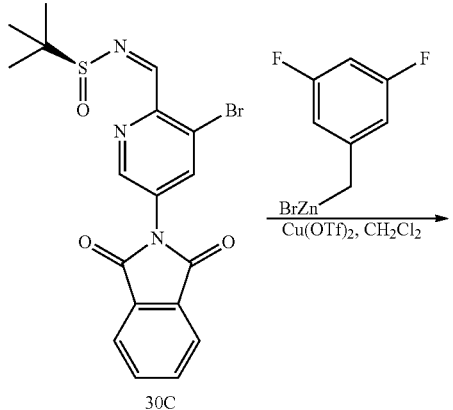

30C

91
-continued
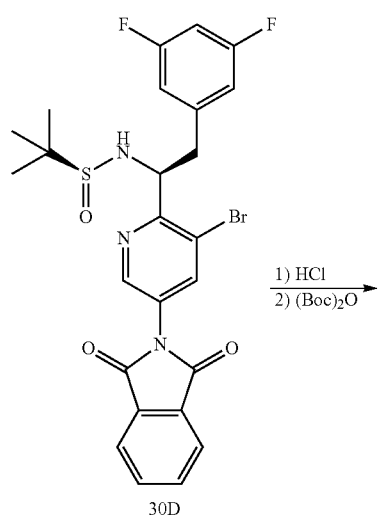
30D
1) HCl
2) (Boc)₂O →
92
-continued
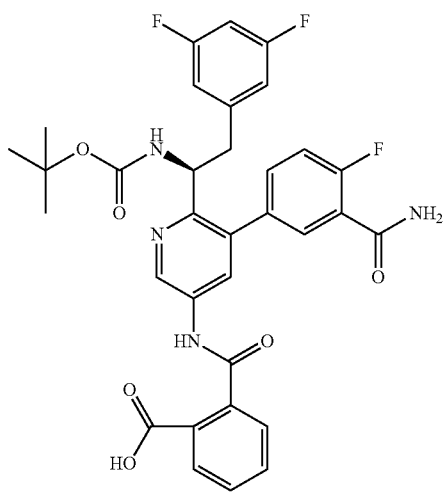
30H
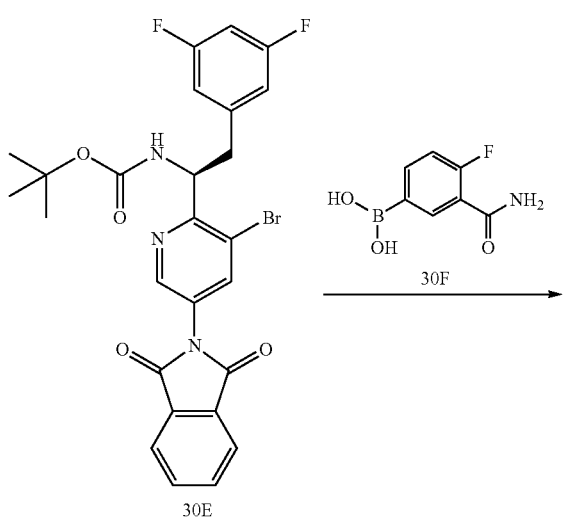
30E
+ 30F → 
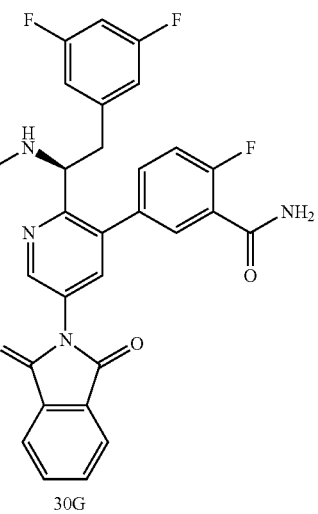
30G
HCl →
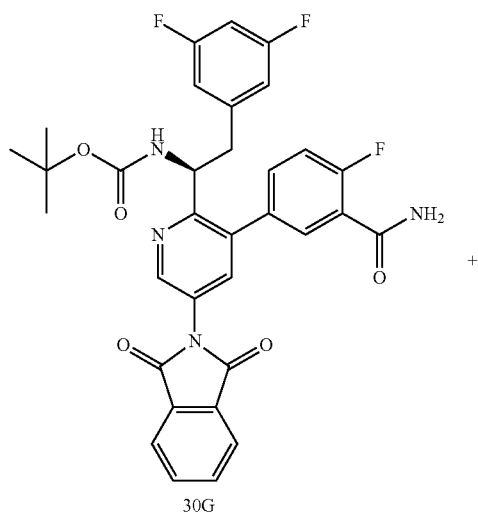
30G
+
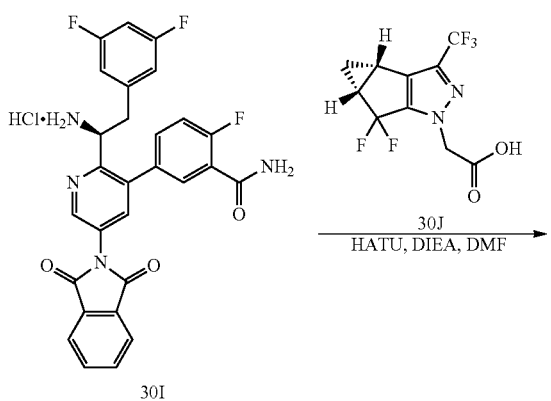
30I
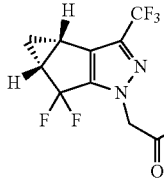
30J
HATU, DIEA, DMF →

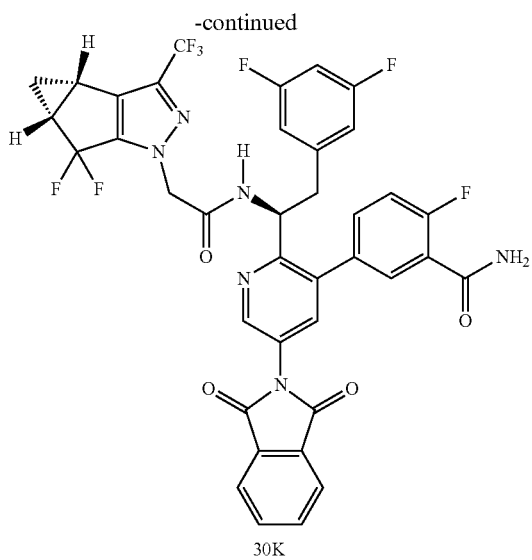

30K

Synthesis of 2-(5-bromo-6-methylpyridin-3-yl)isoindoline-1,3-dione (30A)

A mixture of phthalic anhydride (3.7 g, 25 mmol), 5-bromo-6-methylpyridin-3-amine (3.9 g, 20.85 mmol) and sodium acetate (1.5 g, 25 mmol) in glacial acetic acid (44 ml) was refluxed for overnight. After cooling down to room temperature, the precipitate was collected by vacuum filtration, washed with water, and dried to afford the title compound. MS (m/z) 318.91 [M+H]$^+$.

Synthesis of 3-bromo-5-(1,3-dioxoisoindolin-2-yl)picolinaldehyde (30B)

To 2-(5-bromo-6-methylpyridin-3-yl)isoindoline-1,3-dione (30A, 1.5 g, 4.73 mmol) and selenium dioxide (682 mg, 6.15 mmol) was added 14 mL of DME. The reaction mixture was heated in a 130° C. heating bath for 20 hours. The reaction was repeated on identical scale 4×. The combined reaction mixtures were cooled and the solids filtered off. The filtrate was concentrated to afford 6 g of the title compound. $^1$H NMR (400 MHz, DMSO) δ 10.04 (s, 1H), 8.95 (d, J=1.9 Hz, 1H), 8.41 (d, J=1.7 Hz, 1H), 8.07-7.84 (m, 4H).

Synthesis of (S,Z)—N-((3-bromo-5-(1,3-dioxoisoindolin-2-yl)pyridin-2-yl)methylene)-2-methylpropane-2-sulfinamide (30C)

Copper(II) sulfate (anhydrous, 5.8 g, 36.2 mmol) was added to a solution of 3-bromo-5-(1,3-dioxoisoindolin-2-yl)picolinaldehyde (30B, 6 g, 18 mmol) and (S)-2-methylpropane-2-sulfinamide (2.2 g, 18 mmol) in CH$_2$Cl$_2$ (60 mL). The reaction mixture was stirred at ambient temperature for 2 hours and then filtered and washed with CH$_2$Cl$_2$. The filtrate was concentrated and the residue was purified by silica gel chromatography eluting with EtOAc and methylene chloride to yield the title compound. MS (m/z) 433.87 [M+H]$^+$.

Synthesis of (S)—N-((S)-1-(3-bromo-5-(1,3-dioxoisoindolin-2-yl)pyridin-2-yl)-2-(3,5-difluorophenyl)ethyl)-2-methylpropane-2-sulfinamide (30D)

To a solution of (S,Z)—N-((3-bromo-5-(1,3-dioxoisoindolin-2-yl)pyridin-2-yl)methylene)-2-methylpropane-2-sulfinamide (30C, 3.7 G, 8.5 mmol) and Cu(OTf)$_2$ (154 mg, 0.4 mmol) in methylene chloride (30 ml) at 0° C. was added (3,5-difluorobenzyl)zinc bromide (0.5 M in THF, 25.5 ml, 12.8 mmol) dropwise. The reaction stirred at room temperature for one hour. Ammonium chloride (aq, 100 ml) was added to the reaction and the mixture was extracted with methylene chloride (2×100 ml). The organic layer was dried over Na$_2$SO$_4$ filtered and concentrated (about 1:3 ratio of two diastereomers). The crude was purified by reverse phase HPLC eluting with acetonitrile and water (with 0.1% TFA) to afford the title compound as a single diastereomer. MS (m/z) 563.83 [M+H]$^+$.

Synthesis of (S)-tert-butyl 1-(3-bromo-5-(1,3-dioxoisoindolin-2-yl)pyridin-2-yl)-2-(3,5-difluorophenyl)ethylcarbamate (30E)

(S)—N-((S)-1-(3-bromo-5-(1,3-dioxoisoindolin-2-yl)pyridin-2-yl)-2-(3,5-difluorophenyl)ethyl)-2-methylpropane-2-sulfinamide (30D, 2.6 G, 4.6 mmol) was dissolved in 40 mL of methanol and cooled to 0° C. To it was added 4N HCl/1,4-dioxane (4.6 ml). The reaction mixture was allowed to stir at room temperature for 10 minutes and concentrated to afford product (S)-2-(6-(1-amino-2-(3,5-difluorophenyl)ethyl)-5-bromopyridin-3-yl)isoindoline-1,3-dione hydrochloride. To the mixture of the above HCl salt (~4.6 mmol) and di-tert-butyl dicarbonate (1 g, 4.6 mmol) in 50 mL of CH$_2$Cl$_2$ was added triethylamine (1.28 mL, 9.2 mmol) at 0° C. The reaction mixture was stirred for overnight and concentrated in vacuo. The residue was partitioned between EtOAc and H$_2$O. The organic layer was washed with brine, dried over MgSO4, filtered and concentrated. Then it was purified on silica gel chromatography eluting with EtOAc/hexanes to yield the title compound. MS (m/z) 559.71 [M+H]$^+$.

Synthesis of (S)-tert-butyl 1-(3-(3-carbamoyl-4-fluorophenyl)-5-(1,3-dioxoisoindolin-2-yl)pyridin-2-yl)-2-(3,5-difluorophenyl)ethylcarbamate (30G)

A microwave tube was charged with of (S)-tert-butyl 1-(3-bromo-5-(1,3-dioxoisoindolin-2-yl)pyridin-2-yl)-2-(3,5-difluorophenyl)ethylcarbamate (30E, 50 mg, 0.09 mmol), (3-carbamoyl-4-fluorophenyl)boronic acid (25 mg, 0.13 mmol) and PdCl$_2$[P(Cy)$_3$]$_2$ (3.3 mg, 0.004 mmol). To the mixture was added 1.8 mL of 1,4-dioxane and 0.3 mL of sodium bicarbonate aqueous solution (1M). The system was purged with argon and then the microwave tube was sealed and the reaction mixture was heated up in a microwave synthesizer at 150° C. for 15 min. The above procedure was repeated 2× more; a total 150 mg of compound 30E was used. After cooling, the combined reactions were partitioned between EtOAc and water. The organic layer was separated and washed with brine, then dried over MgSO$_4$, filtered and concentrated. The residue was purified by reverse phase HPLC eluting with acetonitrile and water (with 0.1% TFA) to afford 30H, MS (m/z) 634.81 [M+H]$^+$ and the title compound 30G. MS (m/z) 616.82 [M+H]$^+$.

Synthesis of (S)-5-(2-(1-amino-2-(3,5-difluorophenyl)ethyl)-5-(1,3-dioxoisoindolin-2-yl)pyridin-3-yl)-2-fluorobenzamide hydrochloride (30I)

(S)-tert-butyl 1-(3-(3-carbamoyl-4-fluorophenyl)-5-(1,3-dioxoisoindolin-2-yl)pyridin-2-yl)-2-(3,5-difluorophenyl)ethylcarbamate (30G, 29 mg, 0.047 mmol) was dissolved in 0.5 mL of methanol and cooled to 0° C. To it was added 4N HCl/1,4-dioxane (0.05 ml). The reaction mixture was stirred at room temperature for 10 minutes and concentrated to afford the title product. MS (m/z) 516.96 [M+H]⁺.

Synthesis of 5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-5-(1,3-dioxoisoindolin-2-yl)pyridin-3-yl)-2-fluorobenzamide (30K)

2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (13 mg, 0.045 mmol), (S)-5-(2-(1-amino-2-(3,5-difluorophenyl)ethyl)-5-(1,3-dioxoisoindolin-2-yl)pyridin-3-yl)-2-fluorobenzamide hydrochloride (30I, 25 mg, 0.045 mmol) and HATU (21 mg, 0.054 mmol) were dissolved in 10 mL DMF, cooled to 0° C., then N,N-diisopropylethylamine (0.032 mL, 0.18 mmol) was added dropwise. The reaction mixture was allowed to stir at 0° C. for 5 min, and then partitioned between EtOAc and 5% LiCl aqueous solution. The organic layer was separated, washed with NaHCO₃ (sat'd aq.) and brine. After dried over MgSO₄, it was filtered and concentrated. The residue was purified by RP-HPLC eluting with acetonitrile/H₂O (with 0.1% TFA) to afford the title compound. ¹H NMR (400 MHz, CD₃OD): δ 8.87 (s, 1H), 7.98 (m, 2H), 7.88 (m, 2H), 7.76 (d, 1H), 7.54-7.30 (m, 2H), 7.24 (dd, 1H), 6.67 (t, 1H), 6.39 (m, 2H), 5.51-5.26 (m, 1H), 4.88 (s, 2H), 3.18-2.98 (m, 2H), 2.63-2.41 (m, 2H), 1.40 (m, 1H), 1.11 (m, 1H). MS (m/z) 781.03 [M+H]⁺.

Example 31

Synthesis of 5-(5-amino-2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (31)

Compound 30K (13 mg, 0.017 mmol) was dissolved in 1 ml of ethanol; 0.01 ml of hydrazine monohydrate was added and stirred at room temperature for 2 hours. The solvent was removed and the residue was purified by RP-HPLC eluting with acetonitrile/H₂O (with 0.1% TFA) to afford the title compound. ¹H NMR (400 MHz, CD₃OD) δ 8.07 (d, 1H), 7.38 (m, 2H), 7.28-7.07 (m, 2H), 6.71 (t, 1H), 6.35 (m, 2H), 5.14 (m, 1H), 4.90 (s, 2H), 3.13 (m, 1H), 3.01-2.91 (m, 1H), 2.48 (m, 2H), 1.40 (m, 1H), 1.09 (m, 1H). MS (m/z) 650.94 [M+H]⁺.

Example 32

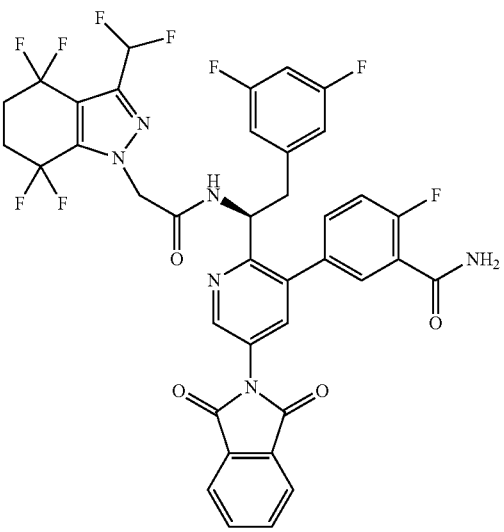

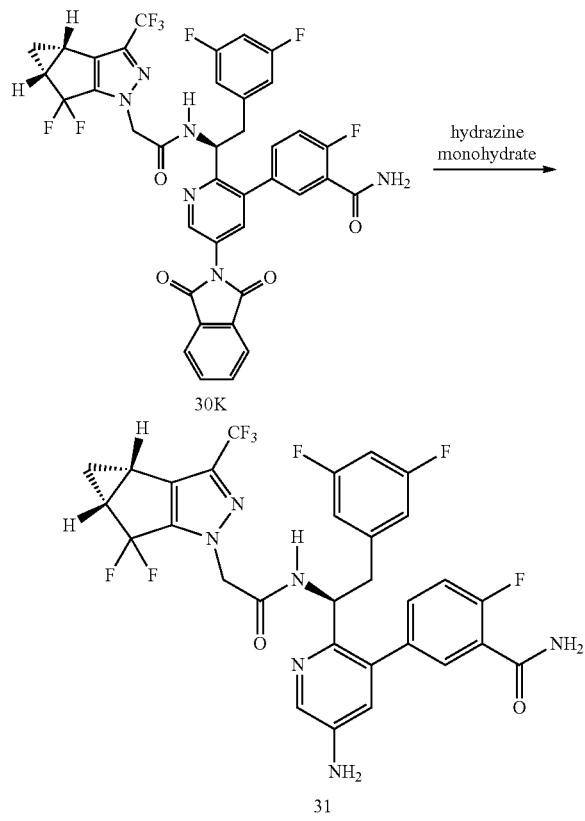

Synthesis of (S)-5-(2-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-5-(1,3-dioxoisoindolin-2-yl)pyridin-3-yl)-2-fluorobenzamide (32)

Compound 32 was prepared according to the method presented in the final step for the synthesis of Example 30 substituting 2-(3-(difluoromethyl)-4,4,7,7-tetrafluoro-4,5,6,7-tetrahydro-1H-indazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, CD₃OD) δ 8.87 (d, 1H), 7.98 (m, 2H), 7.88 (m, 2H), 7.76 (d, 1H), 7.48 (m, 1H), 7.39 (m, 1H), 7.32-7.17 (m, 1H), 6.77 (m, 2H), 6.41 (m, 2H), 5.40 (m, 1H), 5.06 (s, 2H), 3.12 (m, 2H), 2.49 (m, 4H). MS (m/z) 800.99 [M+H]⁺.

Example 33

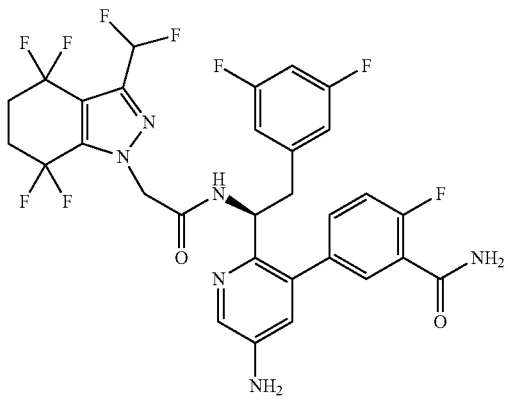

Synthesis of (S)-5-(5-amino-2-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridin-3-yl)-2-fluorobenzamide (33)

Compound 33 was prepared according to the method presented in the synthesis of Example 31 substituting compound 32 for compound 30K. $^1$H NMR (400 MHz, CD$_3$OD) δ 8.08 (d, 1H), 7.39 (m, 2H), 7.28-7.17 (m, 1H), 7.14 (d, 1H), 7.00-6.60 (m, 2H), 6.37 (m, 2H), 5.19-5.01 (m, 3H), 3.12 (m, 1H), 2.99 (m, 1H), 2.66-2.34 (m, 4H). MS (m/z) 671.01 [M+H]$^+$.

Example 34

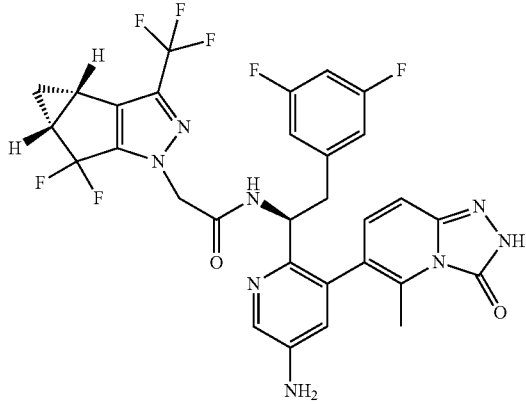

Synthesis of N—((S)-1-(5-amino-3-(5-methyl-3-oxo-2,3-dihydro-[1,2,4]triazolo[4,3-a]pyridin-6-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (34)

Compound 34 was prepared according to the method presented in the synthesis of Example 30 substituting 5-methyl-6-(4,4,5,5-tetramethyl-1,3,2-dioxaborolan-2-yl)-[1,2,4]triazolo[4,3-a]pyridin-3(2H)-one for 3-carbamoyl-4-fluorophenylboronic acid then following the method presented the synthesis of Example 31. $^1$H NMR (400 MHz, methanol-d4): δ 8.14 (dd, 1H), 7.12-6.93 (m, 2H), 6.90-5.77 (m, 4H), 5.11-4.92 (m, 1H), 4.89 (m, 2H), 3.30-3.02 (m, 2H), 2.69-2.08 (m, 5H), 1.43 (m, 1H), 1.10 (m, 1H). MS (m/z) 660.97 [M+H]$^+$

Example 35

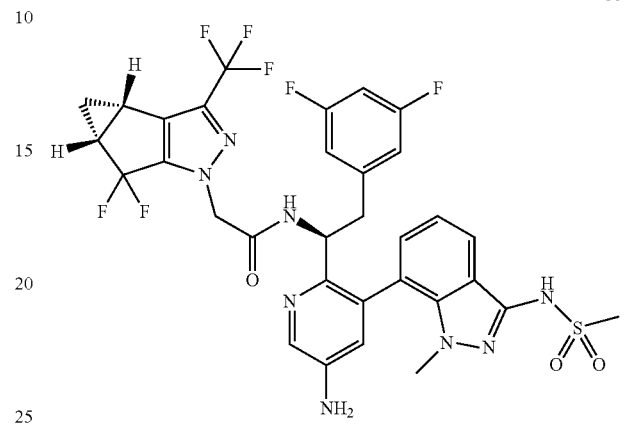

Synthesis of N—((S)-1-(5-amino-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamide (35)

Compound 35 was prepared according to the method presented in the synthesis of Example 30 substituting N-(1-methyl-7-(4,4,5,5-tetramethyl-1,3,2-dioxaborolan-2-yl)-1H-indazol-3-yl)methanesulfonamide for 3-carbamoyl-4-fluorophenylboronic acid then following the method presented the synthesis of Example 31. $^1$H NMR (400 MHz, methanol-d4) δ 8.22 (d, 1H), 7.96-7.74 (m, 1H), 7.23 (d, 1H), 7.10 (dd, 1H), 6.90-6.70 (m, 1H), 6.70-6.51 (m, 1H), 6.39 (m, 2H), 5.23 (m, 1H), 4.87-4.59 (m, 2H), 3.45 (s, 3H), 3.24-3.07 (m, 4H), 3.09-2.88 (m, 1H), 2.67-2.33 (m, 2H), 1.52-1.31 (m, 1H), 1.06 (m, 1H). MS (m/z) 736.98 [M+H]$^+$.

Example 36

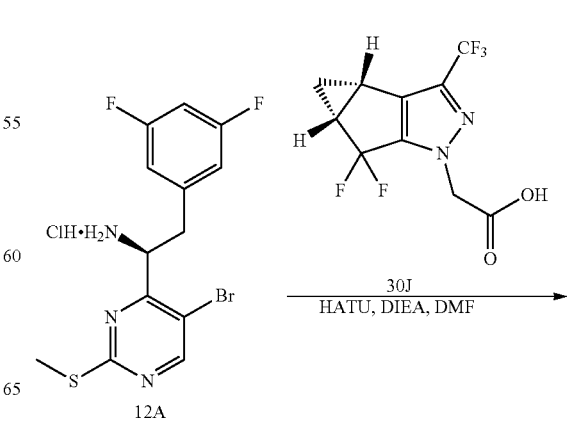

-continued

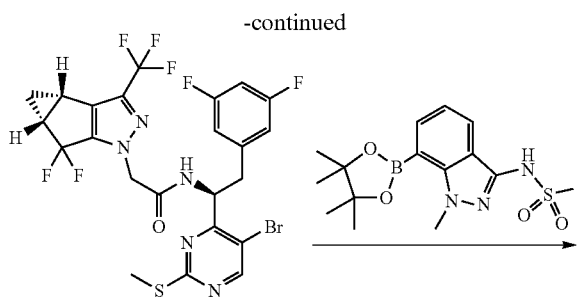

36A

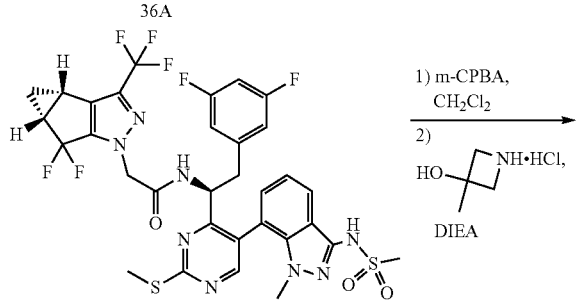

36B

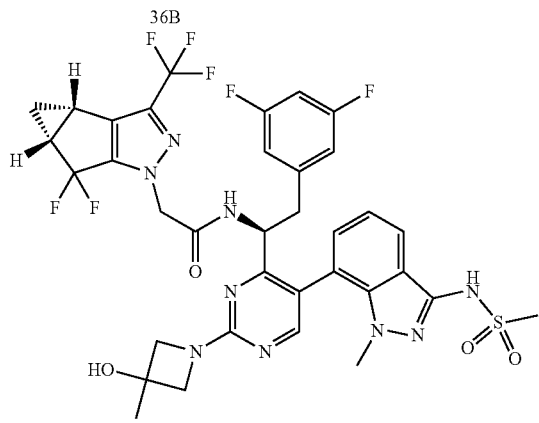

36C

Synthesis of N—((S)-1-(5-bromo-2-(methylthio) pyrimidin-4-yl)-2-(3,5-difluorophenyl)ethyl)-2-((3bS,4aR)-5,5-difluoro-3-(trifluoromethyl)-3b,4,4a, 5-tetrahydro-1H-cyclopropa[3,4]cyclopenta[1,2-c] pyrazol-1-yl)acetamide (36A)

Compound 36A was prepared according to the method presented in the synthesis of Example 30K substituting (S)-1-(5-bromo-2-(methylthio)pyrimidin-4-yl)-2-(3,5-difluorophenyl)ethanamine hydrochloride for compound 30I. MS (m/z) 625.88 [M+H]+.

Synthesis of 2-((3bS,4aR)-5,5-difluoro-3-(trifluoromethyl)-3b,4,4a,5-tetrahydro-1H-cyclopropa[3,4] cyclopenta[1,2-c]pyrazol-1-yl)-N—((S)-2-(3,5-difluorophenyl)-1-(5-(1-methyl-3-(methylsulfonamido)-1H-indazol-7-yl)-2-(methylthio)pyrimidin-4-yl)ethyl)acetamide (36B)

Compound 36B was prepared according to the method presented in the synthesis of Example 30G substituting N-(1-methyl-7-(4,4,5,5-tetramethyl-1,3,2-dioxaborolan-2-yl)-1H-indazol-3-yl)methanesulfonamide for compound 30F. MS (m/z) 768.86 [M+H]+

Synthesis of 2-((3bS,4aR)-5,5-difluoro-3-(trifluoromethyl)-3b,4,4a,5-tetrahydro-1H-cyclopropa[3,4] cyclopenta[1,2-c]pyrazol-1-yl)-N—((S)-2-(3,5-difluorophenyl)-1-(2-(3-hydroxy-3-methylazetidin-1-yl)-5-(1-methyl-3-(methylsulfonamido)-1H-indazol-7-yl)pyrimidin-4-yl)ethyl)acetamide (36C)

Compound 36B (30 mg, 0.039 mmol) was dissolved in 3 mL of CH$_2$Cl$_2$ and to it was added m-CPBA (17.5 mg, 77%, 0.078 mmol). The reaction mixture was allowed to stir at rt for 20 min. To the reaction mixture was added N,N-diisopropylethylamine (0.2 mL, 0.017 mmol) and 3-methylazetidin-3-ol hydrochloride (34 mg, 0.39 mmol). The reaction mixture was allowed to stir at room temperature for 30 min and then partitioned between EtOAc and brine. The organic layer was separated, washed with brine and dried over Na$_2$SO$_4$ and concentrated. The residue was purified by RP-HPLC eluting with acetonitrile/H$_2$O (with 0.1% TFA) to afford the title product. $^1$H NMR (400 MHz, methanol-d4) δ 8.53 (dd, 1H), 8.25 (d, 1H), 7.83 (m, 1H), 7.36-6.52 (m, 3H), 6.47-6.22 (m, 2H), 4.85 (m, 3H), 4.40-3.94 (m, 4H), 3.75-2.67 (m, 8H), 2.51 (m, 2H), 1.60 (s, 3H), 1.51-1.23 (m, 1H), 1.18-0.88 (m, 1H). MS (m/z): 808.01 [M+H]+.

Example 37

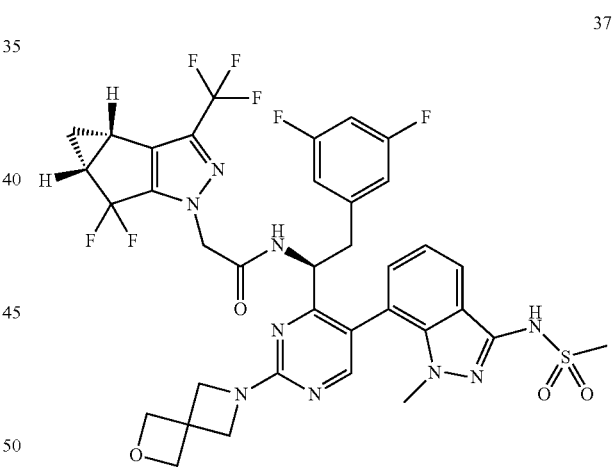

37

Synthesis of 2-((3bS,4aR)-5,5-difluoro-3-(trifluoromethyl)-3b,4,4a,5-tetrahydro-1H-cyclopropa[3,4] cyclopenta[1,2-c]pyrazol-1-yl)-N—((S)-2-(3,5-difluorophenyl)-1-(5-(1-methyl-3-(methylsulfonamido)-1H-indazol-7-yl)-2-(2-oxa-6-azaspiro[3.3]heptan-6-yl)pyrimidin-4-yl)ethyl) acetamide (37)

Compound 37 was prepared according to the method presented in the synthesis of Example 36 substituting 2-oxa-6-azaspiro[3.3]heptane hemioxalate for 3-methylazetidin-3-ol hydrochloride. $^1$H NMR (400 MHz, methanol-d4) δ 8.55 (dd, 1H), 8.24 (d, 1H), 7.82 (m, 1H), 7.45-7.00 (m, 1H), 6.86-6.44 (m, 2H), 6.34 (m, 2H), 5.19 (m, 1H), 4.91 (d, 4H), 4.85 (m, 2H), 4.41 (m, 4H), 3.59-2.72 (m, 8H), 2.49 (m, 2H), 1.61-0.97 (m, 2H). MS (m/z) 819.99 [M+H]⁺.

Example 38

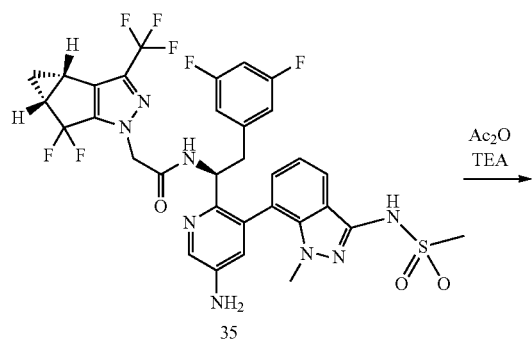

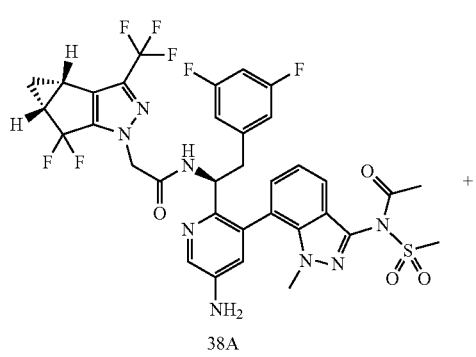

Synthesis of N-(7-(5-amino-2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-1-methyl-1H-indazol-3-yl)-N-(methylsulfonyl)acetamide (38A)

To a solution of Compound 35 (20 mg, 0.027 mmol) in methylene chloride (2 mL) was added acetic anhydride (0.03 mL, 0.27 mmol), triethylamine (0.04 mL, 0.027 mmol), and the reaction mixture was stirred for one hour at room temperature. The solution was partitioned between EtOAc and saturated aqueous sodium bicarbonate. The organic layer was dried over Na₂SO₄, filtered and concentrated. The residue was purified by reverse phase HPLC eluting with acetonitrile and water (with 0.1% TFA) to afford the title compound 38A: ¹H NMR (400 MHz, methanol-d4) δ 8.26 (d, 1H), 7.72 (dd, 1H), 7.18 (m, 1H), 7.09 (d, 1H), 6.76 (tt, 1H), 6.46 (d, 1H), 6.42-6.21 (m, 2H), 4.85-4.52 (m, 3H), 3.50 (m, 6H), 3.12 (m, 1H), 3.00-2.80 (m, 1H), 2.59-2.31 (m, 2H), 1.86 (s, 3H), 1.41 (m, 1H), 1.04 (m, 1H). MS (m/z): 778.95 [M+H]⁺ and 11 mg of compound 38B. MS (m/z) 820.83 [M+H]⁺.

Example 39

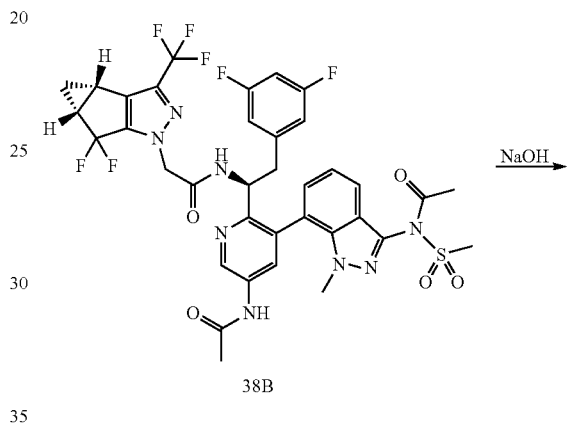

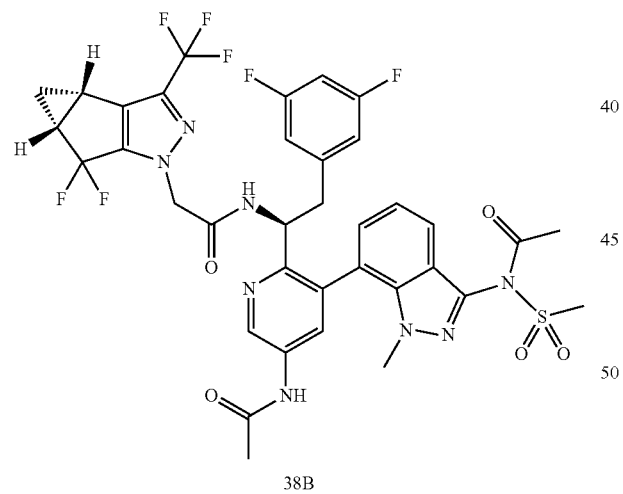

Synthesis of N—((S)-1-(5-acetamido-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (39)

To a solution of compound 38B in ethanol (2 mL) was added 0.5 ml of 15% of NaOH. The reaction mixture was stirred at room temperature for 10 min, and then was partitioned between EtOAc and saturated aqueous sodium bicarbonate. The organic layer was dried over Na₂SO₄, filtered and concentrated. The residue was purified by reverse phase HPLC eluting with acetonitrile and water (with 0.1% TFA) to afford the title compound. $^1$H NMR (400 MHz, methanol-d4) δ 9.07-8.85 (m, 1H), 8.04-7.89 (m, 1H), 7.83 (dd, 1H), 7.07 (m, 1H), 6.74 (tt, 1H), 6.55-6.41 (m, 1H), 6.45-6.00 (m, 2H), 4.85 (m, 3H), 3.45-2.69 (m, 8H), 2.64-2.31 (m, 2H), 2.17 (s, 3H), 1.40 (q, 1H), 1.07 (m, 1H). MS (m/z) 779.97 [M+H]⁺.

Example 40

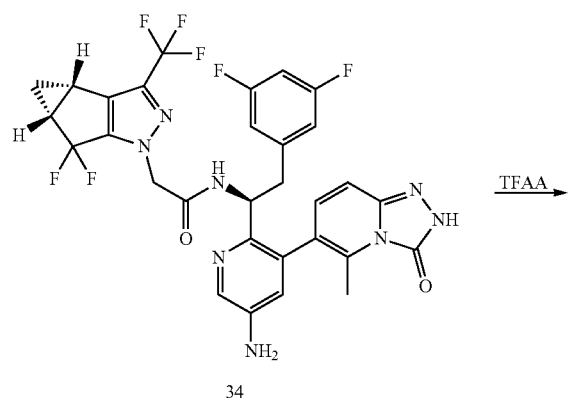

34

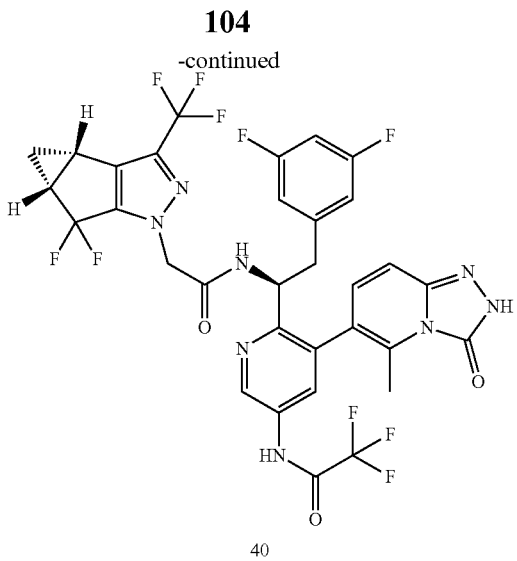

40

Synthesis of N-(6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-5-(5-methyl-3-oxo-2,3-dihydro-[1,2,4]triazolo[4,3-a]pyridin-6-yl)pyridin-3-yl)-2,2,2-trifluoroacetamide (40)

Compound 34 was dissolved in methylene chloride and cooled to 0° C. To it was added pyridine followed by trifluoroacetic anhydride. The reaction mixture was stirred at 0° C. for 10 min then partitioned between EtOAc and brine. The organic layer was separated, dried and concentrated. The residue was purified by RP-HPLC eluting with acetonitrile/H₂O (with 0.1% TFA) to afford the title compound. $^1$H NMR (400 MHz, methanol-d4) δ 9.04 (dd, J=13.1, 2.5 Hz, 1H), 7.85 (dd, J=7.3, 2.5 Hz, 1H), 7.20-5.77 (m, 5H), 5.21 (ddd, J=26.2, 8.8, 6.0 Hz, 1H), 4.85 (s, 2H), 3.24-2.91 (m, 2H), 2.70-1.88 (m, 5H), 1.56-1.27 (m, 1H), 1.11 (m, 1H). MS (m/z) 756.92 [M+H]⁺

Example 41

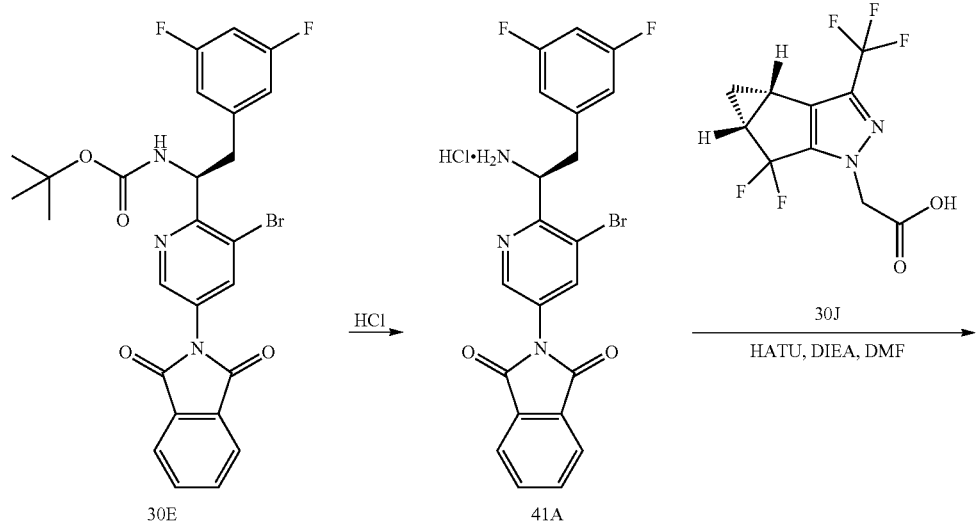

-continued
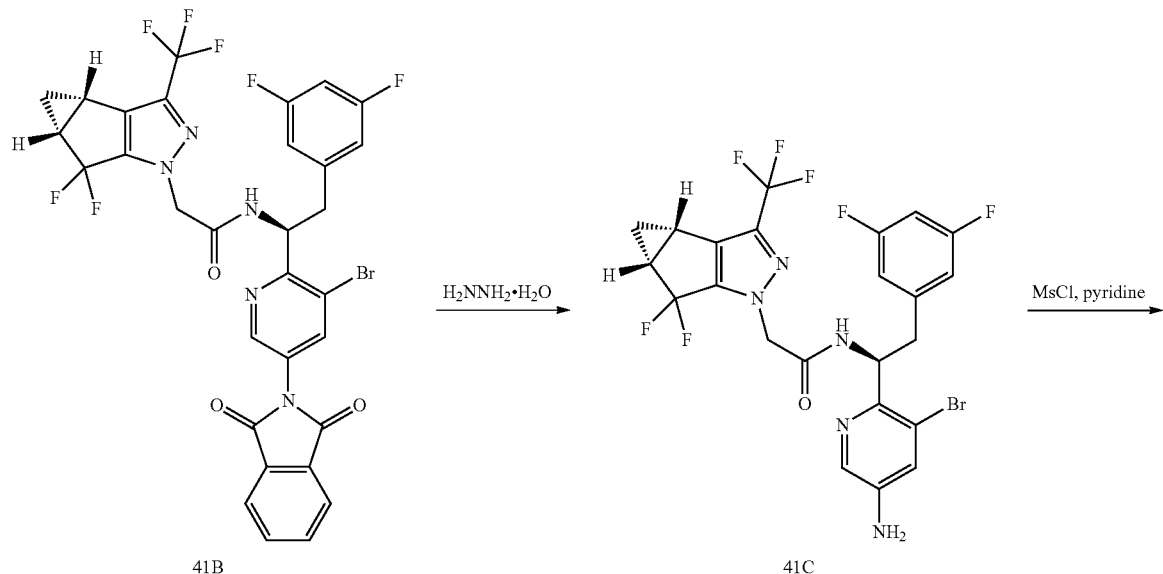
41B
41C
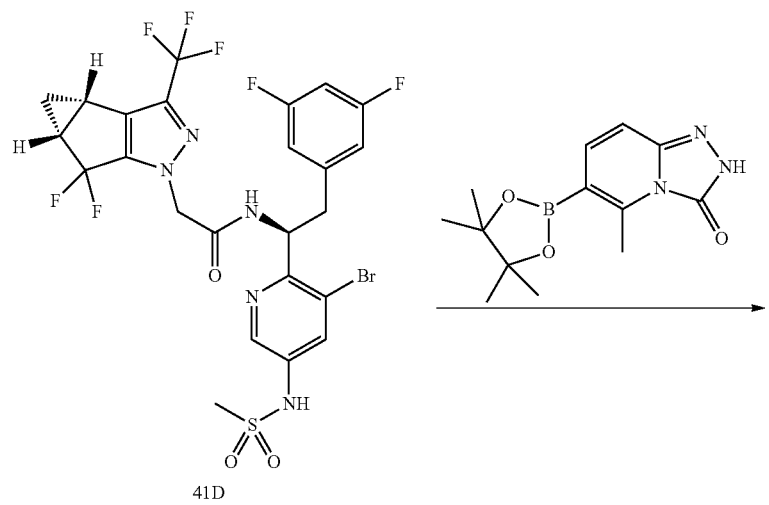
41D
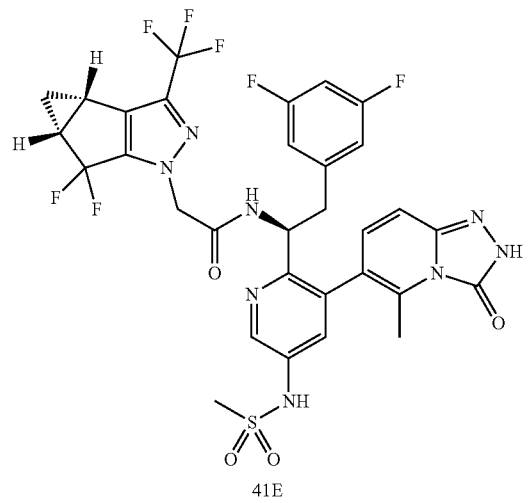 [SMILES: Cc1c(-c2cc(NS(C)(=O)=O)cnc2[C@H](Cc2cc(F)cc(F)c2)NC(=O)Cn2nc(C(F)(F)F)c3c2C(F)(F)[C@@H]2C[C@H]32)ccc2n[nH]c(=O)n12]
41E

Synthesis of (S)-2-(6-(1-amino-2-(3,5-difluorophenyl)ethyl)-5-bromopyridin-3-yl)isoindoline-1,3-dione hydrochloride (41A)

Compound 30E (260 mg, 0.047 mmol) was dissolved in 10 mL of methanol and cooled to 0° C. To it was added 4N HCl/1,4-dioxane (2 ml). The reaction mixture was stirred at room temperature for overnight and concentrated to afford the title product. MS (m/z) 458.00 [M+H]+

Synthesis of N—((S)-1-(3-bromo-5-(1,3-dioxoisoindolin-2-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (41B)

Compound 41B was prepared according to the method presented in the final step for the synthesis of Example 30 substituting compound 41A for compound 30I. MS (m/z) 722.23 [M+H]+

Synthesis of N—((S)-1-(5-amino-3-bromopyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (41C)

To a mixture of Compound 41B (100 mg, 0.14 mmol) in 15 ml of ethanol, 0.05 ml of hydrazine monohydrate was added and the reaction mixture was stirred at room temperature for 10 min. The solvent was removed and the residue was purified by RP-HPLC eluting with acetonitrile/H2O (with 0.1% TFA) to afford the title product. MS (m/z) 592.20 [M+H]+.

Synthesis of N—((S)-1-(3-bromo-5-(methylsulfonamido)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (41D)

Compound 41C (35.6 mg, 0.06 mmol) was dissolved in 1 mL of methylene chloride and cooled to 0° C. To it was added 0.2 mL of pyridine followed by methanesulfonyl chloride (0.007 mL, 0.09 mmol). The reaction mixture was stirred at 0° C. for one hour. LCMS showed complete reaction. It was then partitioned between EtOAc and brine. The organic layer was separated, dried and concentrated to afford the title product. MS (m/z) 670.27 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(5-methyl-3-oxo-2,3-dihydro-[1,2,4]triazolo[4,3-a]pyridin-6-yl)-5-(methylsulfonamido)pyridin-2-yl)ethyl)acetamide (41E)

A microwave tube was charged with N—((S)-1-(3-bromo-5-(methylsulfonamido)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (41D, 20 mg, 0.03 mmol), 5-methyl-6-(4,4,5,5-tetramethyl-1,3,2-dioxaborolan-2-yl)-[1,2,4]triazolo[4,3-a]pyridin-3(2H)-one (12.3 mg, 0.045 mmol) and PdCl2[P(Cy)3]2 (2.2 mg, 0.003 mmol). To the mixture was added 0.6 mL of 1,4-dioxane and 0.09 mL of sodium bicarbonate aqueous solution (1M). The system was purged with argon and then the microwave tube was sealed and the reaction mixture was heated in a microwave synthesizer at 170° C. for 15 min. After cooling, the reaction was partitioned between EtOAc and water. The organic layer was separated and washed with brine, then dried over MgSO4, filtered and concentrated. The residue was purified by reverse phase HPLC eluting with acetonitrile and water (with 0.1% TFA) to afford the title compound. $^1$H NMR (400 MHz, methanol-d4) δ 8.91-8.48 (m, 1H), 7.40 (dd, J=13.1, 2.6 Hz, 1H), 7.07-5.77 (m, 5H), 5.38-5.02 (m, 1H), 4.85 (s, 2H), 3.29-2.92 (m, 5H), 2.66-1.95 (m, 5H), 1.41 (dd, J=8.1, 6.0 Hz, 1H), 1.10 (m, 1H). MS (m/z) 738.92 [M+H]+.

Example 42

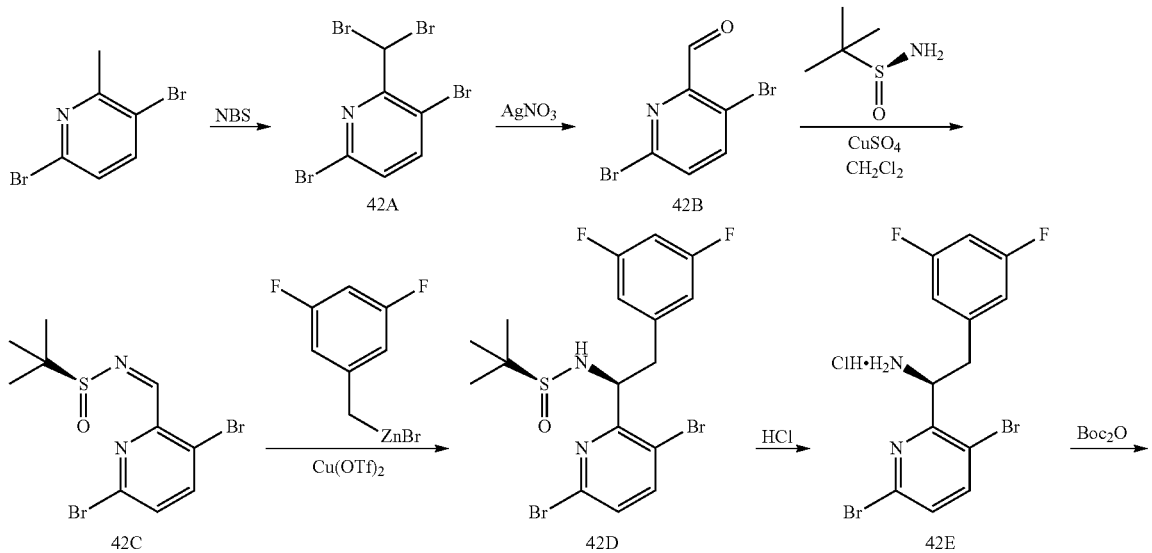

-continued
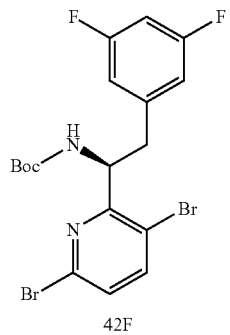 
42F
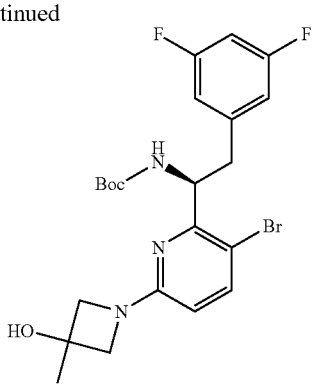 
42G
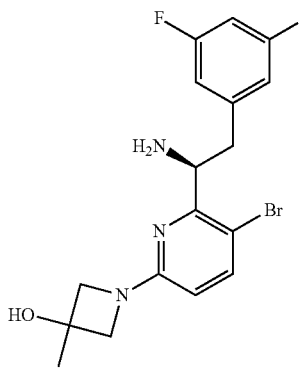 
42H
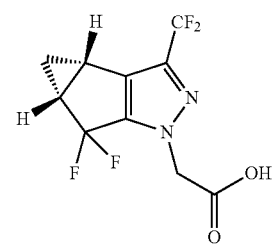 
42I
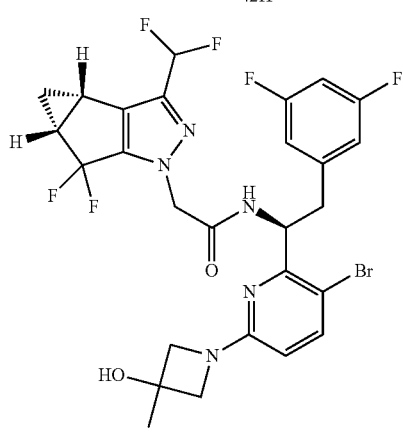 
42J
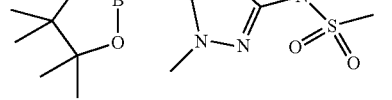
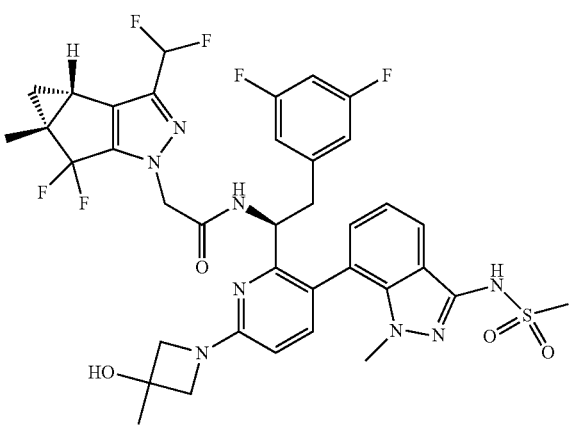 
42K

Synthesis of 3,6-dibromo-2-(dibromomethyl)pyridine (42A)

To a solution of 3,6-dibromo-2-methylpyridine (5.2 g, 21 mmol) in CCl$_4$ (50 mL) was added N-bromosuccinimide (7.57 g, 42 mmol) and 2,2'-azobis(2-methylpropionitrile) (0.70 g, 4.3 mmol). The mixture was heated at 80° C. overnight and cooled to room temperature. The solid was removed by filtration and the filtrate was concentrated under reduced pressure. The product (42A) was obtained after flash chromatography eluding with 0-10 percent EtOAc in hexane (7.36 g). MS (m/z): 409.66 [M+H]$^+$

Synthesis of 3,6-dibromopicolinaldehyde (42B)

A solution of silver nitrate (7.6 g, 45 mmol) in water (24 mL) was added dropwise to a solution of 42A (7.36 g, 18 mmol) in refluxing EtOH (90 mL). The mixture was stirred at 80° C. for 5 hours. After the mixture was cooled to room temperature, it was diluted with water (100 mL), extracted with EtOAc (3 times), dried over Na$_2$SO$_4$, filtered and concentrated under reduced pressure. The crude product (42B, 4.6 g) was directly used for next step. MS (m/z): 265.96. [M+H]$^+$

Synthesis of (S,Z)—N-((3,6-dibromopyridin-2-yl)methylene)-2-methylpropane-2-sulfinamide (42C)

The title compound (42C) was prepared according to the method presented for the synthesis of compound 30C of Example 30 utilizing 42B. MS (m/z) 368.86 [M+H]$^+$

Synthesis of (S)—N—((S)-1-(3,6-dibromopyridin-2-yl)-2-(3,5-difluorophenyl)ethyl)-2-methylpropane-2-sulfinamide (42D)

The title compound (42D) was prepared according to the method presented for the synthesis of compound 30D of Example 30 utilizing 42C. MS (m/z) 496.99 [M+H]$^+$

Synthesis of (S)-tert-butyl 1-(3,6-dibromopyridin-2-yl)-2-(3,5-difluorophenyl)ethylcarbamate (42F)

The title compound was prepared according to the 2 step method presented for the synthesis of compound 30E of Example 30 utilizing 42D.

Synthesis of (S)-tert-butyl (1-(3-bromo-6-(3-hydroxy-3-methylazetidin-1-yl)pyridin-2-yl)-2-(3,5-difluorophenyl)ethyl)carbamate (42G)

(S)-tert-butyl (1-(3,6-dibromopyridin-2-yl)-2-(3,5-difluorophenyl)ethyl)carbamate (150 mg, 0.3 mmol), 3-methylazetidin-3-ol hydrochloride (75 mg, 0.6 mmol) was combined with cesium carbonate (397 mg, 1.2 mmol), palladium diacetate (10 mg, 0.015 mmol) and 2,2'-bis-(diphenylphosphino)-1,1'-binaphthyl (19 mg, 0.03 mmol) in 2 mL of toluene. The system was degassed and purged with argon and heated to 150° C. heating bath for 1 hour, the reaction mixture was cooled and diluted with ethyl acetate. The organic layer was washed with water and brine, and then dried over sodium sulfate. The crude was purified by flash chromatography eluting with EtOAc/hexanes to provided the title compound. MS (m/z) 499.72 [M+H]$^+$.

Synthesis of (S)-1-(6-(1-amino-2-(3,5-difluorophenyl)ethyl)-5-bromopyridin-2-yl)-3-methylazetidin-3-ol (42H)

Compound 42G (64 mg, 0.13 mmol) was dissolved in 2 mL of 20% TFA/methylene chloride. The reaction mixture was stirred at room temperature for 2 hours and then partitioned between EtOAc and saturated aq. NaHCO$_3$. The organic layer was separated and concentrated to afford the title product. MS (m/z) 398.03[M+H]$^+$.

Synthesis of N—((S)-1-(3-bromo-6-(3-hydroxy-3-methylazetidin-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (42J)

2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (33 mg, 0.13 mmol), (S)-1-(6-(1-amino-2-(3,5-difluorophenyl)ethyl)-5-bromopyridin-2-yl)-3-methylazetidin-3-ol (50 mg, 0.13 mmol) and HATU (57 mg, 0.15 mmol) were dissolved in 1 mL of DMF and cooled to 0° C. To it was dropwise added N,N-diisopropylethylamine (0.07 mL, 0.38 mmol). The reaction mixture was allowed to stir at 0° C. for 5 min, and then partitioned between EtOAc and 5% LiCl aqueous solution. The organic layer was separated, washed with NaHCO$_3$ (saturated aqueous) and brine. After dried over MgSO$_4$, it was filtered and concentrated. The residue was purified by silica gel chromatography eluting with EtOAc/hexanes to afford the title product. MS (m/z): 644.33[M+H]$^+$.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylazetidin-1-yl)-3-(1-methyl-3-(methylsulfonamido)-1H-indazol-7-yl)pyridin-2-yl)ethyl)acetamide (42K)

In a microwave tube were charged with of N—((S)-1-(3-bromo-6-(3-hydroxy-3-methylazetidin-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (45 mg, 0.07 mmol), N-(1-methyl-7-(4,4,5,5-tetramethyl-1,3,2-dioxaborolan-2-yl)-1H-indazol-3-yl)methanesulfonamide (36 mg, 0.1 mmol) and PdCl$_2$[P(Cy)$_3$]$_2$ (5 mg, 0.007 mmol). To the mixture was added 1.4 mL of 1,4-dioxane and 0.2 mL of sodium bicarbonate aqueous solution (1M). The system was purged with argon and then the microwave tube was sealed and the reaction mixture was heated up in a microwave synthesizer at 150° C. for 20 min. After cooled down to room temperature, it was partitioned between EtOAc and water. The organic layer was separated and washed with brine, then dried over MgSO$_4$, filtered and concentrated. The residue was purified by reverse phase HPLC eluting with acetonitrile and water (with 0.1% TFA) to afford the title product. $^1$H NMR (400 MHz, methanol-d4) δ 7.79 (dd, 1H), 7.51 (dd, 1H), 7.29-6.45 (m, 5H), 6.48-6.24 (m, 2H), 4.85 (m, 3H), 4.19-3.91 (m, 4H), 3.58-2.75 (m, 8H), 2.49 (m, 2H), 1.61 (d, J=2.2 Hz, 3H), 1.41 (q, J=7.0 Hz, 1H), 1.20-0.83 (m, 1H). MS (m/z) 789.11 [M+H]$^+$.

Example 43

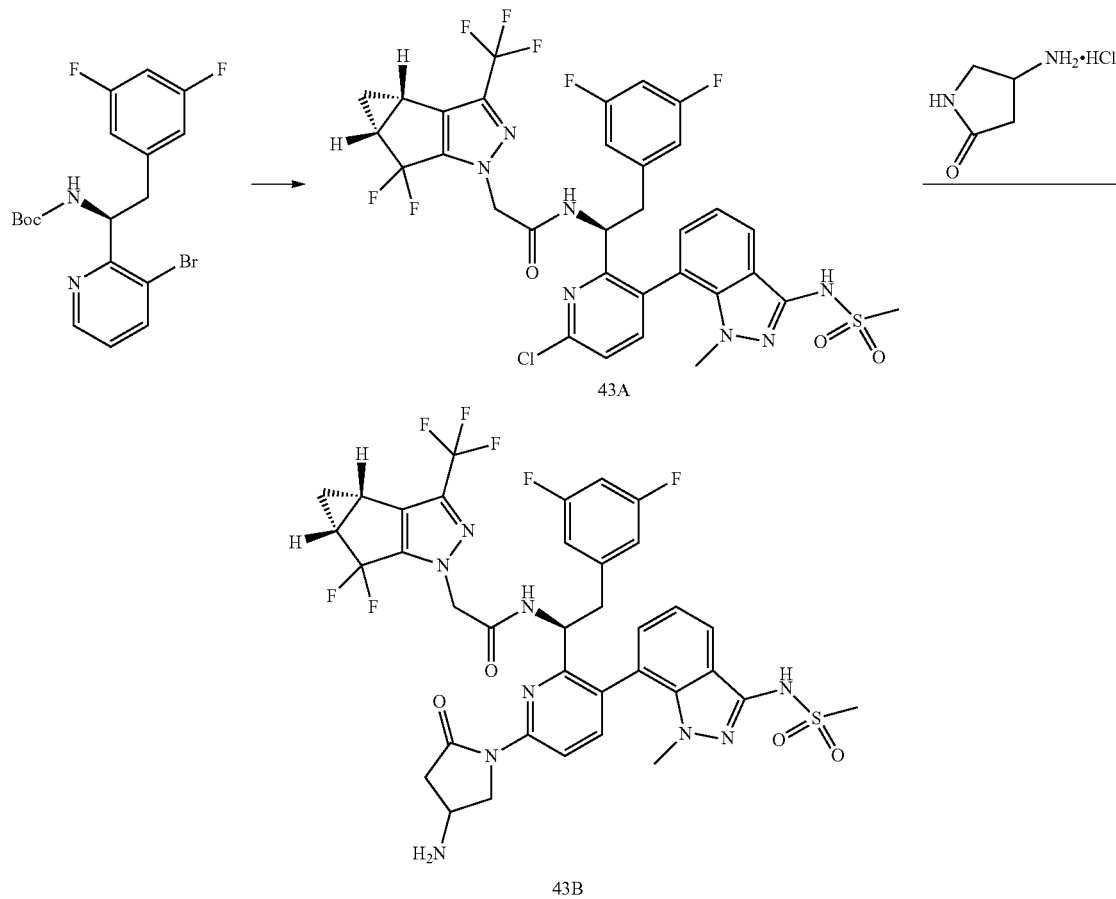

Synthesis of N—((S)-1-(6-chloro-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43A)

Compound 43A was prepared from (S)-tert-butyl (1-(3-bromopyridin-2-yl)-2-(3,5-difluorophenyl)ethyl)carbamate according to the method presented in the synthesis of compound 60B of Example 60 utilizing N-(1-methyl-7-(4,4,5,5-tetramethyl-1,3,2-dioxaborolan-2-yl)-1H-indazol-3-yl)methanesulfonamide.

Synthesis of N-((1S)-1-(6-(4-amino-2-oxopyrrolidin-1-yl)-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43B)

Compound 43B was prepared according to the method presented in the synthesis of compound 42G of Example 42 substituting N—((S)-1-(6-chloro-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43A) for (S)-Atert-butyl (1-(3,6-dibromopyridin-2-yl)-2-(3,5-difluorophenyl)ethyl) carbamate (42F). $^1$H NMR (400 MHz, methanol-d4) δ 8.69-8.34 (m, 2H), 7.91-7.67 (m, 2H), 7.38-6.89 (m, 1H), 6.93-6.52 (m, 1H), 6.48-6.14 (m, 2H), 5.39-4.92 (m, 1H), 4.84-4.70 (m, 2H), 4.69-4.33 (m, 2H), 4.27 (m, 1H), 3.48-2.72 (m, 10H), 2.62-2.28 (m, 2H), 1.61-1.27 (m, 1H), 1.08 (m, 1H). MS (m/z) 820.00[M+H]$^+$.

Example 44

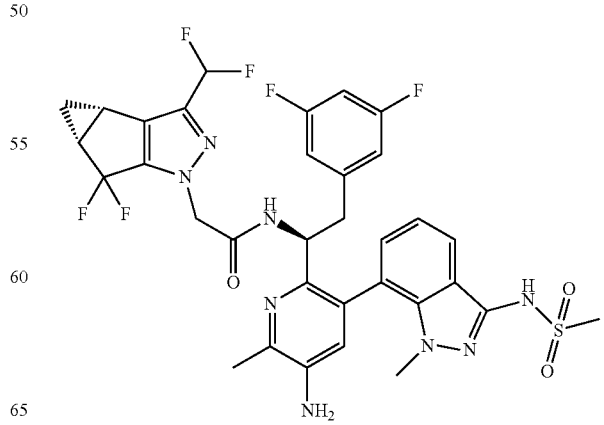

44

Synthesis of N—((S)-1-(5-amino-6-methyl-3-(1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (44)

Compound 44 was prepared according to the method presented in the synthesis of Example 47 substituting N-(1-methyl-7-(4,4,5,5-tetramethyl-1,3,2-dioxaborolan-2-yl)-1H-indazol-3-yl)methanesulfonamide for N-(4-chloro-1-methyl-7-(4,4,5,5-tetramethyl-1,3,2-dioxaborolan-2-yl)-1H-indazol-3-yl)methanesulfonamide to provide the title compound. $^1$H NMR (400 MHz, methanol-d4) δ 7.86-7.78 (m, 1H), 7.17-6.99 (m, 2H), 6.88-6.53 (m, 3H), 6.41-6.34 (m, 2H), 4.81-4.68 (m, 3H), 3.42 (s, 3H), 3.23-2.89 (m, 6H), 2.60 (s, 3H), 2.46 (ddd, 2H), 1.39 (q, 1H), 1.01 (d, 1H). MS (m/z) 733 [M+H]$^+$.

Example 45

45

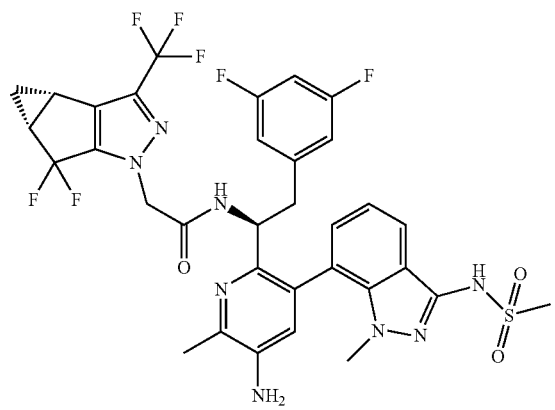

Synthesis of N—((S)-1-(5-amino-6-methyl-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (45)

Compound 45 was prepared according to the method presented for the synthesis of Example 47 substituting N-(1-methyl-7-(4,4,5,5-tetramethyl-1,3,2-dioxaborolan-2-yl)-1H-indazol-3-yl)methanesulfonamide for N-(4-chloro-1-methyl-7-(4,4,5,5-tetramethyl-1,3,2-dioxaborolan-2-yl)-1H-indazol-3-yl)methanesulfonamide and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid for 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid to provide 8 mg of title compound: $^1$H NMR (400 MHz, Methanol-d4) δ 7.83 (dd, 1H), 7.19-7.02 (m, 2H), 6.85-6.70 (m, 1H), 6.53 (d, 1H), 6.38 (d, 2H), 4.83-4.71 (m, 3H), 3.42 (s, 3H), 3.15 (m, 4H), 2.99 (dd, 1H), 2.61 (s, 3H), 2.56-2.45 (m, 2H), 1.42 (d, 1H), 1.05 (d, 1H). MS (m/z) 751 [M+H]$^+$.

Example 46

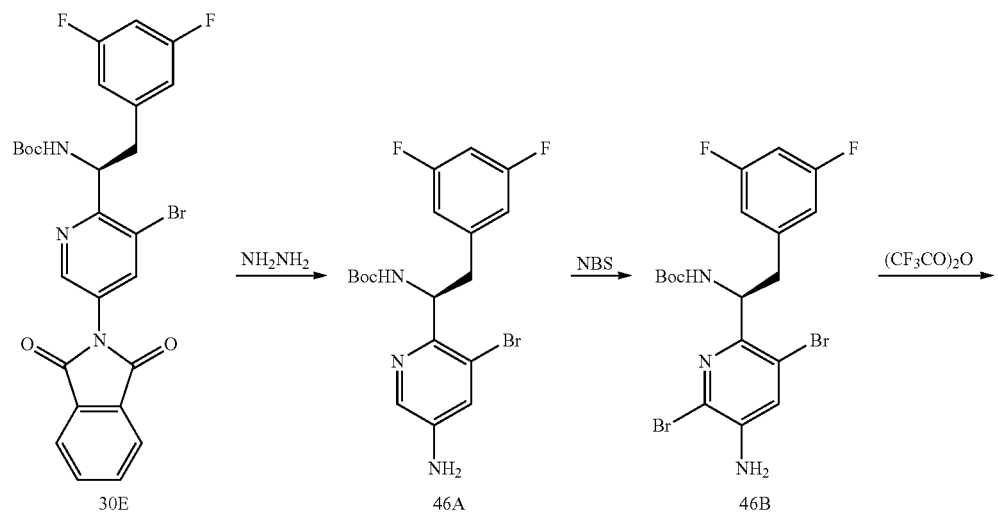

-continued
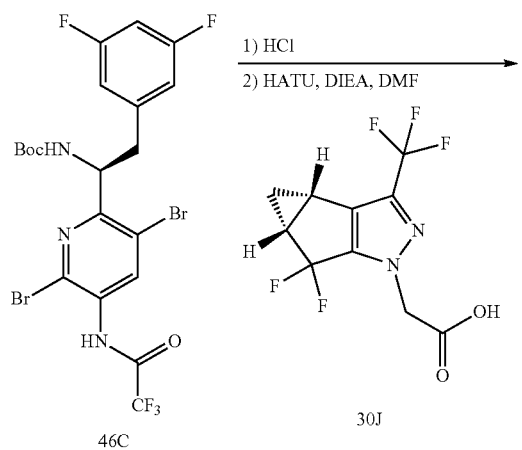
46C 30J
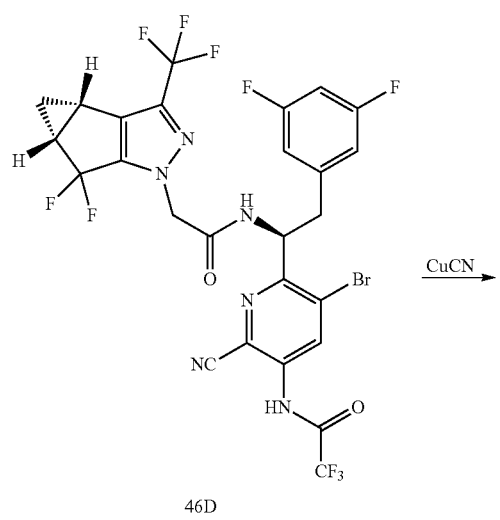
46D
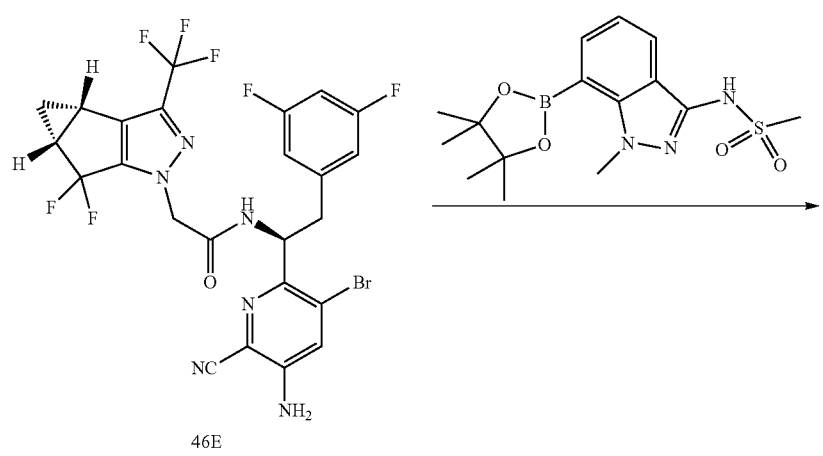
46E

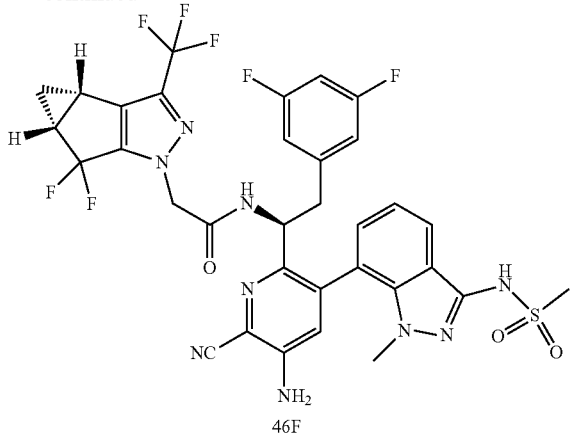

46F

Synthesis of (S)-tert-butyl (1-(5-amino-3-bromopyridin-2-yl)-2-(3,5-difluorophenyl)ethyl)carbamate (46A)

To a mixture of (S)-tert-butyl (1-(3-bromo-5-(1,3-dioxoisoindolin-2-yl)pyridin-2-yl)-2-(3,5-difluorophenyl)ethyl)carbamate (30E, 1.5 g, 2.7 mmol) in 27 ml of ethanol, 0.9 ml of hydrazine monohydrate was added and stirred at room temperature for 2 hours. To the reaction mixture, ethanol was added and filtrated, and the filtrate was concentrated. The residue was diluted with ethyl acetate, and washed with water and then with a saturated sodium chloride solution. The organic layer was dried over anhydrous magnesium sulfate, and then concentrated under reduced pressure. The residue was subjected to silica gel column chromatography to give the title product. MS (m/z) 427.83 [M+H]$^+$.

Synthesis of (S)-tert-butyl (1-(5-amino-3,6-dibromopyridin-2-yl)-2-(3,5-difluorophenyl)ethyl)carbamate (46B)

A solution of (S)-tert-butyl (1-(5-amino-3-bromopyridin-2-yl)-2-(3,5-difluorophenyl)ethyl)carbamate (46A, 960 mg, 2.24 mmol) in 20 mL of acetonitrile was cooled to 0° C. and treated with N-bromosuccinimide (399 mg, 2.24 mmol) as a solution in 20 mL of acetonitrile. After 5 min, the reaction mixture was partitioned with EtOAc and saturated aqueous NaHCO$_3$. The organic layer was separated and washed with brine, then dried over MgSO$_4$ and concentrated in vacuo. The residue was purified by silica gel chromatography eluting with EtOAc/hexanes to afford the title product. MS (m/z): 507.52 [M+H]$^+$.

Synthesis of (S)-tert-butyl (1-(3,6-dibromo-5-(2,2,2-trifluoroacetamido)pyridin-2-yl)-2-(3,5-difluorophenyl)ethyl)carbamate (46C)

A solution of (S)-tert-butyl (1-(5-amino-3,6-dibromopyridin-2-yl)-2-(3,5-difluorophenyl)ethyl)carbamate (500 mg, 0.99 mmol) in 5 mL of 1,4-dioxane at 0° C. was treated with trifluoroacetic anhydride (0.2 mL, 1.5 mmol) followed by potassium carbonate (204 mg, 1.5 mmol). After 5 min, a mixture of 10 mL of 1,4-dioxane and 20 mL of water were added to the reaction. The resulting precipitate was collected by vacuum filtration and washed with water. The solid product was dissolved in methylene chloride, dried over Na$_2$SO$_4$ and filtered. The filtrate was concentrated to afford the title product. MS (m/z) 603.31, [M+H]$^+$.

Synthesis of N-(2,5-dibromo-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2,2,2-trifluoroacetamide (46D)

A mixture of (S)-tert-butyl (1-(3,6-dibromo-5-(2,2,2-trifluoroacetamido)pyridin-2-yl)-2-(3,5-difluorophenyl)ethyl)carbamate (46C, 563 mg, 0.94 mmol) in 5 mL of methylene chloride was cooled down to 0° C. and to it was added 10 mL of 20% TFA/methylene chloride. The reaction was allowed to stir at room temperature for 1 hour and then concentrated to dryness to afford (S)—N-(6-(1-amino-2-(3,5-difluorophenyl)ethyl)-2,5-dibromopyridin-3-yl)-2,2,2-trifluoroacetamide as a TFA salt. 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (265 mg, 0.94 mmol), the amine (TFA salt from last step) and HATU (429 mg, 1.1 mmol) were dissolved in 10 mL DMF, cooled to 0° C., then N,N-diisopropylethylamine (0.84 mL, 4.7 mmol) was added dropwise. The reaction mixture was allowed to stir at 0° C. for 5 min, and then partitioned between EtOAc and 5% LiCl aqueous solution. The organic layer was separated, washed with NaHCO$_3$ (sat'd aq.) and brine. After dried over MgSO$_4$, it was filtered and concentrated to yield the title product. MS (m/z): 767.84 [M+H]$^+$.

Synthesis of N—((S)-1-(5-amino-3-bromo-6-cyanopyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (46E)

In a microwave tube was charged with N-(2,5-dibromo-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2,2,2-trifluoroacetamide (46D, 150 mg, 0.2 mmol) and to it was added cuprous cyanide (35 mg, 0.4 mmol). The reaction mixture was heated at 100° C. heating bath for overnight and then cooled down to room temperature. The reaction mixture was partitioned between EtOAc and water (+1 mL of ammonium hydroxide solution). The organic layer was separated, then washed with water (+0.5 mL of ammonium hydroxide solution) and brine. After dried over Na₂SO₄ and filtered, it was concentrated to dryness to afford crude products which was purified by silica gel chromatography eluting with EtOAc/CH₂Cl₂ afford the title product. MS (m/z): 618.92 [M+H]⁺.

Synthesis of N—((S)-1-(5-amino-6-cyano-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (46F)

Compound 46F was prepared according to the method presented in the synthesis of Example 42D substituting N—((S)-1-(5-amino-3-bromo-6-cyanopyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (46E) for N—((S)-1-(3-bromo-6-(3-hydroxy-3-methylazetidin-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (42C). ¹H NMR (400 MHz, methanol-d4) δ 8.66 (d, J=8.7 Hz, 1H), 7.23-6.96 (m, 2H), 6.86-6.69 (m, 1H), 6.38 (m, 3H), 4.84 (m, 3H), 3.42 (s, 3H), 3.28-2.78 (m, 5H), 2.62-2.30 (m, 2H), 2.08-1.64 (m, 1H), 1.52-1.06 (m, 1H). MS (m/z): 796.09 [M+H]⁺;

Example 47

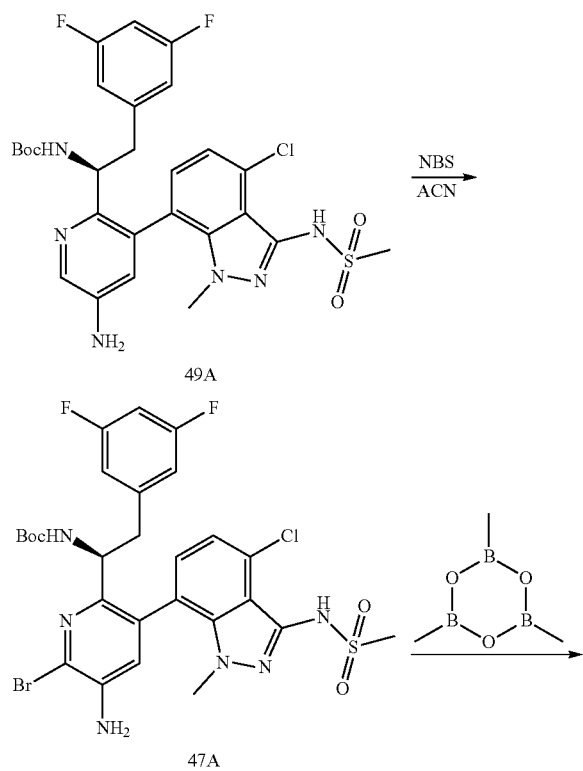

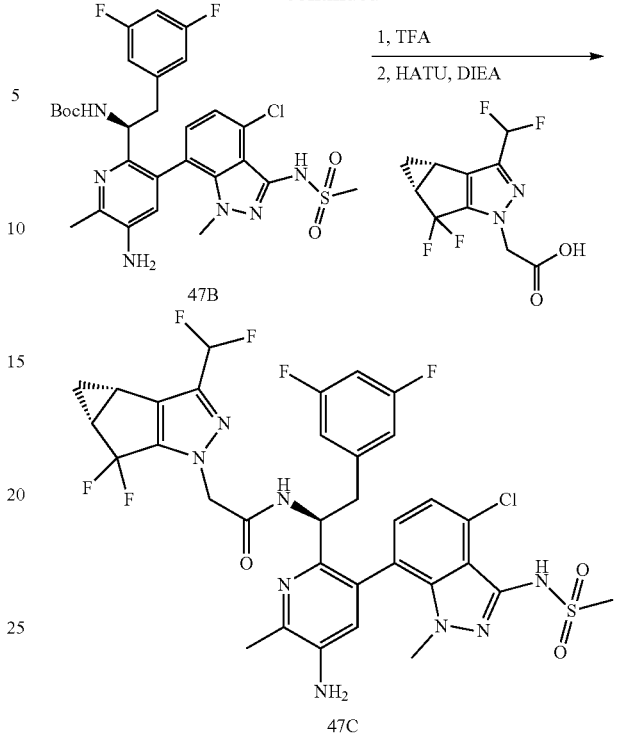

Synthesis of (S)-tert-butyl (1-(5-amino-6-bromo-3-(4-chloro-1-methyl-3-(methylsulfonamido)-1H-indazol-7-yl)pyridin-2-yl)-2-(3,5-difluorophenyl)ethyl) carbamate (47A)

A solution of 49A (225 mg, 0.37 mmol) in 5 mL of acetonitrile was cooled to 0° C. and treated with NBS (0.37 mmol) as a solution in 5 mL of acetonitrile. Check LC/MS until the reaction completed. The reaction mixture was partitioned with EtOAc and saturated aq NaHCO₃, then with brine. The organic layer were dried over MgSO4 and concentrated in vacuo. It was dried under high vacuum to afford the title compound. MS (m/z) 685 [M+H]⁺.

Synthesis of (S)-tert-butyl (1-(5-amino-3-(4-chloro-1-methyl-3-(methylsulfonamido)-1H-indazol-7-yl)-6-methylpyridin-2-yl)-2-(3,5-difluorophenyl)ethyl) carbamate (47B)

To a flask of 47A (255 mg, 0.37 mmol) in dioxane, K₂CO₃ (179 mg, 1.30 mmol), PdCl2(dppf) (27 mg, 0.037 mmol) and trimethyl boroxine (0.052 mL, 0.37 mmol) was added to the mixture. The reaction mixture was heated at 100° C. for 3 h. The reaction was cooled down and the solution partitioned between water and EtOAc. The aqueous phase was extracted with EtOAc and the combined extracts dried, filtered and concentrated in vacuo. The crude product was purified by flash chromatography to provide the title compound. MS (m/z) 621 [M+H]⁺.

Synthesis of N—((S)-1-(5-amino-3-(4-chloro-1-methyl-3-(methylsulfonamido)-1H-indazol-7-yl)-6-methylpyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (47C)

Compound 47C was prepared according to the method presented for the synthesis of compound 49C in Example 49 substituting 47B for 49A to provide title compound. ¹H NMR (400 MHz, methanol-d4) δ 7.23-7.00 (m, 1H), 7.00-6.70 (m, 3H), 6.47-6.17 (m, 3H), 4.79-4.66 (m, 3H), 3.36 (s, 2H), 3.24 (d, 3H), 3.12-2.84 (m, 3H), 2.52 (d, 3H), 2.46 (m, 2H), 1.40 (m, 1H), 1.07 (m, 1H). MS (m/z) 767 [M+H]⁺.

Example 48

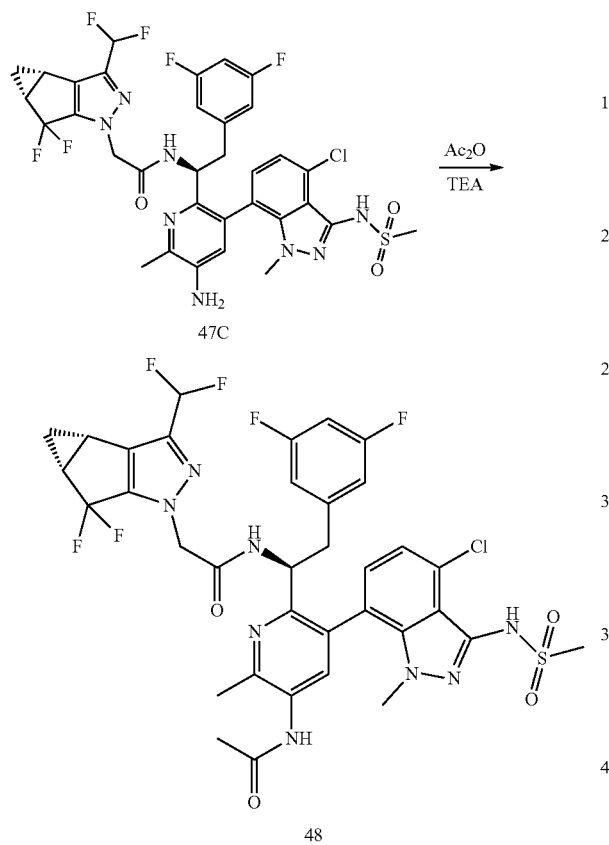

Synthesis of N—((S)-1-(5-acetamido-3-(4-chloro-1-methyl-3-(methylsulfonamido)-1H-indazol-7-yl)-6-methylpyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (48)

To a solution of 47C (12 mg, 0.016 mmol), triethylamine (0.044 mL, 0.313 mmol), and acetic anhydride (0.03 mL, 0.313 mmol) in DCM (1 mL) was stirred for overnight. NaOH (0.3 mL of 10% aq solution) and methanol (0.5 mL) were added to the solution. The reaction mixture was stirred at for 1 h. The mixture was filtered and the filtrate was purified on prep reverse phase HPLC using 20-80% B over 20 min (A=0.1% TFA/H₂O; B=0.1% TFA/Acetonitrile) to provide the title compound: ¹H NMR (400 MHz, Methanol-d4) δ 7.77 (d, 1H), 7.17-7.02 (m, 1H), 6.90-6.36 (m, 5H), 5.27-4.92 (m, 1H), 4.80-4.70 (m, 2H), 3.38 (s, 2H), 3.24 (d, 3H), 3.17-2.93 (m, 3H), 2.64 (d, 3H), 2.45 (ddd, 2H), 2.18 (d, 3H), 1.39 (m, 1H), 1.02 (m, 1H). MS (m/z) 809 [M+H]⁺.

Example 49

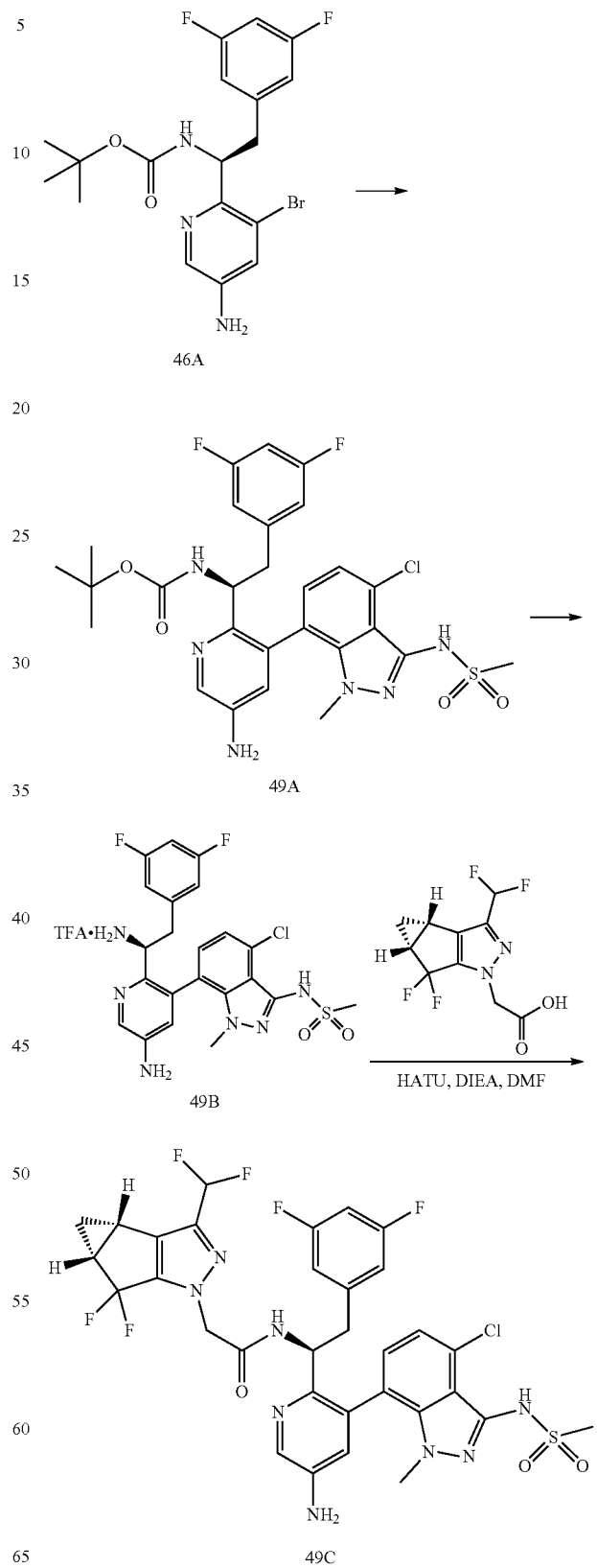

Synthesis of (S)-tert-butyl (1-(5-amino-3-(4-chloro-1-methyl-3-(methylsulfonamido)-1H-indazol-7-yl)pyridin-2-yl)-2-(3,5-difluorophenyl)ethyl)carbamate (49A)

In a microwave tube were charged with of (S)-tert-butyl (1-(5-amino-3-bromopyridin-2-yl)-2-(3,5-difluorophenyl)ethyl)carbamate (46A, 350 mg, 0.8 mmol), N-(4-chloro-1-methyl-7-(4,4,5,5-tetramethyl-1,3,2-dioxaborolan-2-yl)-1H-indazol-3-yl)methanesulfonamide (410 mg, 1.06 mmol) and $PdCl_2[P(Cy)_3]_2$ (18 mg, 0.025 mmol). To the mixture was added 16 mL of 1,4-dioxane and 4.9 mL of sodium bicarbonate aqueous solution (1M). The system was purged with argon and then the microwave tube was sealed and the reaction mixture was heated up in a heating bath at 150° C. for 1 hour. After cooling to room temperature, the reaction was partitioned between EtOAc and water. The organic layer was separated and washed with brine, then dried over $MgSO_4$, filtered and concentrated. The residue was purified by silica gel chromatography eluting with EtOAc/hexanes to afford the title product. MS (m/z): 606.88 $[M+H]^+$.

Synthesis of (S)—N-(7-(5-amino-2-(1-amino-2-(3,5-difluorophenyl)ethyl)pyridin-3-yl)-4-chloro-1-methyl-1H-indazol-3-yl)methanesulfonamide TFA salt (49B)

Compound 49A (60 mg) was dissolved in 2 mL of DCM and to it was added 0.3 mL of TFA. The reaction mixture was stirred at room temperature for 1 hour. The solvent was removed to afford the title product. MS (m/z): 507.00 $[M+H]^+$.

Synthesis of N—((S)-1-(5-amino-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (49C)

Compound 49B (60 mg, 0.1 mmol) was dissolved in 1 mL of DMF and cooled to 0° C. To it was added N,N-diisopropylethylamine (0.09 mL, 0.5 mmol) followed by a solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (26 mg, 0.1 mmol) and HATU (56.5 mg, 0.15 mmol) in 1 mL of DMF. To it was added 0.5 mL of ethanol and 0.1 mL of 15% NaOH aqueous solution and stirred for 5 min. The reaction mixture was acidified with 5% citric acid and then extracted with EtOAc. The organic layer was separated, dried over $Na_2SO_4$, filtered and concentrated. The residue was purified by RP-HPLC eluting with acetonitrile/$H_2O$ (with 0.1% TFA) to afford the title compound: $^1$H NMR (400 MHz, methanol-d4) δ 8.23 (dd, 1H), 7.09 (q, 1H), 6.97 (d, 1H), 6.83-6.53 (m, 2H), 6.37 (m, 2H), 6.17 (d, 1H), 4.80-4.66 (m, 3H), 3.38 (s, 2H), 3.06 (dd, 1H), 2.97 (d, 4H), 2.91 (m, 1H), 2.55-2.42 (m, 2H), 1.44-1.34 (m, 1H), 1.12-1.00 (m, 1H). MS (m/z) 753.14 $[M+H]^+$.

Examples 50 and 51

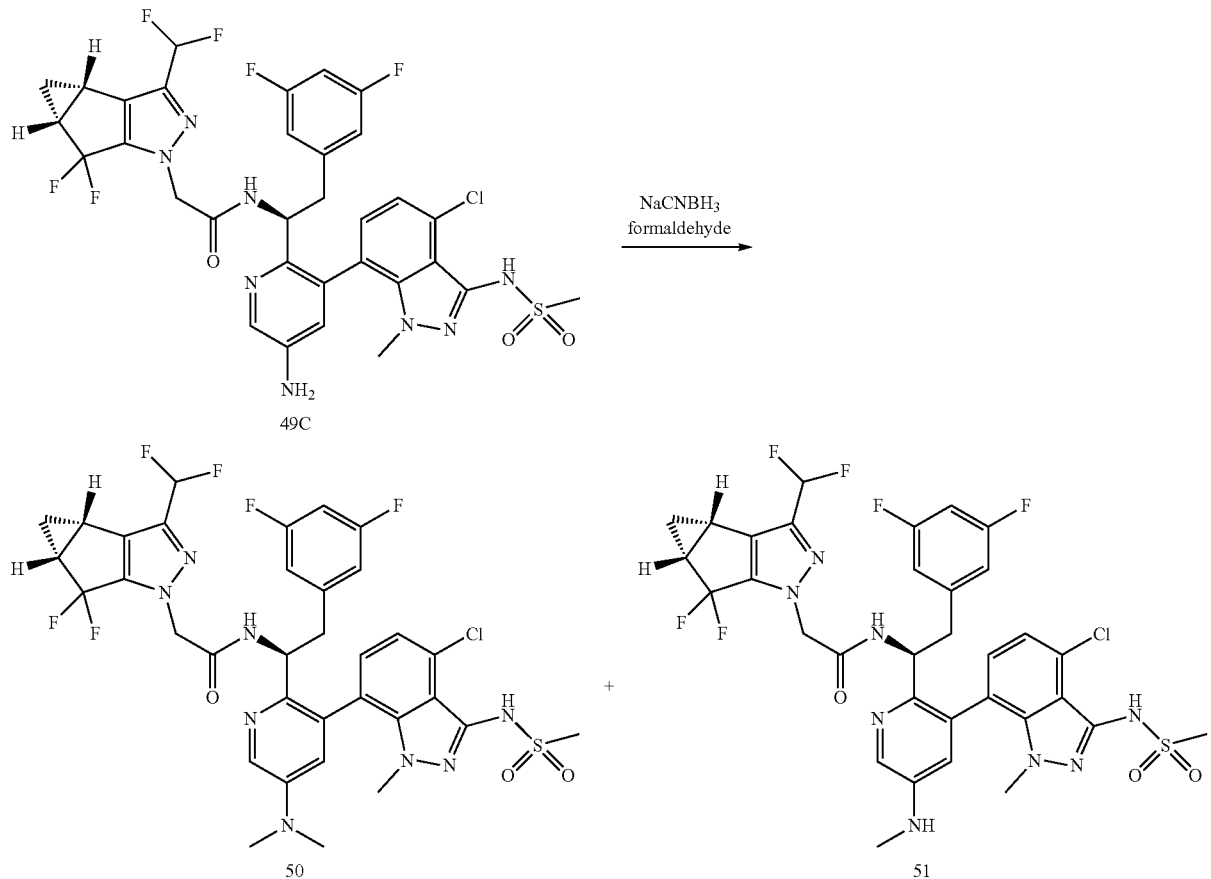

Synthesis of N—((S)-1-(3-(4-chloro-1-methyl-3-(methylsulfonamido)-1H-indazol-7-yl)-5-(dimethylamino)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50) and N—((S)-1-(3-(4-chloro-1-methyl-3-(methylsulfonamido)-1H-indazol-7-yl)-5-(methylamino)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (51)

Sodium cyanoborohydride (0.16 mL, 1M in THF) was added slowly at room temperature to a solution of N—((S)-1-(5-amino-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (49C, 39 mg, 0.052 mmol) and formaldehyde (0.04 mL, 37 percent in H₂O) in acetonitrile (0.5 ml). The mixture was stirred at room temperature for 15 min and it was basified with aqueous Na₂CO₃ and extracted with EtOAc. The organic layer was washed with water, dried over Na₂SO₄ and concentrated under reduced pressure. The residue was purified by RP-HPLC eluting with acetonitrile/H₂O (with 0.1% TFA) to afford the title compounds.

Compound 50: 3.3 mg. $^1$H NMR (400 MHz, methanol-d4) δ 8.28 (d, J=3.0 Hz, 1H), 7.18 (d, J=2.9 Hz, 1H), 7.06 (d, J=7.6 Hz, 1H), 6.89-6.52 (m, 2H), 6.41 (m, 3H), 4.82-4.64 (m, 3H), 3.41 (s, 3H), 3.23 (s, 3H), 3.19-2.83 (m, 8H), 2.46 (m, 2H), 1.38 (m, 1H), 1.02 (m, 1H). MS (m/z): 781.34 [M+H]$^+$.

Compound 51: 1.4 mg. $^1$H NMR (400 MHz, methanol-d4) δ 8.17 (d, J=2.8 Hz, 1H), 7.02 (d, J=7.6 Hz, 1H), 6.89 (d, J=2.8 Hz, 1H), 6.85-6.48 (m, 2H), 6.44-6.34 (m, 2H), 6.29 (d, J=7.6 Hz, 1H), 4.78-4.53 (m, 3H), 3.41 (s, 3H), 3.23 (s, 3H), 3.16-2.88 (m, 2H), 2.82 (s, 3H), 2.61-2.33 (m, 2H), 1.38 (m, 1H), 1.17-0.72 (m, 1H). MS (m/z): 767.06 [M+H]$^+$.

Example 52

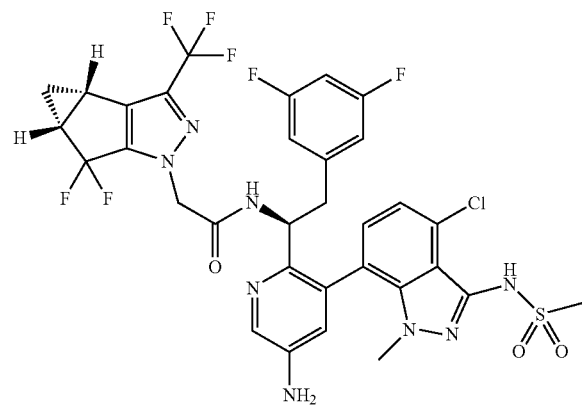

52

Synthesis of N—((S)-1-(5-amino-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (52)

Compound 52 was prepared according to the method presented in the synthesis of Example 49D substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, methanol-d4) δ 8.21 (m, 1H), 7.35-7.14 (m, 1H), 7.15-6.95 (m, 1H), 6.88-6.57 (m, 1H), 6.54-5.94 (m, 3H), 5.06 (dd, J=9.7, 5.6 Hz, 1H), 4.83-4.65 (m, 2H), 3.51-2.73 (m, 8H), 2.63-2.30 (m, 2H), 1.42 (m, 1H), 1.26-0.75 (m, 1H). MS (m/z): 771.11 [M+H]$^+$.

Example 53

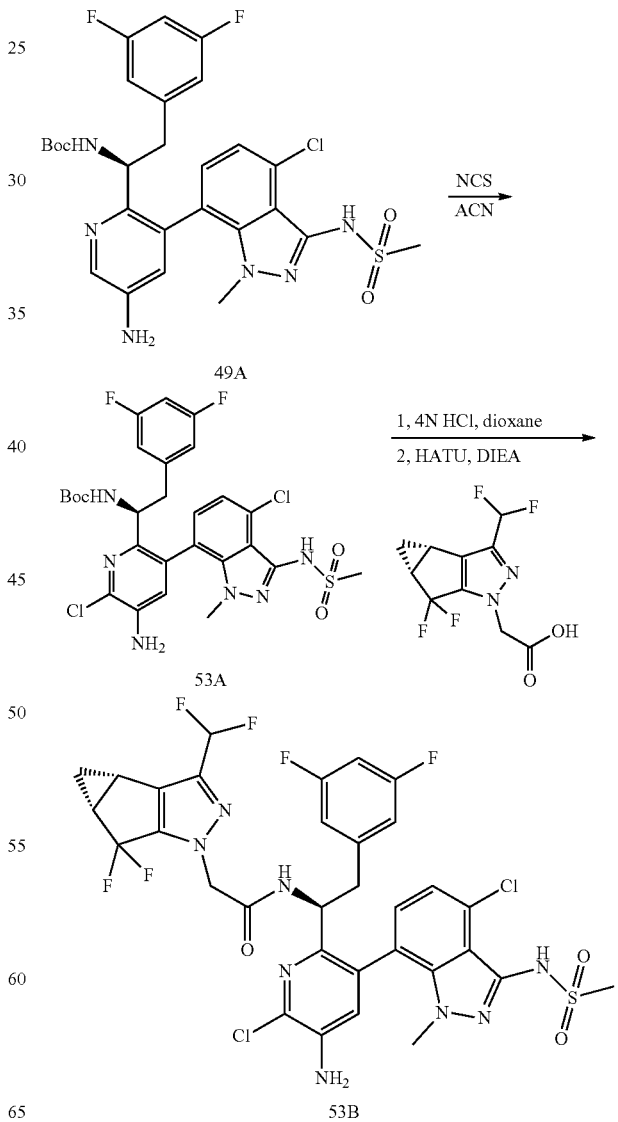

Synthesis of (S)-tert-butyl (1-(5-amino-6-chloro-3-(4-chloro-1-methyl-3-(methylsulfonamido)-1H-indazol-7-yl)pyridin-2-yl)-2-(3,5-difluorophenyl)ethyl) carbamate (53A)

A solution of 49A (300 mg, 0.49 mmol) in 5 mL of acetonitrile was cooled to 0° C. and treated with NCS (0.49 mmol). The reaction was heated to 60° C. overnight. The reaction mixture was partitioned with EtOAc and aqueous saturated NaHCO$_3$, then washed with brine. The organic layer were dried over MgSO$_4$ and concentrated in vacuo. The crude product was purified by flash chromatography to provide the title compound. MS (m/z) 641 [M+H]$^+$.

Synthesis of N—((S)-1-(5-amino-6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (53B)

Compound 53B was prepared according to the method presented for the synthesis of compound 49C in Example 49 substituting 53A for 49A to provide the title compound: $^1$H NMR (400 MHz, methanol-d4) δ 7.17-6.94 (m, 2H), 6.87-6.54 (m, 2H), 6.53-6.19 (m, 3H), 4.96 (s, 1H), 4.72 (dd, 2H), 3.41 (s, 2H), 3.24 (d, 3H), 3.16-2.88 (m, 3H), 1.38 (dt, 1H), 1.13-0.99 (m, 1H). MS (m/z) 787 [M+H]$^+$.

Example 54

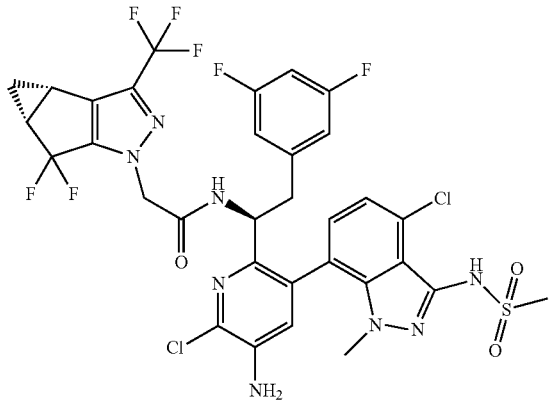

Synthesis of N—((S)-1-(5-amino-6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (54)

Compound 54 was prepared from compound 53A according to the method presented for the synthesis of Example 49 substituting 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid for 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid to provide 13 mg of title compound: $^1$H NMR (400 MHz, Methanol-d4) δ 7.12-6.94 (m, 2H), 6.81-6.60 (m, 1H), 6.55-6.35 (m, 2H), 6.25 (d, 1H), 5.01-4.90 (m, 1H), 4.76 (t, 2H), 3.41 (s, 2H), 3.24 (d, 3H), 3.15-2.88 (m, 3H), 2.48 (q, 2H), 1.47-1.38 (m, 1H), 1.16-1.04 (m, 1H). MS (m/z) 805 [M+H]$^+$.

Example 55

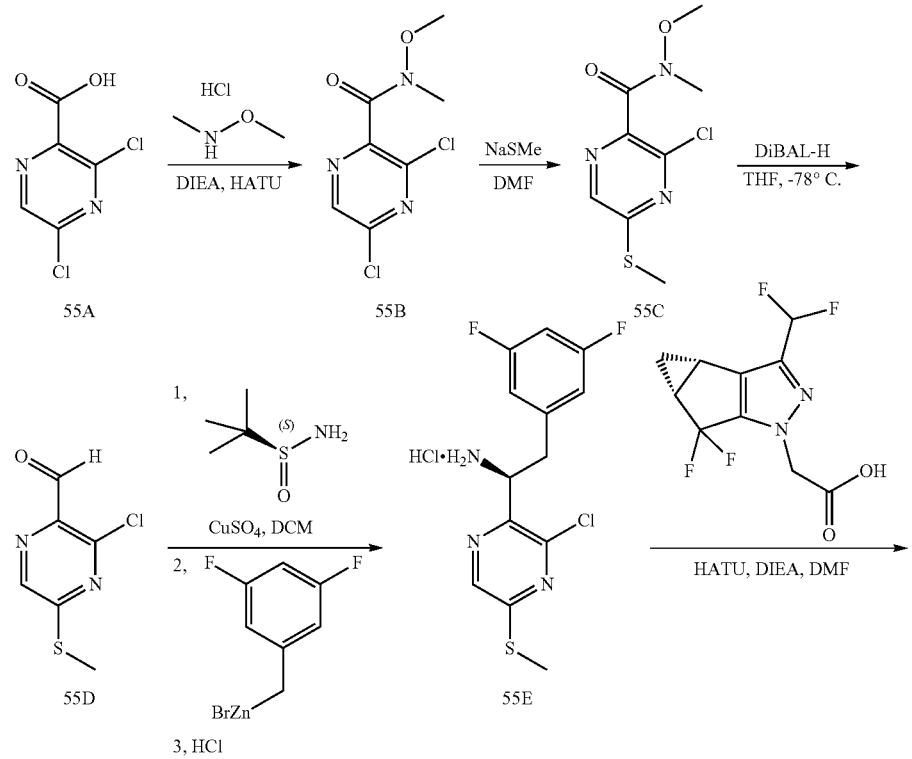

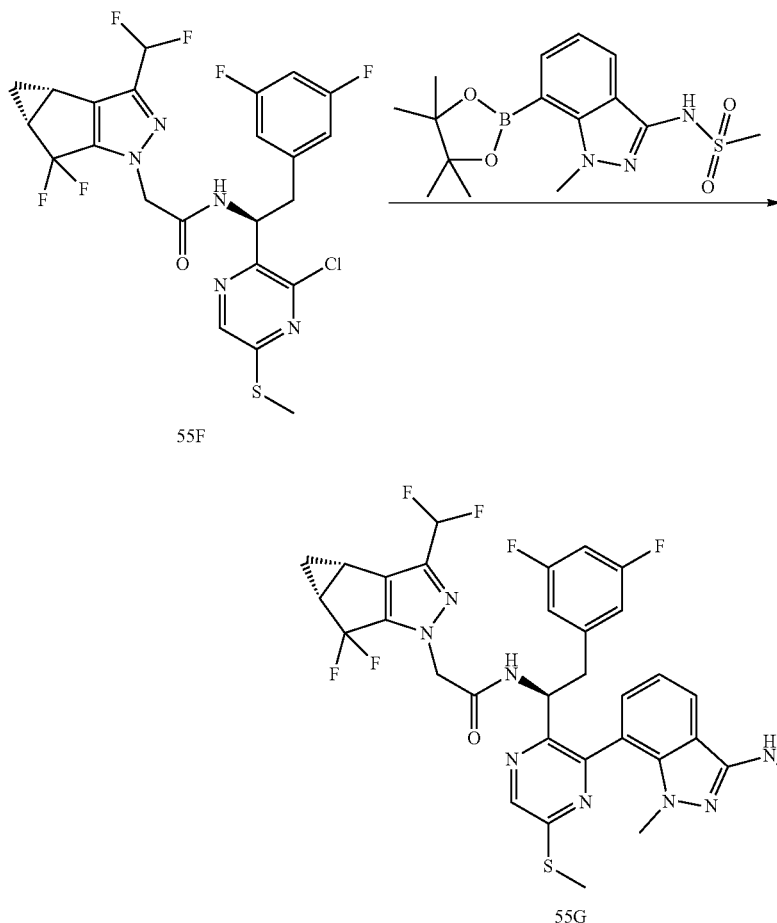

Synthesis of 3,5-dichloro-N-methoxy-N-methylpyrazine-2-carboxamide (55B)

To a solution of 55A (10 g, 51.82 mmol) and HATU (21.67 g, 57 mmol) in DMF (50 mL), DIEA (19.86 mL, 114 mmol) was added. After 30 minutes, N,O-dimethylhydroxylamine hydrochloride (6.09 g, 62.18 mmol) was added to the solution. The mixture was stirred for overnight. Water (300 mL) was added and extracted with EtOAc three times (100 mL). The crude product purified by flash chromatography to afford the desired product. MS (m/z) 236 [M+H]$^+$.

Synthesis of 3-chloro-N-methoxy-N-methyl-5-(methylthio)pyrazine-2-carboxamide (55C)

To a solution of 55B (2 g, 8.47 mmol) in DMF (10 mL), 1 eq. of sodium methanethiolate was added to the solution. After 5 hours, 0.5 eq. of sodium methanethiolate was added to the suspension. The reaction was stirred overnight then diluted with EtOAc and washed with NaHCO$_3$ (aq) and brine. The organic layer was concentrated and purified by flash chromatography to provide the title compound. MS (m/z) 248 [M+H]$^+$.

Synthesis of 3-chloro-5-(methylthio)pyrazine-2-carbaldehyde (55D)

To a solution of 55C (750 mg, 3.03 mmol) in THF at 78° C., DIBAL-H (3.33 mL, 3.33 mmol) in toluene was added to the solution slowly. Then, it was stirred for 2 hours at 78° C. HCl (4 mL, 1 N) was added to the solution and warmed to 0° C. The mixture was stirred for 20 minutes at 0° C. then extracted with EtOAc twice. The organic layer was dried and concentrated to provide the crude product which was used without further purification. MS (m/z) 189 [M+H]$^+$.

Synthesis of (S)—N—((S)-1-(3-chloro-5-(methylthio)pyrazin-2-yl)-2-(3,5-difluorophenyl)ethyl)-2-methylpropane-2-sulfinamide (55E)

Compound 55E was prepared according to the method presented for the synthesis of Example 30 substituting 3-chloro-5-(methylthio)pyrazine-2-carbaldehyde for 30B to provide the title compound. MS (m/z) 420 [M+H]$^+$.

Synthesis of N—((S)-1-(3-chloro-5-(methylthio)pyrazin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (55F)

Compound 55F was prepared according to the method presented in the synthesis of Example 30 substituting 55E for 30I to provide the title compound. MS (m/z) 562 [M+H]$^+$.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-5-(methylthio)pyrazin-2-yl)ethyl)acetamide (55G)

Compound 55G was prepared according to the method presented in the synthesis of Example 30 substituting 55F for 30E and N-(1-methyl-7-(4,4,5,5-tetramethyl-1,3,2-dioxaborolan-2-yl)-1H-indazol-3-yl)methanesulfonamide for 30F to provide the title compound: $^1$H NMR (400 MHz, methanol-d4) δ 8.68 (d, 1H), 7.98-7.76 (m, 1H), 7.56-7.38 (m, 1H), 7.33-7.08 (m, 1H), 6.89-6.50 (m, 3H), 6.30 (s, 1H), 5.65-5.41 (m, 1H), 4.85 (d, 2H), 3.62 (d, 1H), 3.35 (d, 1H), 3.23-2.93 (m, 5H), 2.60-2.32 (m, 4H), 2.00-1.75 (m, 2H), 1.41-1.31 (m, 1H), 1.01 (m, 1H). MS (m/z) 751 [M+H]$^+$.

The title compound (56) was prepared according to the method presented for the synthesis of compound 57G of Example 57 utilizing 2-((3bS,4aR)-5,5-difluoro-3-(trifluoromethyl)-3b,4,4a,5-tetrahydro-1H-cyclopenta[3,4]cyclopenta[1,2-c]pyrazol-1-yl)acetic acid (30J) and 2-aminoethanol. $^1$H NMR (400 MHz, methanol-d$_4$) δ 7.53 (m, 1H), 7.16-6.22 (m, 6H), 5.13 (m, 1H), 4.95-4.88 (m, 4H), 3.86-3.81 (m, 2H), 3.72-3.56 (m, 2H), 3.48-3.47 (m, 2H), 3.24 (m, 3H), 3.18-3.11 (m, 2H), 3.02-2.90 (m, 1H), 2.69 (m, 2H), 2.55-2.42 (m, 2H), 1.44-1.38 (m, 1H), 1.10 (m, 1H). MS (m/z) 815.15 [M+H]$^+$.

Example 56

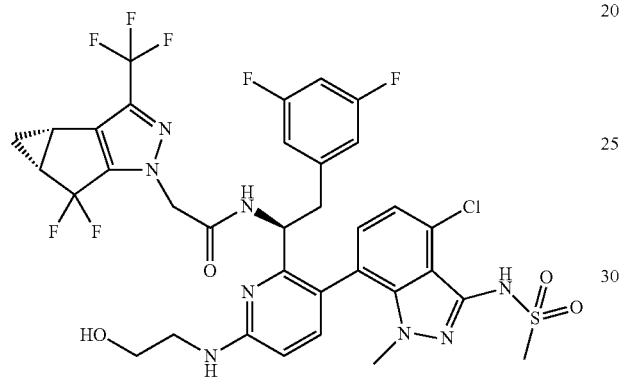

Example 57

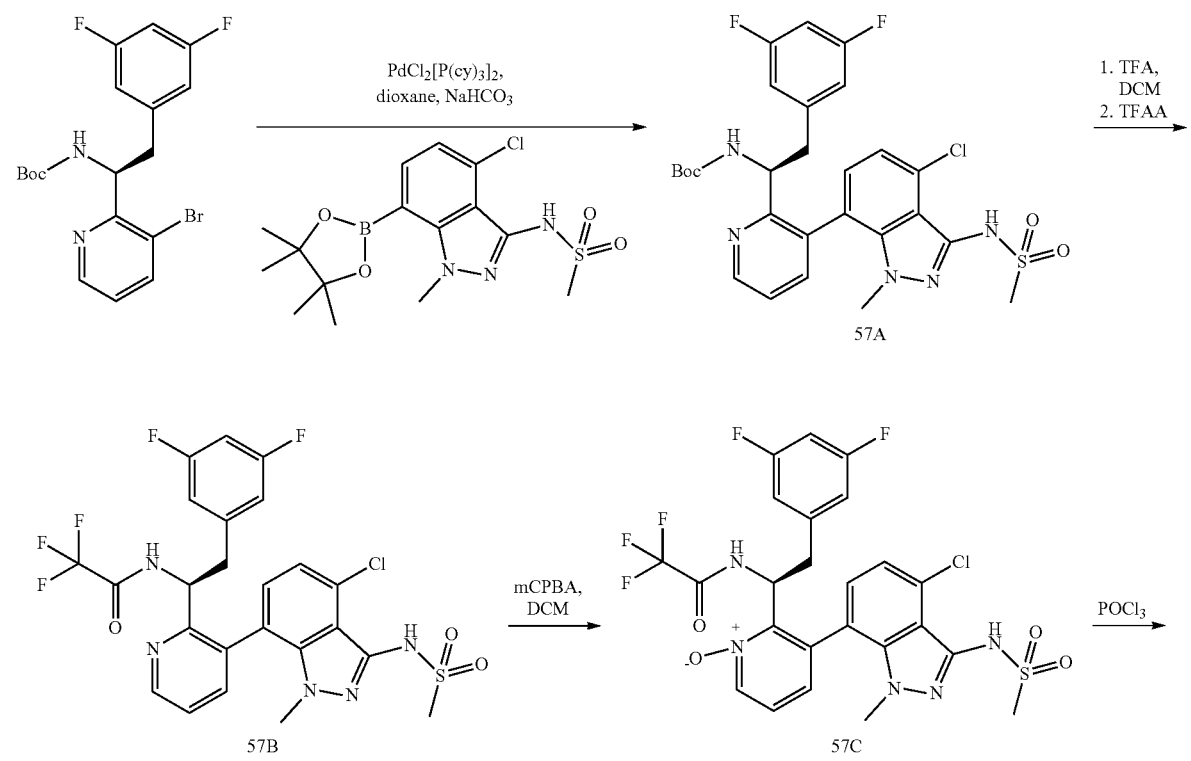

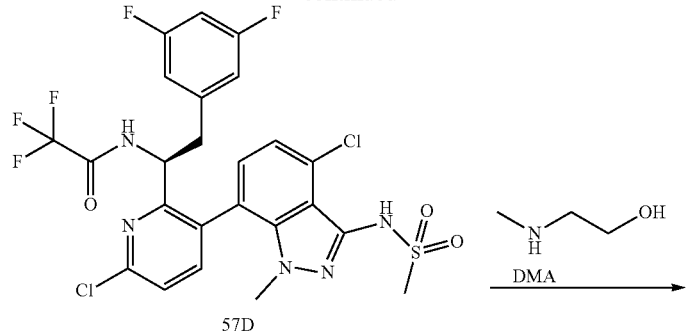
57D
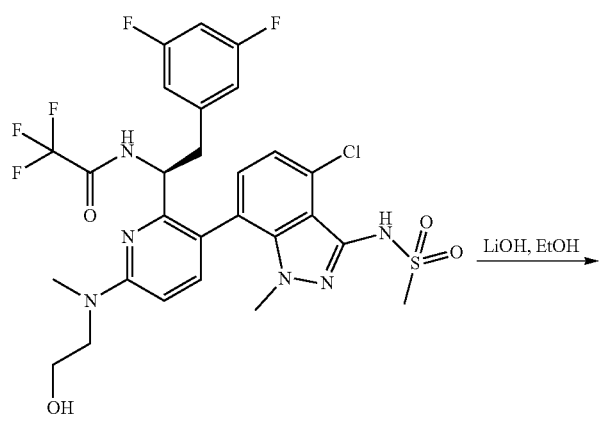
57E
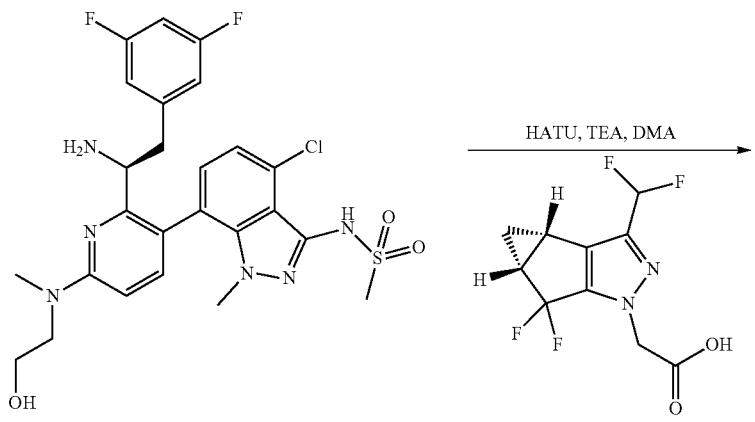
57F
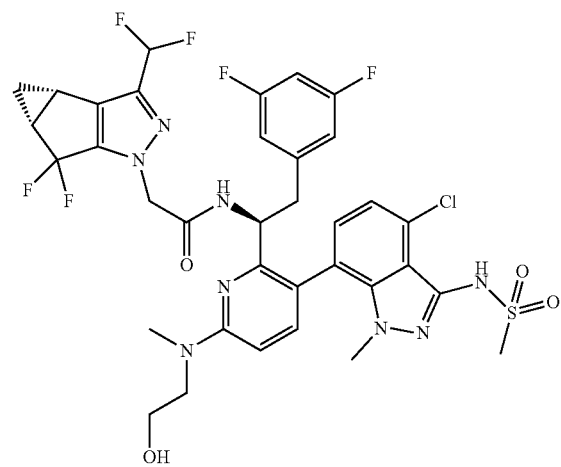
57G

Synthesis of (S)-tert-butyl (1-(3-(4-chloro-1-methyl-3-(methylsulfonamido)-1H-indazol-7-yl)pyridin-2-yl)-2-(3,5-difluorophenyl)ethyl)carbamate (57A)

(S)-tert-butyl (1-(3-bromopyridin-2-yl)-2-(3,5-difluorophenyl)ethyl)carbamate (1.0 g, 2.42 mmol), N-(4-chloro-1-methyl-7-(4,4,5,5-tetramethyl-1,3,2-dioxaborolan-2-yl)-1H-indazol-3-yl)methanesulfonamide (1.12 g, 2.90 mmol), and PdCl$_2$[P(cy)$_3$]$_2$ (89.0 mg, 0.121 mmol) were suspended in 1,4-dioxane (108 mL) and 1.0 M aqueous NaHCO$_3$ (36 mL). The reaction mixture was degassed by bubbling argon for 5 minutes then sealed and heated 150° C. for 15 minutes in a microwave reactor. Upon cooling, the reaction mixture was diluted with water and extracted with three portions of EtOAc. The combined organic layers were dried over Na$_2$SO$_4$, filtered, concentrated in vacuo, and purified by silica gel column chromatography, eluting with 0-100% EtOAc in hexanes to give the title compound. MS (m/z) 591.72 [M+H]$^+$.

Synthesis of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (57B)

To (S)-tert-butyl (1-(3-(4-chloro-1-methyl-3-(methylsulfonamido)-1H-indazol-7-yl)pyridin-2-yl)-2-(3,5-difluorophenyl)ethyl)carbamate (57A, 3.39 g, 5.73 mmol) in DCM (5 mL) was added trifluoroacetic acid (5 mL). The reaction mixture was stirred at room temperature for 2.5 hours. Upon complete removal of the Boc protecting group, trifluoroacetic anhydride (2.02 mL, 14.31 mmol) was added. The reaction mixture was stirred at room temperature for 30 minutes. Upon completion, the reaction mixture was filtered through celite, concentrated in vacuo, taken in EtOAc, and carefully neutralized with 1M aqueous NaHCO$_3$ until the aqueous layer was at pH 10. The organic layer was collected and the aqueous layer extracted once more with EtOAc. The combined organic layers were dried over Na$_2$SO$_4$, filtered, concentrated in vacuo, and purified by silica gel column chromatography, eluting with 0-100% EtOAc in hexanes to give the title compound. MS (m/z) 588.14 [M+H]$^+$.

Synthesis of (S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (57C)

To a solution of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (57B, 8.0 g, 13.61 mmol) in DCM (70 mL) was added mCPBA (3.659 g, 16.33 mmol) in 4 portions over a 15 minute period. The reaction mixture was stirred at room temperature for 16 hours. Upon completion, the reaction was quenched with 1M aqueous NaHSO$_3$ and saturated aqueous NaHCO$_3$. The organic layer was collected and the aqueous layer was extracted an additional time with DCM. The combined organic layers were dried over Na$_2$SO$_4$, filtered, concentrated in vacuo, and purified by silica gel column chromatography, eluting with 50-100% EtOAc in hexanes to give the title compound. MS (m/z) 604.10 [M+H]$^+$.

Synthesis of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (57D)

(S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (57C, 1.0 g, 1.66 mmol) was treated with POCl$_3$ (2.32 mL, 24.84 mmol). The reaction mixture was stirred at 115° C. for 2 hours. Upon cooling, the reaction was concentrated in vacuo, taken in DCM, and vigorously stirred with saturated aqueous NaHCO$_3$ for 1 hour. The organic layer was collected, and the aqueous layer was extracted an additional time with DCM. The combined organic layers were dried over Na$_2$SO$_4$, filtered, concentrated in vacuo, and purified by silica gel column chromatography, eluting with 0-100% EtOAc in hexanes to give the title compound. MS (m/z) 622.13 [M+H]$^+$.

Synthesis of (S)—N-(1-(3-(4-chloro-1-methyl-3-(methylsulfonamido)-1H-indazol-7-yl)-6-((2-hydroxyethyl)(methyl)amino)pyridin-2-yl)-2-(3,5-difluorophenyl)ethyl)-2,2,2-trifluoroacetamide (57E)

To a solution of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (57D, 50 mg, 0.08 mmol) in DMA (1 mL) was added 2-(methylamino)ethanol (64.5 µL, 0.803 mmol). The reaction mixture was heated to 150° C. for 2 hours. The crude mixture was concentrated in vacuo and used without further purification. MS (m/z) 661.16 [M+H]$^+$.

Synthesis of (S)—N-(7-(2-(1-amino-2-(3,5-difluorophenyl)ethyl)-6-((2-hydroxyethyl)(methyl)amino)pyridin-3-yl)-4-chloro-1-methyl-1H-indazol-3-yl)methanesulfonamide (57F)

To a solution of crude (S)—N-(1-(3-(4-chloro-1-methyl-3-(methylsulfonamido)-1H-indazol-7-yl)-6-((2-hydroxyethyl)(methyl)amino)pyridin-2-yl)-2-(3,5-difluorophenyl)ethyl)-2,2,2-trifluoroacetamide (57E) in EtOH (1 mL) was added aqueous 2M lithium hydroxide (0.4 mL). The reaction was heated at 130° C. in a microwave reactor for 5 minutes. Upon cooling, aqueous 2N HCl was added until the solution became slightly acidic (pH 4-5). The reaction mixture was then concentrated and taken up in equal volumes of EtOAc and saturated aqueous NaHCO$_3$. The organic layer was collected and the aqueous layer was extracted with a second volume of EtOAc. The combined organic layers were dried over Na$_2$SO$_4$, filtered, concentrated in vacuo, and used without further purification. MS (m/z) 565.09 [M+H]$^+$.

Synthesis of N—((S)-1-(3-(4-chloro-1-methyl-3-(methylsulfonamido)-1H-indazol-7-yl)-6-((2-hydroxyethyl)(methyl)amino)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (57G)

To a solution of crude (S)—N-(7-(2-(1-amino-2-(3,5-difluorophenyl)ethyl)-6-((2-hydroxyethyl)(methyl)amino)pyridin-3-yl)-4-chloro-1-methyl-1H-indazol-3-yl)methanesulfonamide (57F, 10 mg, 0.018 mmol assuming 100% purity) in DMA (0.5 mL) was added triethylamine (7.4 µL, 0.053 mmol), followed by 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (3.7 mg, 0.014 mmol) and HATU (3.4 mg, 0.009 mmol). After stirring for 5 minutes, additional HATU (3.4 mg, 0.009 mmol) was added. After stirring for an additional 5 minutes, the reaction mixture was filtered and purified by reverse phase HPLC, eluting with 5-100% acetonitrile in water with 0.1% TFA. Fractions containing the product were pooled and lyophilized to provide the TFA salt of the product. $^1$H NMR (400 MHz, methanol-$d_4$) δ 7.49-6.22 (m, 8H), 5.23-5.08 (m, 1H), 4.82-4.70 (m, 2H), 4.06-3.67 (m, 3H), 3.44 (s, 2H), 3.28-3.08 (m, 9H), 2.97 (s, 1H), 2.56-2.41 (m, 2H), 1.47-1.33 (m, 1H), 1.13-0.98 (m, 1H). MS (m/z) 811.16 [M+H]$^+$.

romethyl)-3b,4,4a,5-tetrahydro-1H-cyclopropa[3,4]cyclopenta[1,2-c]pyrazol-1-yl)acetic acid (30J). $^1$H NMR (400 MHz, Methanol-$d_4$) δ 7.43-6.05 (m, 7H), 5.18-5.09 (m, 1H), 4.85-4.75 (m 2H), 4.04-3.69 (m, 3H), 3.42 (s, 2H), 3.27-3.20 (m, 6H), 3.20-3.11 (m, 2H), 3.05 (s, 1H), 2.95 (s, 1H), 2.61-2.43 (m, 2H), 1.51-1.35 (m, 1H), 1.11 (m, 1H). MS (m/z) 829.20 [M+H]$^+$.

Example 58

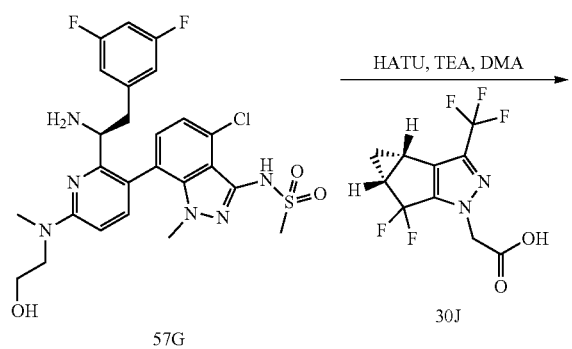

Example 59

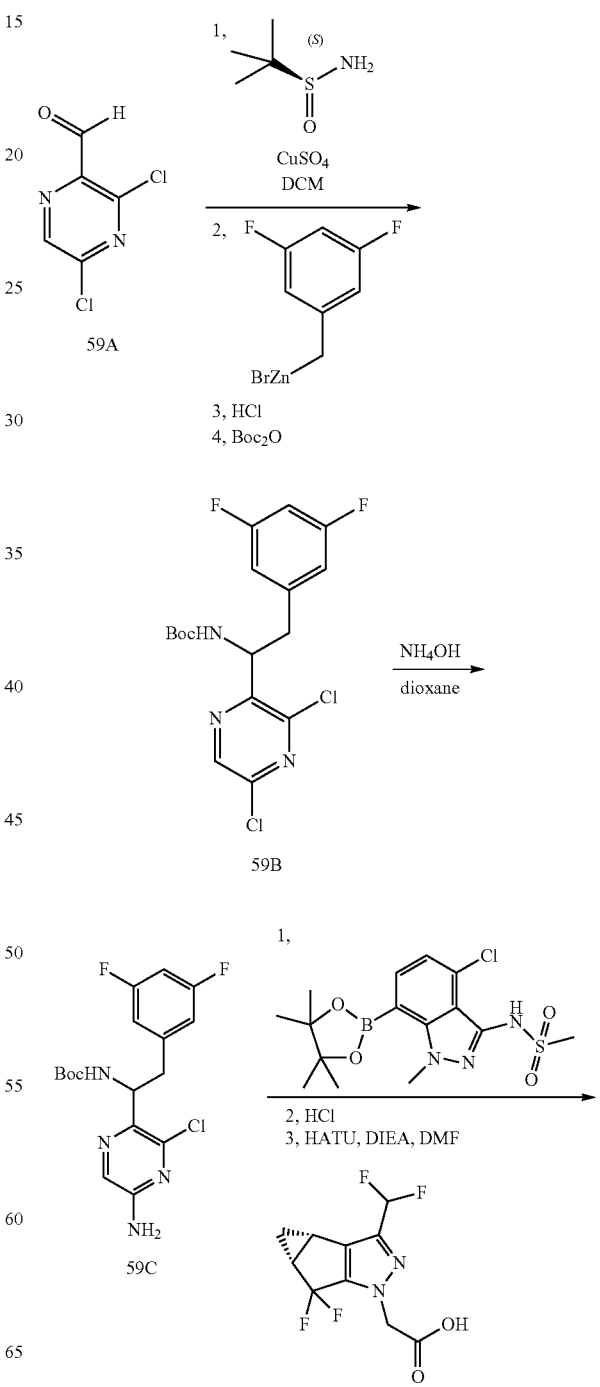

Synthesis of N—((S)-1-(3-(4-chloro-1-methyl-3-(methylsulfonamido)-1H-indazol-7-yl)-6-((2-hydroxyethyl)(methyl)amino)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamide (58)

The title compound (58) was prepared according to the method presented for the synthesis of compound 57G of Example 57 utilizing 2-((3bS,4aR)-5,5-difluoro-3-(trifluo-

141

-continued

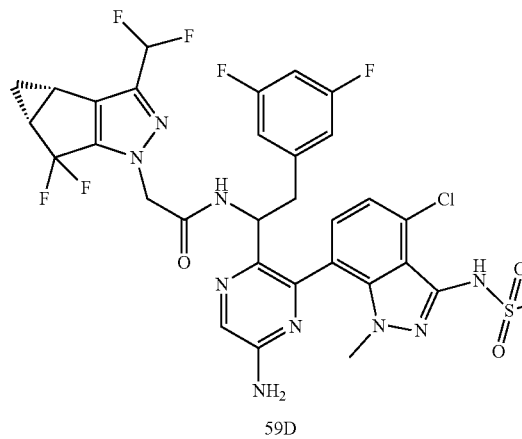

59D

Synthesis of tert-butyl (1-(3,5-dichloropyrazin-2-yl)-
2-(3,5-difluorophenyl)ethyl)carbamate (59B)

Compound 59B was prepared according to the method presented for the synthesis of compound 30E in Example 30 substituting 3,5-dichloropyrazine-2-carbaldehyde for 30B to provide 59B. MS (m/z) 404 [M+H]$^+$.

Synthesis of tert-butyl (1-(5-amino-3-chloropyrazin-2-yl)-2-(3,5-difluorophenyl)ethyl)carbamate (59C)

In a high pressure reaction vessel, a suspension of 59B (300 mg, 0.742 mmol) in dioxane (2 mL) was treated with ammonium hydroxide (28%) (3 mL) and heated at 90° C. overnight. Solvents were removed and the crude was purified by flash chromatography to provide the title compound: $^1$H NMR (400 MHz, methanol-d4) δ 8.17 (d, 1H), 7.33-6.97 (m, 2H), 6.84-6.31 (m, 4H), 5.25 (m, 1H), 4.65 (s, 1H), 3.42 (d, 2H), 3.27-2.96 (m, 6H), 2.47 (m, 2H), 1.38 (m, 1H), 1.05 (m, 1H). MS (m/z) 385 [M+H]$^+$.

Synthesis of N-(1-(5-amino-3-(4-chloro-1-methyl-3-(methylsulfonamido)-1H-indazol-7-yl)pyrazin-2-yl)-
2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (59D)

Compound 59D was prepared according to the method presented for the synthesis of Example 30 substituting 59C for 30E and N-(4-chloro-1-methyl-7-(4,4,5,5-tetramethyl-1,3,2-dioxaborolan-2-yl)-1H-indazol-3-yl)methanesulfonamide for 30F to provide the title compound. MS (m/z) 754 [M+H]$^+$.

142

Example 60

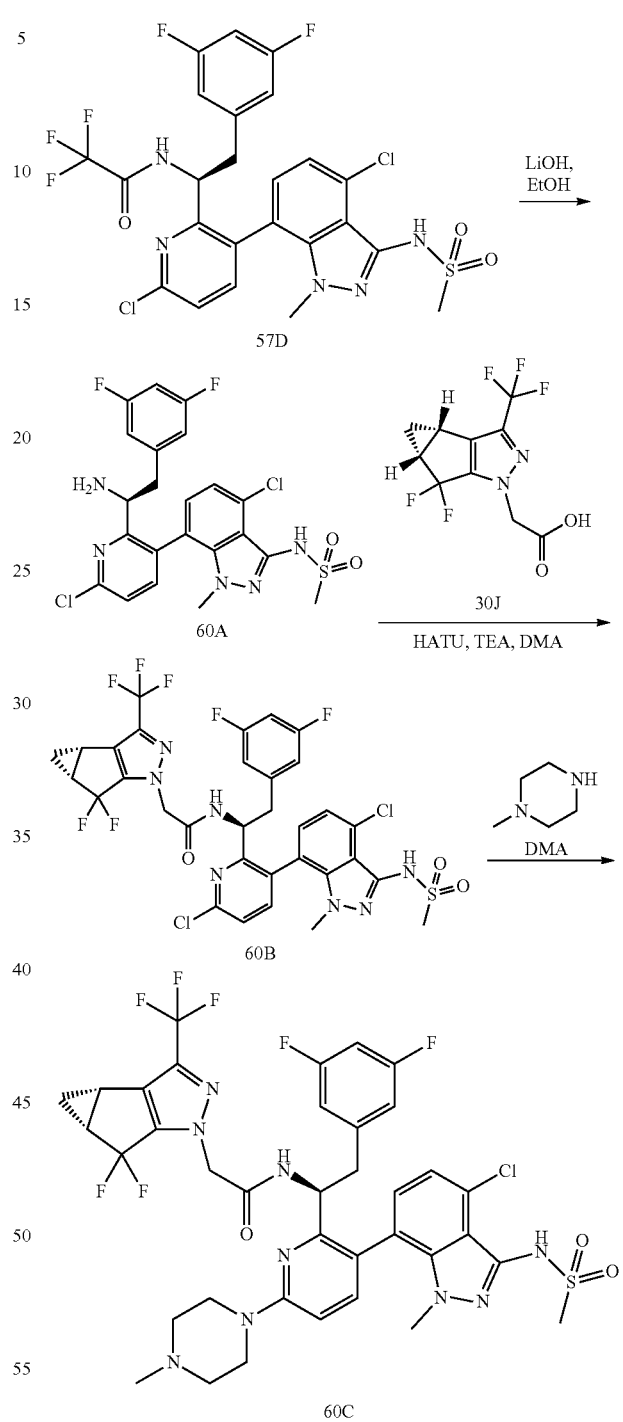

Synthesis of (S)—N-(7-(2-(1-amino-2-(3,5-difluorophenyl)ethyl)-6-chloropyridin-3-yl)-4-chloro-1-methyl-1H-indazol-3-yl)methanesulfonamide (60A)

To a solution of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (57D, 870 mg, 1.40 mmol) in EtOH (16 mL) was added 2M aqueous LiOH (7.0 mL, 13.98 mmol). The reaction was heated in a microwave reactor at 130° C. for 10 minutes. Upon cooling, the reaction mixture was acidified with 2N aqueous HCl until at pH 5. The reaction mixture was then concentrated in vacuo and taken in EtOAc. To the solution was added saturated aqueous NaHCO₃ until the aqueous layer was at pH 10. The organic layer was collected, and the aqueous layer was extracted an additional time with EtOAc. The combined organic layers were dried over Na₂SO₄, filtered, concentrated in vacuo, and used without further purification. MS (m/z) 526.06 [M+H]⁺.

Synthesis of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60B)

To a solution of crude (S)—N-(7-(2-(1-amino-2-(3,5-difluorophenyl)ethyl)-6-chloropyridin-3-yl)-4-chloro-1-methyl-1H-indazol-3-yl)methanesulfonamide (60A, 400 mg, 0.76 mmol) in DMA (6 mL) was added triethylamine (0.32 mL, 2.28 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (30J, 0.61 mmol), then HATU (173.4 mg, 0.46 mmol). The reaction mixture was stirred at room temperature for 15 minutes, then additional HATU (86.7 mg, 0.23 mmol) was added. The reaction mixture was stirred at room temperature for an additional 15 minutes. Upon completion, the reaction mixture was concentrated in vacuo and purified by silica gel column chromatography, eluting with 0-100% EtOAc in hexanes to give the title compound (60B). MS (m/z) 790.05 [M+H]⁺.

Synthesis of N—((S)-1-(3-(4-chloro-1-methyl-3-(methylsulfonamido)-1H-indazol-7-yl)-6-(4-methylpiperazin-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (60C)

To a solution of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (60B, 20 mg, 0.025 mmol) in DMA (0.5 mL) was added 1-methylpiperazine (28 µL, 0.253 mmol). The reaction mixture was heated at 130° C. for 3 hours. Upon cooling, the reaction mixture was filtered and purified by reverse phase HPLC, eluting with 5-100% acetonitrile in water with 0.1% TFA. Fractions containing the product were pooled and lyophilized to provide the TFA salt of the product. ¹H NMR (400 MHz, methanol-d₄) δ 8.47 (dd, J=45.5, 8.5 Hz, 1H), 7.53 (dd, J=14.6, 8.6 Hz, 1H), 7.16-6.22 (m, 7H), 4.95-4.88 (m, 1H), 4.83-4.67 (m, 5H), 3.79-3.62 (m, 2H), 3.38 (s, 2H), 3.27-3.20 (m, 4H), 3.20-3.11 (m, 1H), 3.07-3.02 (m, 4H), 3.02-2.90 (m, 1H), 2.62-2.41 (m, 2H), 1.51-1.37 (m, 1H), 1.10 (d, J=31.7 Hz, 1H). MS (m/z) 854.21 [M+H]⁺.

Example 61

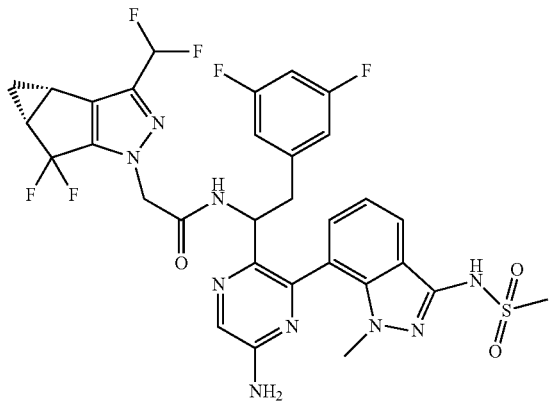

Synthesis of N-(1-(5-amino-3-(1-methyl-3-(methylsulfonamido)-1H-indazol-7-yl)pyrazin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (61)

Compound 61 was prepared according to the method presented in the synthesis of Example 59 substituting N-(1-methyl-7-(4,4,5,5-tetramethyl-1,3,2-dioxaborolan-2-yl)-1H-indazol-3-yl)methanesulfonamide for N-(4-chloro-1-methyl-7-(4,4,5,5-tetramethyl-1,3,2-dioxaborolan-2-yl)-1H-indazol-3-yl)methanesulfonamide to provide 17 mg of title compound: ¹H NMR (400 MHz, methanol-d4) 8.19 (d, 1H), 7.83 (d, 1H), 7.43-6.97 (m, 2H), 6.91-6.24 (m, 5H), 5.29 (m, 1H), 4.66 (m, 1H), 3.42 (d, 2H), 3.26-2.94 (m, 6H), 2.59-2.37 (m, 2H), 1.38 (m, 1H), 1.05 (m, 1H). MS (m/z) 720 [M+H]⁺

Example 62

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:
1. A compound of formula I:

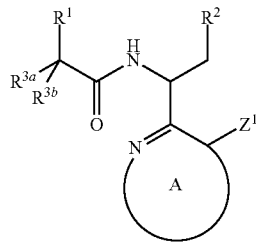

wherein:
A is

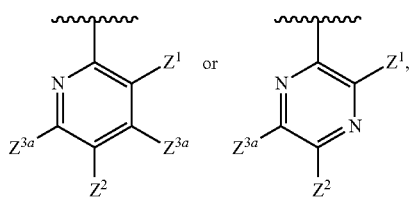

wherein each $Z^{3a}$ is independently selected from H or $Z^3$;

$R^1$ is a bicyclic-heteroaryl or tricyclic-heteroaryl, wherein the bicyclic-heteroaryl or tricyclic-heteroaryl has 4-9 carbon atoms and 1-5 heteroatoms selected from nitrogen, sulfur, and oxygen, and wherein the bicyclic-heteroaryl or tricyclic-heteroaryl of $R^1$ is optionally substituted with 1, 2, 3, 4, or 5 $Z^4$ groups;

$R^2$ is phenyl optionally substituted with 1, 2, or 3 $Z^5$ groups;

each $R^{3a}$ and $R^{3b}$ is independently selected from H, halogen, $(C_1-C_3)$alkyl, and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is phenyl, monocyclic-heteroaryl or bicyclic-heterocycle, wherein the monocyclic-heteroaryl or bicyclic-heterocycle has 4-8 carbon atoms and 1-3 heteroatoms and, wherein any phenyl, monocyclic-heteroaryl or bicyclic-heterocycle of $Z^1$ is optionally substituted with 1, 2, 3, 4, or 5 $Z^{1a}$ or $Z^{1b}$;

each $Z^{1a}$ is independently selected from halogen, —CN, —$OR_{n1}$, —$OC(O)R_{p1}$, —$OC(O)NR_{q1}R_{r1}$, —$SR_{n1}$, —$S(O)R_{p1}$, —$S(O)_2OH$, —$S(O)_2R_{p1}$, —$S(O)_2NR_{q1}R_{r1}$, —$NR_{q1}R_{r1}$, —$NR_{n1}COR_{p1}$, —$NR_{n1}CO_2R_{p1}$, —$NR_{n1}CONR_{q1}R_{r1}$, —$NR_{n1}S(O)_2R_{p1}$, —$NR_{n1}S(O)_2OR_{p1}$, —$NR_{n1}S(O)_2NR_{q1}R_{r1}$, $NO_2$, —$C(O)R_{n1}$, —$C(O)OR_{n1}$, —$C(O)NR_{q1}R_{r1}$ and —$S(O)_2NR_{n1}COR_{p1}$;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with 1, 2, 3, 4, or 5 $Z^{1c}$ groups;

each $Z^{1c}$ is independently selected from halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O)_2NR_{q2}R_{r2}$, $NO_2$, —$C(O)R_{n2}$, —$C(O)OR_{n2}$, and —$C(O)NR_{q2}R_{r2}$;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R_{n1}$ is independently selected from H, $(C_1-C_8)$alkyl, $(C_2-C_8)$alkenyl, and $(C_2-C_8)$alkynyl, wherein any $(C_1-C_8)$alkyl, $(C_2-C_8)$alkenyl and $(C_2-C_8)$alkynyl of $R_{n1}$ is optionally substituted with 1, 2, 3, 4, or 5 $Z^{1c}$ groups;

each $R_{p1}$ is independently selected from $(C_1-C_8)$alkyl, $(C_2-C_8)$alkenyl, and $(C_2-C_8)$alkynyl, wherein any $(C_1-C_8)$alkyl, $(C_2-C_8)$alkenyl and $(C_2-C_8)$alkynyl of $R_{p1}$ is optionally substituted with 1, 2, 3, 4, or 5 $Z^{1c}$ groups;

$R_{q1}$ and $R_{r1}$ are each independently selected from H, $(C_1-C_8)$alkyl, $(C_2-C_8)$alkenyl, $(C_2-C_8)$alkynyl, wherein any $(C_1-C_8)$alkyl, $(C_2-C_8)$alkenyl and $(C_2-C_8)$alkynyl of $R_{q1}$ or $R_{r1}$ is optionally substituted with 1, 2, 3, 4, or 5 $Z^{1c}$ groups;

each $R_{n2}$ is independently selected from H, $(C_1-C_8)$alkyl, $(C_2-C_8)$alkenyl, $(C_2-C_8)$alkynyl, $(C_1-C_8)$haloalkyl and $(C_1-C_8)$heteroalkyl;

each $R_{p2}$ is independently selected from $(C_1-C_8)$alkyl, $(C_2-C_8)$alkenyl, $(C_2-C_8)$alkynyl, $(C_1-C_8)$haloalkyl and $(C_1-C_8)$heteroalkyl;

$R_{q2}$ and $R_{r2}$ are each independently selected from H, $(C_1-C_8)$alkyl, $(C_2-C_8)$alkenyl, $(C_2-C_8)$alkynyl, $(C_1-C_8)$haloalkyl and $(C_1-C_8)$heteroalkyl;

$Z^2$ is selected from —$OR_{s3}$, —$OC(O)R_{p3}$, —$OC(O)NR_{q3}R_{r3}$, —$SR_{n3}$, —$S(O)R_{p3}$, —$S(O)_2R_{p3}$, —$S(O)_2NR_{q3}R_{r3}$, —$NR_{q3}R_{r3}$, —$NR_{n3}COR_{p3}$, —$NR_{n3}CO_2R_{p3}$, —$NR_{n3}S(O)_2R_{p3}$, —$NR_{n3}S(O)_2OR_{p3}$ and —$NR_{n3}S(O)_2NR_{q3}R_{r3}$;

each $Z^{2a}$ is independently selected from halogen, —CN, —$OR_{n4}$, —$OC(O)R_{p4}$, —$OC(O)NR_{q4}R_{r4}$, —$SR_{n4}$, —$S(O)R_{p4}$, —$S(O)_2OH$, —$S(O)_2R_{p4}$, —$S(O)_2NR_{q4}R_{r4}$, —$NR_{q4}R_{r4}$, —$NR_{n4}COR_{p4}$, —$NR_{n4}CO_2R_{p4}$, —$NR_{n4}CONR_{q2}R_{r4}$, —$NR_{n4}S(O)_2R_{p4}$, —$NR_{n4}S(O)_2OR_{p4}$, —$NR_{n4}S(O)_2NR_{q4}R_{r4}$, $NO_2$, —$C(O)R_{n4}$, —$C(O)OR_{n4}$, and —$C(O)NR_{q4}R_{r4}$;

each $Z^{2b}$ is independently selected from $(C_1-C_4)$alkyl, $(C_1-C_4)$heteroalkyl and $(C_1-C_4)$haloalkyl;

each $Z^{2c}$ is independently selected from halogen, —CN, —$OR_{n4}$, —$OC(O)R_{p4}$, —$OC(O)NR_{q4}R_{r4}$, —$SR_{n4}$, —$S(O)R_{p4}$, —$S(O)_2OH$, —$S(O)_2R_{p4}$, —$S(O)_2NR_{q4}R_{r4}$, —$NR_{q4}R_{r4}$, —$NR_{n4}COR_{p4}$, —$NR_{n4}CO_2R_{p4}$, —$NR_{n4}CONR_{q4}R_{r4}$, —$NR_{n4}S(O)_2R_{p4}$, —$NR_{n4}S(O)_2OR_{p4}$, —$NR_{n4}S(O)_2NR_{q4}R_{r4}$, $NO_2$, —$C(O)R_{n4}$, —$C(O)OR_{n4}$, —$C(O)NR_{q4}R_{r4}$;

each $R_{n3}$ is independently selected from H, $(C_1-C_4)$alkyl, $(C_2-C_4)$alkenyl, and $(C_2-C_4)$alkynyl, wherein any $(C_1-C_4)$alkyl, $(C_2-C_4)$alkenyl or $(C_2-C_4)$alkynyl of $R_{n3}$ is optionally substituted with 1, 2, 3, 4, or 5 $Z^{2a}$ groups;

each $R_{p3}$ is independently selected from $(C_1-C_4)$alkyl, $(C_1-C_4)$haloalkyl, $(C_2-C_4)$alkenyl, and $(C_2-C_4)$alkynyl, wherein any $(C_1-C_4)$alkyl, $(C_2-C_4)$alkenyl and $(C_2-C_4)$alkynyl of $R_{p3}$ is optionally substituted with 1, 2, 3, 4, or 5 $Z^{2a}$ groups;

$R_{q3}$ and $R_{r3}$ are each independently selected from H, $(C_1-C_4)$alkyl, and $(C_2-C_4)$alkenyl, wherein any $(C_1-C_4)$alkyl and $(C_2-C_4)$alkenyl of $R_{q3}$ or $R_{r3}$ is optionally substituted with 1, 2, 3, 4, or 5 $Z^{2a}$ groups, or $R_{q3}$ and $R_{r3}$ together with the nitrogen to which they are attached form a heterocycle or heteroaryl selected from triazolyl, aziridinyl, azetidinyl, pyrrolidinyl, piperidinyl, homopiperidinyl, morpholinyl, piperazinyl, isoindolinyl, 2-oxa-6-azaspiro[3.3]heptanyl, and imidazolidinyl wherein the triazolyl, aziridinyl, azetidinyl, pyrrolidinyl, piperidinyl, homopiperidinyl, morpholinyl, piperazinyl, isoindolinyl, 2-oxa-6-azaspiro[3.3]heptanyl, and imidazolidinyl is optionally substituted with 1, 2, 3, 4, or 5 $Z^{2b}$, $Z^{2c}$, or oxo groups;

each $R_{s3}$ is independently selected from $(C_2-C_4)$alkenyl or $(C_2-C_4)$alkynyl, wherein any $(C_2-C_4)$alkenyl or $(C_2-C_4)$alkynyl of $R_{s3}$ is optionally substituted with 1, 2, 3, 4, or 5 $Z^{2a}$ groups, or $R_{s3}$ is $(C_1-C_4)$alkyl substituted with 1, 2, 3, 4, or 5 $Z^{2a}$ groups;

each $R_{n4}$ is independently selected from H, $(C_1-C_4)$alkyl, $(C_2-C_8)$alkenyl, $(C_2-C_8)$alkynyl, $(C_1-C_4)$haloalkyl and $(C_1-C_4)$heteroalkyl;

each $R_{p4}$ is independently selected from $(C_1-C_8)$alkyl, $(C_2-C_4)$alkenyl, $(C_2-C_4)$alkynyl, $(C_1-C_4)$haloalkyl and $(C_1-C_4)$heteroalkyl;

$R_{q4}$ and $R_{r4}$ are each independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl;

each $Z^3$ is independently selected from halogen, $(C_1-C_4)$alkyl, —OH, —CN, $(C_1-C_4)$heteroalkyl and $(C_1-C_4)$haloalkyl;

each $Z^4$ is independently selected from $(C_1-C_8)$alkyl, $(C_2-C_8)$alkenyl, $(C_2-C_8)$alkynyl, halogen, —CN, —$OR_{n5}$, —$OC(O)R_{p5}$, —$OC(O)NR_{q5}R_{r5}$, —$SR_{n5}$, —$S(O)R_{p5}$, —$S(O)_2OH$, —$S(O)_2R_{p5}$, —$S(O)_2NR_{q5}R_{r5}$, —$NR_{q5}R_{r5}$, —$NR_{n5}COR_{p5}$, —$NR_{n5}CO_2R_{p5}$, —$NR_{n5}CONR_{q5}R_{r5}$, —$NR_{n5}S(O)_2R_{p5}$, —$NR_{n5}S(O)_2OR_{p5}$, —$NR_{n5}S(O)_2NR_{q5}R_{r5}$, $NO_2$, —$C(O)R_{n5}$, —$C(O)OR_{n5}$, —$C(O)NR_{q5}R_{r5}$ and —$B(OR_{q5})(OR_{r5})$, wherein any $(C_1-C_8)$alkyl, $(C_2-C_8)$alkenyl and $(C_2-C_8)$alkynyl of $Z^4$ is optionally substituted with 1, 2, 3, 4, or 5 $Z^{4a}$ groups;

each $Z^{4a}$ is independently selected from halogen, —CN, —$OR_{n6}$, —$OC(O)R_{p6}$, —$OC(O)NR_{q6}R_{r6}$, —$SR_{n6}$, —$S(O)R_{p6}$, —$S(O)_2OH$, —$S(O)_2R_{p6}$, —$S(O)_2NR_{q6}R_{r6}$, —$NR_{q6}R_{r6}$, —$NR_{n6}COR_{p6}$, —$NR_{n6}CO_2R_{p6}$, —$NR_{n6}CONR_{q6}R_{r6}$, —$NR_{n6}S(O)_2R_{p6}$, —$NR_{n6}S(O)_2OR_{p6}$, —$NR_{n6}S(O)_2NR_{q6}R_{r6}$, $NO_2$, —$C(O)R_{n6}$, —$C(O)OR_{n6}$, and —$C(O)NR_{q6}R_{r6}$;

each $Z^{4b}$ is independently selected from $(C_1-C_4)$alkyl, $(C_2-C_4)$alkenyl and $(C_2-C_4)$alkynyl, wherein any $(C_1-C_4)$alkyl, $(C_2-C_4)$alkenyl and $(C_2-C_4)$alkynyl of $Z^{4b}$ is optionally substituted with 1, 2, 3, 4, or 5 $Z^{4c}$ groups;

each $Z^{4c}$ is independently selected from halogen, —CN, —$OR_{n7}$, —$OC(O)R_{p7}$, —$OC(O)NR_{q7}R_{r7}$, —$SR_{n7}$, —$S(O)R_{p7}$, —$S(O)_2OH$, —$S(O)_2R_{p7}$, —$S(O)_2NR_{q7}R_{r7}$, —$NR_{q7}R_{r7}$, —$NR_{n7}COR_{p7}$, —$NR_{n7}CO_2R_{p7}$, —$NR_{n7}CONR_{q7}R_{r7}$, —$NR_{n7}S(O)_2R_{p7}$, —$NR_{n7}S(O)_2OR_{p7}$, $NR_{n7}S(O)_2NR_{q7}R_{r7}$, $NO_2$, —$C(O)R_{n7}$, —$C(O)OR_{n7}$, —$C(O)NR_{q7}R_{r7}$ and $(C_1-C_4)$heteroalkyl;

each $Z^{4d}$ is independently selected from $(C_1-C_4)$alkyl, $(C_2-C_4)$alkenyl, $(C_2-C_4)$alkynyl, and $(C_1-C_4)$haloalkyl;

each $R_{n5}$ is independently selected from H, $(C_1-C_4)$alkyl, $(C_2-C_4)$alkenyl, $(C_2-C_4)$alkynyl, wherein any $(C_1-C_4)$alkyl, $(C_2-C_4)$alkenyl and $(C_2-C_4)$alkynyl of $R_{n5}$ is optionally substituted with 1, 2, 3, 4, or 5 $Z^{4a}$ groups;

each $R_{p5}$ is independently selected from $(C_1-C_4)$alkyl, $(C_2-C_4)$alkenyl, and $(C_2-C_4)$alkynyl, wherein any $(C_1-C_4)$alkyl, $(C_2-C_4)$alkenyl or $(C_2-C_4)$alkynyl of $R_{p5}$ is optionally substituted with 1, 2, 3, 4, or 5 $Z^{4a}$ groups;

$R_{q5}$ and $R_{r5}$ are each independently selected from H, $(C_1-C_4)$alkyl, $(C_2-C_4)$alkenyl, and $(C_2-C_4)$alkynyl, wherein any $(C_1-C_4)$alkyl, $(C_2-C_4)$alkenyl and $(C_2-C_4)$alkynyl of $R_{q5}$ or $R_{r5}$ is optionally substituted with 1, 2, 3, 4, or 5 $Z^{4a}$ groups;

each $R_{n6}$ is independently selected from H, $(C_1-C_4)$alkyl, $(C_2-C_4)$alkenyl, and $(C_2-C_4)$alkynyl, wherein any $(C_1-C_4)$alkyl, $(C_2-C_4)$alkenyl and $(C_2-C_4)$alkynyl of $R_{n6}$ is optionally substituted with 1, 2, 3, 4, or 5 $Z^{4c}$ groups;

each $R_{p6}$ is independently selected from $(C_1-C_4)$alkyl, $(C_2-C_4)$alkenyl, and $(C_2-C_4)$alkynyl, wherein any $(C_1-C_4)$alkyl, $(C_2-C_4)$alkenyl and $(C_2-C_4)$alkynyl of $R_{p6}$ is optionally substituted with 1, 2, 3, 4, or 5 $Z^{4c}$ groups;

$R_{q6}$ and $R_{r6}$ are each independently selected from H, $(C_1-C_4)$alkyl, $(C_2-C_4)$alkenyl, and $(C_2-C_4)$alkynyl, wherein any $(C_1-C_4)$alkyl, $(C_2-C_4)$alkenyl and $(C_2-C_4)$alkynyl of $R_{q6}$ or $R_{r6}$ is optionally substituted with 1, 2, 3, 4, or 5 $Z^{4c}$ groups;

each $R_{n7}$ is independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl;

each $R_{p7}$ is independently selected from $(C_1-C_4)$alkyl, $(C_2-C_4)$alkenyl, $(C_2-C_4)$alkynyl, $(C_1-C_4)$haloalkyl and $(C_1-C_4)$heteroalkyl;

$R_{q7}$ and $R_{r7}$ are each independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl, each $Z^5$ is independently selected from $(C_1-C_6)$alkyl, halogen, —CN, and —$OR_{n8}$, wherein any $(C_1-C_6)$alkyl of $Z^5$ is optionally substituted with 1, 2, 3, 4, or 5 halogen; and each $R_{n8}$ is independently selected from H, $(C_1-C_3)$alkyl, and $(C_1-C_3)$haloalkyl;

or a salt thereof.

2. The compound of claim 1, or a salt thereof, wherein $R^{3a}$ and $R^{3b}$ are each H.

3. The compound of claim 1, or a salt thereof, wherein $R^2$ is 3,5-difluorophenyl.

4. The compound of claim 1 which is a compound of formula Ie:

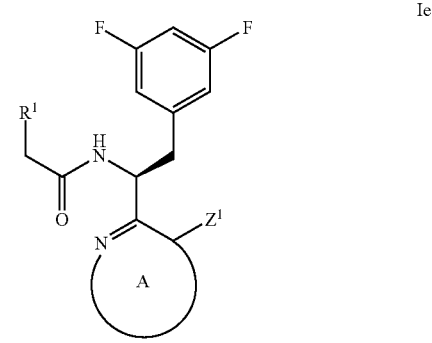

or a salt thereof.

5. The compound of claim 1, or a salt thereof, wherein each $Z^{1a}$ is independently halogen, —$OR_{n1}$, —$S(O)_2NR_{q1}R_{r1}$, —$NR_{q1}R_{r1}$, —$NR_{n1}S(O)_2R_{p1}$ or —$C(O)NR_{q1}R_{r1}$, and each $Z^{1b}$ is $(C_1-C_3)$alkyl, wherein any $(C_1-C_3)$alkyl of $Z^{1b}$ is optionally substituted with one $Z^{1c}$ group.

6. The compound of claim 1, or a salt thereof, wherein $Z^1$ is:

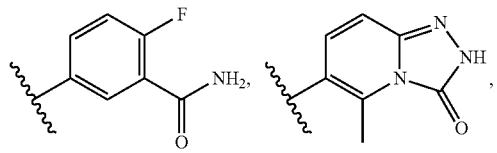

-continued

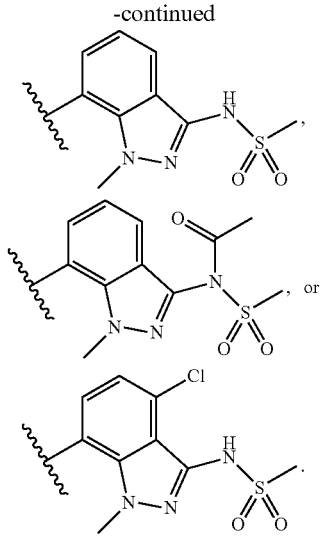

7. The compound of claim 1, or a salt thereof, wherein $Z^2$ is —$NR_{q3}R_{r3}$.

8. The compound of claim 1, or a salt thereof, wherein $R_{q3}$ and $R_{r3}$ are each independently selected from H and $(C_1$-$C_4)$ alkyl wherein any $(C_1$-$C_4)$alkyl of $R_{q3}$ or $R_{r3}$ is optionally substituted with 1, 2, 3, 4, or 5 $Z^{2a}$ groups, or $R_{q3}$ and $R_{r3}$ together with the nitrogen to which they are attached form a heterocycle or heteroaryl selected from triazolyl, azetidinyl, pyrrolidinyl, piperidinyl, morpholinyl, piperazinyl, isoindolinyl, 2-oxa-6-azaspiro[3.3]heptanyl, and imidazolidinyl wherein the triazolyl, azetidinyl, pyrrolidinyl, piperidinyl, morpholinyl, piperazinyl, isoindolinyl, 2-oxa-6-azaspiro [3.3]heptanyl, and imidazolidinyl is optionally substituted with 1, 2, 3, 4, or 5 $Z^{2b}$, $Z^{2c}$, or oxo groups.

9. The compound of claim 1, or a salt thereof, wherein $Z^2$ is selected from:

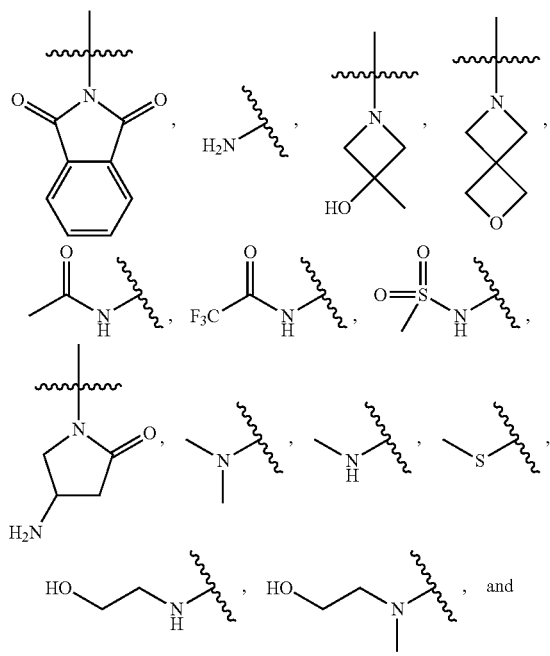

-continued

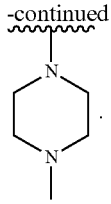

10. The compound of claim 1, or a salt thereof, wherein $R^1$ is a bicyclic-heteroaryl, wherein the bicyclic-heteroaryl of $R^1$ contains at least one partially unsaturated ring.

11. The compound of claim 1, or a salt thereof, wherein each $Z^4$ is independently selected from $(C_1$-$C_6)$alkyl and halogen, wherein any $(C_1$-$C_6)$alkyl of $Z^3$ is optionally substituted with 1, 2, 3, 4, or 5 halogen.

12. The compound of claim 1, or a salt thereof, wherein $R^1$ is selected from:

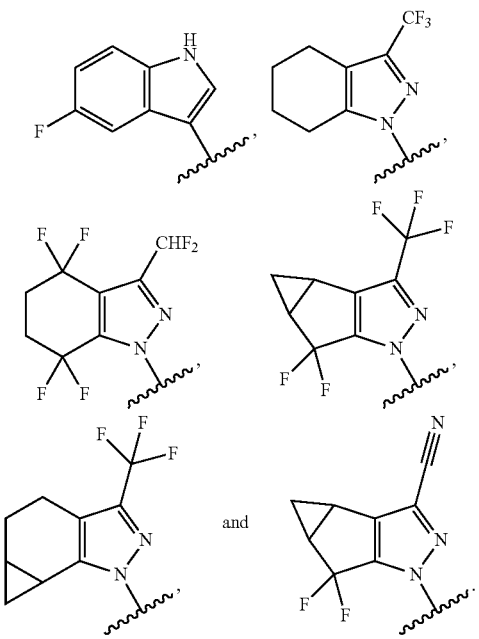

13. A compound, in which the compound is:

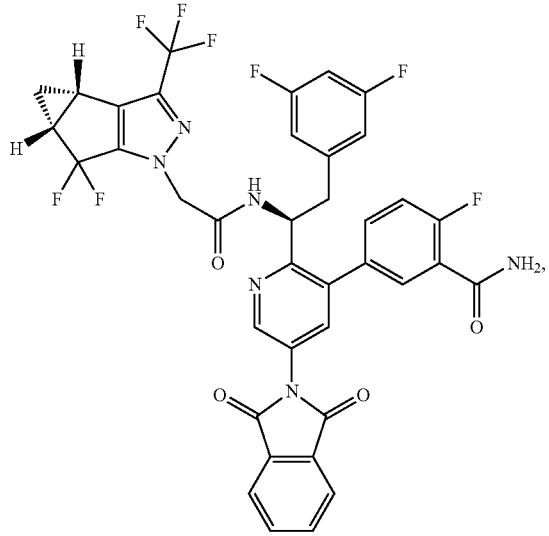

153
-continued
154
-continued
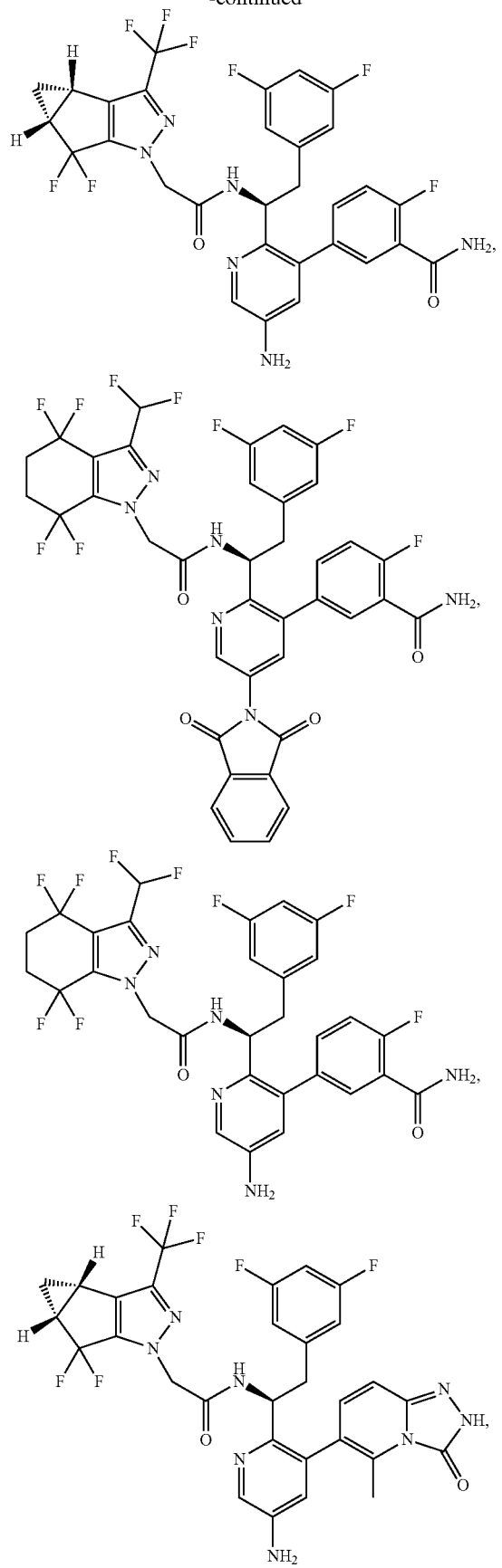
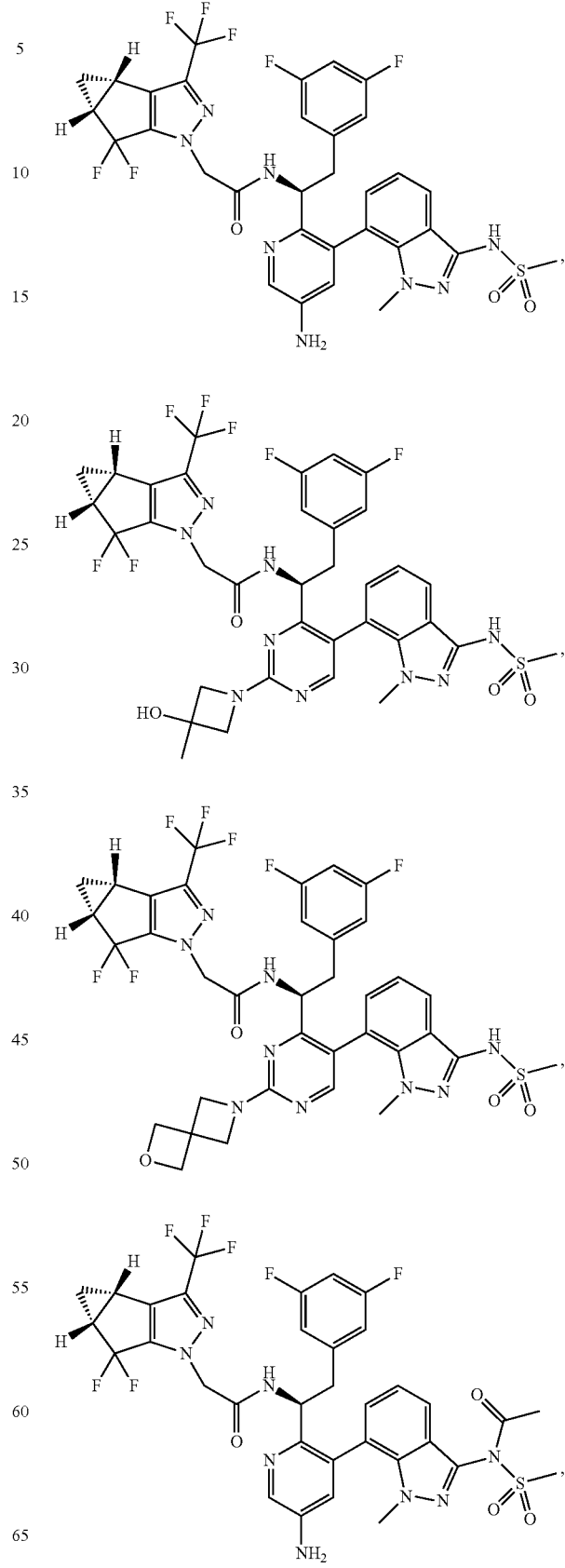

155
-continued
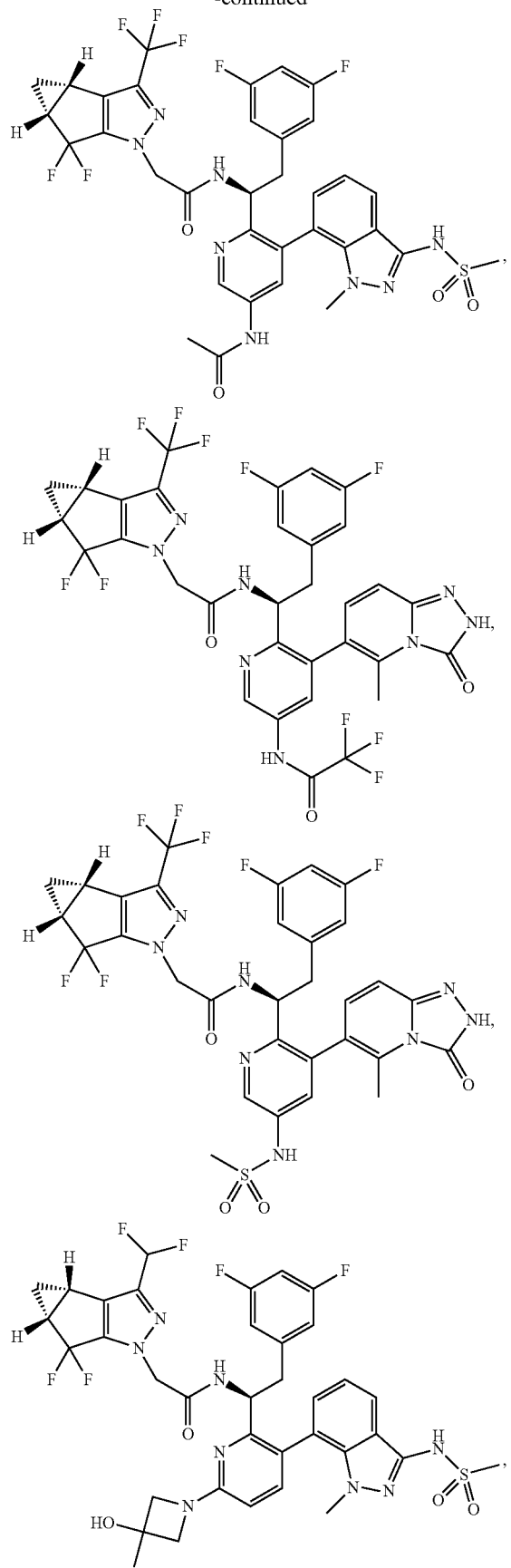
156
-continued
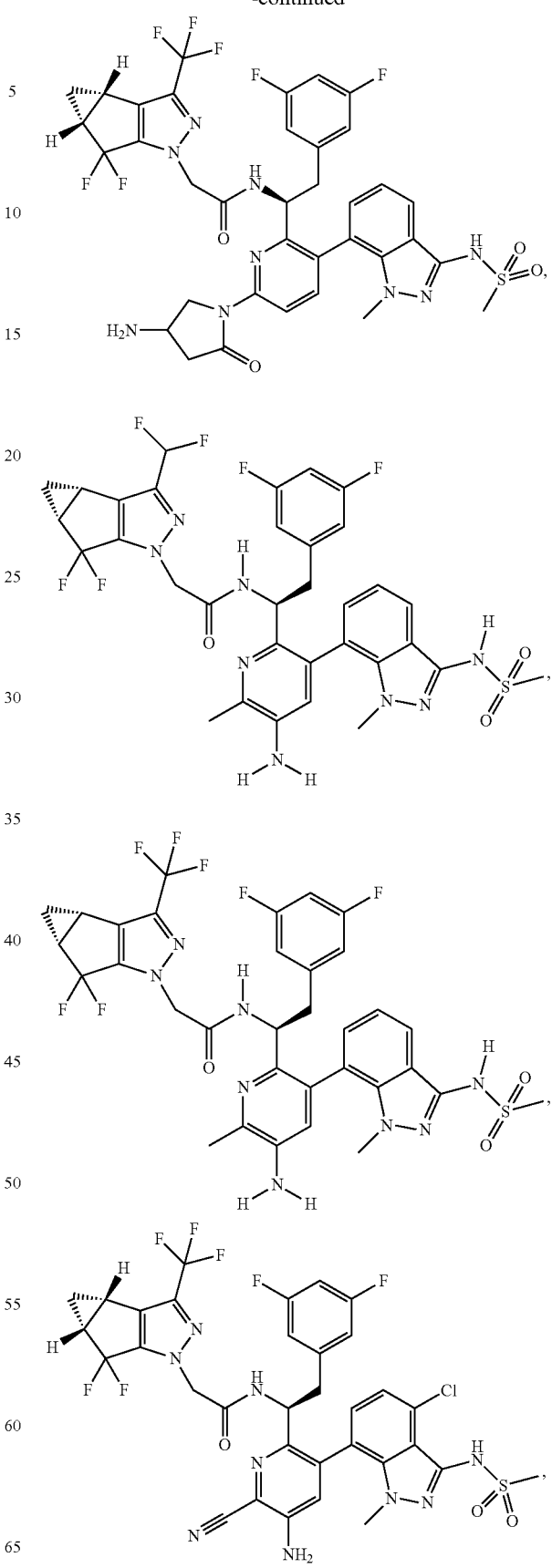

157
-continued
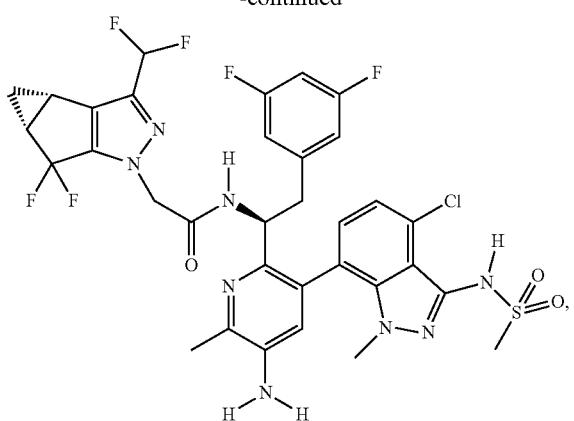
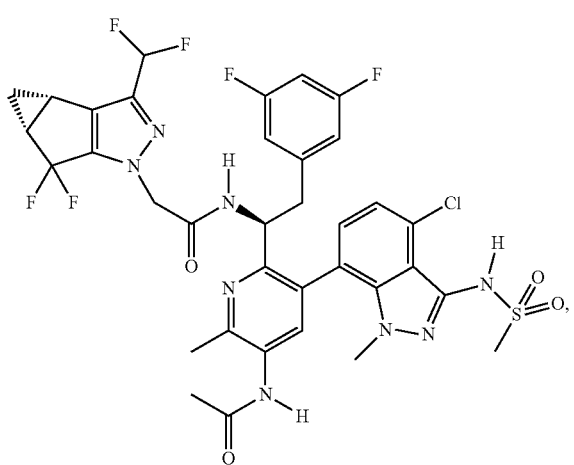
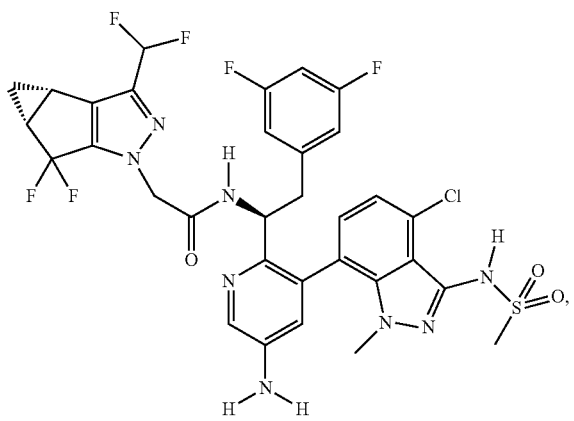
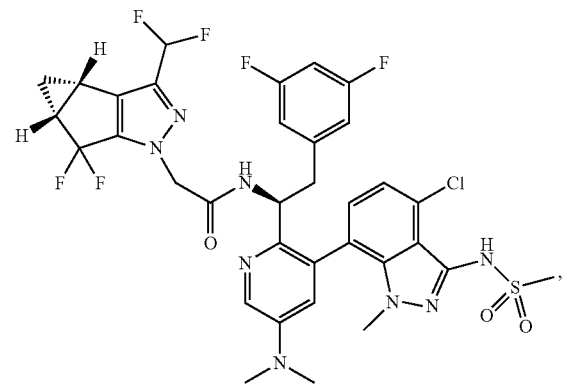
158
-continued
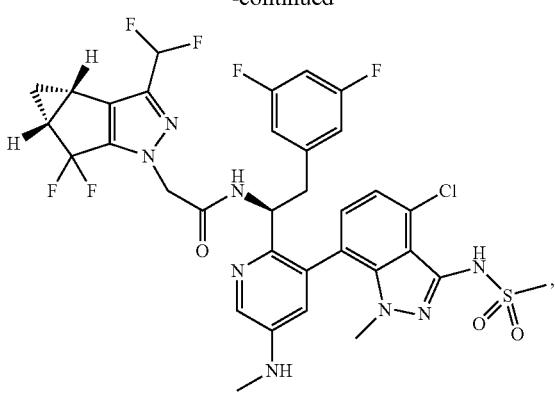
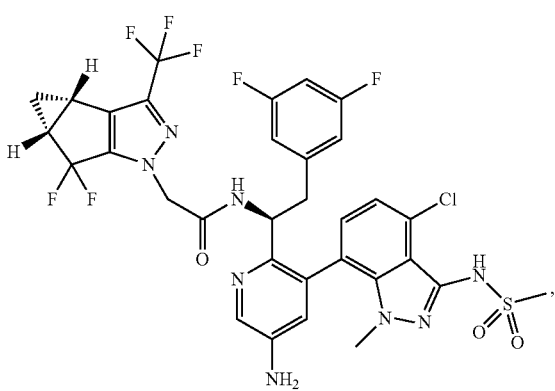
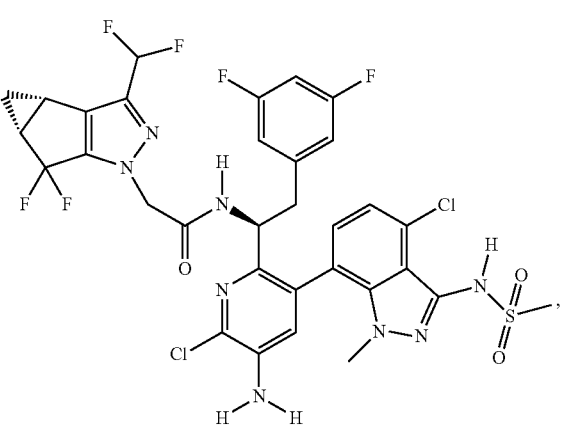
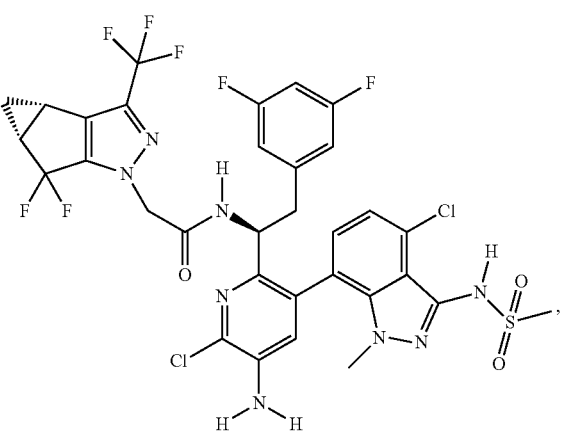

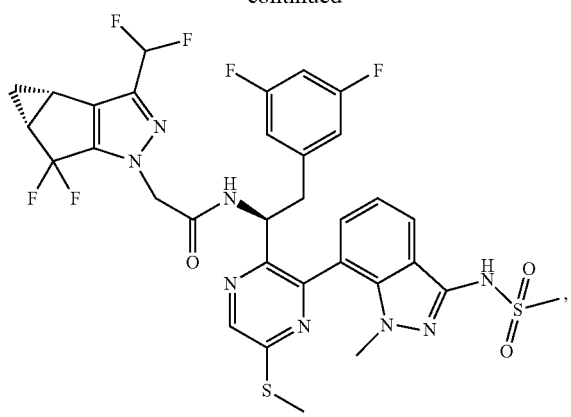
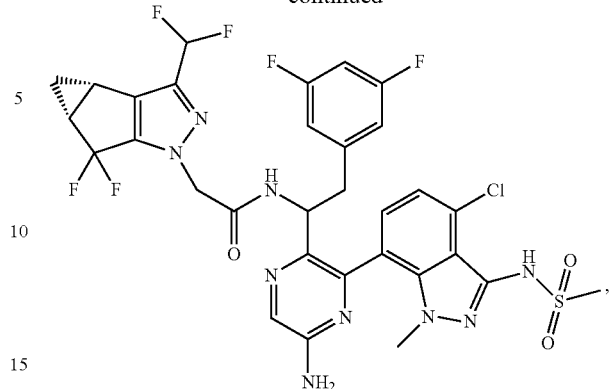
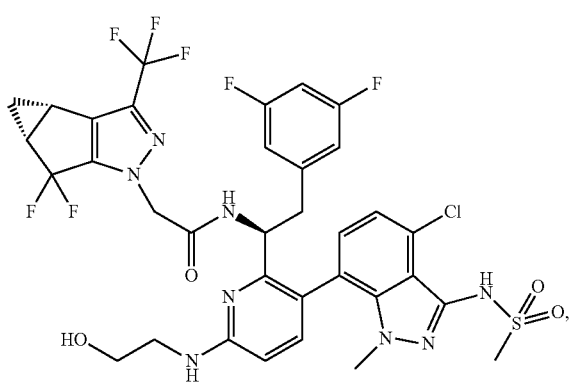
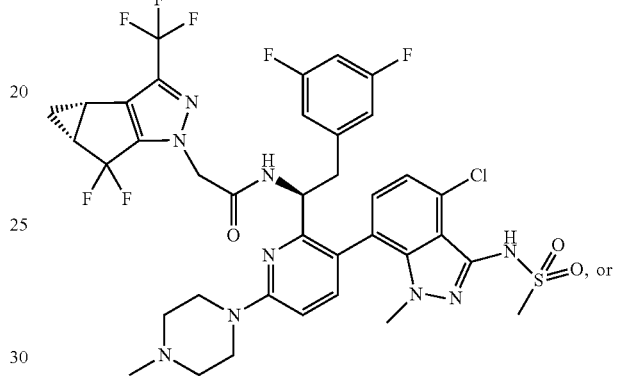
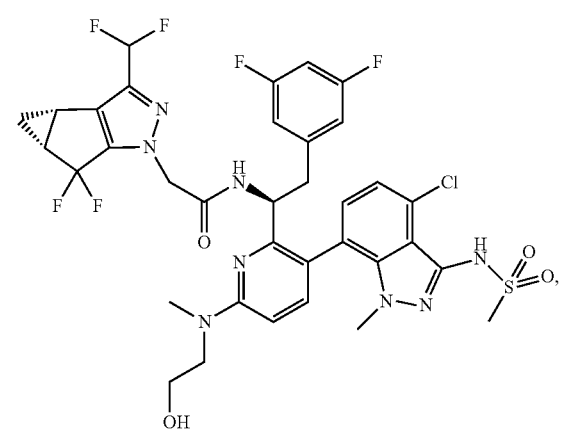
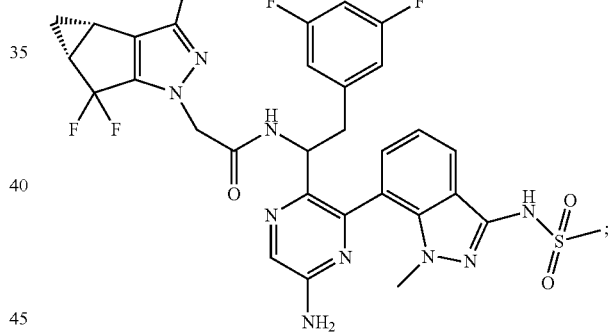
and pharmaceutically acceptable salts thereof.
14. A compound of formula If:
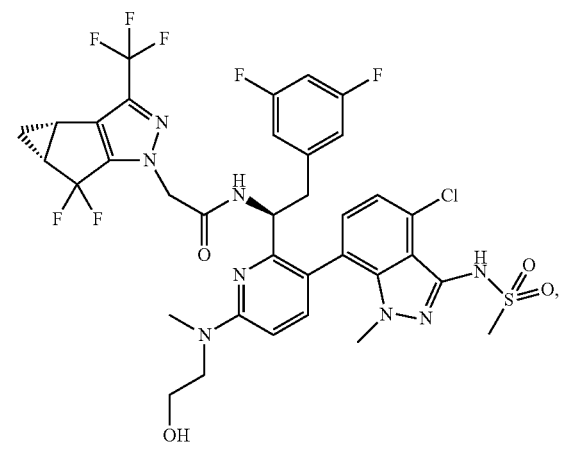
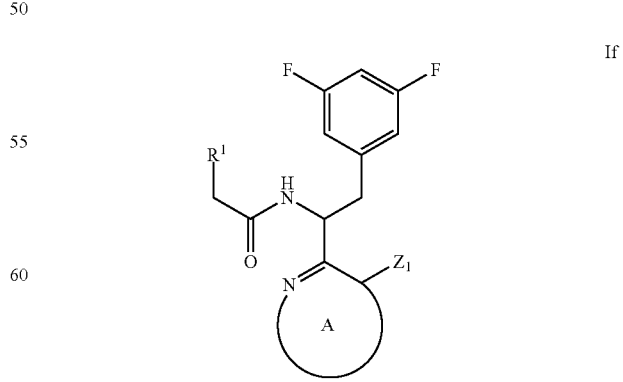
A is pyridinyl, pyrimidinyl, pyrazinyl or pyridazinyl, wherein any pyridinyl, pyrimidinyl, pyrazinyl or pyridazinyl of A is substituted with one $Z^1$ group, one $Z^2$ group, and optionally substituted with $Z^3$ group;
$R^1$ is

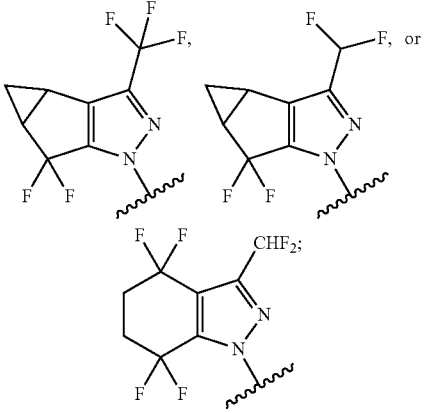

$Z^1$ is phenyl, pyradinyl, indazolyl, or triazolopyridinyl, wherein any phenyl, pyradinyl, indazolyl, or triazolopyridinyl, of $Z^1$ is optionally substituted with 1 to 3 substituents independently selected from $(C_1\text{-}C_8)$alkyl, oxo, halogen, —C(O)NH$_2$, —NHS(O)$_2$CH$_3$, or —N(COCH$_3$)(S(O)$_2$CH$_3$);

$Z^2$ is —NR$_{q3}$R$_{r3}$, —NHCOR$_{p3}$, —NHCO$_2$R$_{p3}$, —NHS(O)$_2$R$_{p3}$, —NHS(O)$_2$OR$_{p3}$, —NHS(O)$_2$NR$_{q3}$R$_{r3}$, or —SCH$_3$;

R$_{q3}$ and R$_{r3}$ are each independently H or $(C_1\text{-}C_4)$alkyl, wherein any $(C_1\text{-}C_4)$alkyl of R$_{q3}$ or R$_{r3}$ is optionally substituted with —OH, or R$_{q3}$ and R$_{r3}$ together with the nitrogen to which they are attached form a heterocycle or heteroaryl selected from triazolyl, azetidinyl, pyrrolidinyl, piperidinyl, morpholinyl, piperazinyl, isoindolinyl, 2-oxa-6-azaspiro[3.3]heptanyl, and imidazolidin 1 wherein the triazolyl, azetidinyl, pyrrolidinyl, piperidinyl, morpholinyl, piperazinyl, isoindolinyl, 2-oxa-6-azaspiro[3.3]heptanyl, and imidazolidinyl, is optionally substituted with 1 to 3 substituents independently selected from $(C_1\text{-}C_4)$alkyl, —OH, —NH$_2$, or oxo;

R$_{p3}$ is $(C_1\text{-}C_4)$alkyl or $(C_1\text{-}C_4)$haloalkyl; and each $Z^3$ is independently halogen, $(C_1\text{-}C_4)$alkyl, —OH, —CN, $(C_1\text{-}C_4)$heteroalkyl or $(C_1\text{-}C_4)$haloalkyl;

or a pharmaceutically acceptable salt thereof.

15. A pharmaceutical composition comprising a compound of claim 1, or a pharmaceutically acceptable salt thereof, and a pharmaceutically acceptable carrier.

16. A method for treating an HIV infection in a mammal comprising administering a therapeutically effective amount of a compound of claim 1, or a pharmaceutically acceptable salt thereof, to the mammal.

17. A method for treating an HIV infection in a mammal comprising administering to the mammal in need thereof a therapeutically effective amount of a compound of claim 1, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

* * * * *